(12) United States Patent
Ha et al.

(10) Patent No.: US 10,910,567 B2
(45) Date of Patent: Feb. 2, 2021

(54) DOUBLE SPIRO-TYPE COMPOUND AND ORGANIC LIGHT EMITTING DIODE COMPRISING SAME

(71) Applicant: LG Chem, Ltd., Seoul (KR)

(72) Inventors: Jae Seung Ha, Daejeon (KR); Sung Kil Hong, Daejeon (KR); Sang Duk Suh, Daejeon (KR)

(73) Assignee: LG Chem, Ltd.

( * ) Notice: Subject to any disclaimer, the term of this patent is extended or adjusted under 35 U.S.C. 154(b) by 352 days.

(21) Appl. No.: 15/764,417

(22) PCT Filed: Oct. 7, 2016

(86) PCT No.: PCT/KR2016/011233
§ 371 (c)(1),
(2) Date: Mar. 29, 2018

(87) PCT Pub. No.: WO2017/061810
PCT Pub. Date: Apr. 13, 2017

(65) Prior Publication Data
US 2018/0287073 A1 Oct. 4, 2018

(30) Foreign Application Priority Data

Oct. 7, 2015 (KR) .......................... 10-2015-0141233

(51) Int. Cl.
*H01L 51/00* (2006.01)
*C09K 11/06* (2006.01)
*H01L 51/50* (2006.01)
*C07C 13/72* (2006.01)
*C07D 405/04* (2006.01)
*C07D 405/10* (2006.01)
*C07D 409/04* (2006.01)
*C07D 409/10* (2006.01)
*C07D 487/04* (2006.01)

(52) U.S. Cl.
CPC .......... *H01L 51/0073* (2013.01); *C07C 13/72* (2013.01); *C07D 405/04* (2013.01); *C07D 405/10* (2013.01); *C07D 409/04* (2013.01); *C07D 409/10* (2013.01); *C07D 487/04* (2013.01); *C09K 11/06* (2013.01); *H01L 51/00* (2013.01); *H01L 51/0052* (2013.01); *H01L 51/0058* (2013.01); *H01L 51/0067* (2013.01); *H01L 51/0072* (2013.01); *H01L 51/0074* (2013.01); *H01L 51/50* (2013.01); *C09K 2211/1018* (2013.01); *H01L 51/0077* (2013.01); *H01L 51/5012* (2013.01); *H01L 51/5016* (2013.01); *H01L 51/5076* (2013.01); *H01L 51/5092* (2013.01)

(58) Field of Classification Search
CPC ............................. H01L 51/007; C07C 13/72
See application file for complete search history.

(56) References Cited

U.S. PATENT DOCUMENTS

| | | | |
|---|---|---|---|
| 2009/0162612 A1 * | 6/2009 | Hatwar | H01L 51/5048 428/156 |
| 2013/0256645 A1 | 10/2013 | Min et al. | |
| 2014/0027757 A1 | 1/2014 | Yamada et al. | |
| 2014/0103322 A1 | 4/2014 | Watanabe et al. | |
| 2014/0225040 A1 | 8/2014 | Parham et al. | |
| 2016/0163991 A1 | 6/2016 | Suzuki et al. | |

FOREIGN PATENT DOCUMENTS

| | | |
|---|---|---|
| EP | 2799515 A1 | 11/2014 |
| JP | 2012229195 A | 11/2012 |
| JP | 2012240951 A | 12/2012 |
| KR | 20140118849 A | 10/2014 |
| KR | 20150010016 A | 1/2015 |
| WO | 02088274 A1 | 11/2002 |
| WO | 2012141229 A1 | 10/2012 |
| WO | 2013017189 A1 | 2/2013 |
| WO | 2015009076 A1 | 1/2015 |

OTHER PUBLICATIONS

Extended European Search Report including Written Opinion for Application No. EP16853926.0 dated Mar. 14, 2019.
Search report from International Application No. PCT/KR2016/011233, dated Jan. 20, 2017.

* cited by examiner

*Primary Examiner* — Peter F Godenschwager
(74) *Attorney, Agent, or Firm* — Lerner, David, Littenberg, Krumholz & Mentlik, LLP

(57) ABSTRACT

The present specification provides a double spiro structured compound and an organic light emitting device including the same.

20 Claims, 1 Drawing Sheet

[Figure 1]
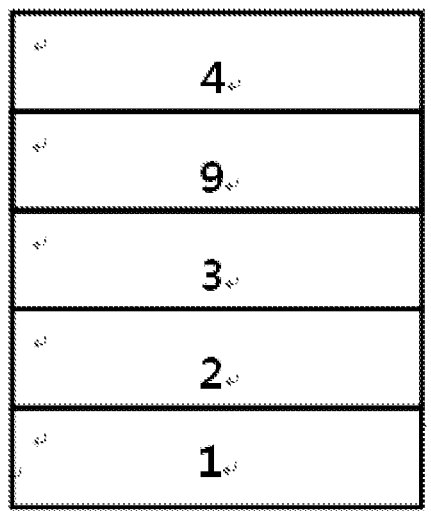
[Figure 2]
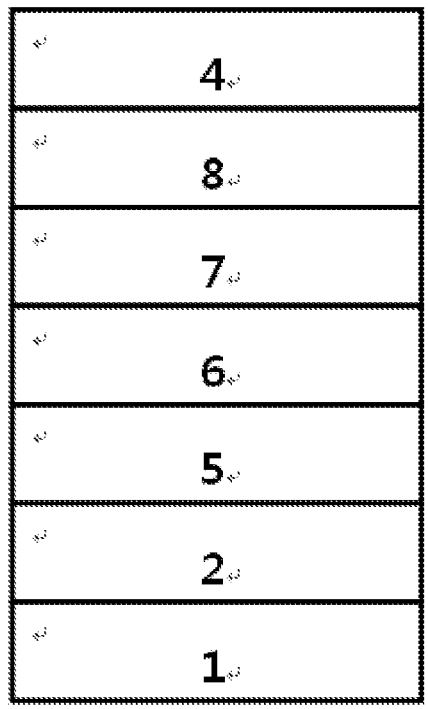

DOUBLE SPIRO-TYPE COMPOUND AND ORGANIC LIGHT EMITTING DIODE COMPRISING SAME

CROSS-REFERENCE TO RELATED APPLICATION

The present invention is a national phase entry under 35 U.S.C. § 371 of International Application No. PCT/KR2016/011233 filed on Oct. 7, 2016, which claims priority from Korean Patent Application No. 10-2015-0141233 filed on Oct. 7, 2015, the entire contents of which are incorporated herein by reference.

TECHNICAL FIELD

The present specification relates to a double spiro compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

DETAILED DESCRIPTION OF THE INVENTION

Technical Problem

The present specification describes a double spiro structured compound and an organic light emitting device including the same.

Technical Solution

An exemplary embodiment of the present specification provides an organic light emitting device including: an anode; a cathode provided to face the anode; and an organic material layer including a light emitting layer provided between the anode and the cathode, in which the organic material layer further includes an organic material layer provided between the light emitting layer and the cathode and including a compound of the following Chemical Formula 1:

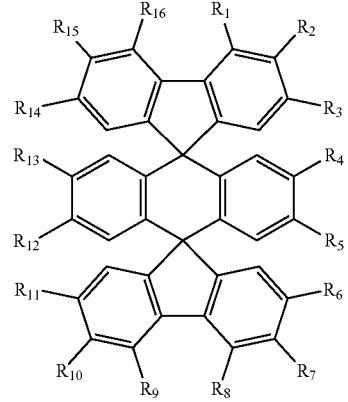

[Chemical Formula 1]

In Chemical Formula 1,
at least one of R1 to R16 combines with an adjacent group to form a ring of Chemical Formula 1-1,

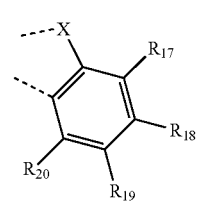

[Chemical Formula 1-1]

X is O or S, and
a group, which does not form the ring of Chemical Formula 1-1 among R1 to R16, and R17 to R20 are the same as or different from each other, and are each independently hydrogen; deuterium; a halogen group; a nitrile group; a nitro group; a hydroxy group; a carbonyl group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

Advantageous Effects

The compound described in the present specification may be used as a material for an organic material layer of an organic light emitting device. The compound according to at least one exemplary embodiment may improve efficiency, achieve low driving voltage and/or improve lifetime characteristics in the organic light emitting device. In particular, the compound described in the present specification may be used as a material for electron transport or electron injection.

BRIEF DESCRIPTION OF DRAWINGS

FIG. 1 illustrates an example of an organic light emitting device composed of a substrate 1, a positive electrode 2, a light emitting layer 3, an organic material layer 9 including the compound of Chemical Formula 1, and a negative electrode 4.

FIG. 2 illustrates an example of an organic light emitting device composed of a substrate 1, a positive electrode 2, a hole injection layer 5, a hole transport layer 6, a light emitting layer 7, an electron transport layer 8, and a negative electrode 4.

EXPLANATION OF REFERENCE NUMERALS AND SYMBOLS

1: Substrate
2: Positive electrode
3: Light emitting layer
4: Negative electrode
5: Hole injection layer
6: Hole transport layer
7: Light emitting layer
8: Electron transport layer
9: Organic material layer including compound of Chemical Formula 1

BEST MODE

Hereinafter, the present specification will be described in more detail.

An exemplary embodiment of the present specification provides an organic light emitting device including: an anode; a cathode provided to face the anode; and an organic material layer including a light emitting layer provided between the anode and the cathode, in which the organic material layer further includes an organic material layer provided between the light emitting layer and the cathode and including the compound of Chemical Formula 1.

Examples of the substituents will be described below, but are not limited thereto.

In the present specification, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or being unsubstituted or substituted with a substituent to which two or more substituents among the substituents exemplified above are linked. For example, "the substituent to which two or more substituents are linked" may be a biphenyl group. That is, the biphenyl group may also be an aryl group, and may be interpreted as a substituent to which two phenyl groups are linked.

In the present specification, an "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, examples of a halogen group include fluorine, chlorine, bromine or iodine.

In the present specification, the number of carbon atoms of a carbonyl group is not particularly limited, but is preferably 1 to 40. Specifically, the carbonyl group may be a compound having the following structures, but is not limited thereto.

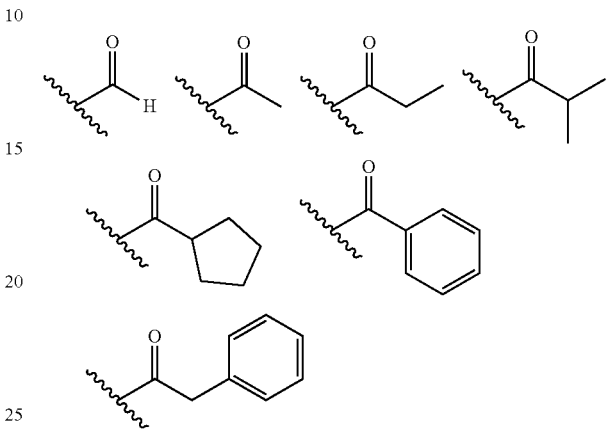

In the present specification, for an ester group, the oxygen of the ester group may be substituted with a straight-chained, branch-chained, or cyclic alkyl group having 1 to 40 carbon atoms, or an aryl group having 6 to 30 carbon atoms. Specifically, the ester group may be a compound having the following structural formulae, but is not limited thereto.

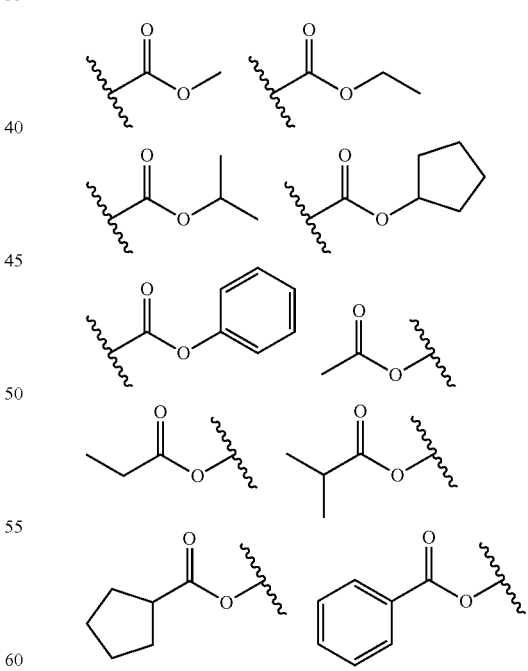

In the present specification, the number of carbon atoms of an imide group is not particularly limited, but is preferably 1 to 25. Specifically, the imide group may be a compound having the following structures, but is not limited thereto.

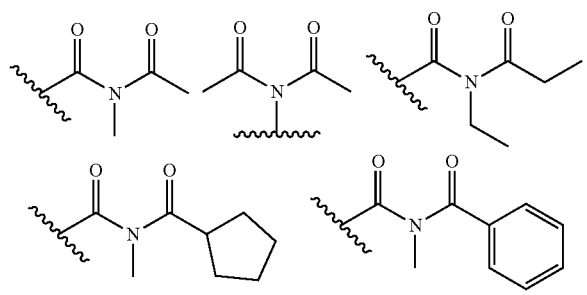

In the present specification, a silyl group may be represented by a chemical formula of —SiR$_a$R$_b$R$_c$, and R$_a$, R$_b$, and R$_c$ may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be represented by a chemical formula of —BR$_a$R$_b$R$_c$, and R$_a$, R$_b$, and R$_c$ may be each hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group, and the like, but are not limited thereto.

In the present specification, the alkyl group may be straight-chained or branch-chained, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 4-methylhexyl, 5-methylhexyl, and the like, but are not limited thereto.

In the present specification, the alkoxy group may be straight-chained, branch-chained, or cyclic. The number of carbon atoms of the alkoxy group is not particularly limited, but is preferably 1 to 40. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

A substituent including an alkyl group, an alkoxy group, and other alkyl group moieties described in the present specification includes both a straight-chained form and a branch-chained form.

In the present specification, the alkenyl group may be straight-chained or branch-chained, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 40. According to yet another exemplary embodiment, the number of carbon atoms of the cycloalkyl group is 3 to 20. According to still yet another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the number of carbon atoms of an alkylamine group is not particularly limited, but is preferably 1 to 40. Specific examples of the alkylamine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group, and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group, and may be a polycyclic aryl group. The arylamine group including two or more aryl groups may include a monocyclic aryl group, a polycyclic aryl group, or both a monocyclic aryl group and a polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group, and may be a polycyclic heterocyclic group. The heteroarylamine group including two or more heterocyclic groups may include a monocyclic heterocyclic group, a polycyclic heterocyclic group, or both a monocyclic heterocyclic group and a polycyclic heterocyclic group.

In the present specification, an arylheteroarylamine group means an amine group substituted with an aryl group and a heterocyclic group.

In the present specification, examples of an arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group, and may be a polycyclic aryl group. The arylphosphine group including two or more aryl groups may include a monocyclic aryl group, a polycyclic aryl group, or both a monocyclic aryl group and a polycyclic aryl group.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. Examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, a fluorenyl group may be substituted, and two substituents may combine with each other to form a spiro structure.

When the fluorenyl group is substituted, the fluorenyl group may be a spiro fluorenyl group such as

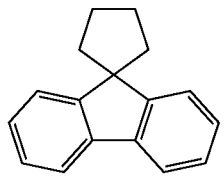 and 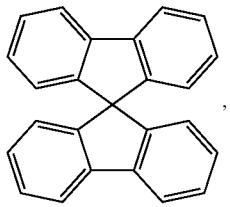

and a substituted fluorenyl group such as

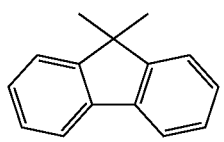

(a 9,9-dimethylfluorenyl group),

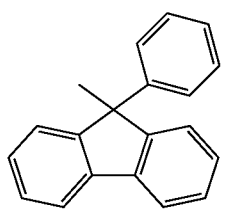 [SMILES: CC1(c2ccccc2)c2ccccc2-c2ccccc21]

(a 9-methyl-9-phenylfluorenyl group), and

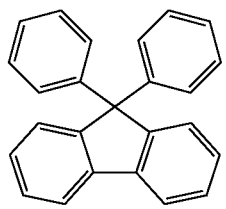 [SMILES: c1ccc(C2(c3ccccc3)c3ccccc3-c3ccccc32)cc1]

(a 9,9-diphenylfluorenyl group). However, the fluorenyl group is not limited thereto.

In the present specification, a heterocyclic group is a heterocyclic group including one or more of N, O, P, S, Si, and Se as a hetero atom, and the number of carbon atoms thereof is not particularly limited, but is preferably 1 to 60. According to an exemplary embodiment, the number of carbon atoms of the heterocyclic group is 1 to 30. Examples of the heterocyclic group include a pyridyl group, a pyrrole group, a pyrimidyl group, a pyridazinyl group, a furanyl group, a thiophenyl group, an imidazole group, a pyrazole group, an oxazole group, an isoxazole group, a triazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a triazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acrydyl group, a xanthenyl group, a phenanthridinyl group, a diaza naphthalenyl group, a triazaindenyl group, an indole group, an indolinyl group, an indolizinyl group, a phthalizinyl group, a pyrido pyrimidinyl group, a pyrido pyrazinyl group, a pyrazino pyrazinyl group, a benzothiazole group, a benzoxazole group, a benzimidazole group, a benzothiophene group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzoimidazoquinazoline group, or a benzoimidazophenanthridine group, and the like, but are not limited thereto.

In the present specification, a nitrogen-containing heterocyclic group is a heterocyclic group including at least one or more nitrogen atoms as a ring member, and examples of a monocyclic nitrogen-containing heterocyclic group include a pyridine group, a pyrimidine group, and a triazine group. Further, examples of a polycyclic nitrogen-containing heterocyclic group include a benzimidazole group, a benzoxazole group, a benzothiazole group, a phenazinyl group, a phenoxazine group, a phenanthridine group, a phenanthroline group, a phenothiazine group, an imidazopyridine group, an imidazophenanthridine group, a benzoimidazoquinazoline group, a benzoimidazophenanthridine group, and the like.

In the present specification, the above-described description on the aryl group may be applied to an aryl group in an aryloxy group, an arylthioxy group, an arylsulfoxy group, an arylphosphine group, an aralkyl group, an aralkylamine group, an aralkenyl group, an alkylaryl group, an arylamine group, and an arylheteroarylamine group.

In the present specification, the above-described description on the alkyl group may be applied to an alkyl group in an alkylthioxy group, an alkylsulfoxy group, an aralkyl group, an aralkylamine group, an alkylaryl group, and an alkylamine group.

In the present specification, the above-described description on the heterocyclic group may be applied to a heteroaryl group in a heteroaryl group, a heteroarylamine group, and an arylheteroarylamine group, except for an aromatic group.

In the present specification, the above-described description on the alkenyl group may be applied to an alkenyl group in an aralkenyl group.

In the present specification, the above-described description on the aryl group may be applied to an arylene group except for a divalent arylene group.

In the present specification, the above-described description on the heterocyclic group may be applied to a heteroarylene group except for a divalent heteroarylene group.

In the present specification, combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; or a fused ring thereof.

In the present specification, an aliphatic hydrocarbon ring means a ring composed of only carbon and hydrogen atoms as a ring which is not an aromatic group. Specifically, examples of the aliphatic hydrocarbon ring include cyclopropane, cyclobutane, cyclobutene, cyclopentane, cyclopentene, cyclohexane, cyclohexene, 1,4-cyclohexadiene, cycloheptane, cycloheptene, cyclooctane, cyclooctene, and the like, but are not limited thereto.

In the present specification, an aromatic hydrocarbon ring means an aromatic ring composed only of carbon and hydrogen atoms. Specifically, examples of the aromatic hydrocarbon ring include benzene, naphthalene, anthracene, phenanthrene, perylene, fluoranthene, triphenylene, phenalene, pyrene, tetracene, chrysene, pentacene, fluorene, indene, acenaphthylene, benzofluorene, spirofluorene, and the like, but are not limited thereto.

In the present specification, an aliphatic hetero ring means an aliphatic ring including one or more hetero atoms. Specifically, examples of the aliphatic hetero ring include oxirane, tetrahydrofuran, 1,4-dioxane, pyrrolidine, piperidine, morpholine, oxepane, azocane, thiocane, and the like, but are not limited thereto. In the present specification, an aromatic hetero ring means an aromatic ring including one or more hetero atoms. Specifically, examples of the aromatic hetero ring include pyridine, pyrrole, pyrimidine, pyridazine, furan, thiophene, imidazole, pyrazole, oxazole, isoxazole, triazole, isothiazole, triazole, oxadiazole, thiadiazole, dithiazole, tetrazole, pyran, thiopyran, diazine, oxazine, triazine, dioxine, triazine, tetrazine, isoquinoline, quinoline, quinol, quinazoline, quinoxaline, naphthyridine, acridine, phenanthridine, diaza naphthalene, triazaindene, indole, indolizine, benzothiazole, benzoxazole, benzoimidazole, benzothiophene, benzofuran, dibenzothiophene, dibenzofuran, carbazole, benzocarbazole, dibenzocarbazole, phenazine, imidazopyridine, phenoxazine, phenanthridine, indolocarbazole, indenocarbazole, and the like, but are not limited thereto.

In the present specification, the aliphatic hydrocarbon ring, the aromatic hydrocarbon ring, the aliphatic hetero ring, and the aromatic hetero ring may be monocyclic or polycyclic.

According to an exemplary embodiment of the present specification, at least one of $R_1$ to $R_{16}$ combines with an adjacent group to form the ring of Chemical Formula 1-1.

According to an exemplary embodiment of the present specification, at least one of $R_6$ to $R_{11}$ combines with an adjacent group to form the ring of Chemical Formula 1-1.

According to an exemplary embodiment of the present specification, a group, which does not form the ring of Chemical Formula 1-1 among $R_1$ to $R_{16}$, and $R_{17}$ to $R_{20}$ are the same as or different from each other, and are each independently hydrogen; deuterium; a halogen group; a nitrile group; a nitro group; a hydroxy group; a carbonyl group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

According to an exemplary embodiment of the present specification, at least one of a group, which does not form the ring of Chemical Formula 1-1 among $R_1$ to $R_{16}$, and $R_{17}$ to $R_{20}$ is represented by -$(L)_p$-A, and p, L, and A are the same as those defined in the following Chemical Formulae 2 to 7.

According to an exemplary embodiment of the present specification, at least one of groups, which do not form the ring of Chemical Formula 1-1 among $R_6$ to $R_{11}$, is represented by -$(L)_p$-A, and p, L, and A are the same as those defined in the following Chemical Formulae 2 to 7.

According to an exemplary embodiment of the present specification, at least one of $R_6$ to $R_{11}$ combines with an adjacent group to form the ring of Chemical Formula 1-1, at least one of groups, which do not form the ring of Chemical Formula 1-1 among $R_6$ to $R_{11}$, is represented by -$(L)_p$-A, and p, L, and A are the same as those defined in the following Chemical Formulae 2 to 7.

According to an exemplary embodiment of the present specification, at least one of $R_6$ to $R_8$ combines with an adjacent group to form the ring of Chemical Formula 1-1, at least one of $R_9$ to $R_{11}$ is represented by -$(L)_p$-A, and p, L, and A are the same as those defined in the following Chemical Formulae 2 to 7.

According to an exemplary embodiment of the present specification, the compound represented by Chemical Formula 1 may be represented by any one of the following Chemical Formulae 2 to 7.

Chemical Formula 2

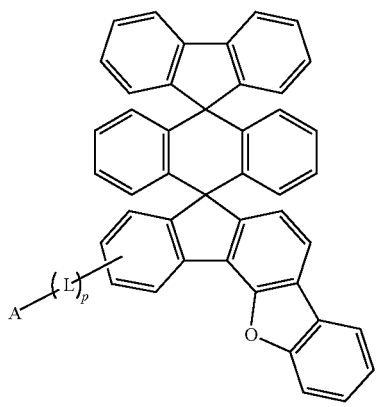

Chemical Formula 5

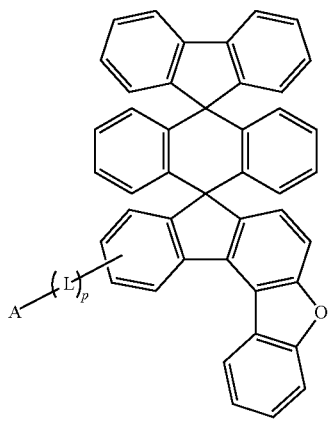

Chemical Formula 3

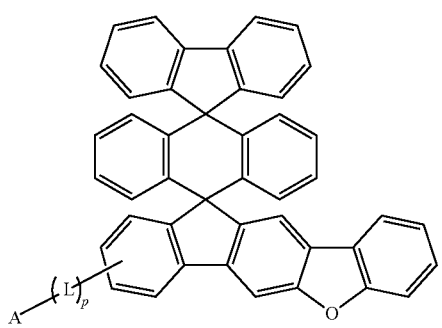

Chemical Formula 6

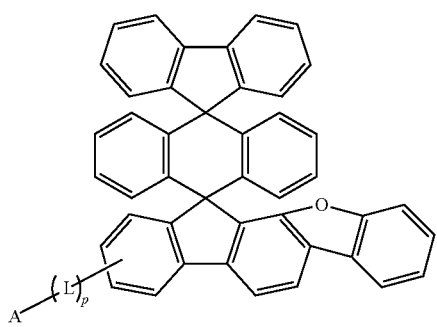

Chemical Formula 4

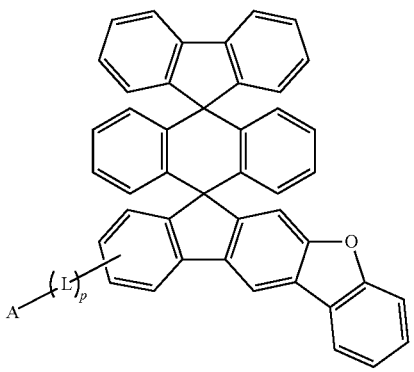

Chemical Formula 7

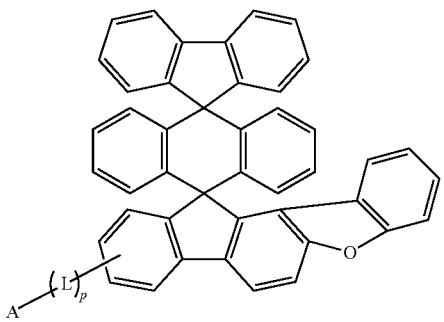

In Chemical Formulae 2 to 7, p is an integer of 0 to 5,

L is a direct bond; a substituted or unsubstituted arylene group; or a substituted or unsubstituted heteroarylene group, A is hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, and when p is 2 or more, Ls are the same as or different from each other.

According to an exemplary embodiment of the present specification, the compound represented by Chemical Formula 1 may be represented by any one of the following Chemical Formulae 8 to 13.

Chemical Formula 8

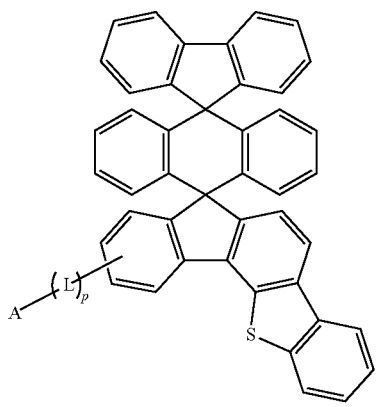

Chemical Formula 11

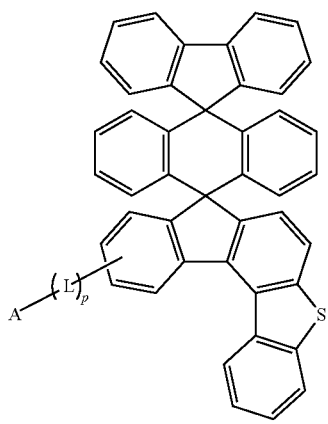

Chemical Formula 9

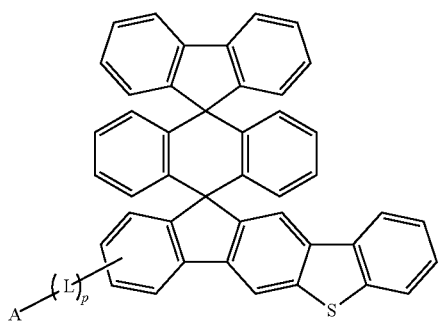

Chemical Formula 12

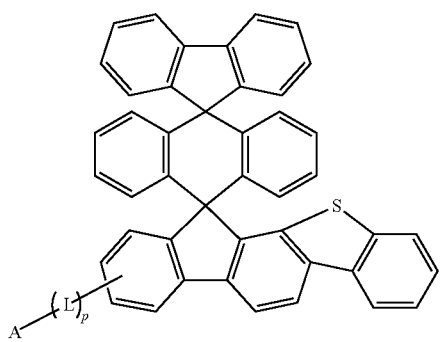

Chemical Formula 10

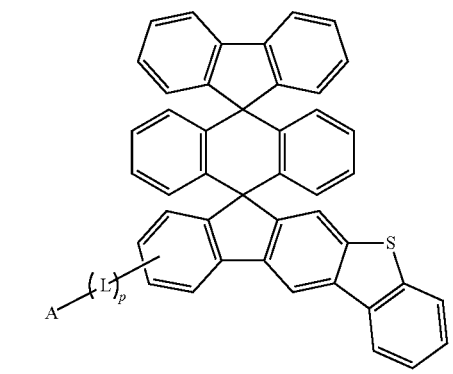

Chemical Formula 13

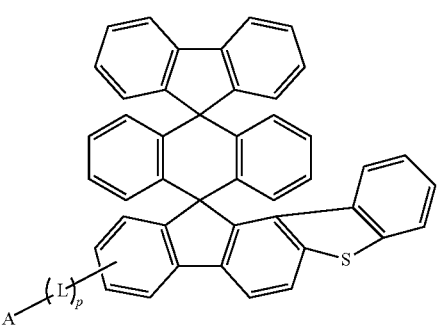

In Chemical Formulae 8 to 13, p, L, and A are each the same as that defined in Chemical Formulae 2 to 7.

According to an exemplary embodiment of the present specification, the compound represented by Chemical Formula 1 may be represented by any one of the following Chemical Formulae 2-1 to 2-4, Chemical Formulae 3-1 to 3-4, and Chemical Formulae 4-1 to 4-4.

Chemical Formula 2-1

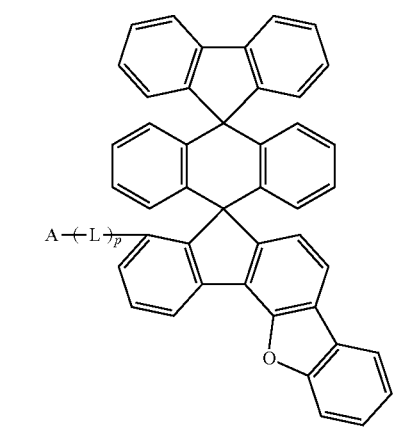

Chemical Formula 3-1
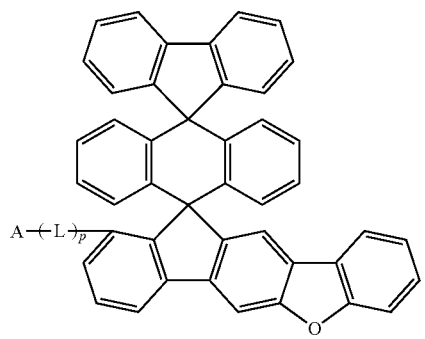
Chemical Formula 4-1
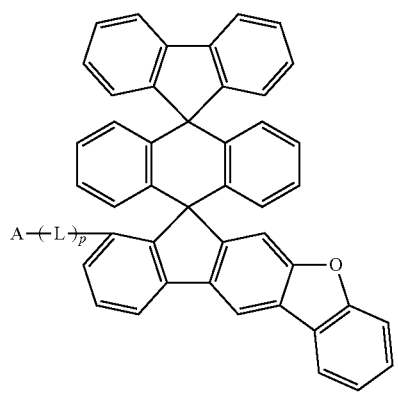
Chemical Formula 2-2
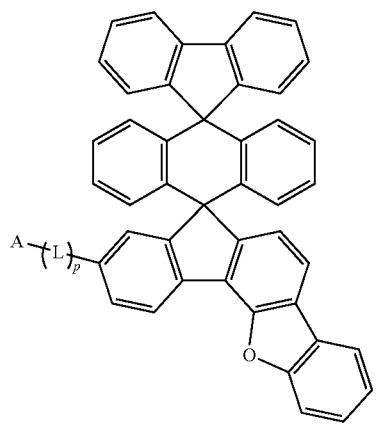
Chemical Formula 3-2
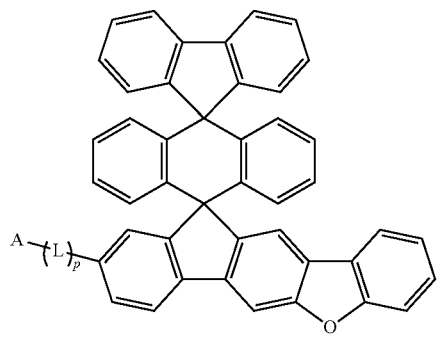
Chemical Formula 4-2
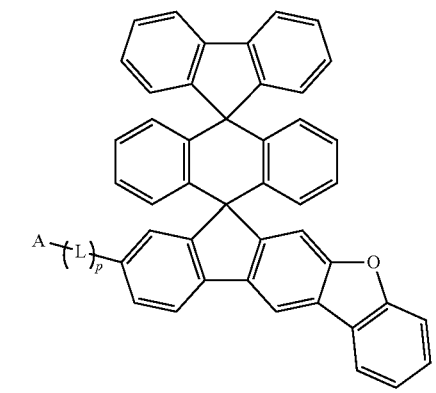
Chemical Formula 2-3
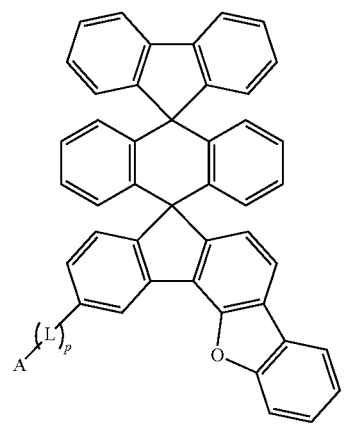
Chemical Formula 3-3
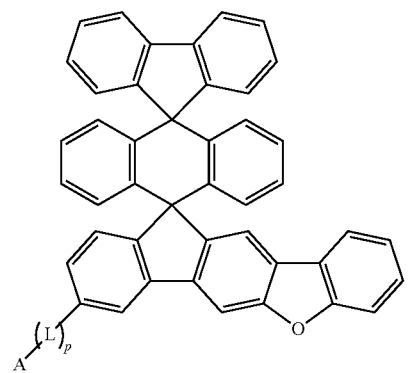
Chemical Formula 4-3
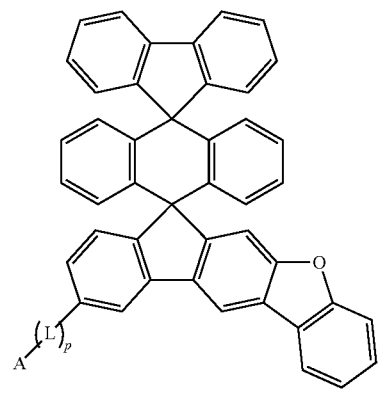

Chemical Formula 2-4

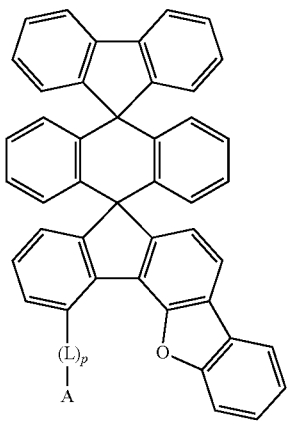

Chemical Formula 3-4

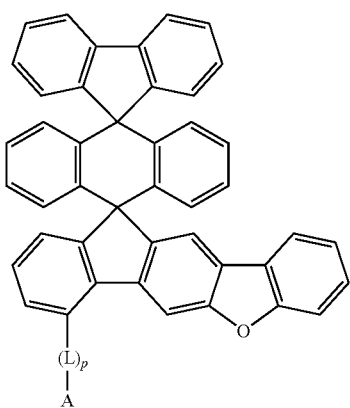

Chemical Formula 4-4

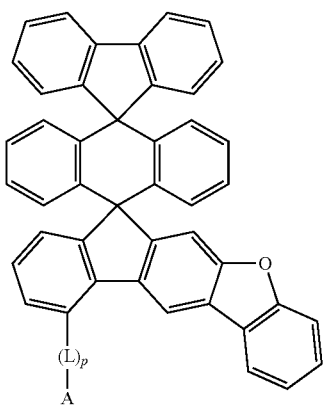

Chemical Formula 5-1

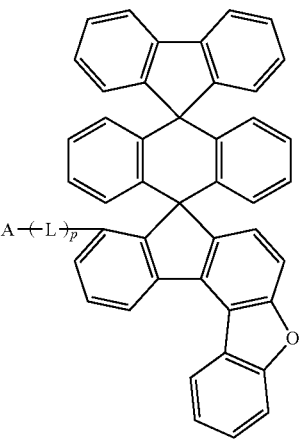

Chemical Formula 6-1

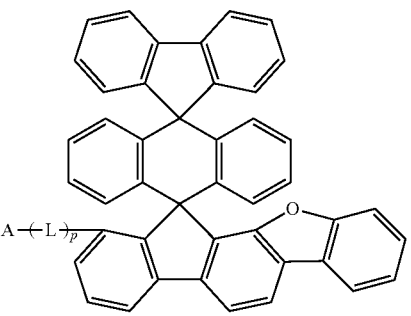

Chemical Formula 7-1

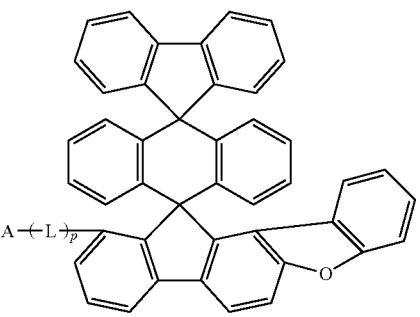

Chemical Formula 5-2

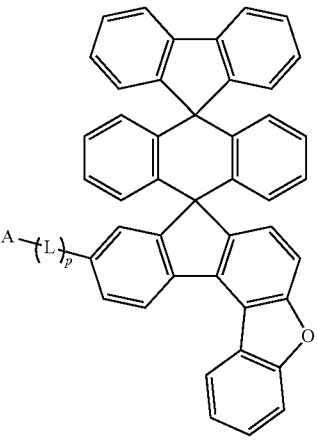

In Chemical Formulae 2-1 to 2-4, Chemical Formulae 3-1 to 3-4, and Chemical Formulae 4-1 to 4-4, p, L, and A are each the same as that defined in Chemical Formulae 2 to 7.

According to an exemplary embodiment of the present specification, the compound represented by Chemical Formula 1 may be represented by any one of the following Chemical Formulae 5-1 to 5-4, Chemical Formulae 6-1 to 6-4, and Chemical Formulae 7-1 to 7-4.

Chemical Formula 6-2
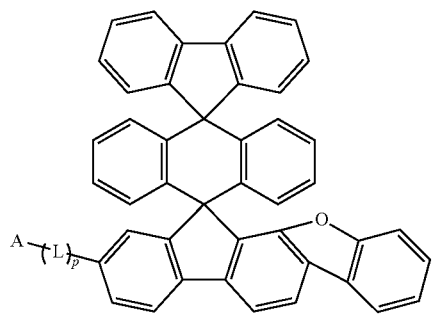
Chemical Formula 7-2
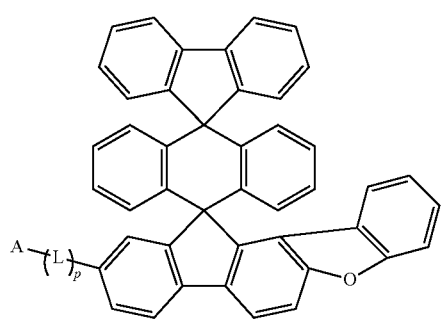
Chemical Formula 5-3
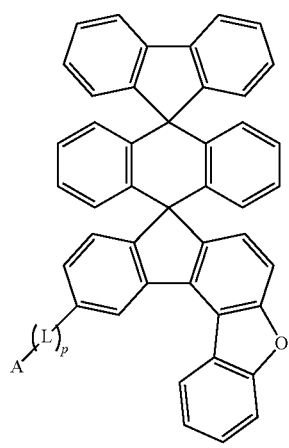
Chemical Formula 6-3
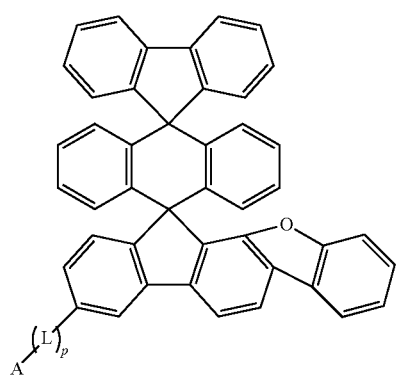
Chemical Formula 7-3
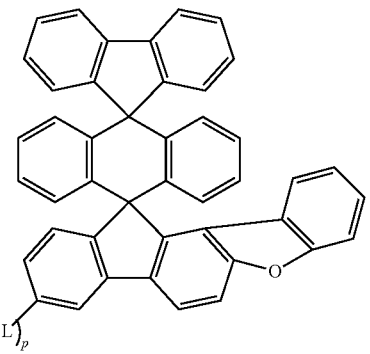
Chemical Formula 5-4
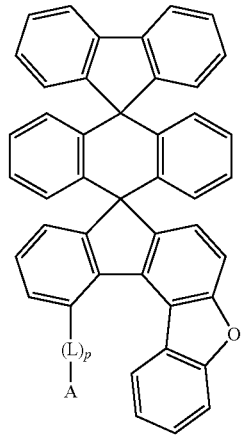
Chemical Formula 6-4
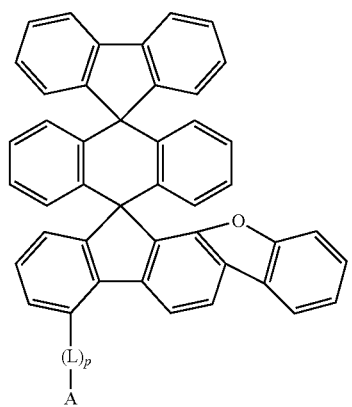
Chemical Formula 7-4
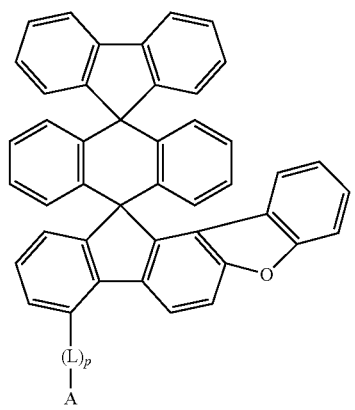

In Chemical Formulae 5-1 to 5-4, Chemical Formulae 6-1 to 6-4, and Chemical Formulae 7-1 to 7-4, p, L, and A are each the same as that defined in Chemical Formulae 2 to 7.

According to an exemplary embodiment of the present specification, the compound represented by Chemical Formula 1 may be represented by any one of the following Chemical Formulae 8-1 to 8-4, Chemical Formulae 9-1 to 9-4, and Chemical Formulae 10-1 to 10-4.

Chemical Formula 8-1

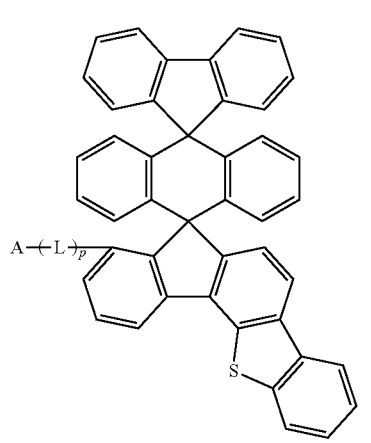

Chemical Formula 9-1

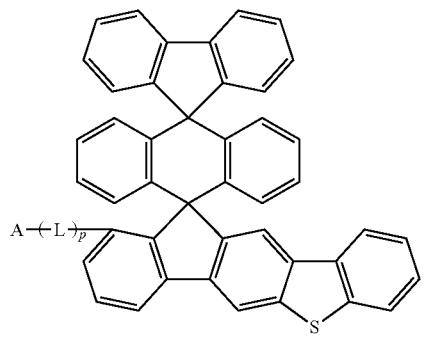

Chemical Formula 10-1

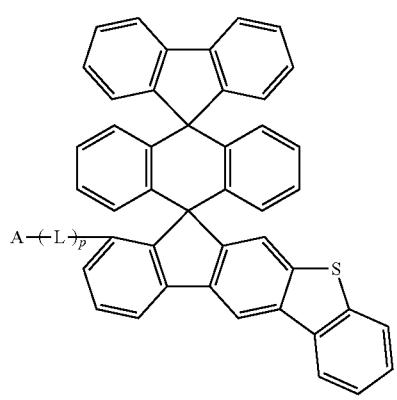

Chemical Formula 8-2

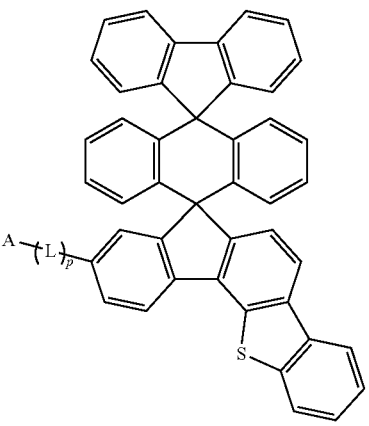

Chemical Formula 9-2

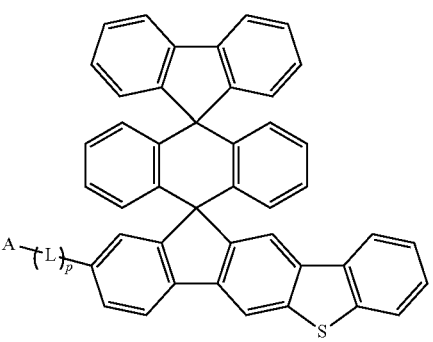

Chemical Formula 10-2

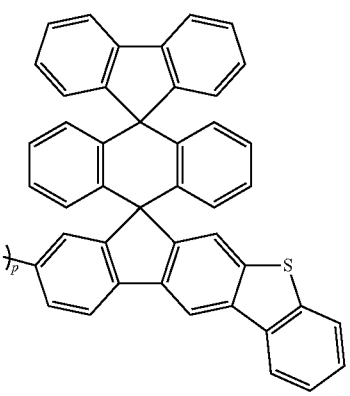

Chemical Formula 8-3

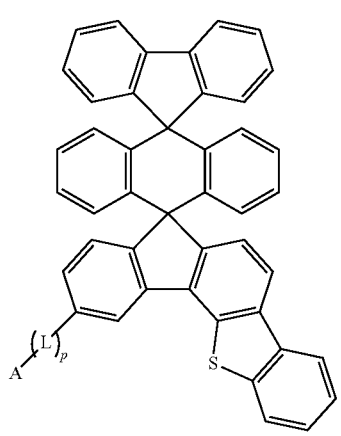

Chemical Formula 9-3

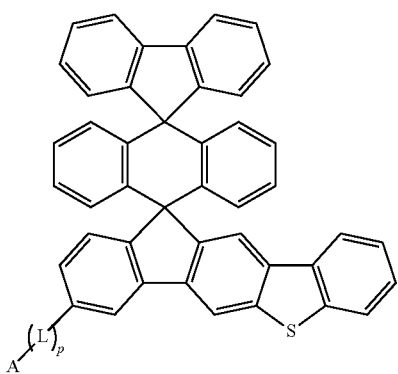

Chemical Formula 10-3

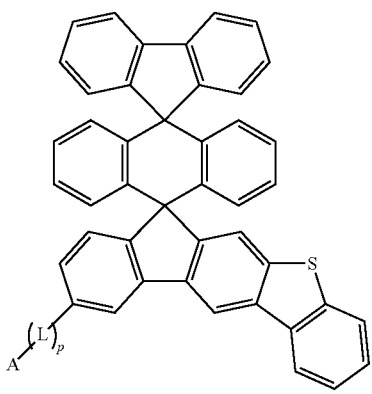

Chemical Formula 8-4

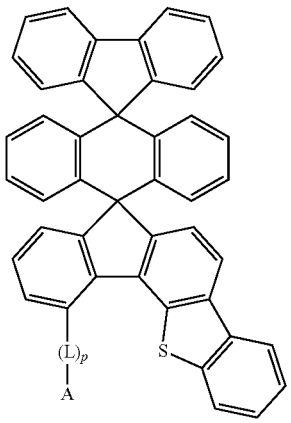

Chemical Formula 9-4

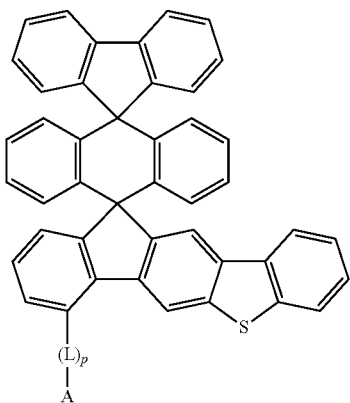

Chemical Formula 10-4

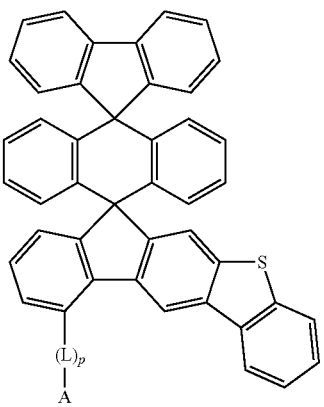

In Chemical Formulae 8-1 to 8-4, Chemical Formulae 9-1 to 9-4, and Chemical Formulae 10-1 to 10-4, p, L, and A are each the same as that defined in Chemical Formulae 2 to 7.

According to an exemplary embodiment of the present specification, the compound represented by Chemical Formula 1 may be represented by any one of the following Chemical Formulae 11-1 to 11-4, Chemical Formulae 12-1 to 12-4, and Chemical Formulae 13-1 to 13-4.

Chemical Formula 11-1

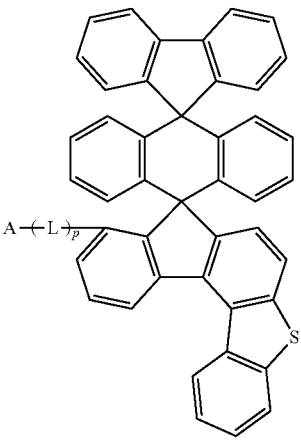

Chemical Formula 12-1

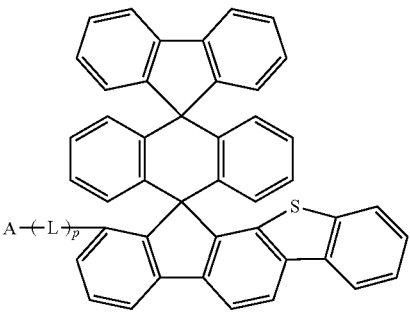

Chemical Formula 13-1
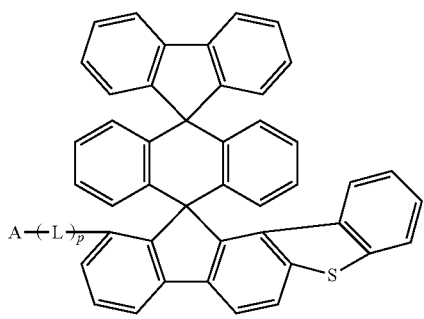
Chemical Formula 11-2
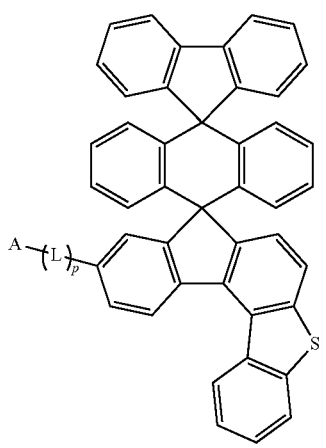
Chemical Formula 12-2
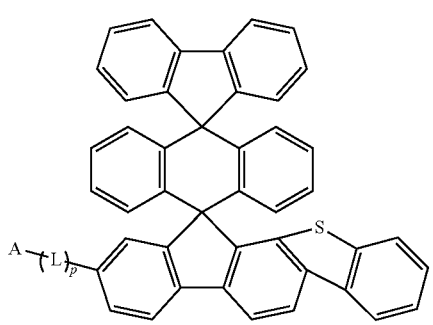
Chemical Formula 13-2
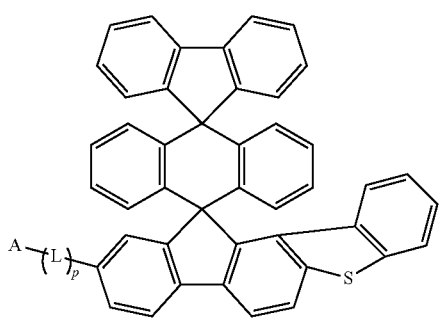
Chemical Formula 11-3
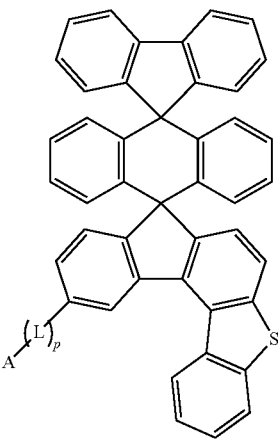
Chemical Formula 12-3
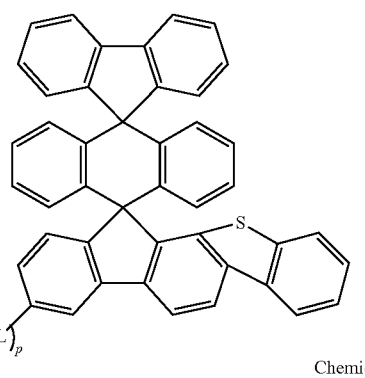
Chemical Formula 13-3
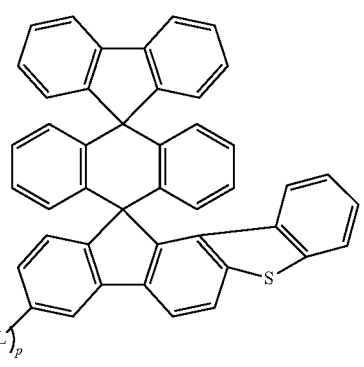
Chemical Formula 11-4
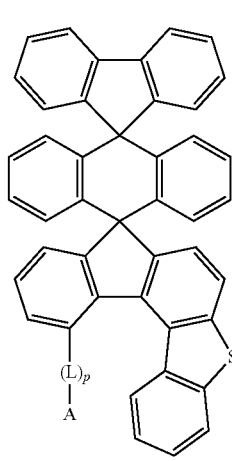

Chemical Formula 12-4

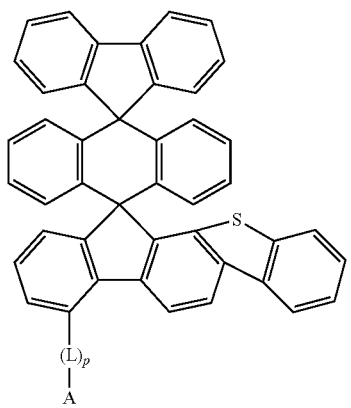

Chemical Formula 13-4

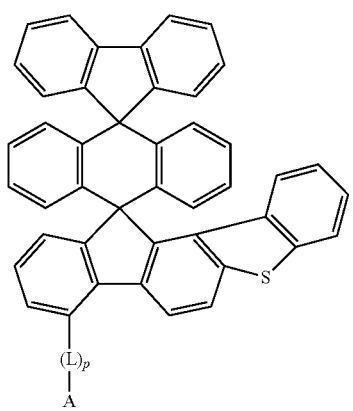

In Chemical Formulae 11-1 to 11-4, Chemical Formulae 12-1 to 12-4, and Chemical Formulae 13-1 to 13-4, p, L, and A are each the same as that defined in Chemical Formulae 2 to 7.

In an exemplary embodiment of the present invention, L is a direct bond; a substituted or unsubstituted arylene group; or a substituted or unsubstituted heteroarylene group.

In an exemplary embodiment of the present invention, L is a direct bond; a substituted or unsubstituted arylene group having 6 to 60 carbon atoms; or a substituted or unsubstituted heteroarylene group having 1 to 60 carbon atoms.

In an exemplary embodiment of the present invention, L is a direct bond; a substituted or unsubstituted monocyclic or polycyclic arylene group having 6 to 30 carbon atoms; or a substituted or unsubstituted monocyclic or polycyclic heteroarylene group having 1 to 30 carbon atoms.

In an exemplary embodiment of the present invention, L is a direct bond; a substituted or unsubstituted phenylene group; a substituted or unsubstituted biphenylylene group; a substituted or unsubstituted terphenylene group; a substituted or unsubstituted quarterphenylene group; a substituted or unsubstituted naphthylene group; a substituted or unsubstituted anthracenylene group; a substituted or unsubstituted phenanthrenylene group; a substituted or unsubstituted triphenylene group; a substituted or unsubstituted pyrenylene group; a substituted or unsubstituted fluorenylenyl group; a substituted or unsubstituted dibenzofuranylene group; a substituted or unsubstituted dibenzothiophenylene group; or a substituted or unsubstituted carbazolylene group.

In an exemplary embodiment of the present specification, L may be a direct bond; or any one selected from the following structures, and the following structures may be additionally substituted.

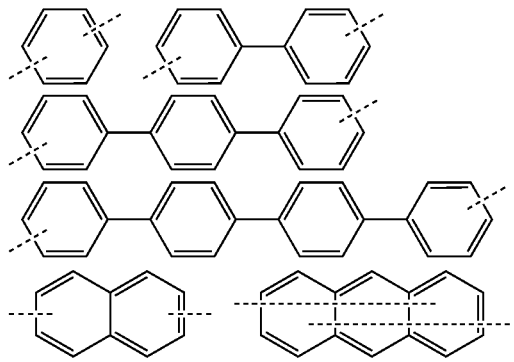

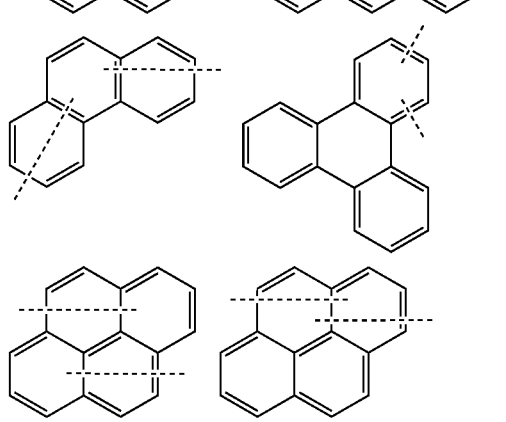

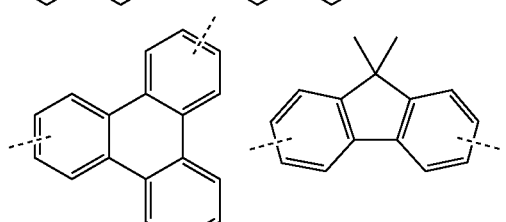

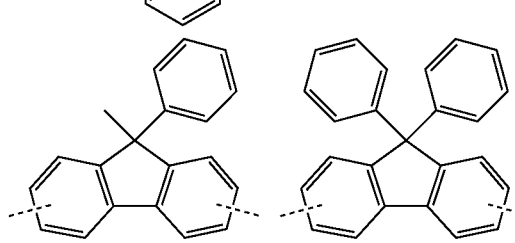

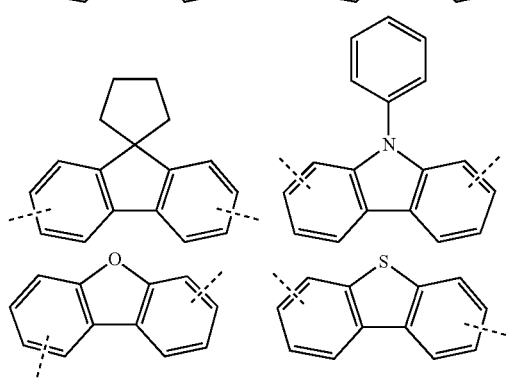

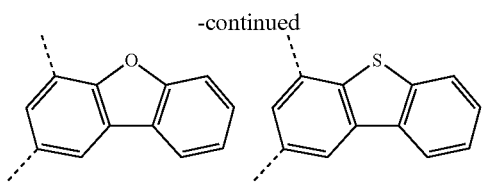

The dotted line in the structural formulae is an adjacent group, for example, the core structure of Chemical Formula 1; another L when p is 2 or more; or a moiety bonded to A.

Specifically, the structures may be unsubstituted or substituted with one or more substituents selected from the group consisting of deuterium; a halogen group; a nitrile group; a nitro group; a hydroxy group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

In an exemplary embodiment of the present invention, L is a direct bond; or a substituted or unsubstituted phenylene group.

In an exemplary embodiment of the present invention, A is hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

According to an exemplary embodiment of the present invention, A is hydrogen; deuterium; a substituted or unsubstituted aryl group having 6 to 60 carbon atoms; or a substituted or unsubstituted heterocyclic group having 1 to 60 carbon atoms.

According to an exemplary embodiment of the present invention, A is hydrogen; deuterium; a substituted or unsubstituted monocyclic or polycyclic aryl group having 6 to 30 carbon atoms; or a substituted or unsubstituted monocyclic or polycyclic heterocyclic group having 1 to 60 carbon atoms.

In an exemplary embodiment of the present invention, A is hydrogen; deuterium; a monocyclic nitrogen-containing heterocyclic group which is unsubstituted or substituted with one or more substituents selected from the group consisting of an aryl group and a heterocyclic group; or a substituted or unsubstituted polycyclic heterocyclic group which is unsubstituted or substituted with one or more substituents selected from the group consisting of an aryl group and a heterocyclic group.

In an exemplary embodiment of the present invention, A is hydrogen; deuterium; a pyridine group which is unsubstituted or substituted with one or more substituents selected from the group consisting of a phenyl group, a biphenyl group, a naphthyl group, a 9,9-dimethylfluorenyl group, and a pyridine group; a pyrimidine group which is unsubstituted or substituted with one or more substituents selected from the group consisting of a phenyl group, a biphenyl group, a naphthyl group, a 9,9-dimethylfluorenyl group, and a pyridine group; a triazinyl group which is unsubstituted or substituted with one or more substituents selected from the group consisting of a phenyl group, a biphenyl group, a naphthyl group, a 9,9-dimethylfluorenyl group, and a pyridine group; a quinoline group which is unsubstituted or substituted with one or more substituents selected from the group consisting of a phenyl group, a biphenyl group, a naphthyl group, a 9,9-dimethylfluorenyl group, and a pyridine group; a quinazoline group which is unsubstituted or substituted with one or more substituents selected from the group consisting of a phenyl group, a biphenyl group, a naphthyl group, a 9,9-dimethylfluorenyl group, and a pyridine group; a benzimidazole group which is unsubstituted or substituted with one or more substituents selected from the group consisting of a phenyl group, a biphenyl group, a naphthyl group, a 9,9-dimethylfluorenyl group, and a pyridine group; a benzoxazole group which is unsubstituted or substituted with one or more substituents selected from the group consisting of a phenyl group, a biphenyl group, a naphthyl group, a 9,9-dimethylfluorenyl group, and a pyridine group; a benzothiazole group which is unsubstituted or substituted with one or more substituents selected from the group consisting of a phenyl group, a biphenyl group, a naphthyl group, a 9,9-dimethylfluorenyl group, and a pyridine group; a phenanthridine group which is unsubstituted or substituted with one or more substituents selected from the group consisting of a phenyl group, a biphenyl group, a naphthyl group, a 9,9-dimethylfluorenyl group, and a pyridine group; a phenanthroline group which is unsubstituted or substituted with one or more substituents selected from the group consisting of a phenyl group, a biphenyl group, a naphthyl group, a 9,9-dimethylfluorenyl group, and a pyridine group; or a benzoimidazoquinazoline group which is unsubstituted or substituted with one or more substituents selected from the group consisting of a phenyl group, a biphenyl group, a naphthyl group, a 9,9-dimethylfluorenyl group, and a pyridine group.

In an exemplary embodiment, when A is a substituted or unsubstituted heteroaryl group, A may be represented by the following Structural Formula 1 or Structural Formula 2, but is not limited thereto.

[Structural Formula 1]

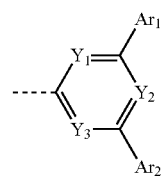

[Structural Formula 2]

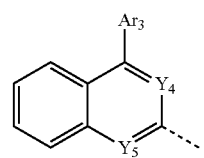

In Structural Formulae 1 and 2, Y1 to Y5 are the same as or different from each other, and are each independently N or CH, at least one of Y1 to Y3 is N, and at least one of Y4 and Y5 is N, and Ar1 to Ar3 are the same as or different from each other, and are each independently hydrogen; a substituted or unsubstituted aryl group; or a substituted or unsubstituted heterocyclic group, and specifically, may be further substituted with an aryl group or a heterocyclic group.

In an exemplary embodiment of the present invention, A may be hydrogen, deuterium, or any one selected from the following structures, and the following structures may be additionally substituted.

B-1
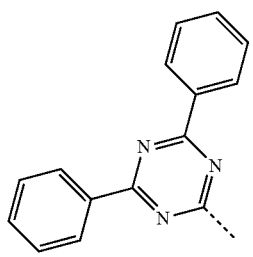

B-2
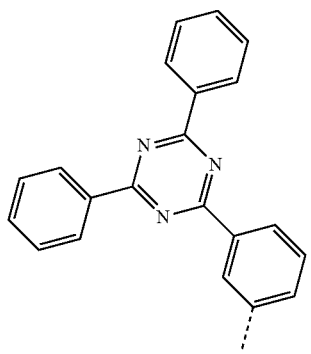

B-3
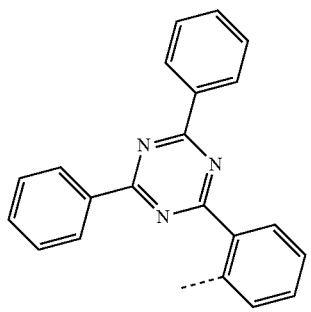

B-4
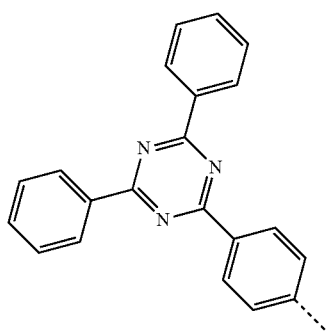

B-5
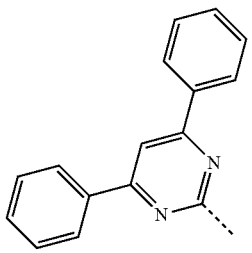

B-6
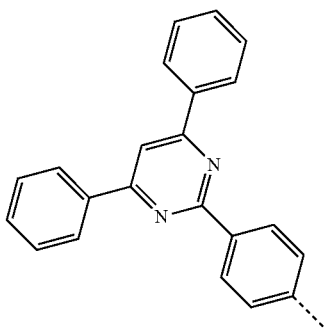

B-7
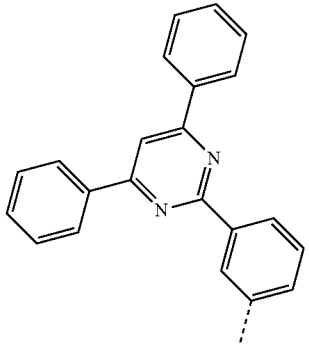

B-8
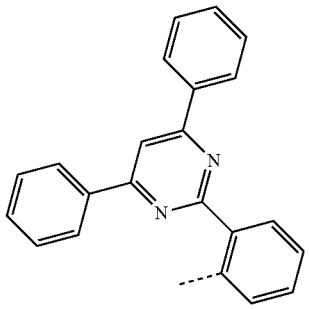

B-9
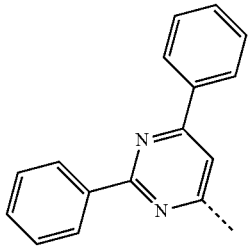

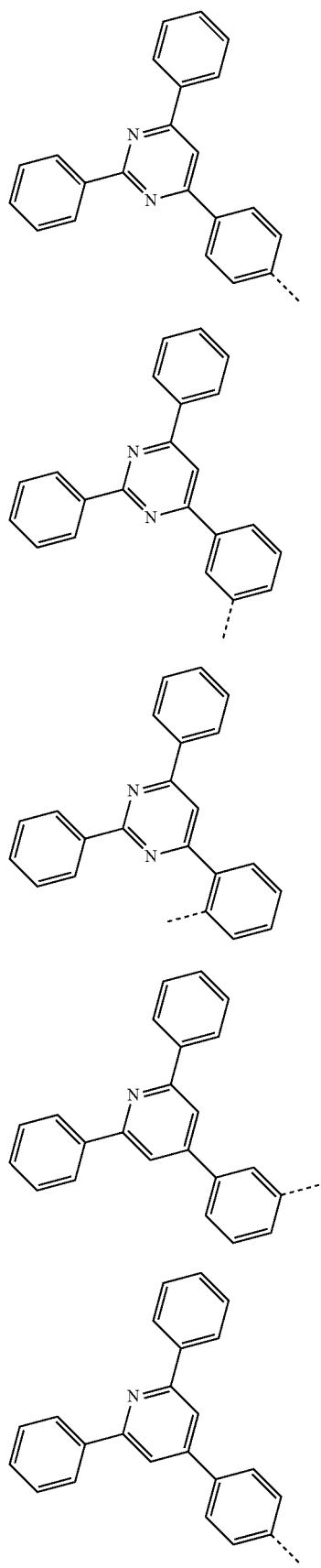
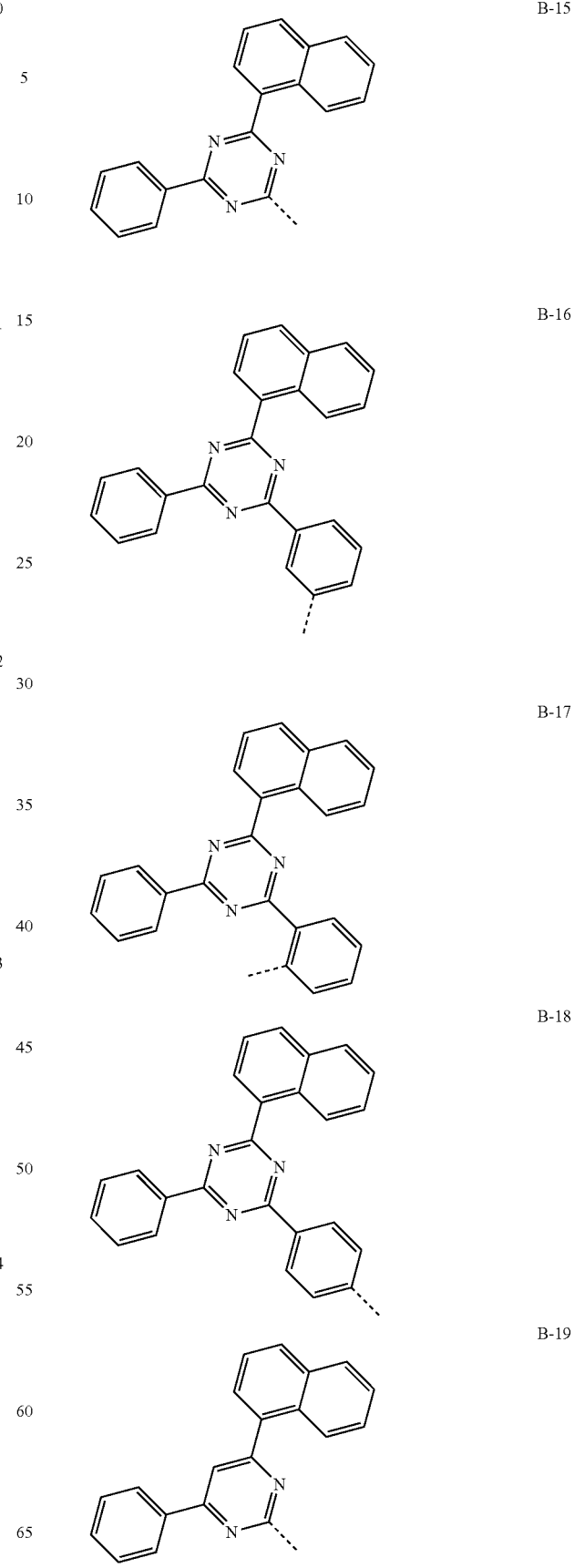

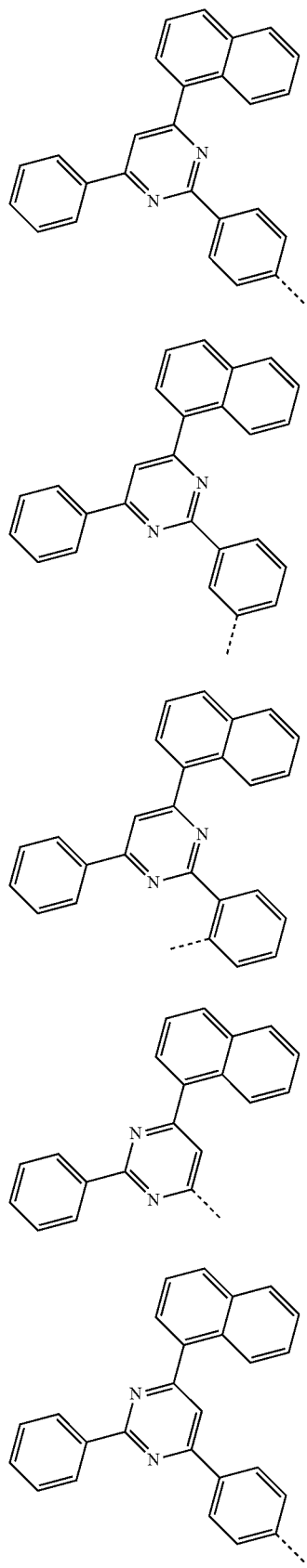
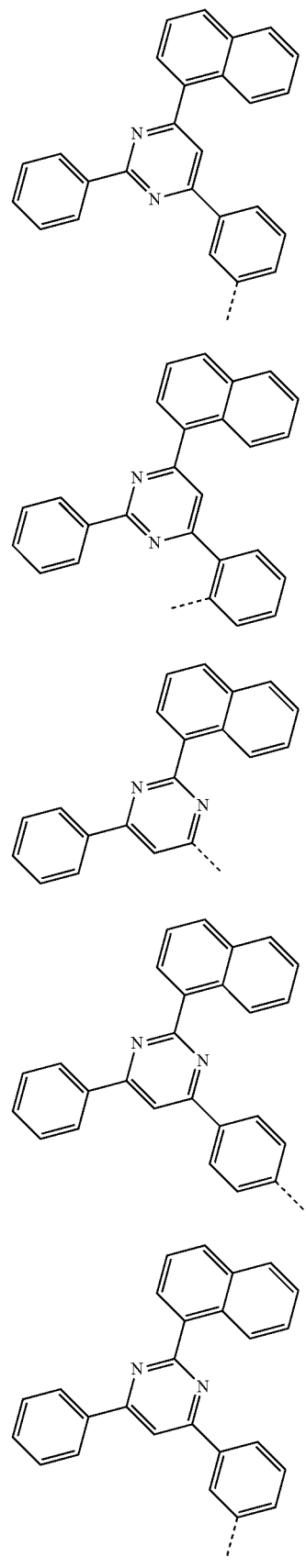

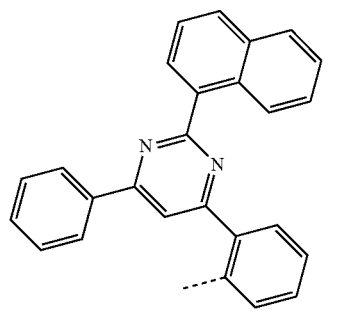
B-30
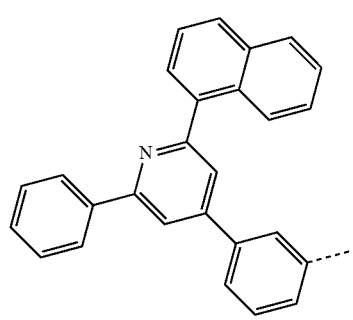
B-31
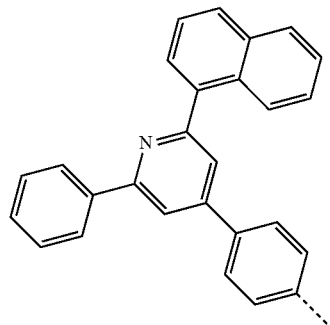
B-32
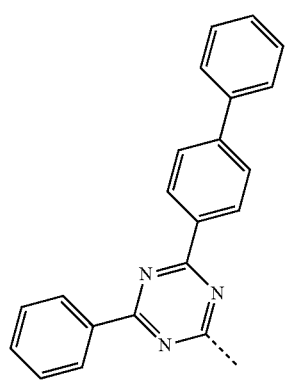
B-33
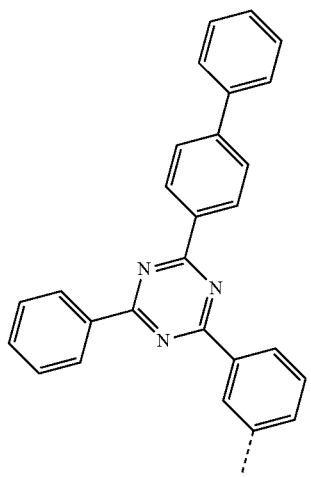
B-34
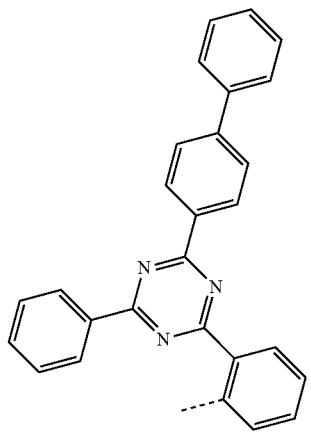
B-35
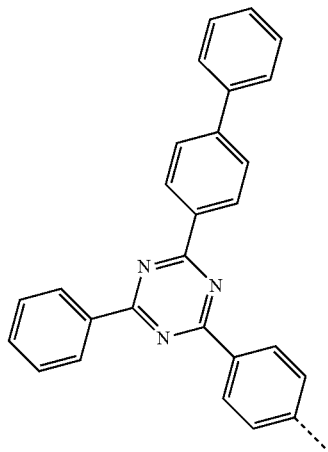
B-36

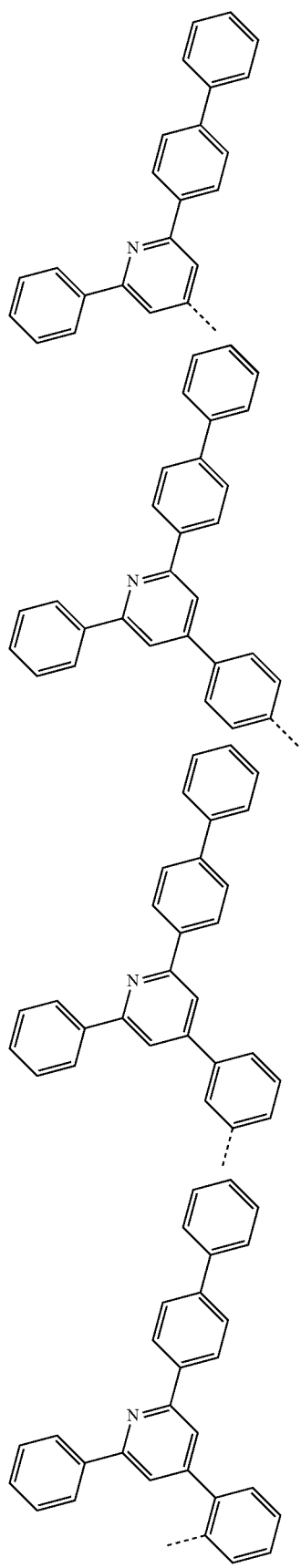
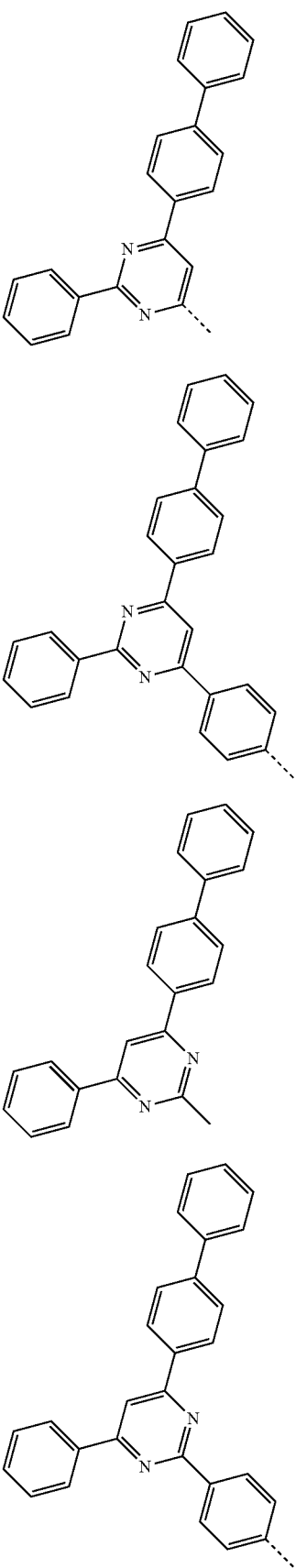

B-45
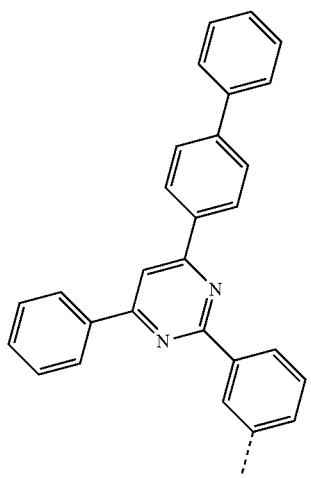
B-46
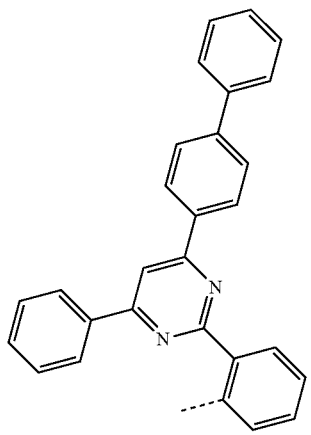
B-47
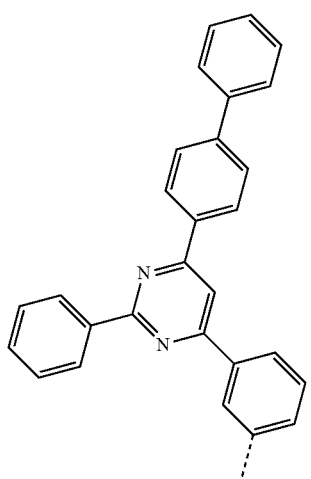
B-48
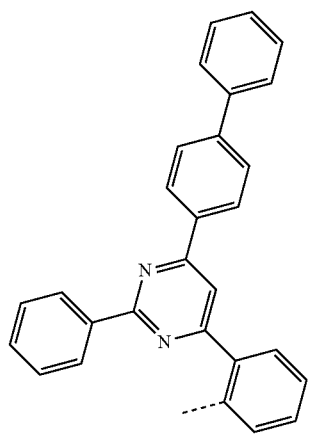
B-49
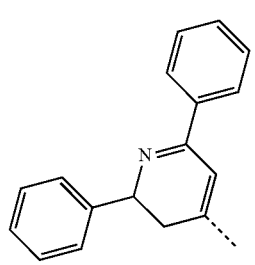
B-50
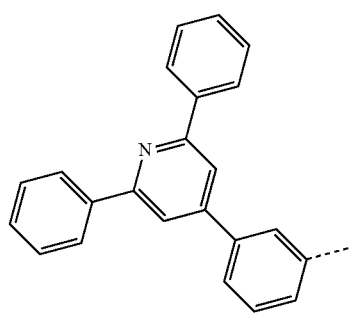
B-51
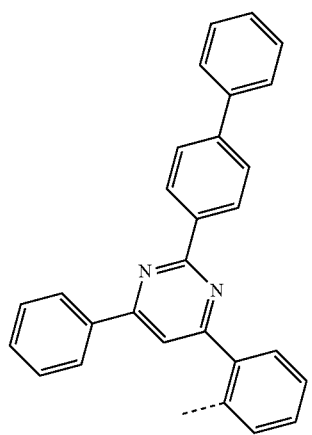

B-52, B-53, B-54, B-55, B-56, B-57, B-58, B-59

B-60 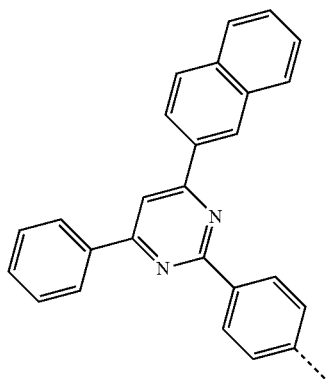
B-61 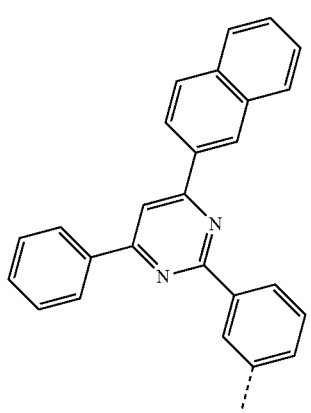
B-62 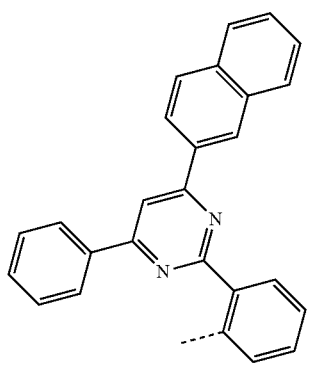
B-63 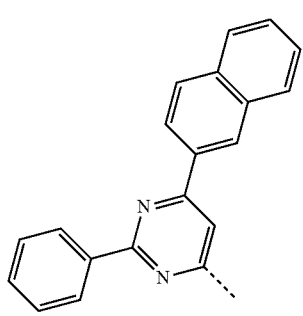
B-64 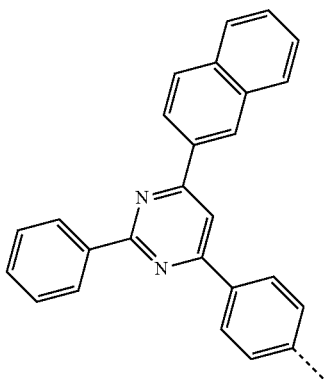
B-65 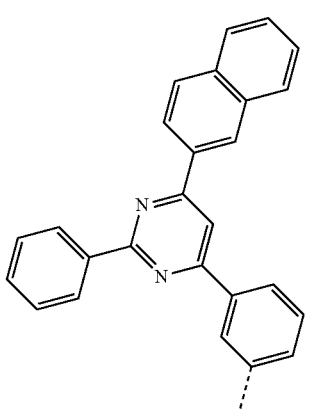
B-66 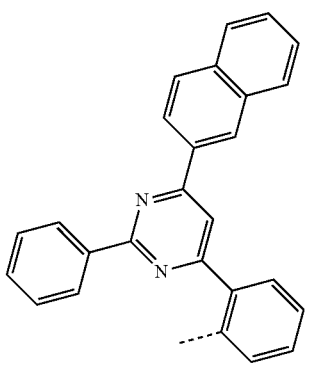
B-67 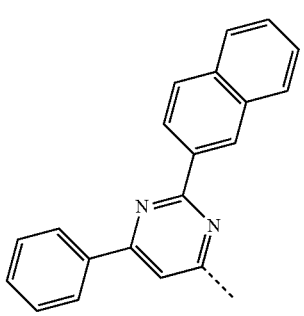

-continued
B-68
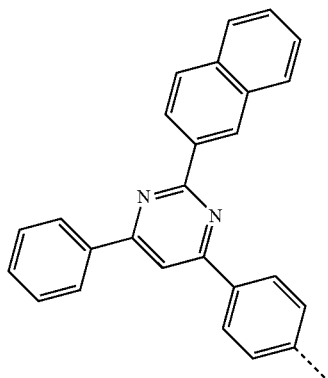
B-69
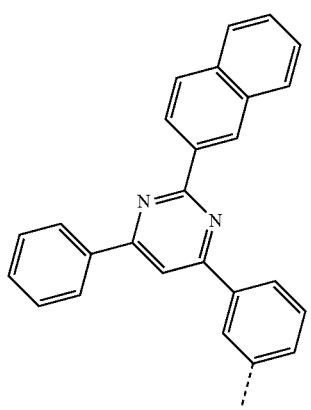
B-70
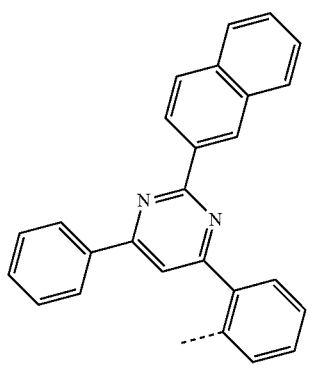
B-71
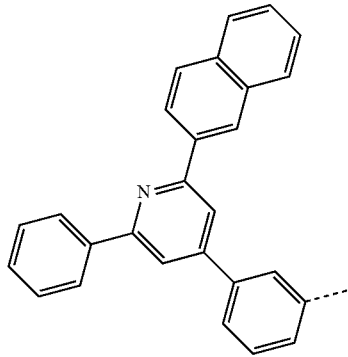
-continued
B-72
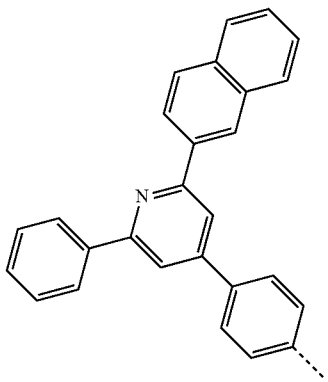
B-73
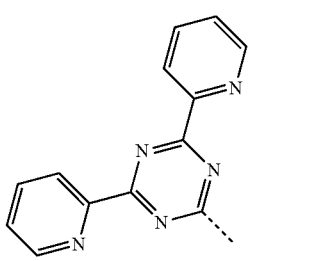
B-74
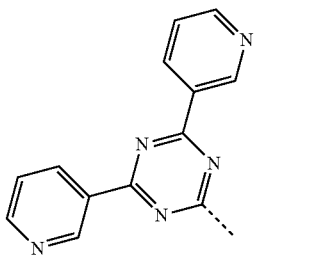
B-75
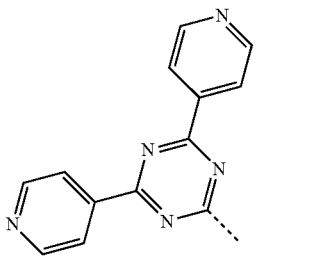
B-76
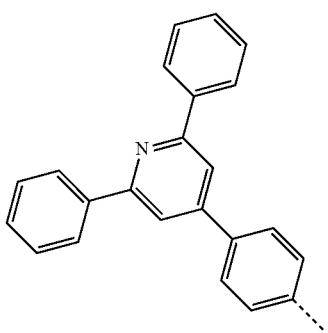

B-77
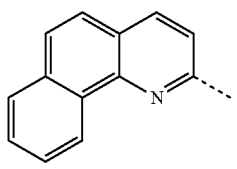
B-78
B-79
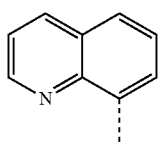
B-80
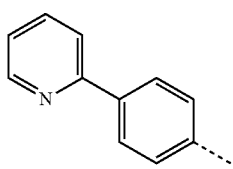
B-80
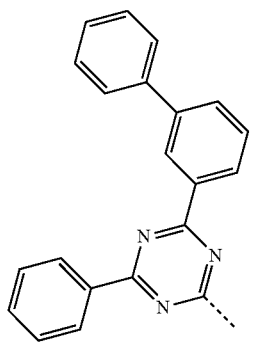
B-81
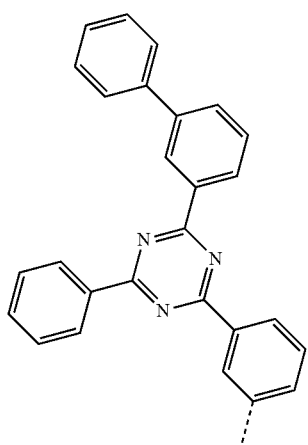
B-82
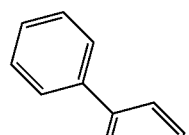
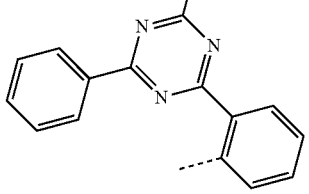
B-83
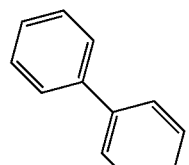
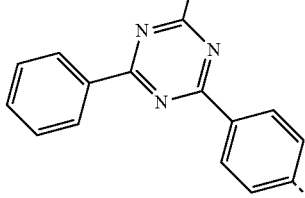
B-84
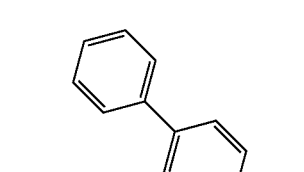
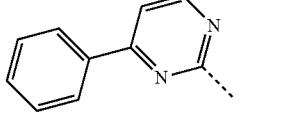
B-85
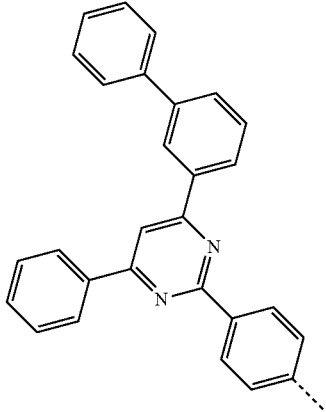

B-86
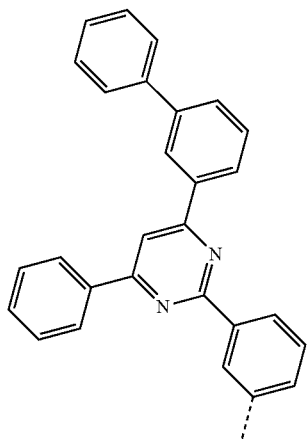
B-87
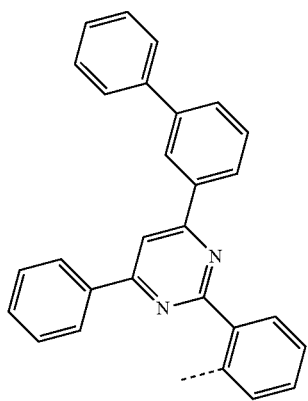
B-88
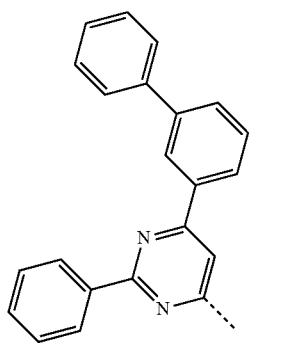
B-89
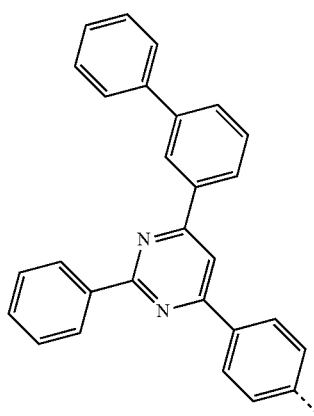
B-90
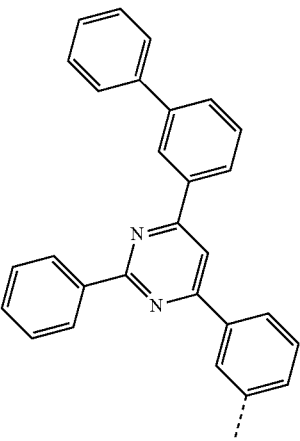
B-91
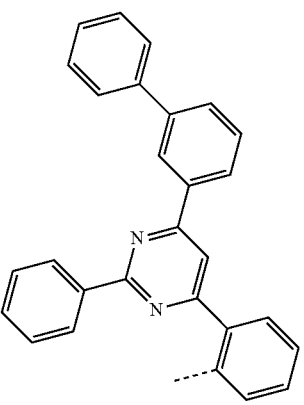
B-92
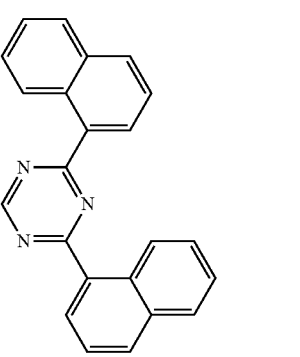
B-93
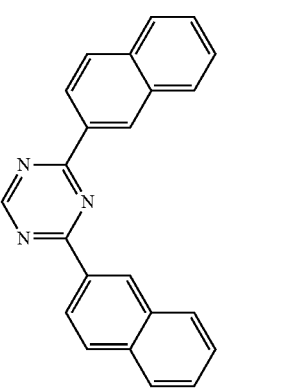

B-94
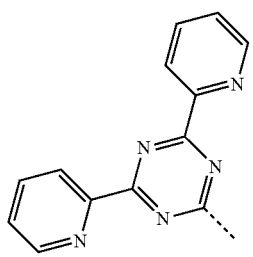
B-95
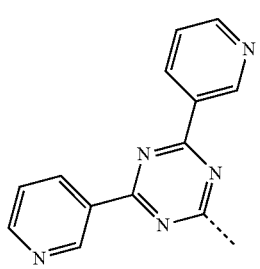
B-96
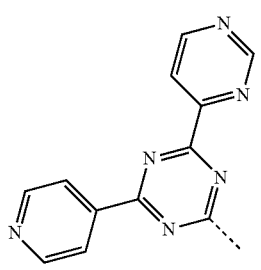
B-97
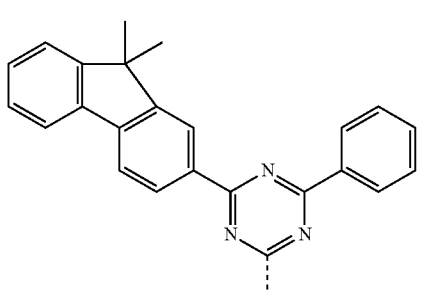
B-98
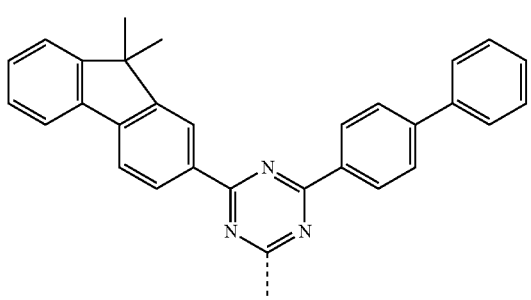
B-99
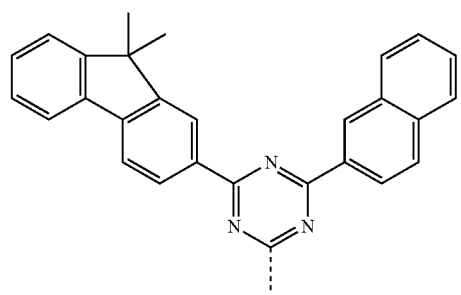
B-100
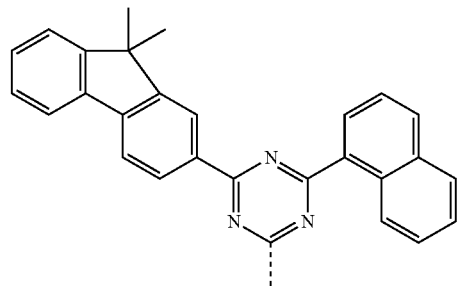
B-101
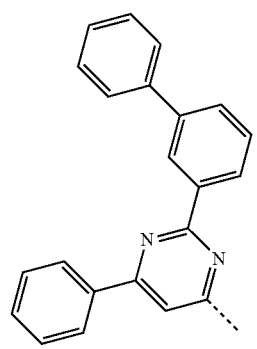
C-1
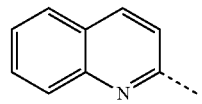
C-2
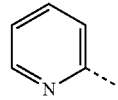
C-3
C-4
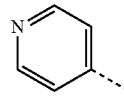
C-5
C-6
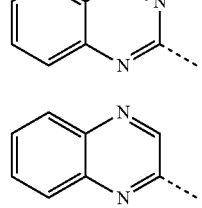

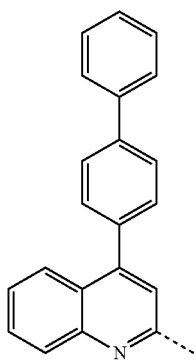
C-7
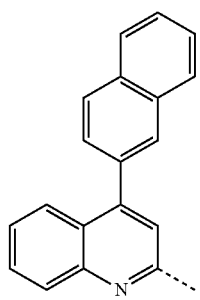
C-12
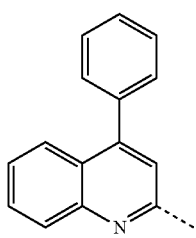
C-8
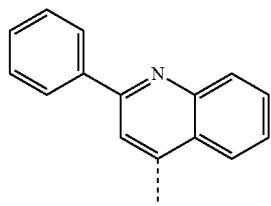
C-13
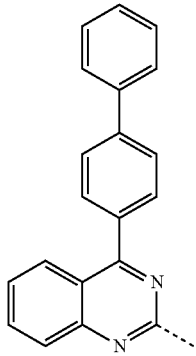
C-9
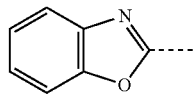
C-14
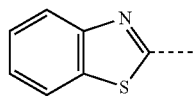
C-15
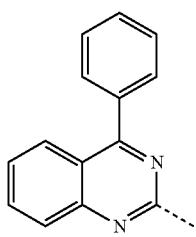
C-10
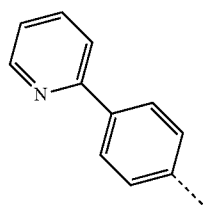
C-16
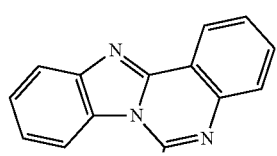
C-17
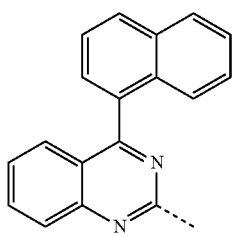
C-11
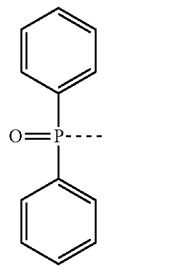
C-18

C-19 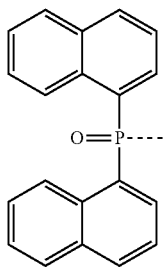

C-20 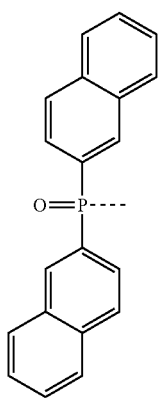

C-21 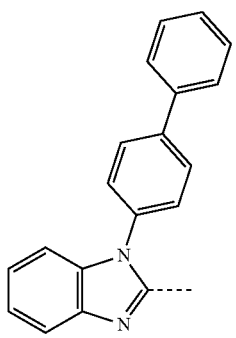

C-22 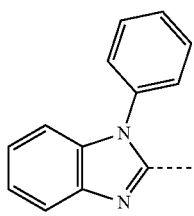

C-23 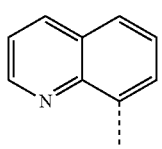

C-24 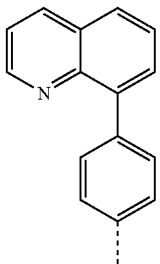

C-25 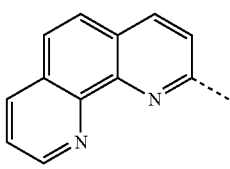

The dotted line in the structural formulae is an adjacent group, for example, the core structure of Chemical Formula 1, or a moiety bonded to L.

Specifically, the structures may be unsubstituted or substituted with one or more substituents selected from the group consisting of deuterium; a halogen group; a nitrile group; a nitro group; a hydroxy group; a carbonyl group; an ester group; an imide group; an amine group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

In an exemplary embodiment of the present invention, the compound of Chemical Formula 1 may be any one selected from the following compounds.

1

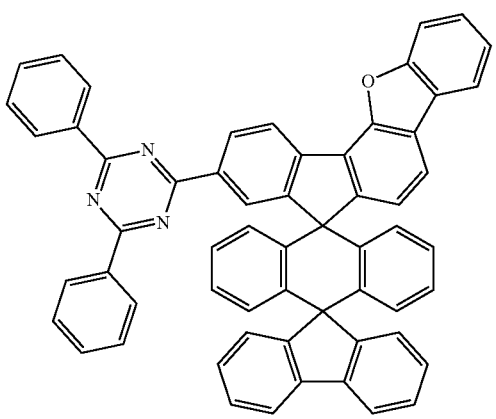

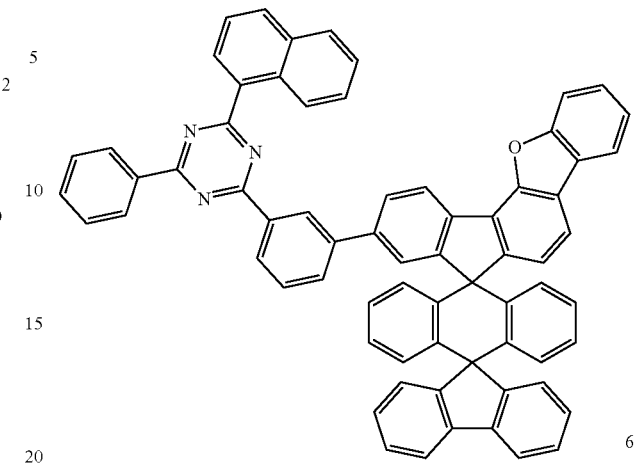
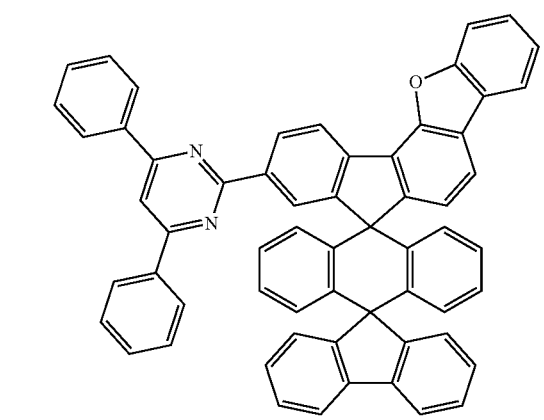
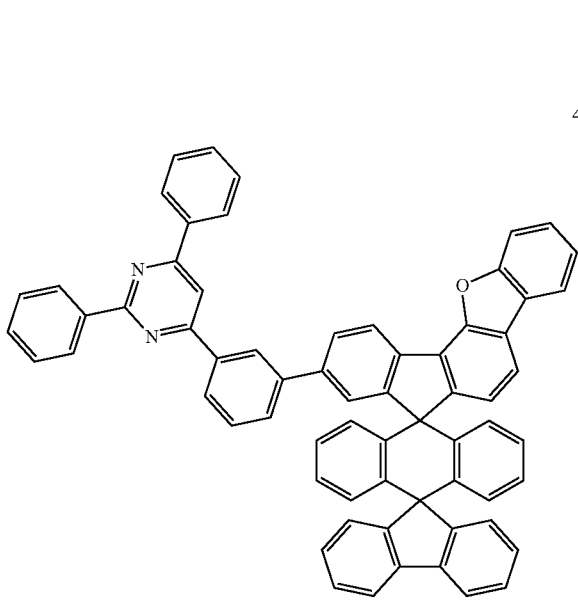
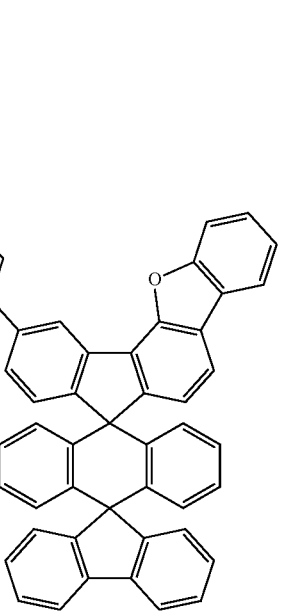

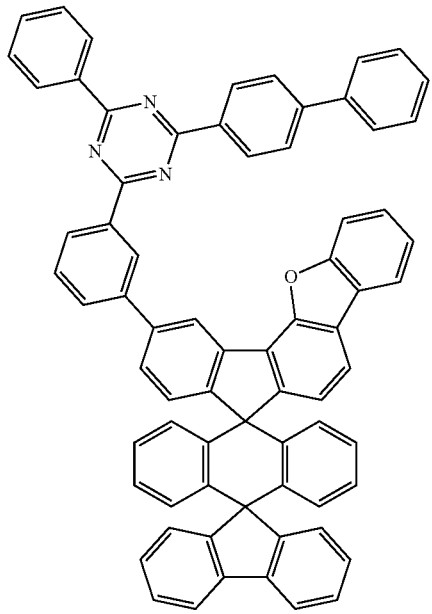
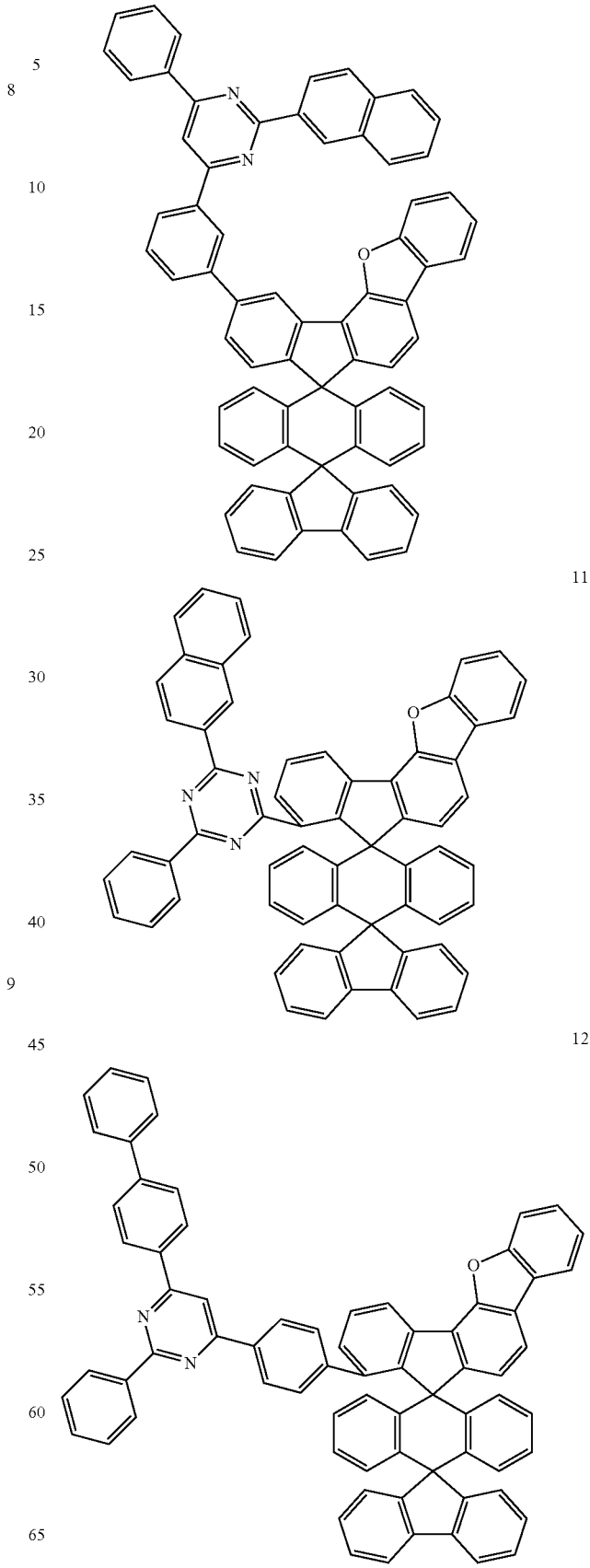

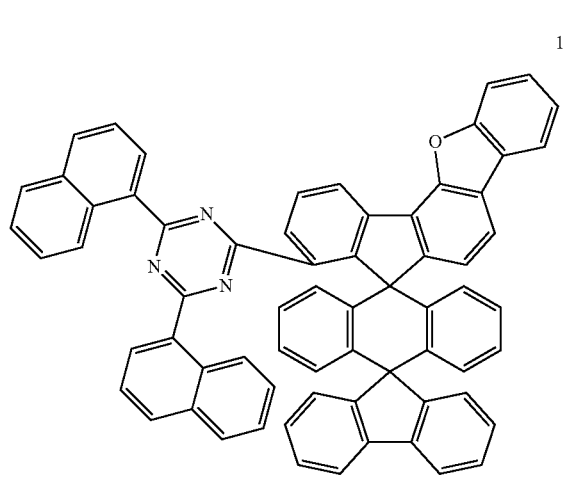
13
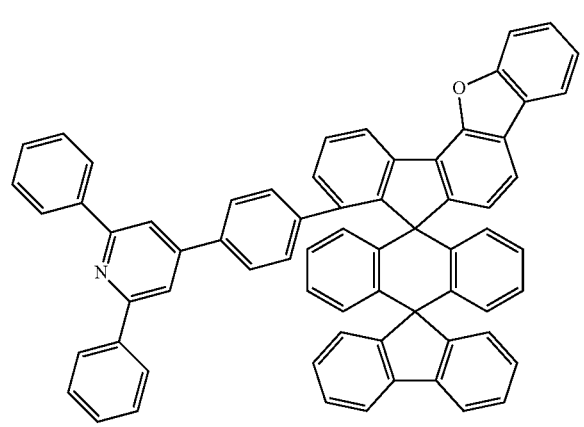
14
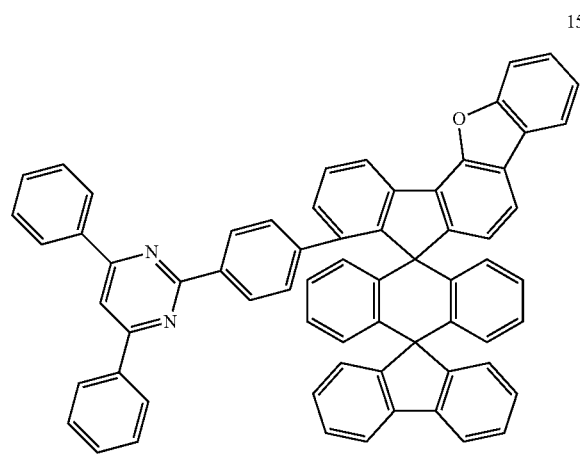
15
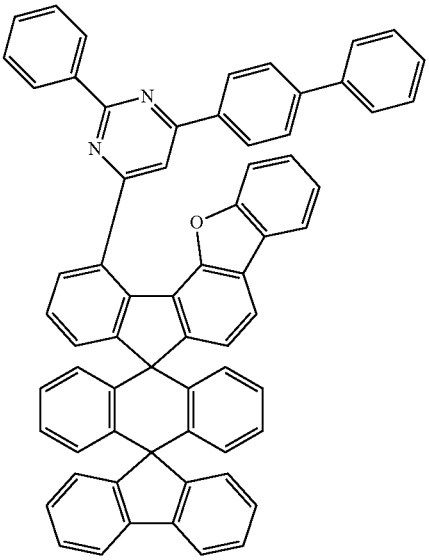
16
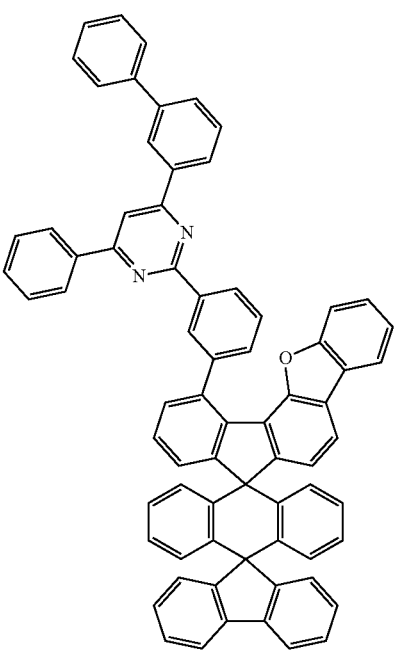
17

18
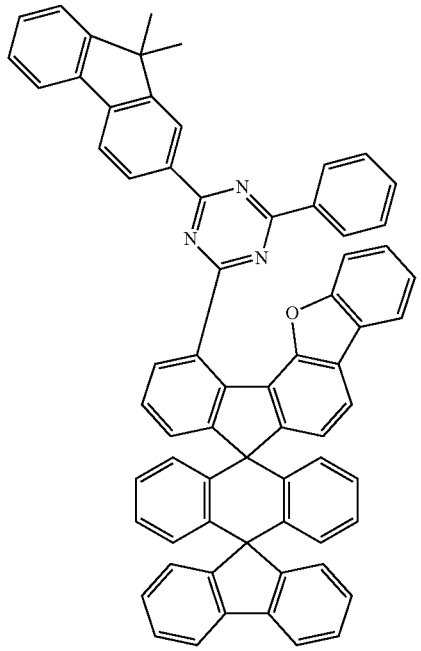
19
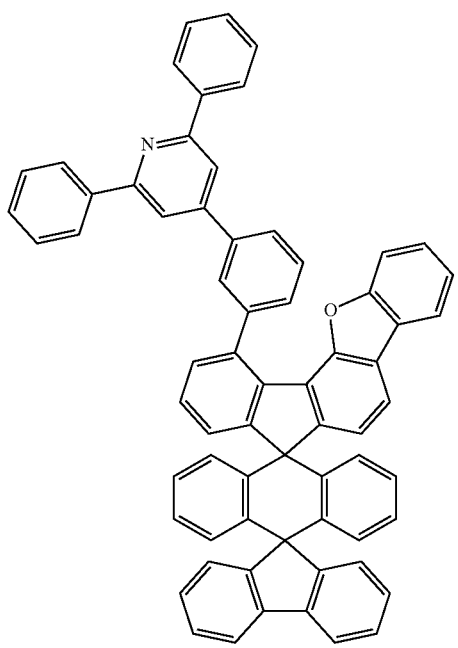
20
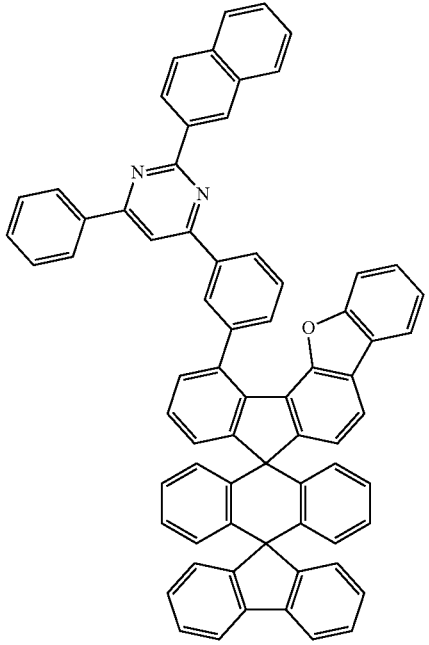
21
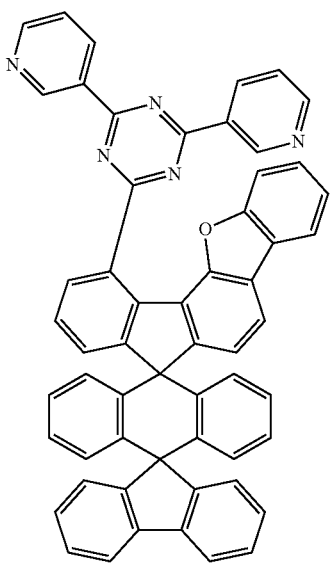
22
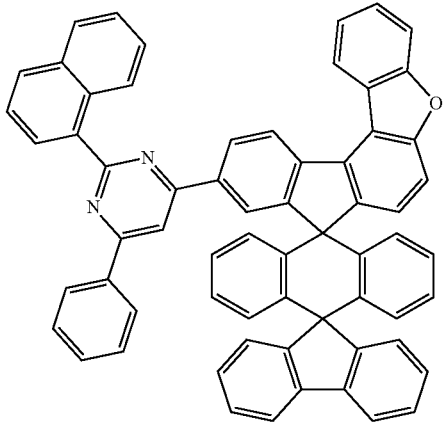

23
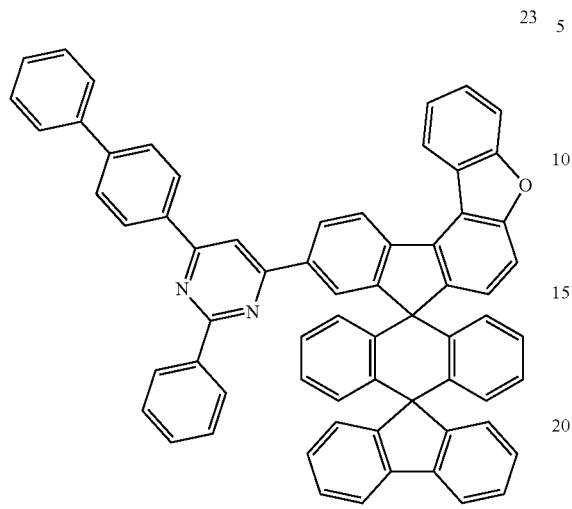
26
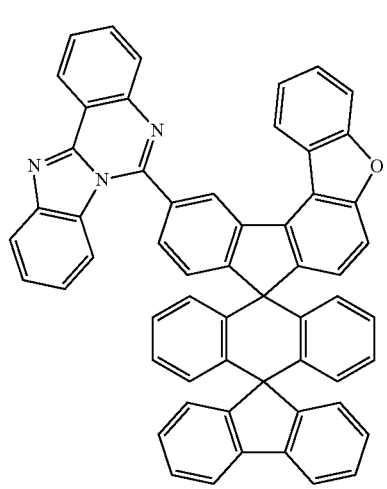
24
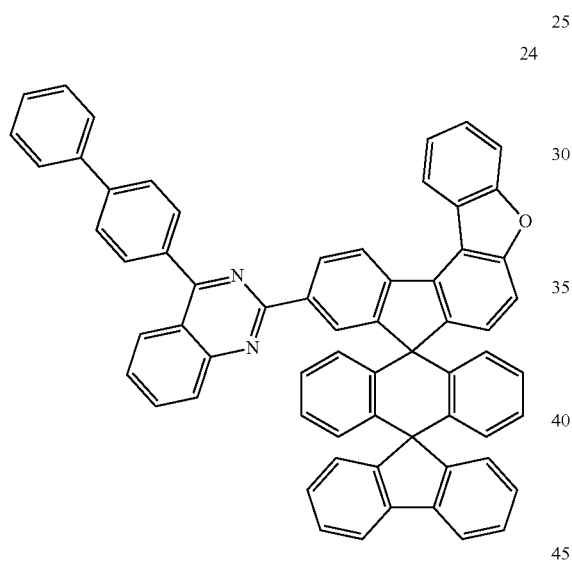
27
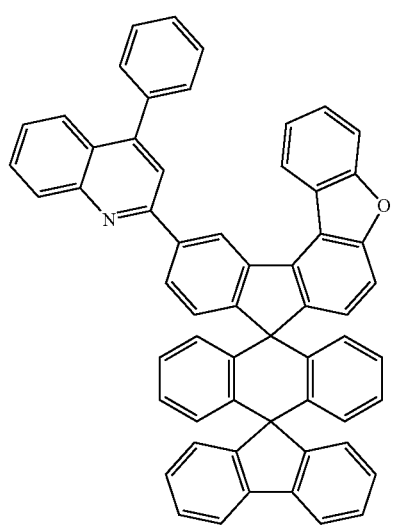
25
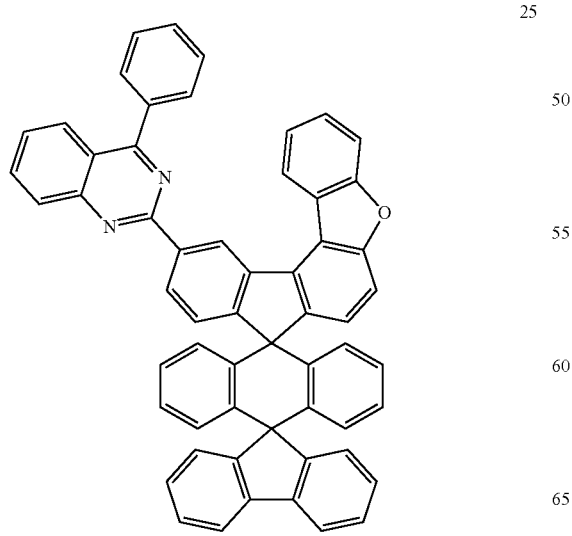
28
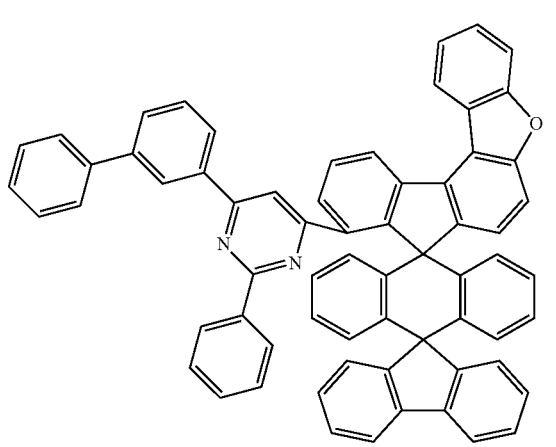

29
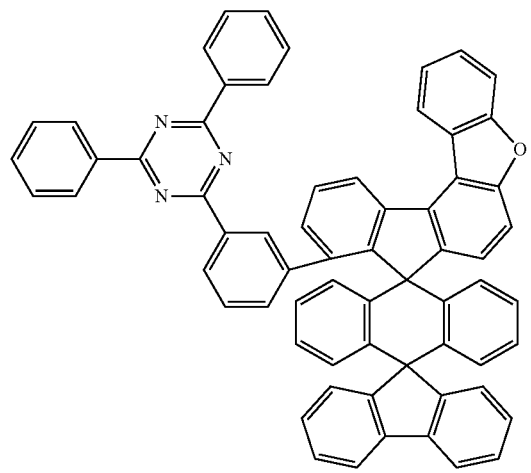
30
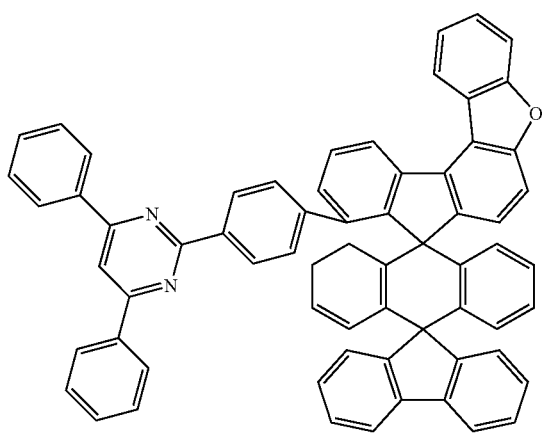
31
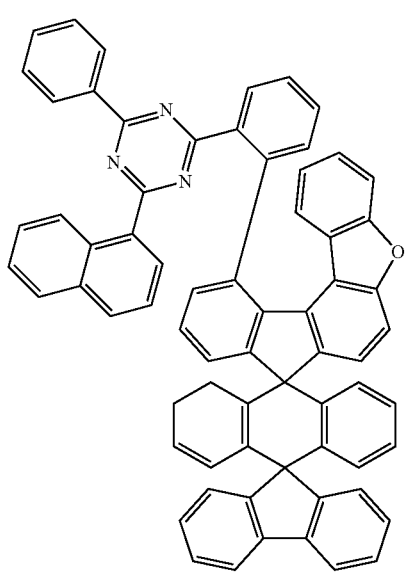
32
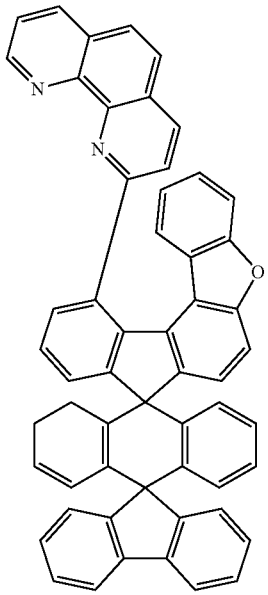
33
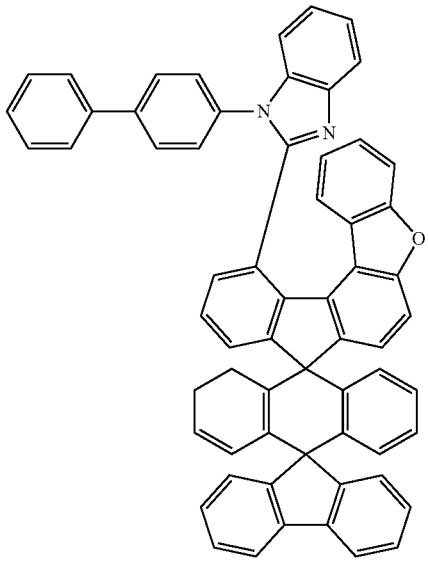
34
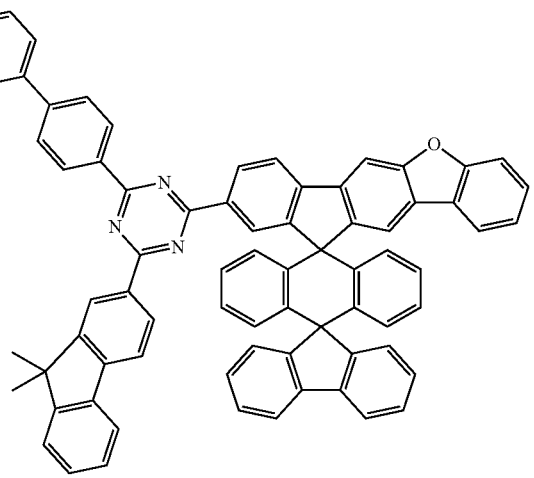

35
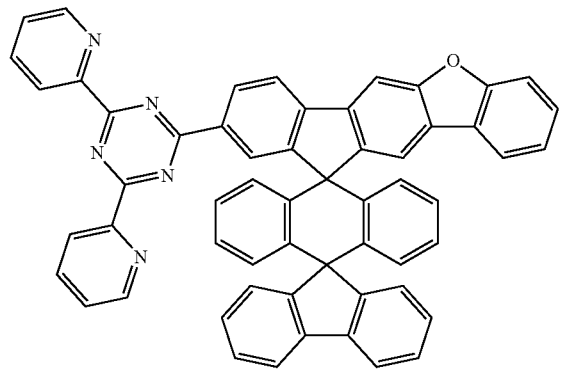
36
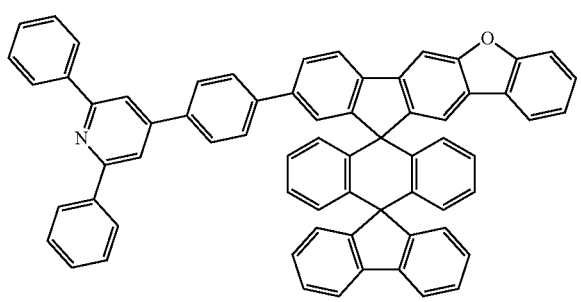
37
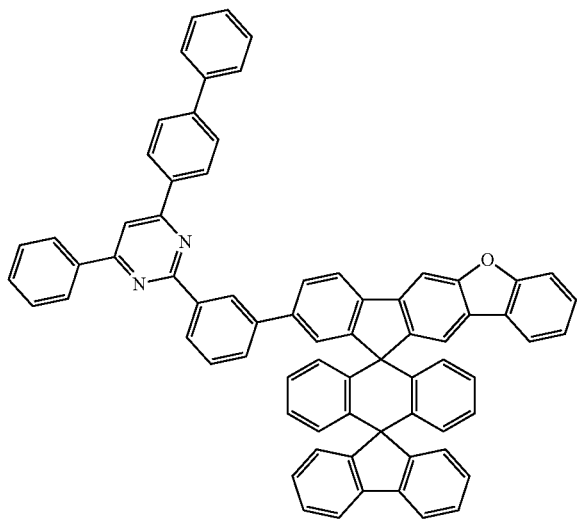
38
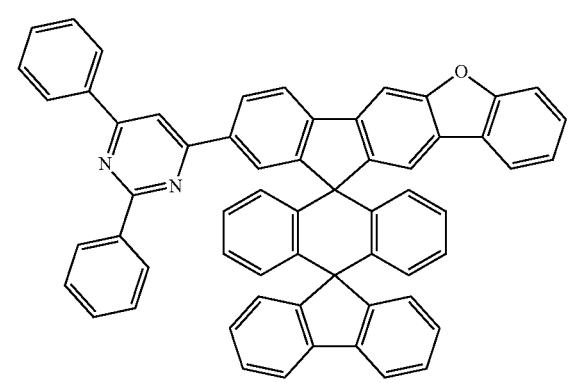
39
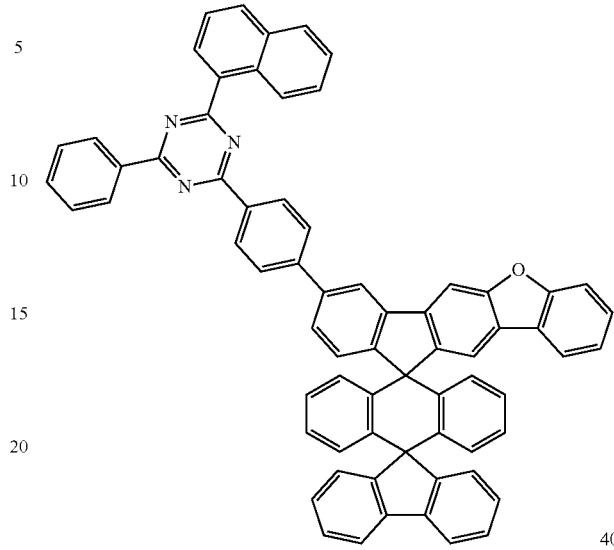
40
35
41

-continued
42
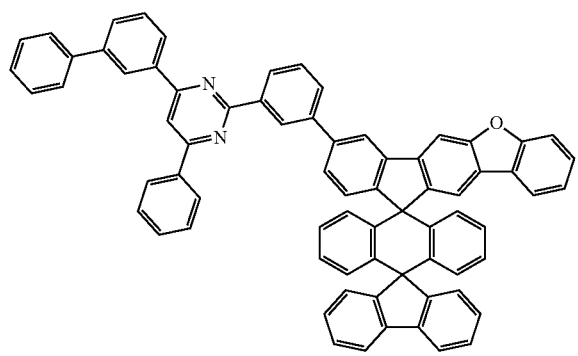
43
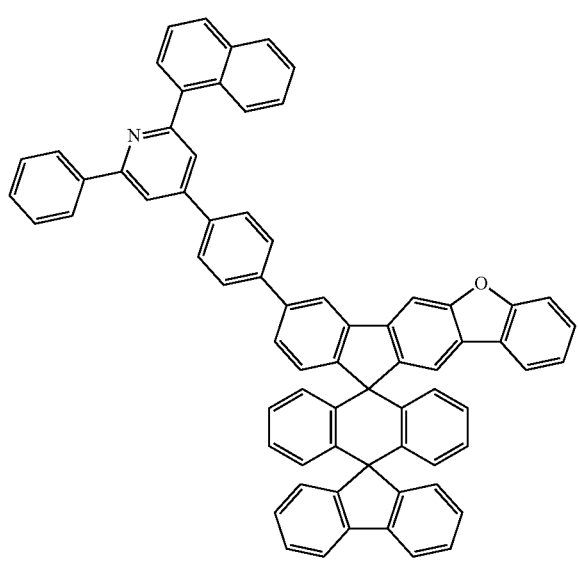
44
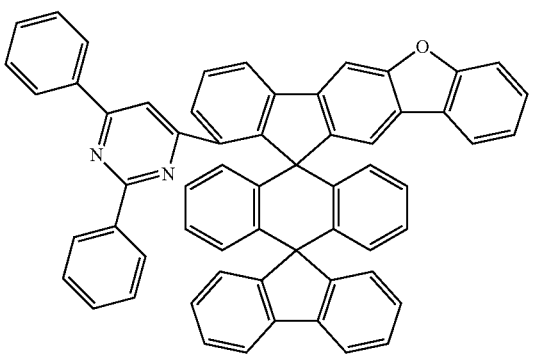
45
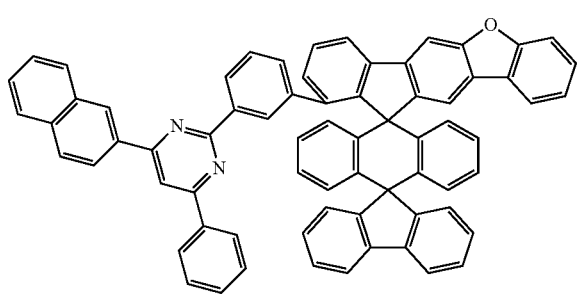
-continued
46
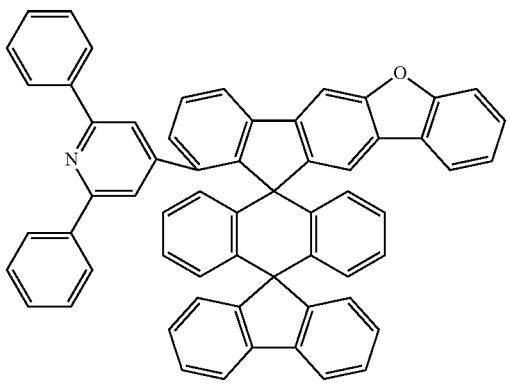
47
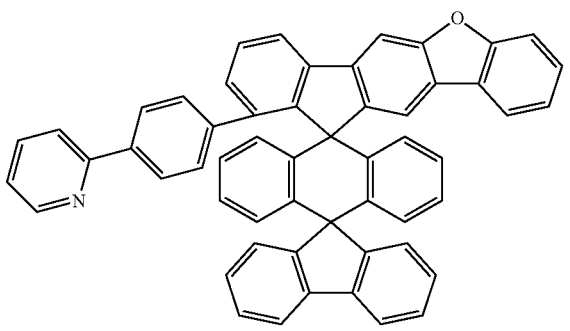
48
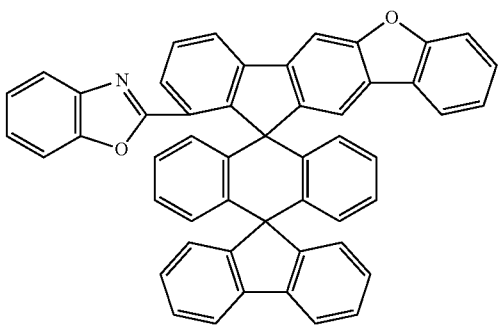
49
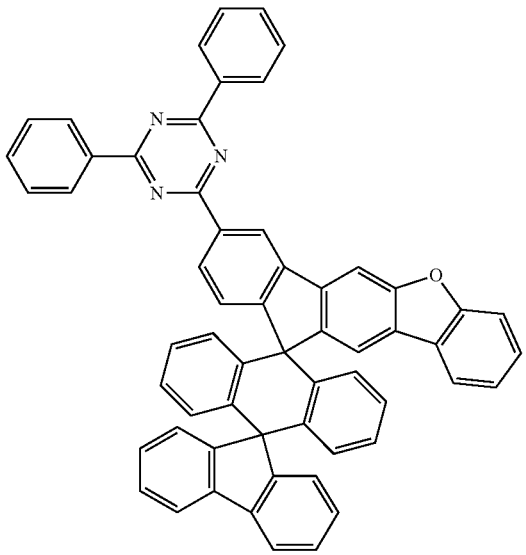

50
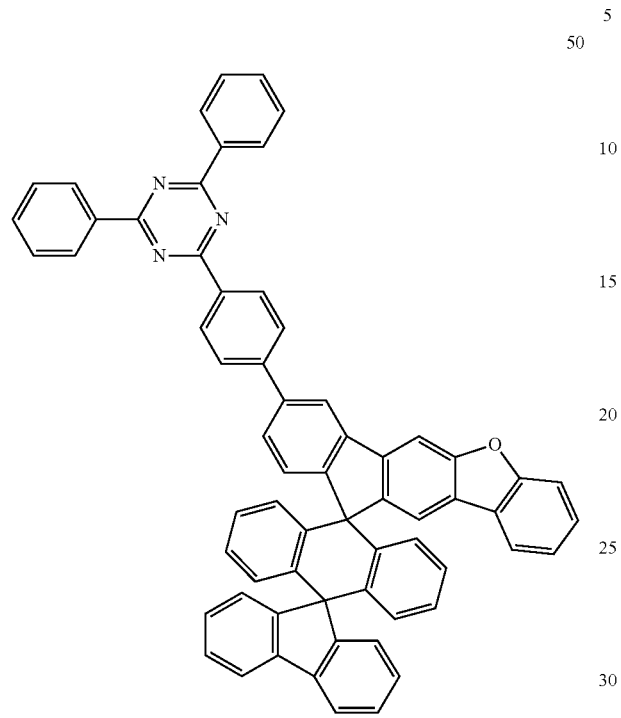
51
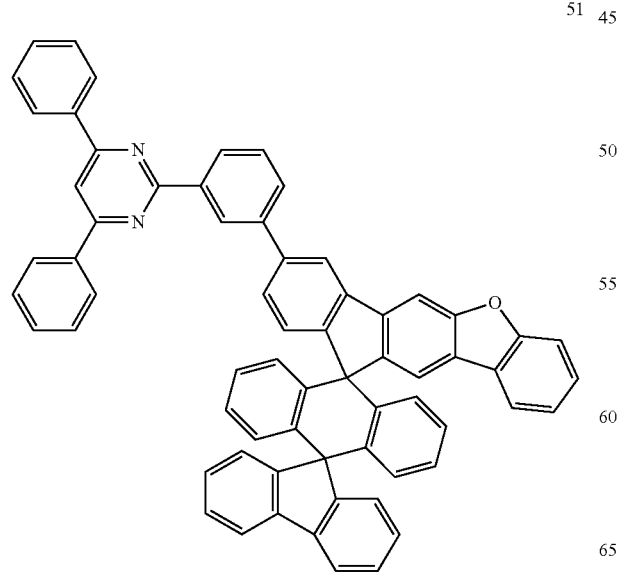
52
53
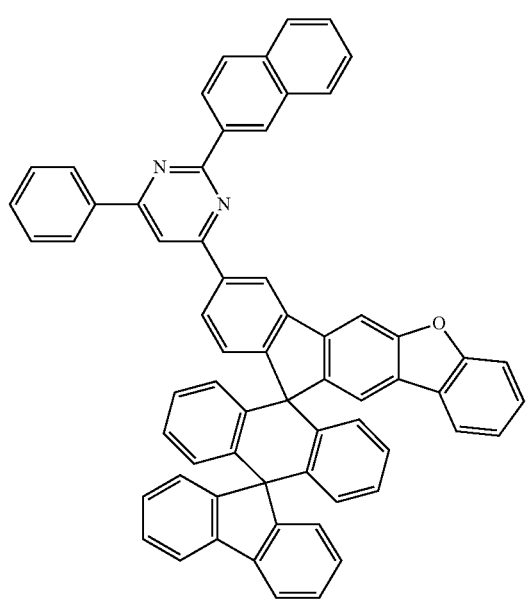

54
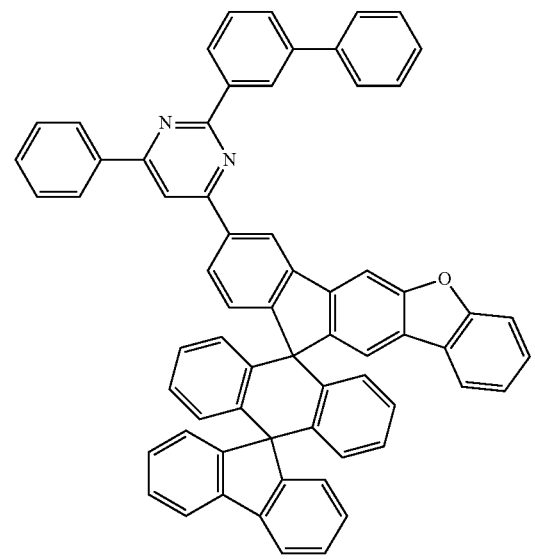
55
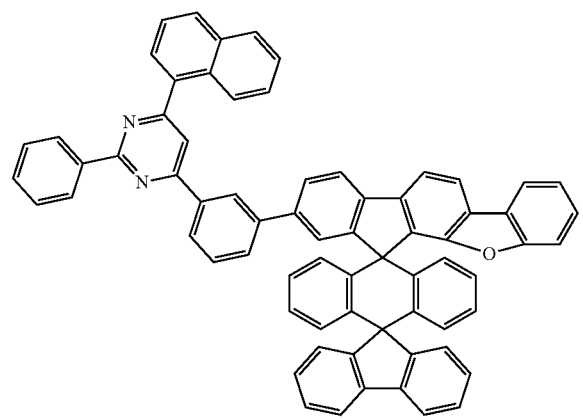
56
57
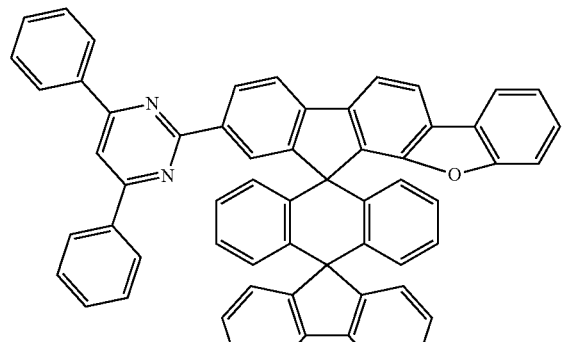
58
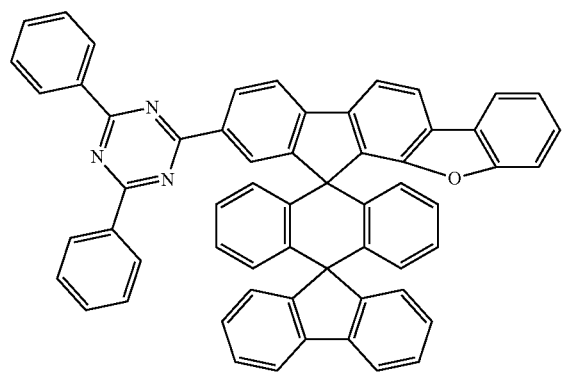
59
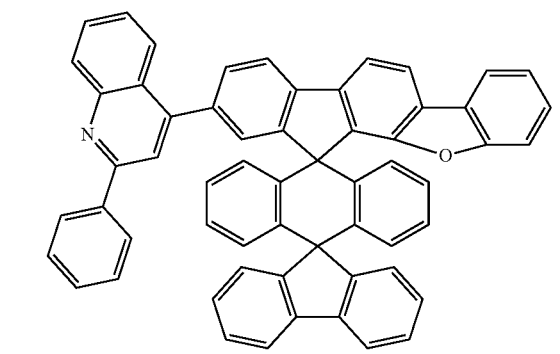
60
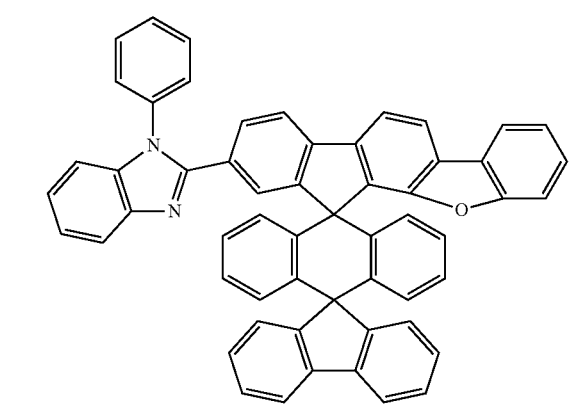

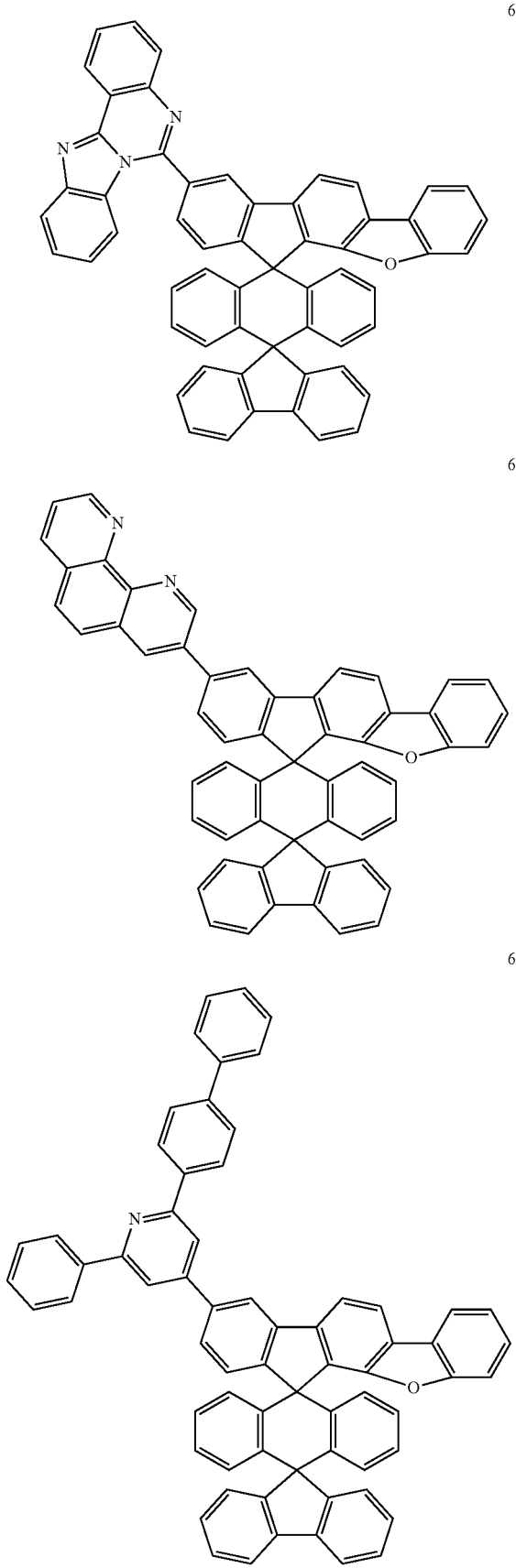
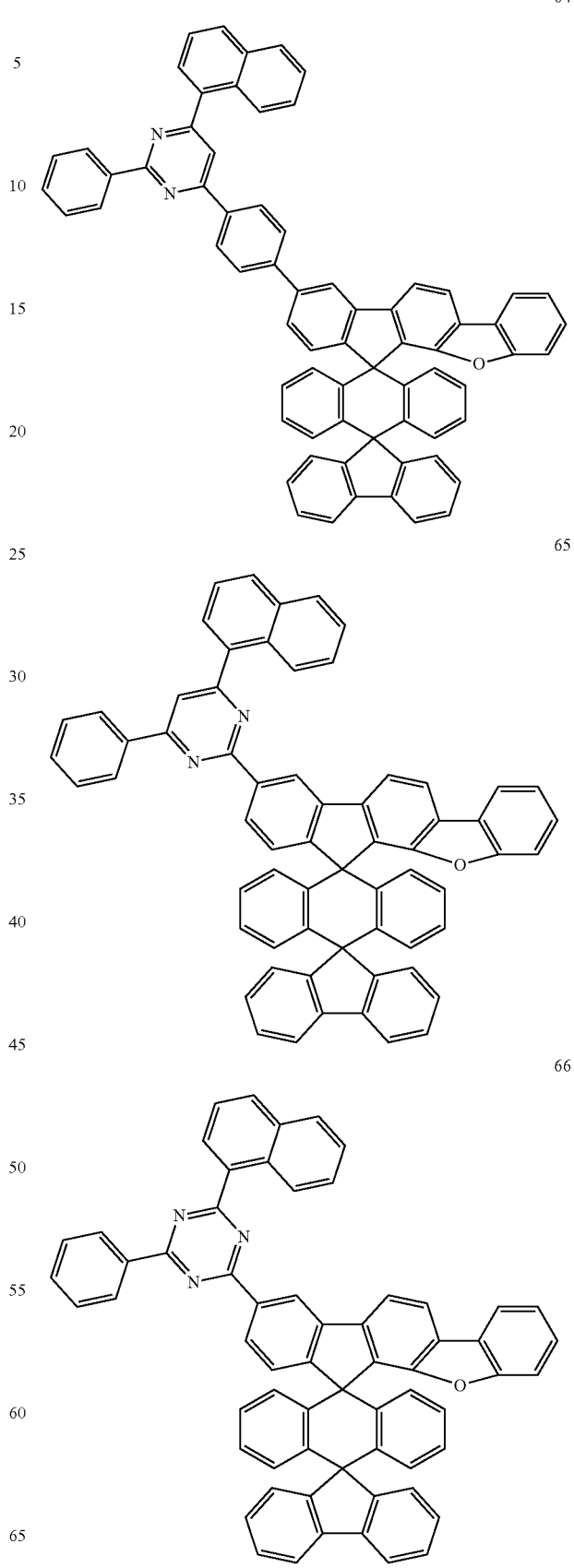

81
-continued
67
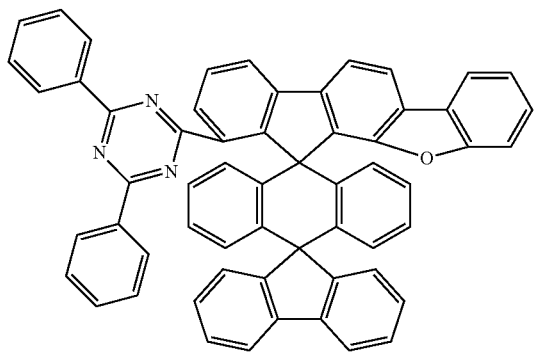
68
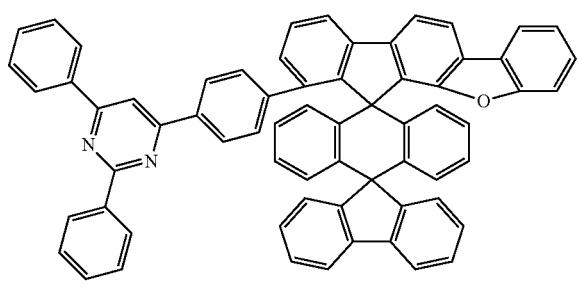
69
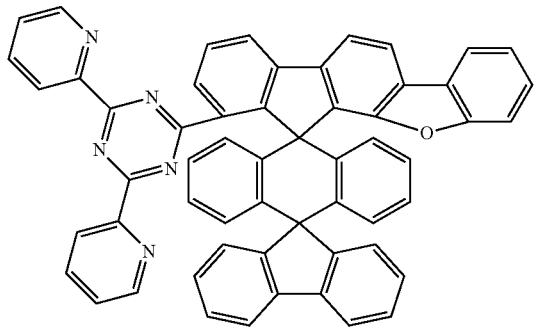
70
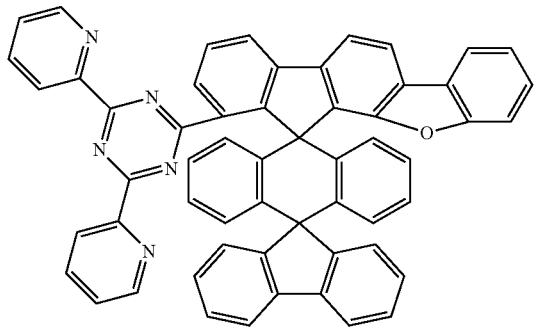
82
-continued
71
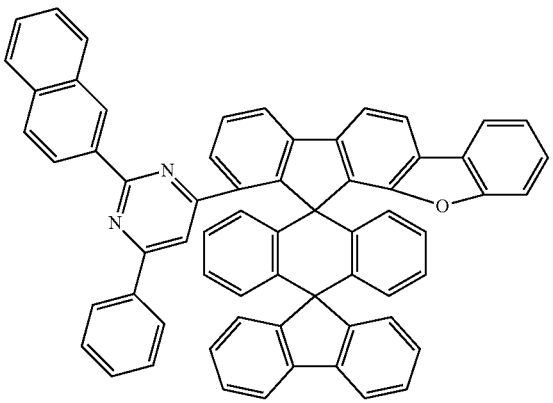
72
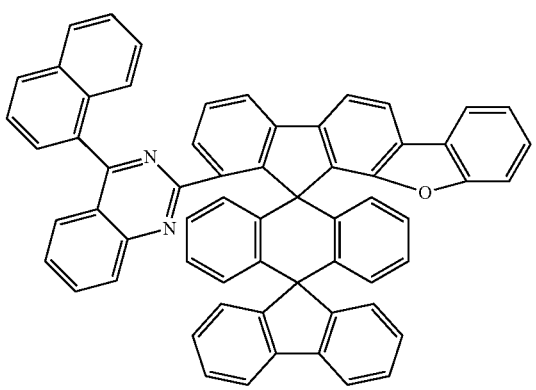
73
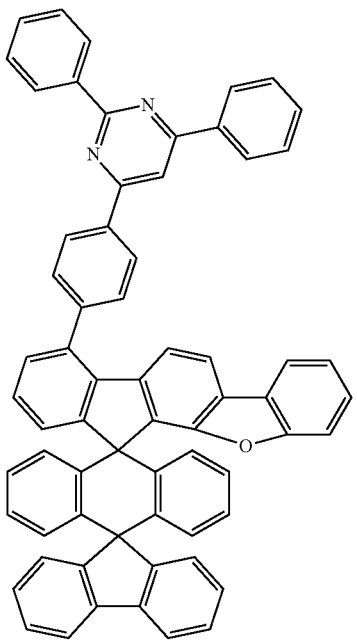

74
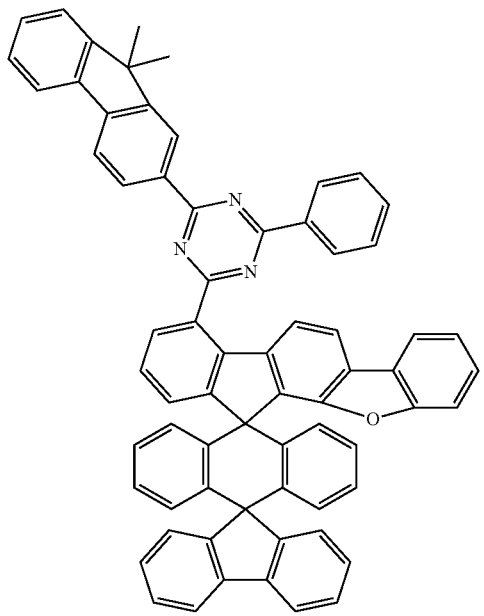
75
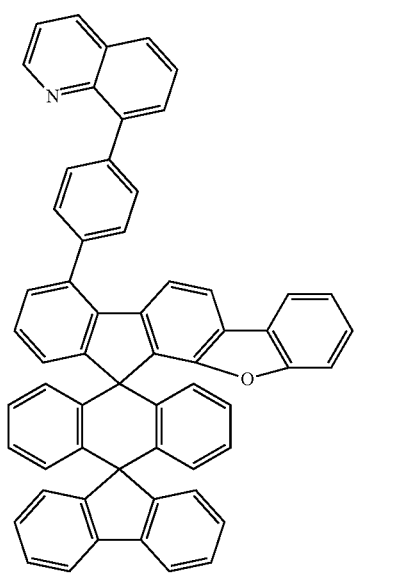
76
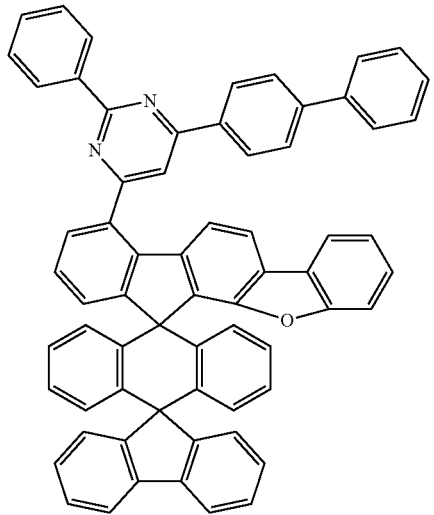
77
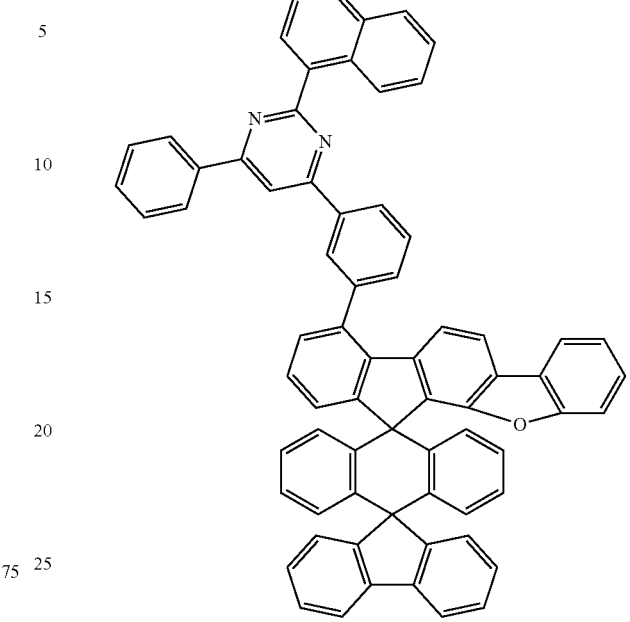
78
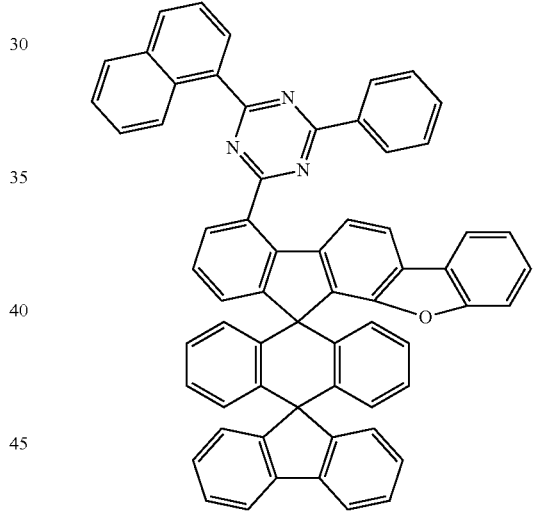
79
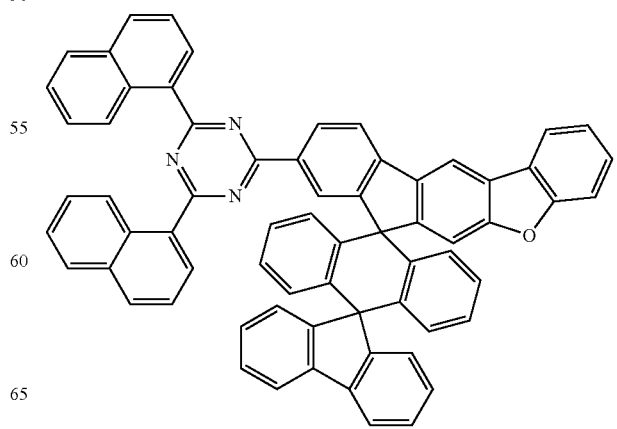

85
-continued
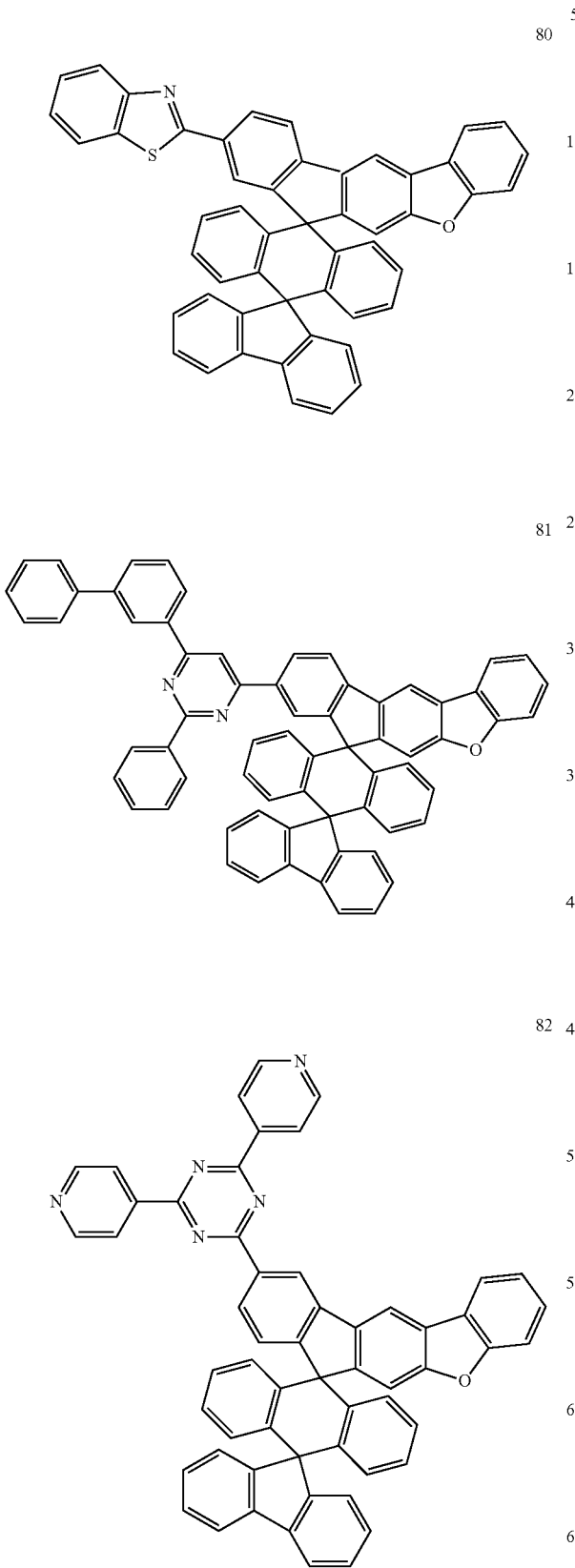
80
81
82
86
-continued
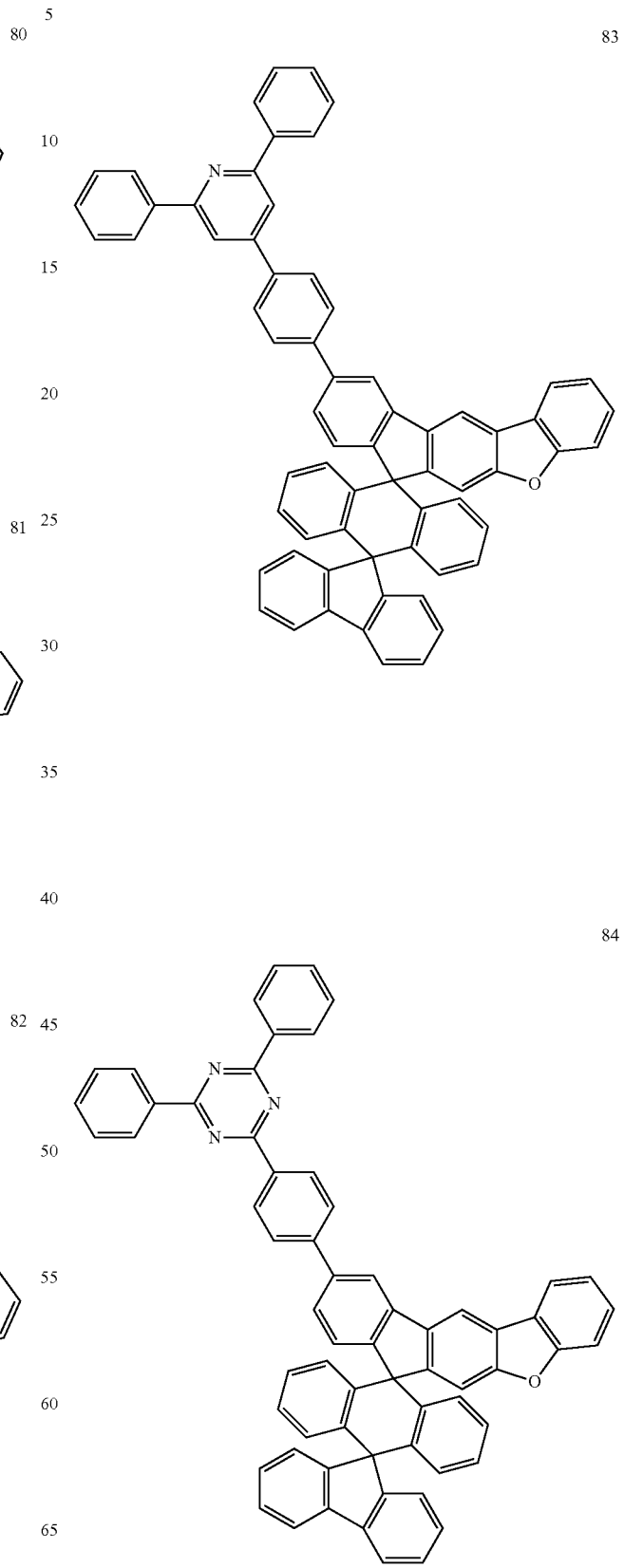
83
84

87
-continued
88
-continued
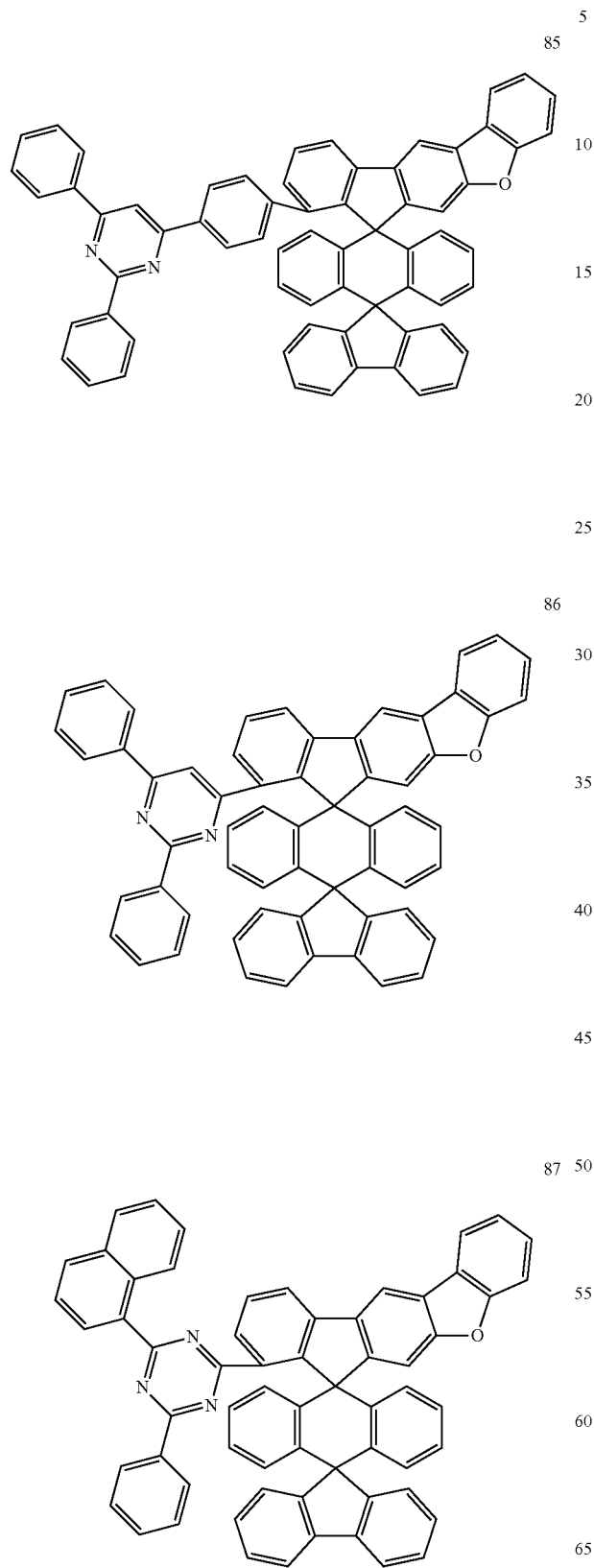
85
86
87
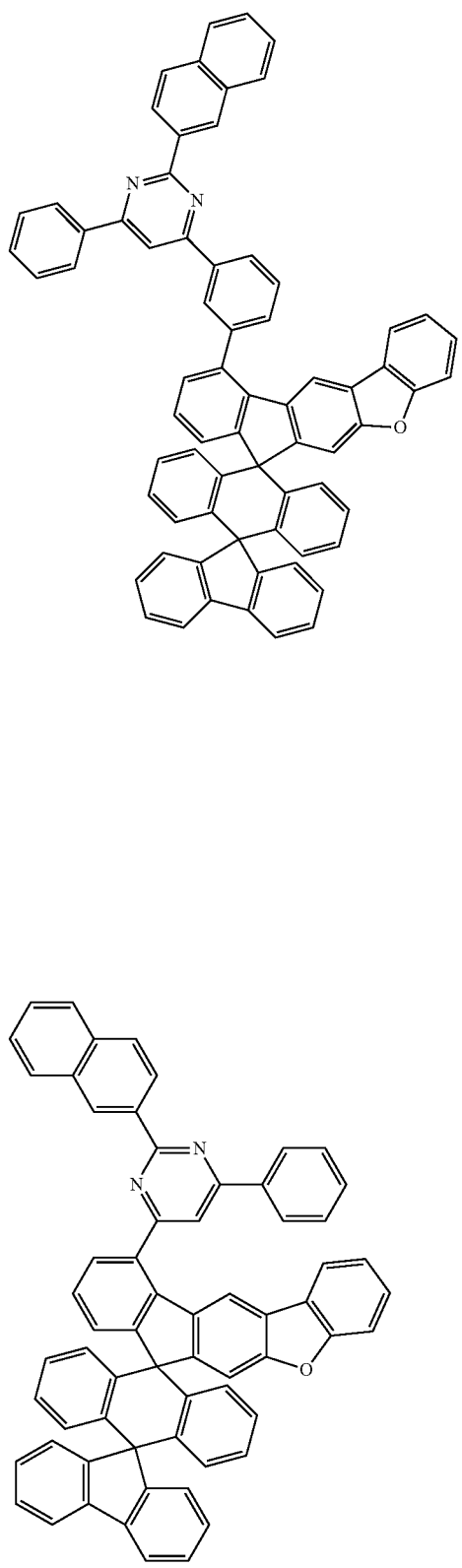
88
89

-continued
90
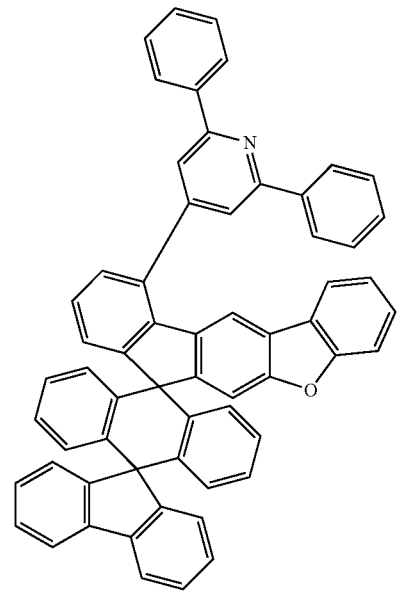
91
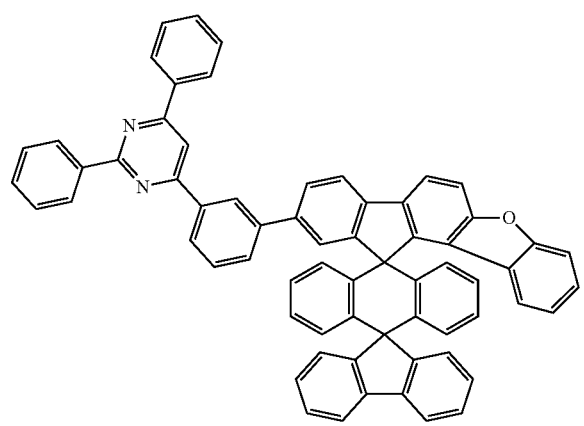
92
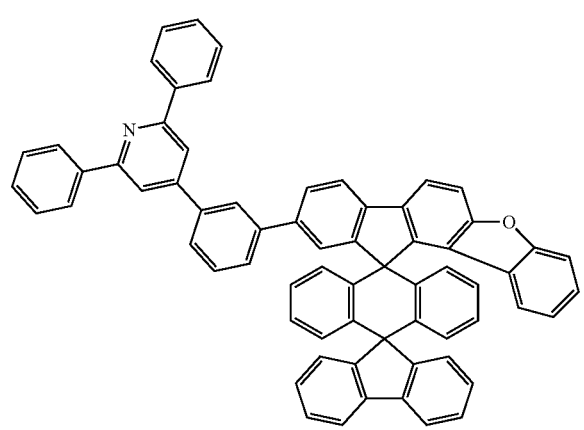
-continued
93
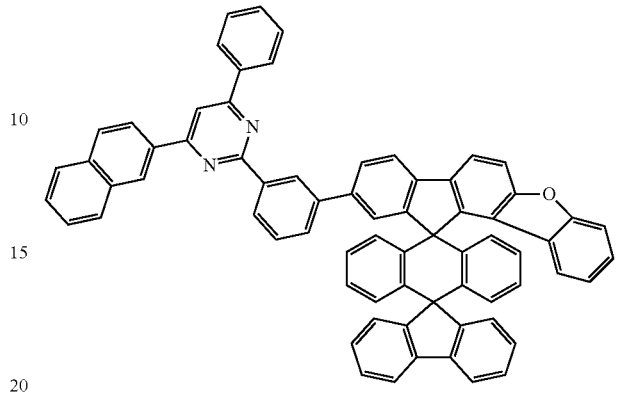
94
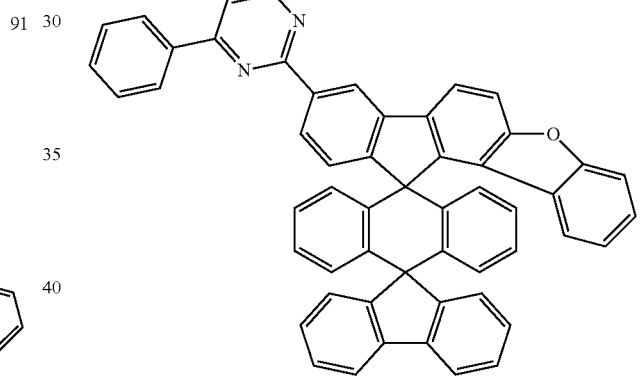
95
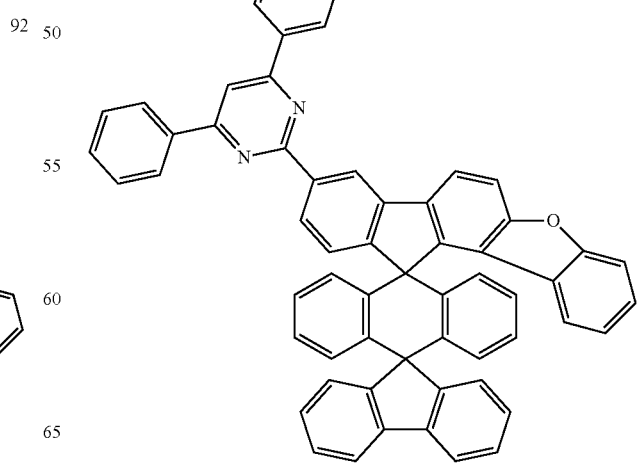

91
-continued
96
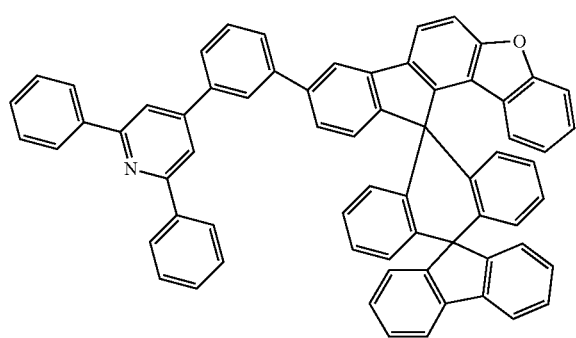
97
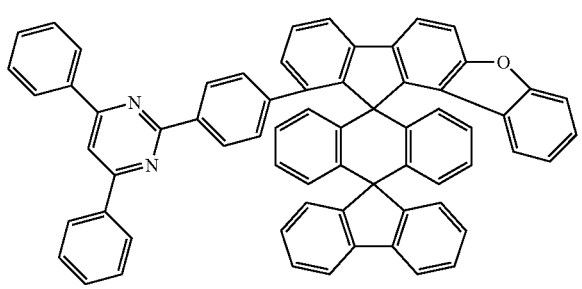
98
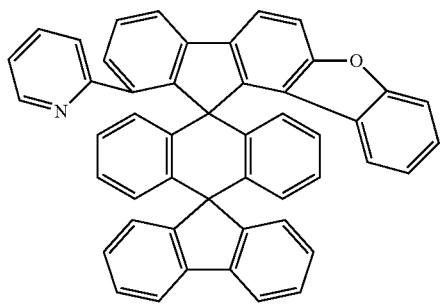
99
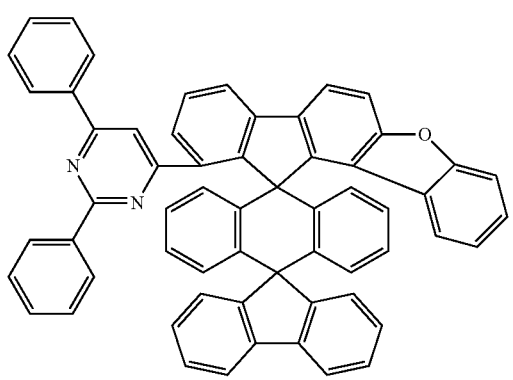
92
-continued
100
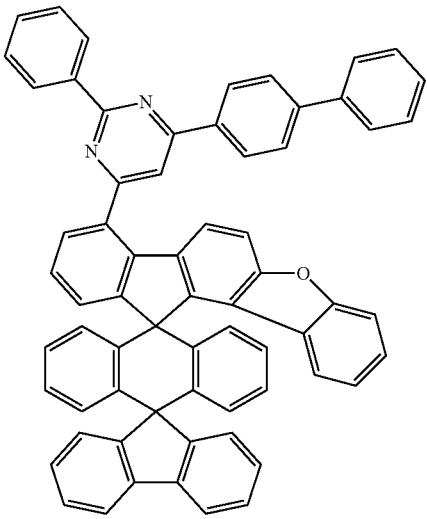
101
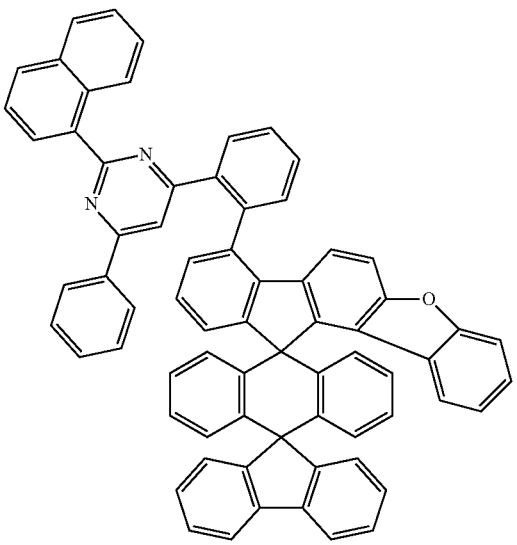
102
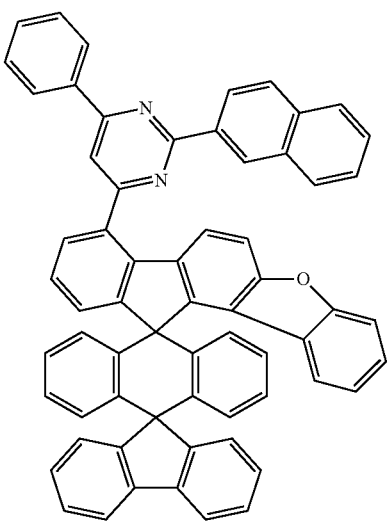

103
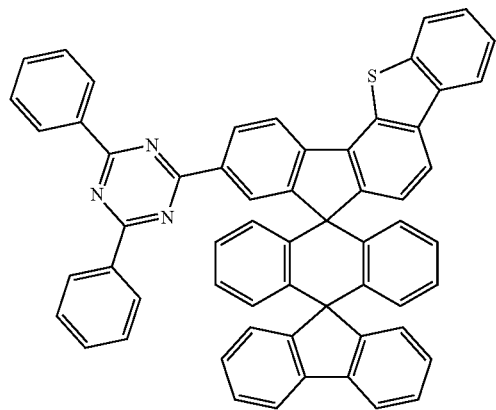
104
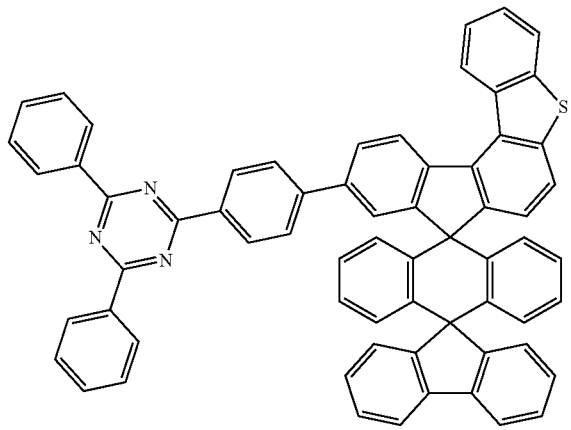
105
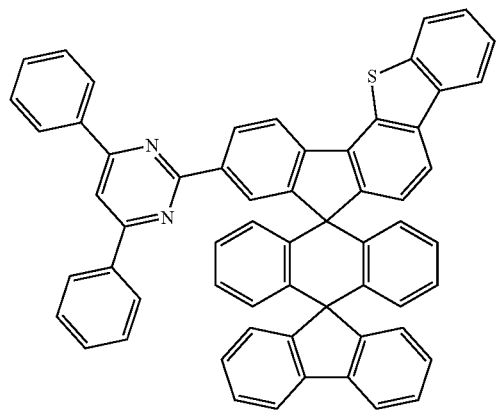
106
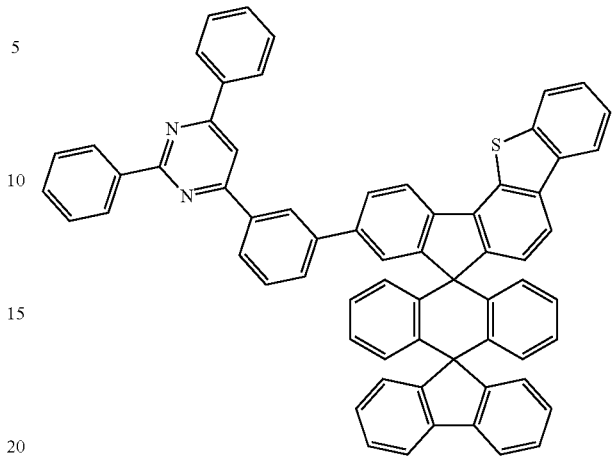
107
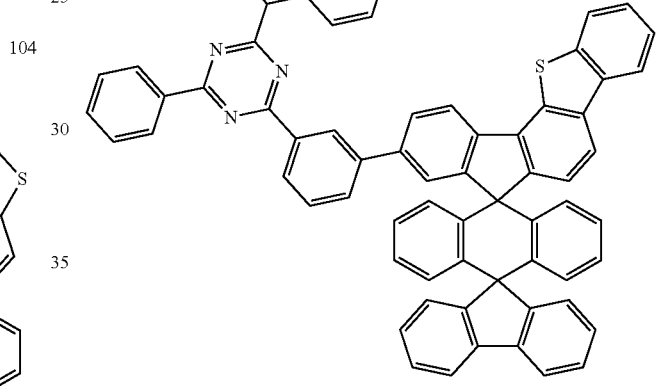
108
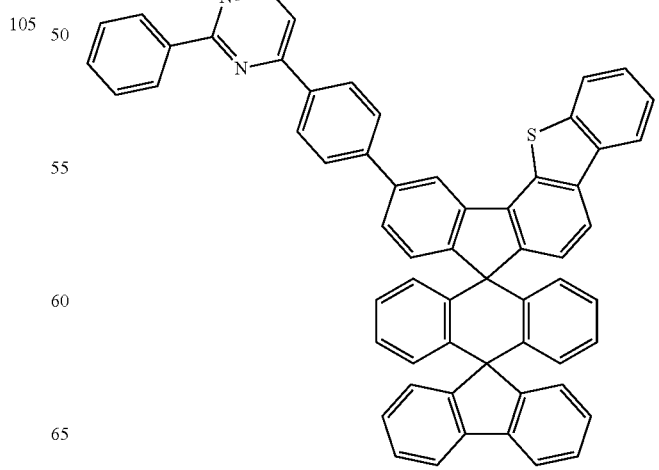

95
-continued
109
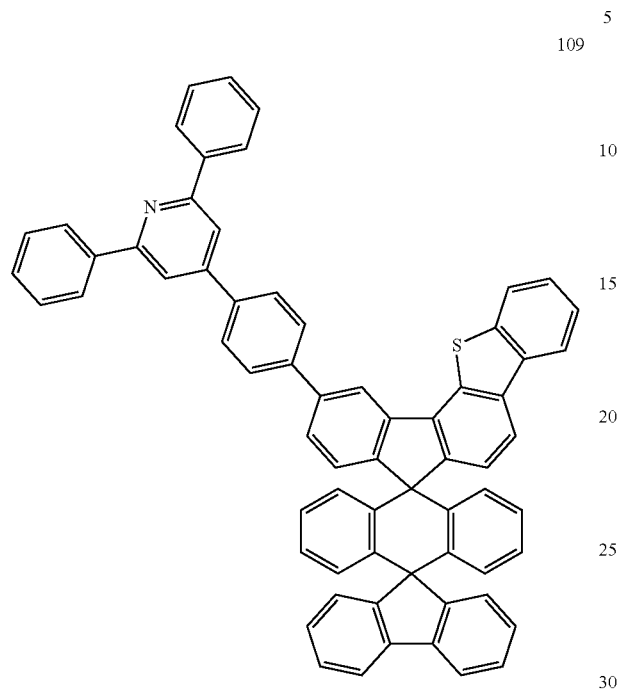
110
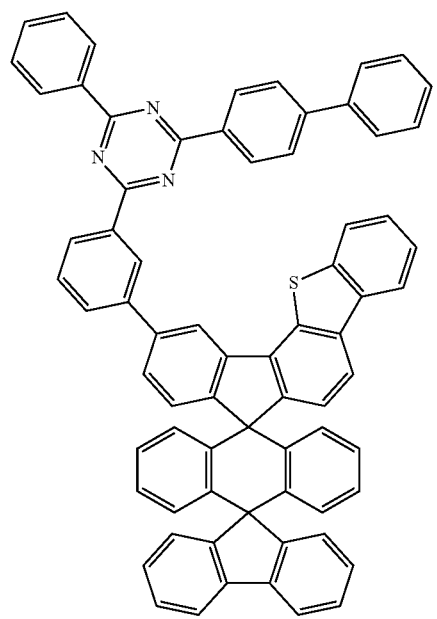
96
-continued
111
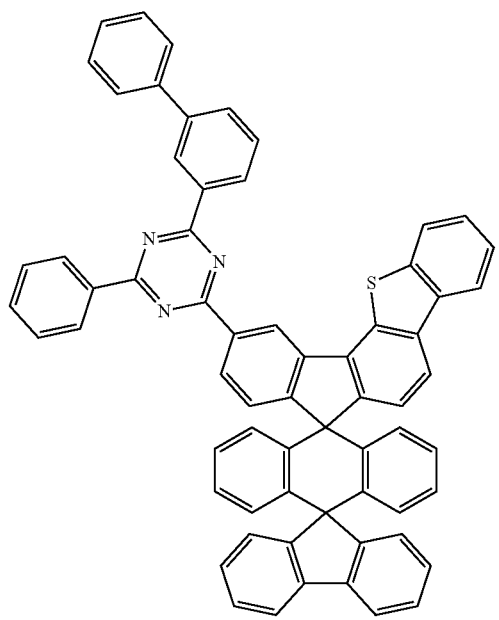
112
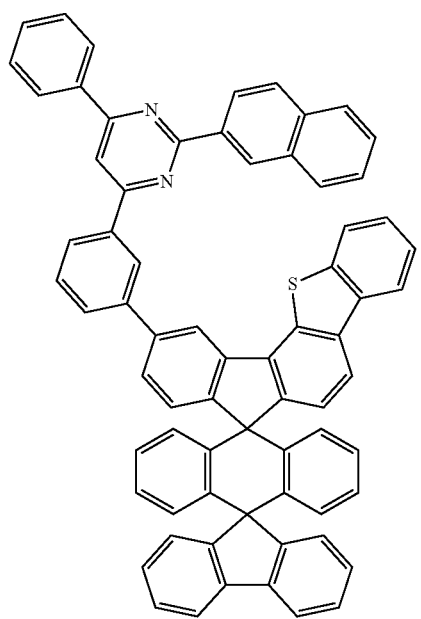

-continued
113
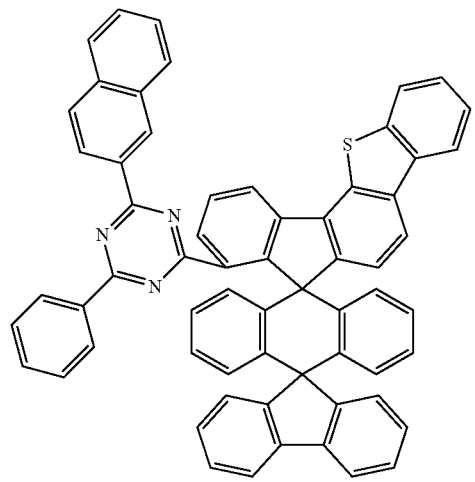
114
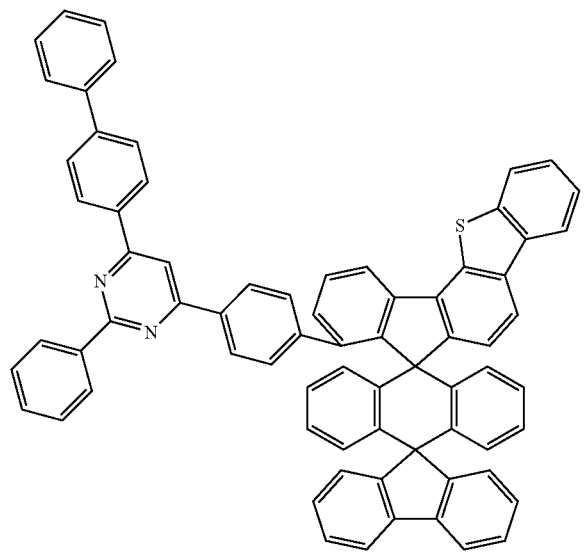
115
116
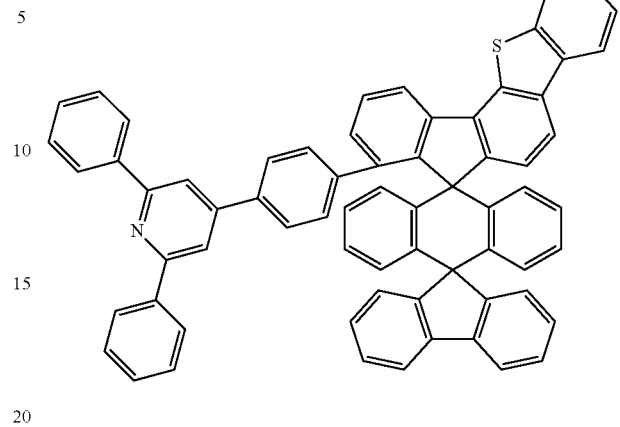
117
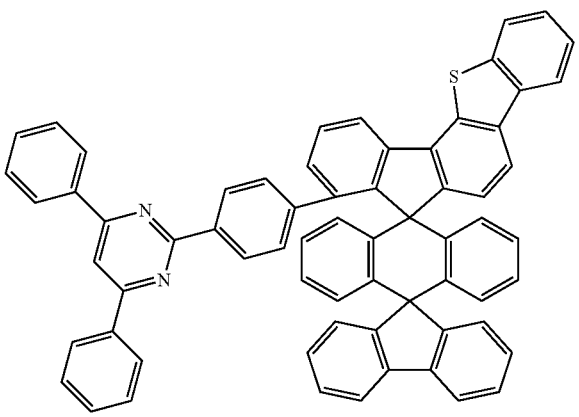
118
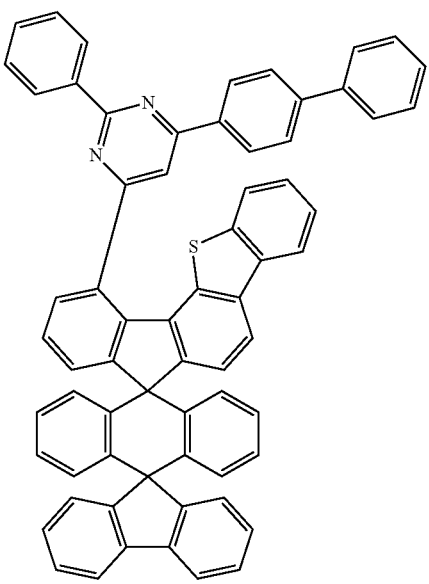

119 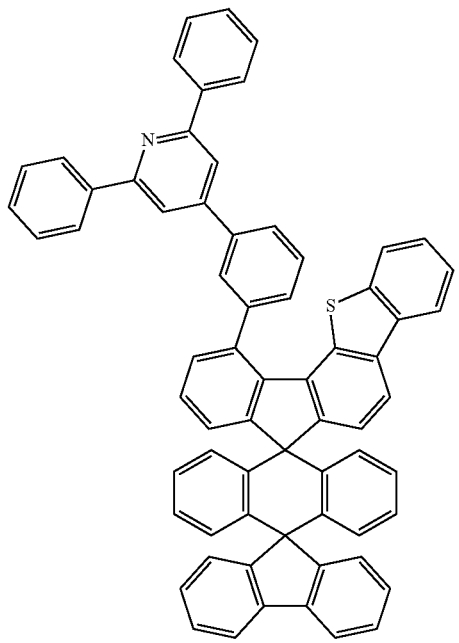
120 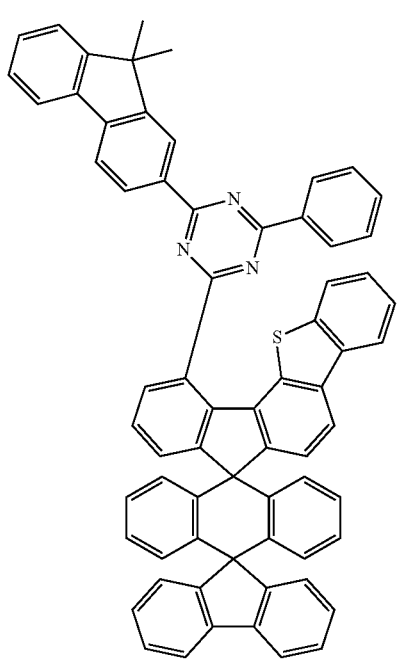
121 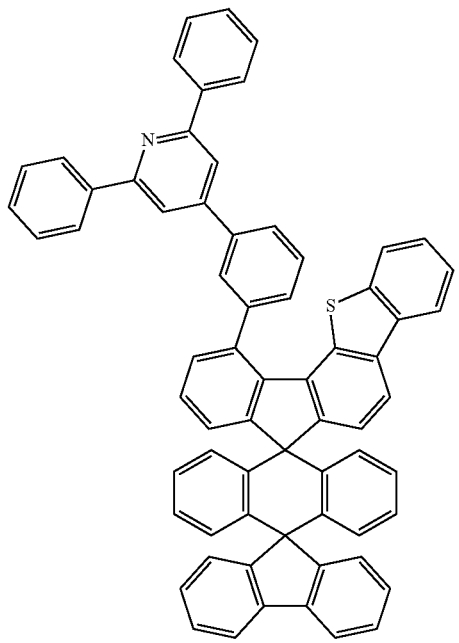
122 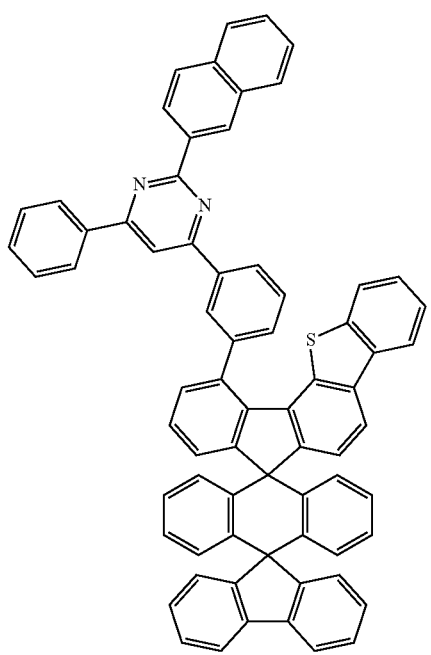

101
-continued
123
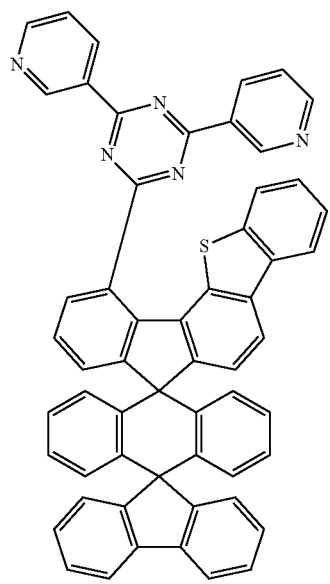
124
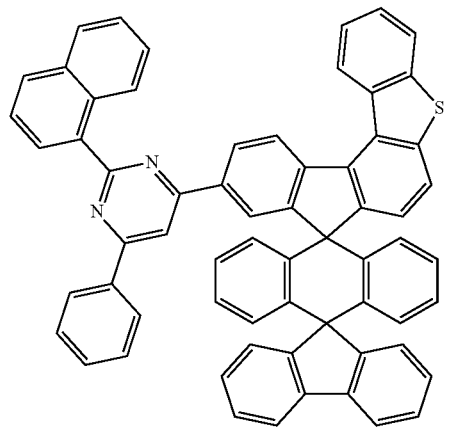
125
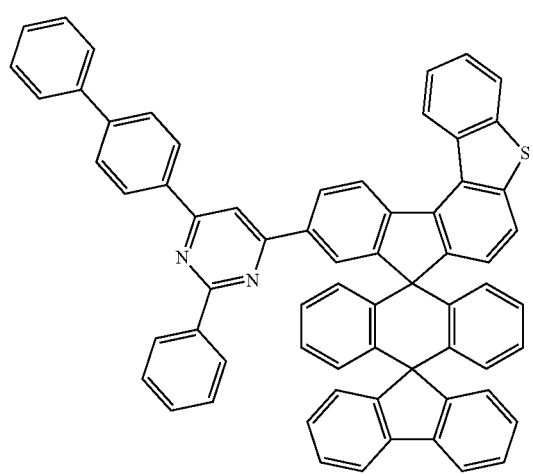
102
-continued
126
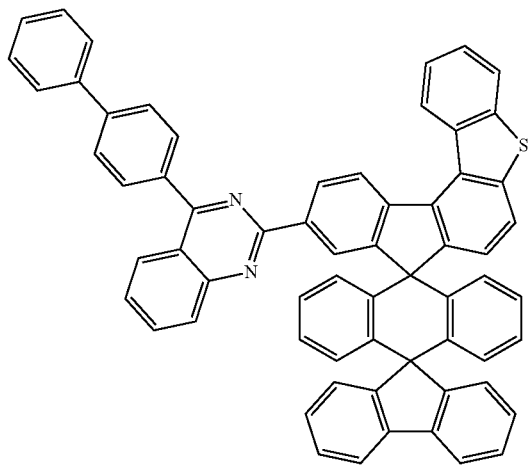
127
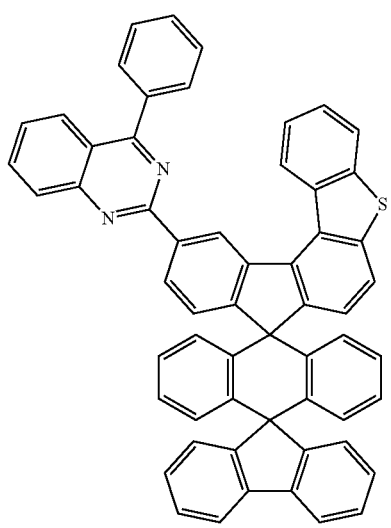
128
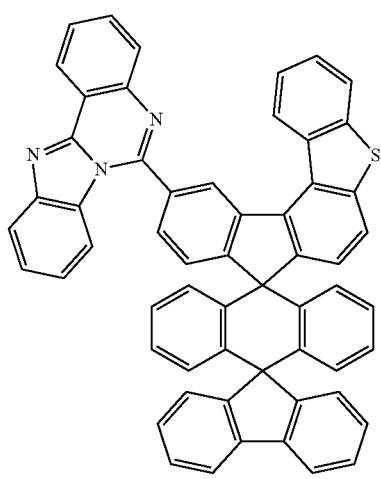

-continued
129
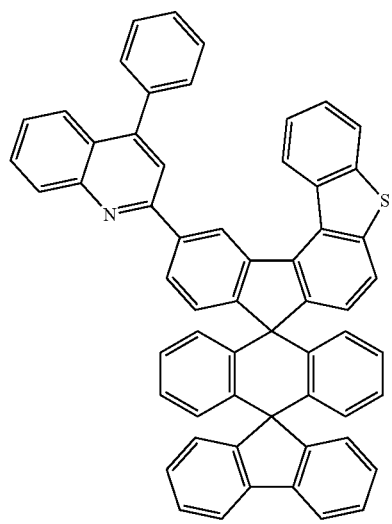
130
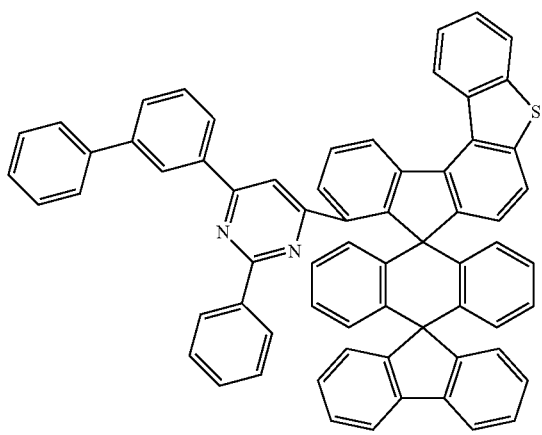
131
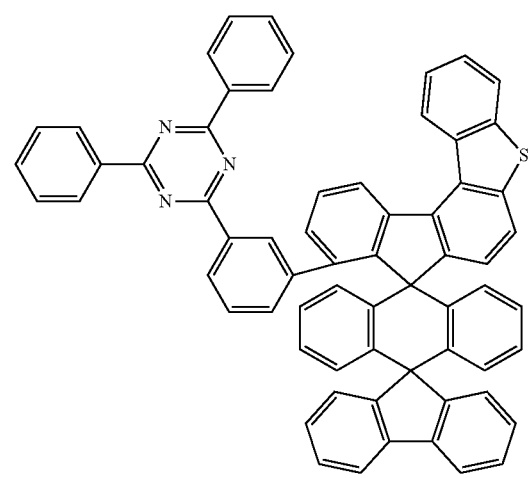
-continued
132
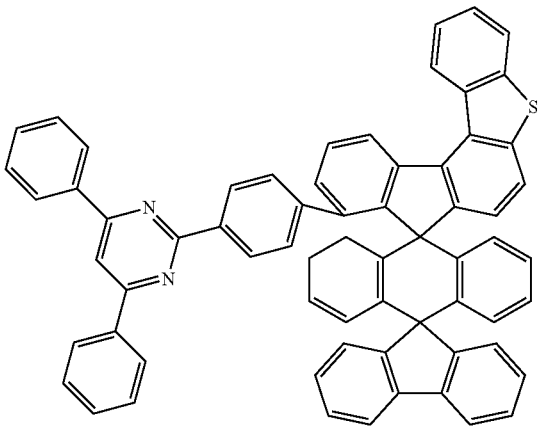
133
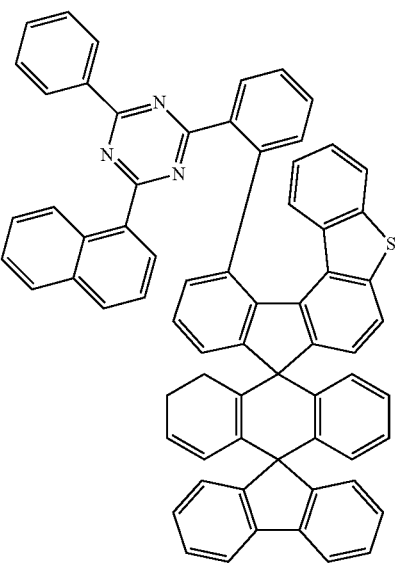
134
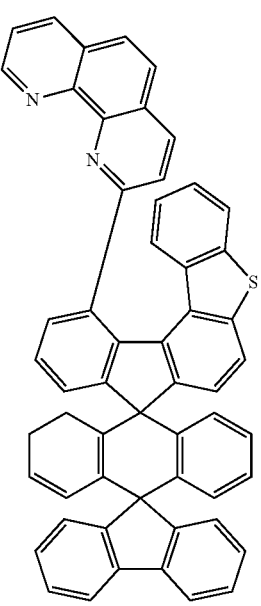

135
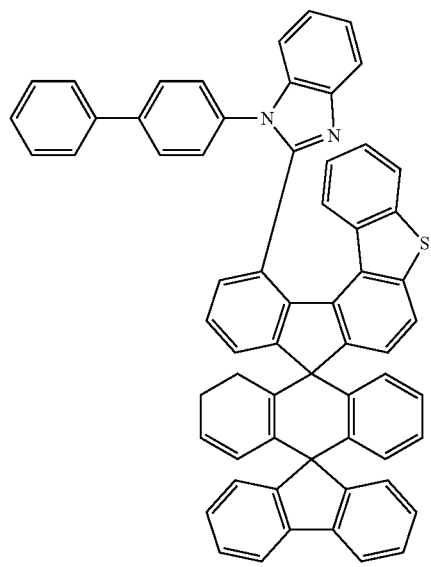
136
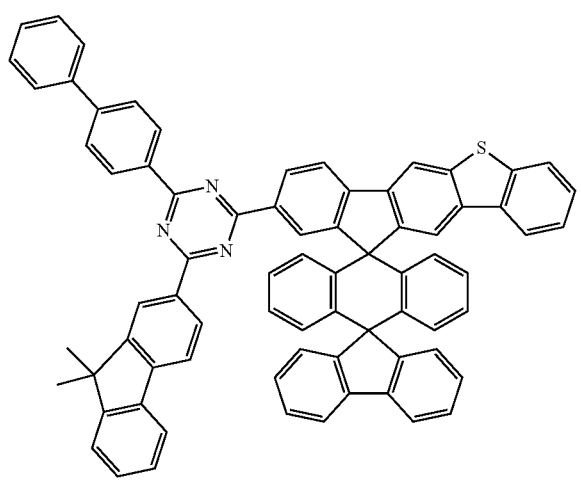
137
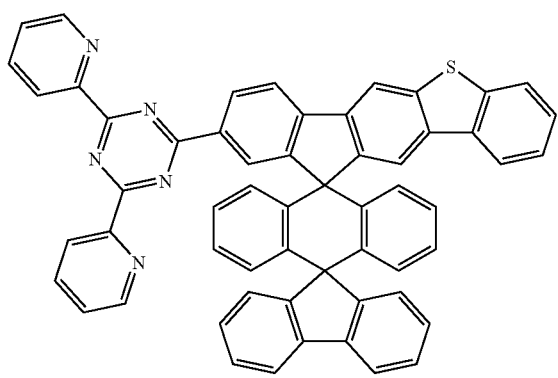
138
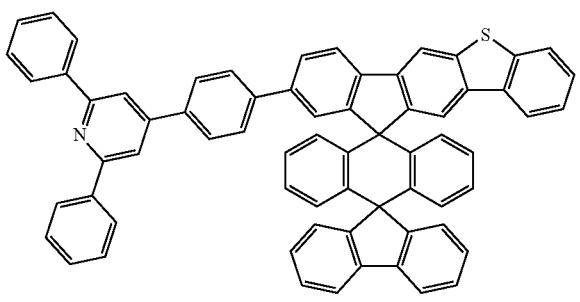
139
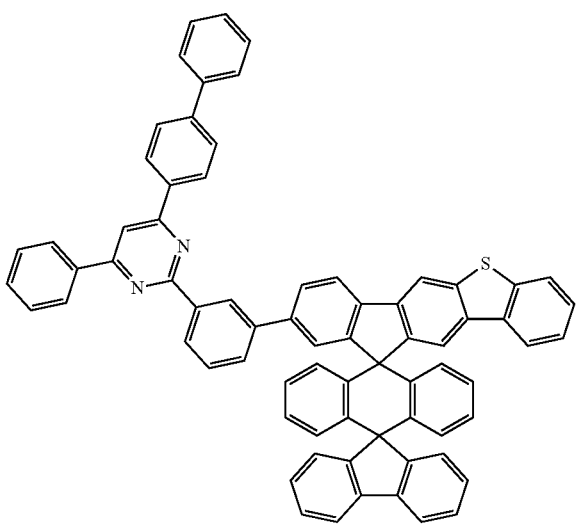
140
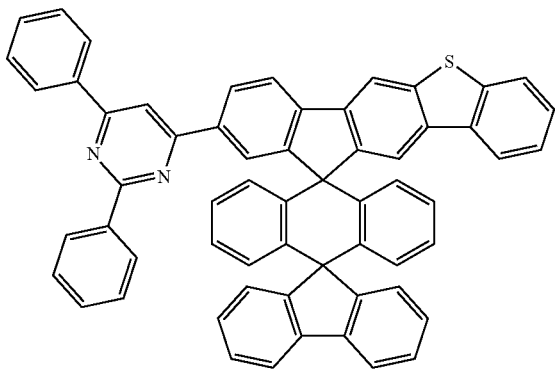

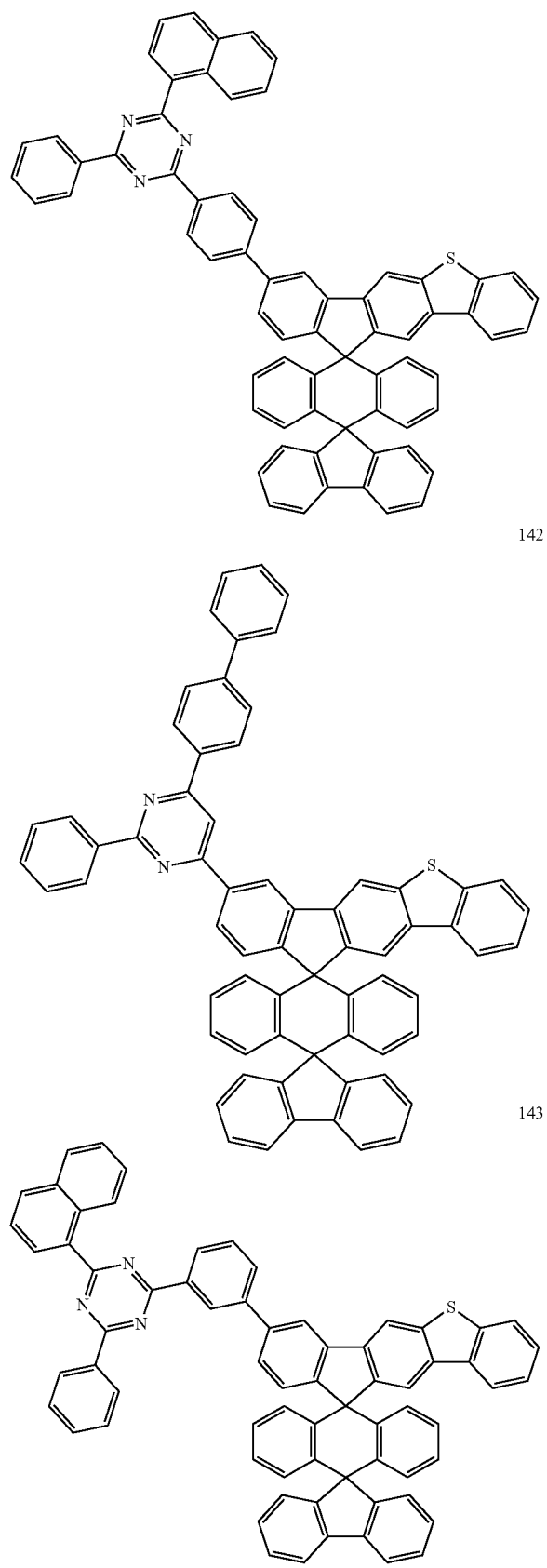
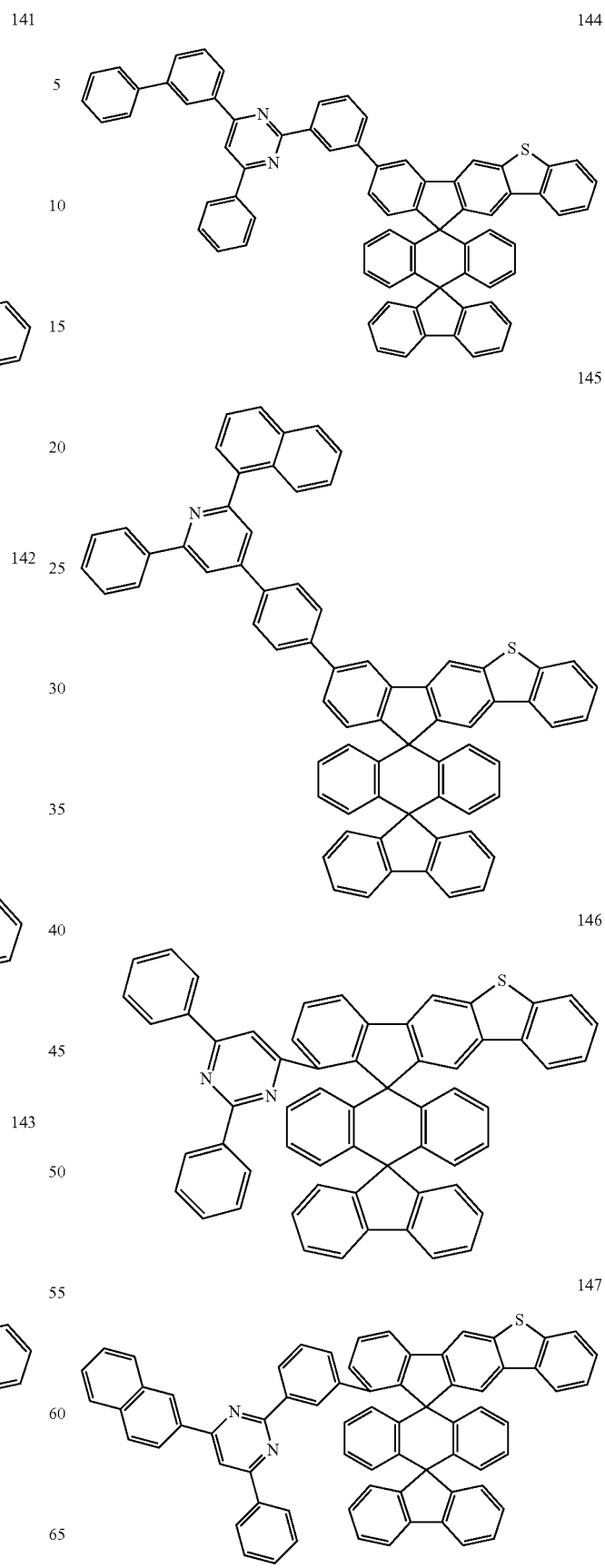

148
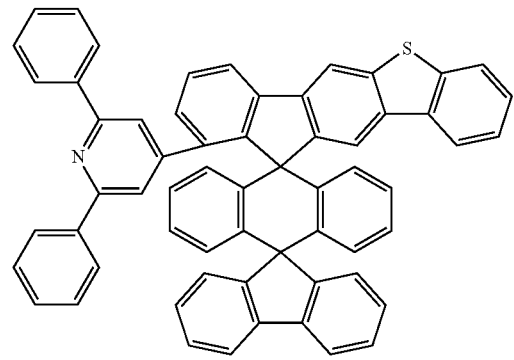
149
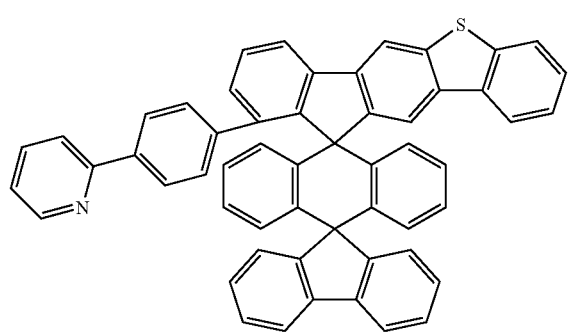
150
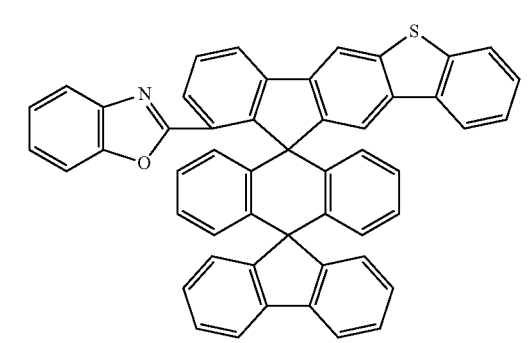
151
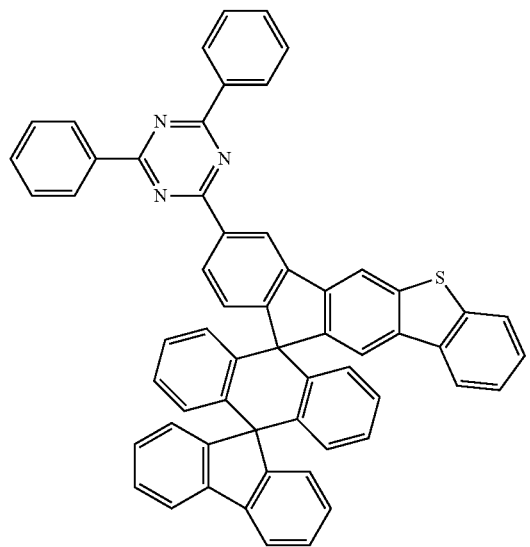
152
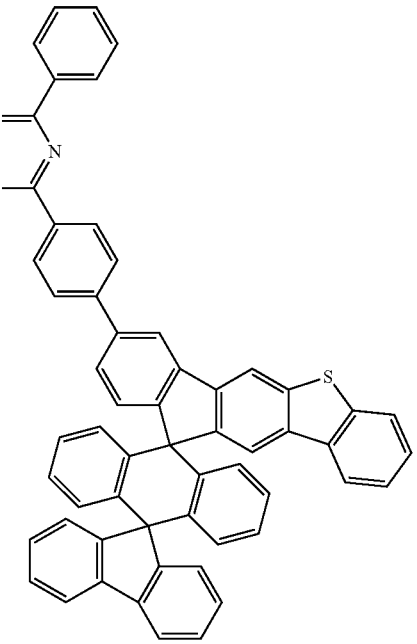
153
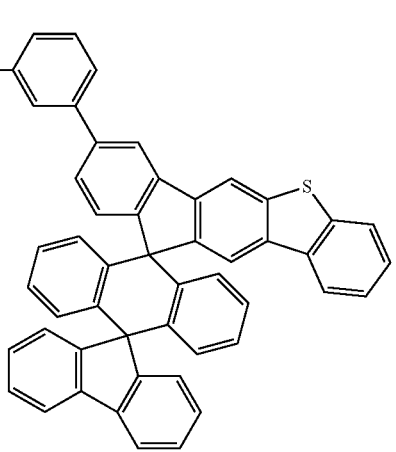

154
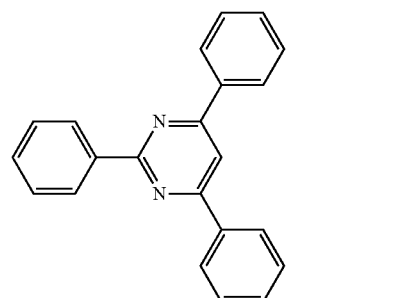
155
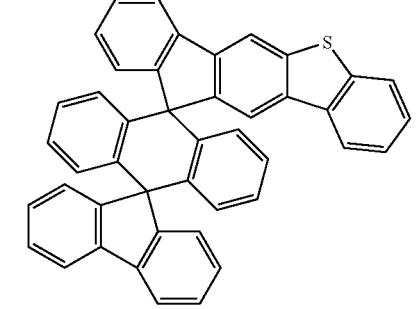
156
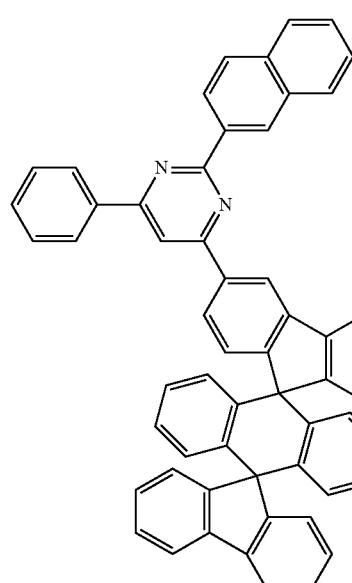
157
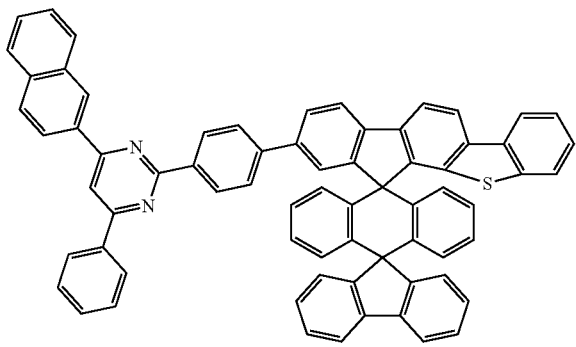
158
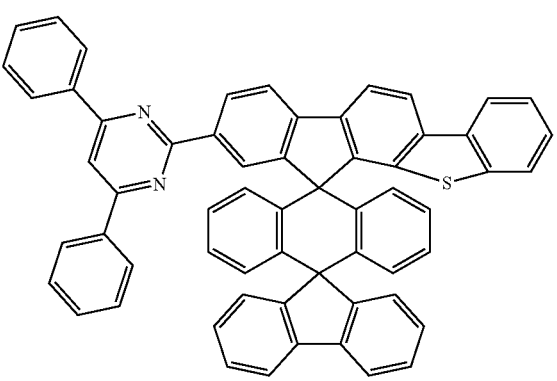
159
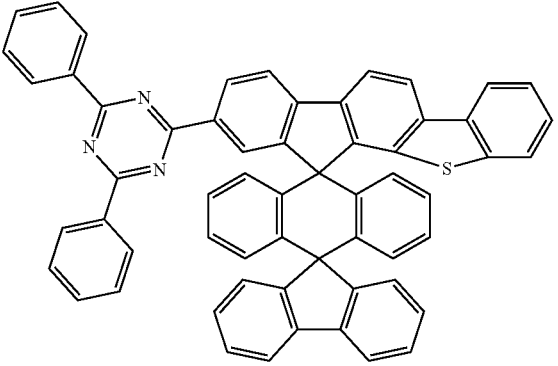
160
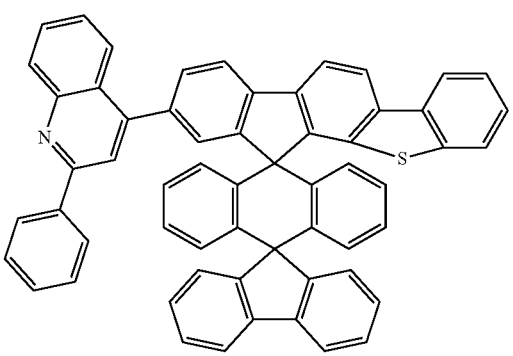

113
-continued
161
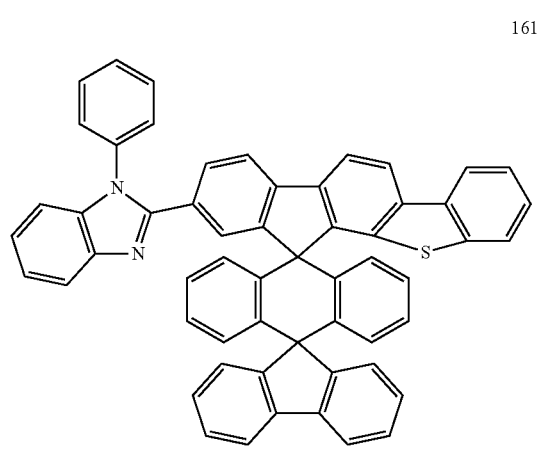
162
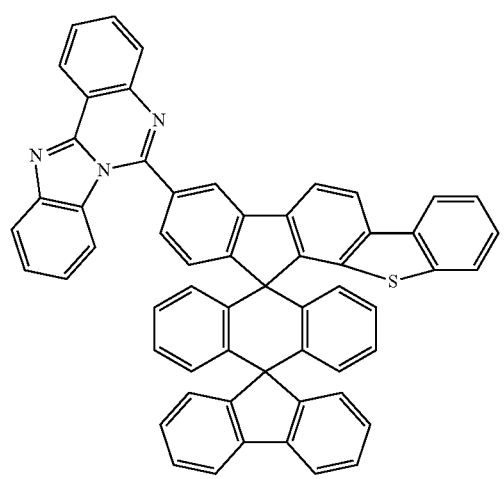
163
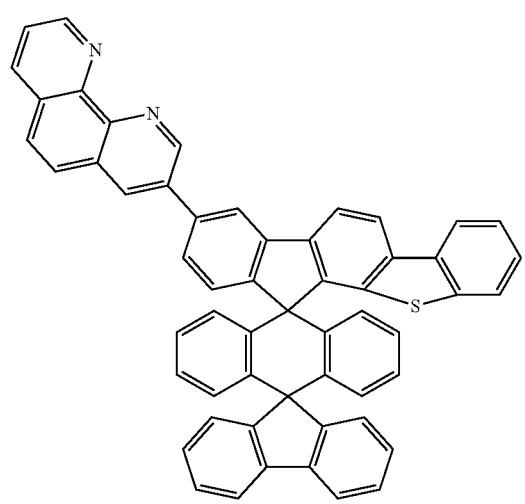
114
-continued
164
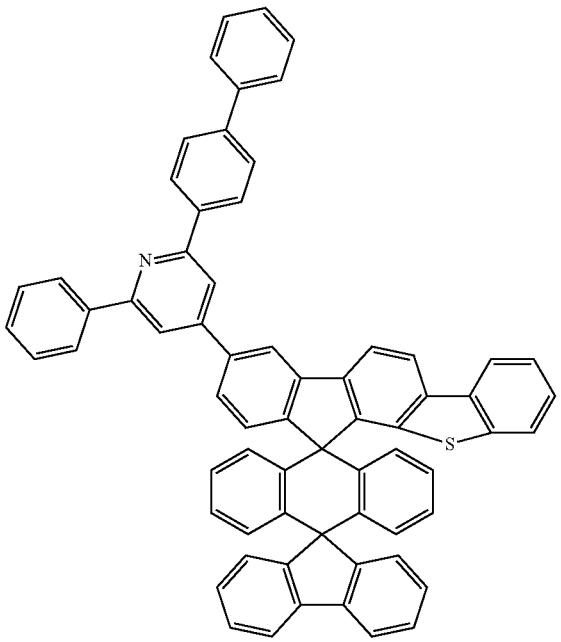
165
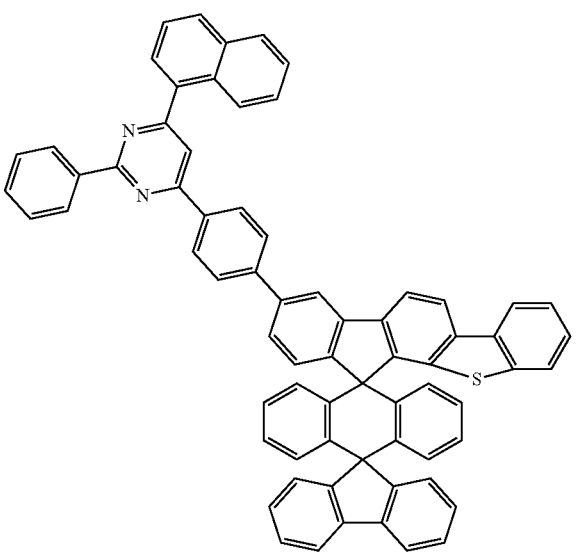

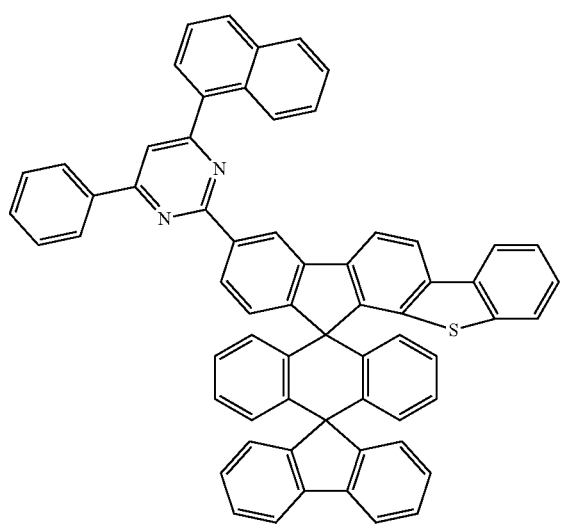
166
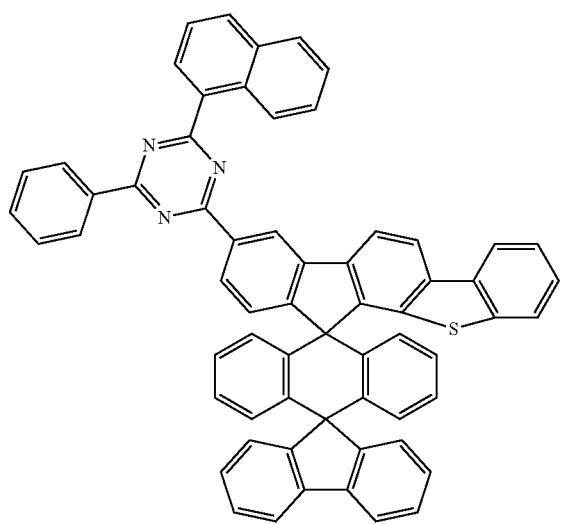
167
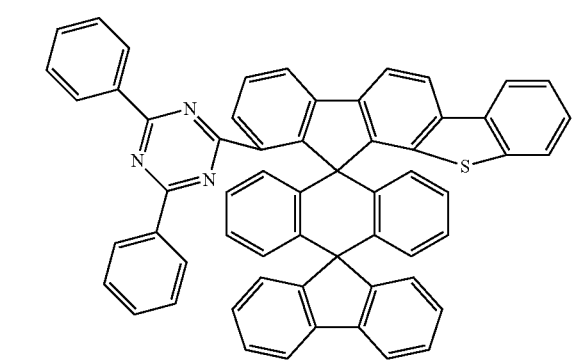
168
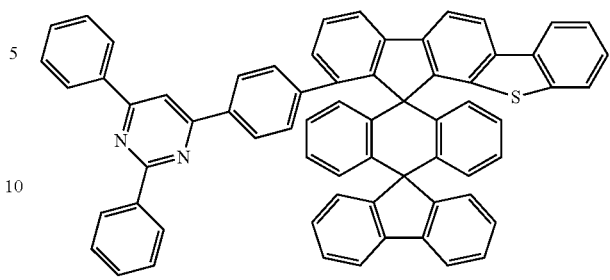
169
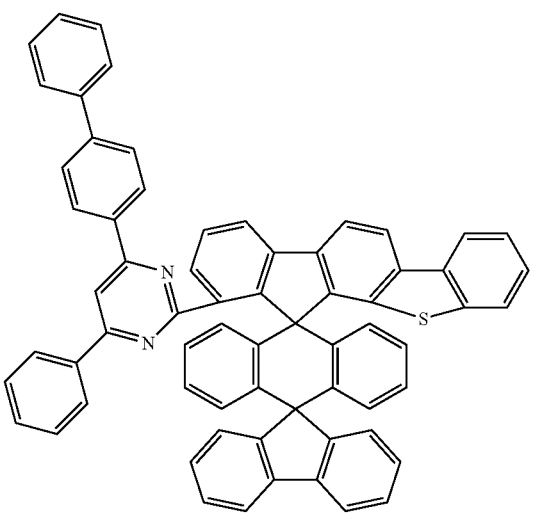
170
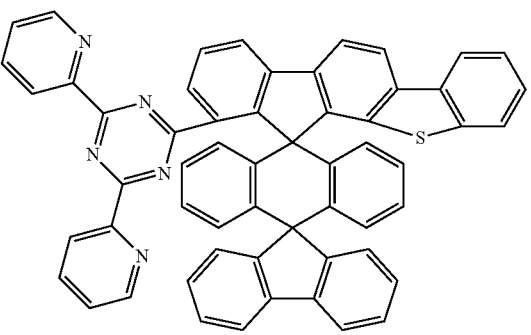
171
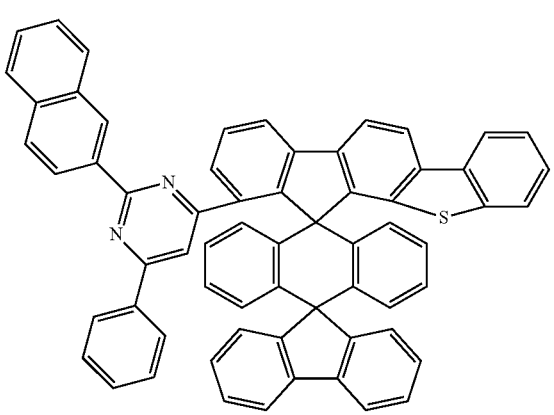
172

173
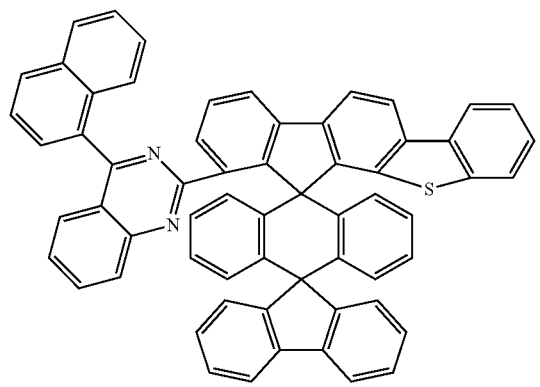
174
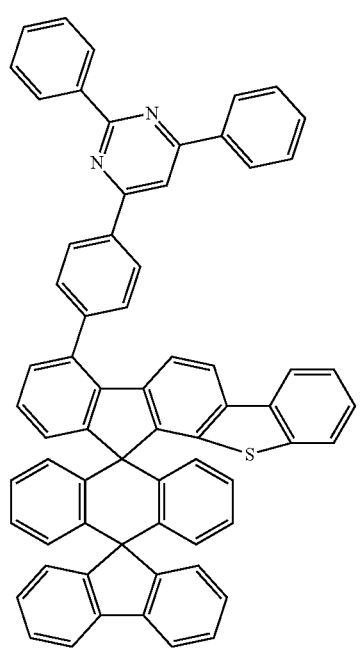
175
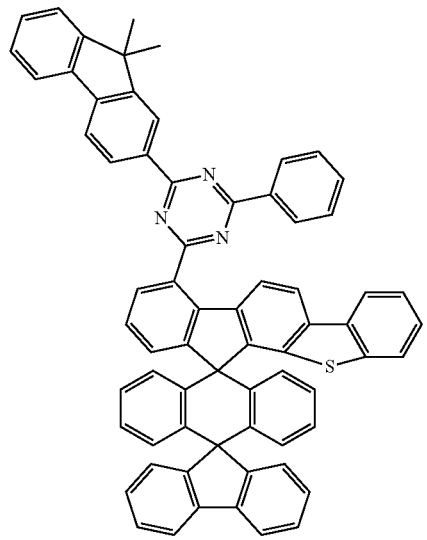
176
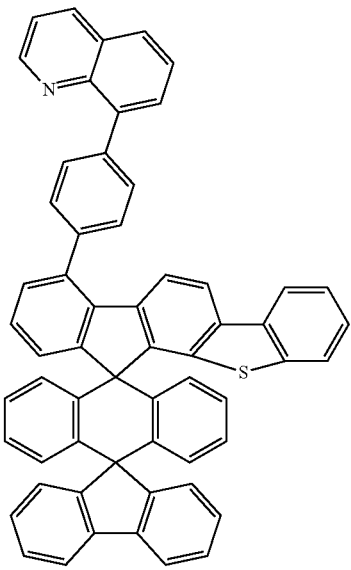
177
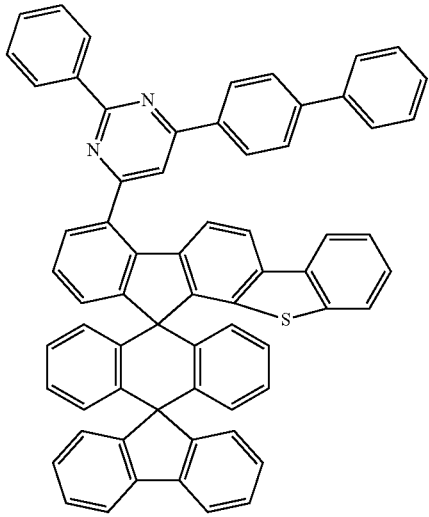
178
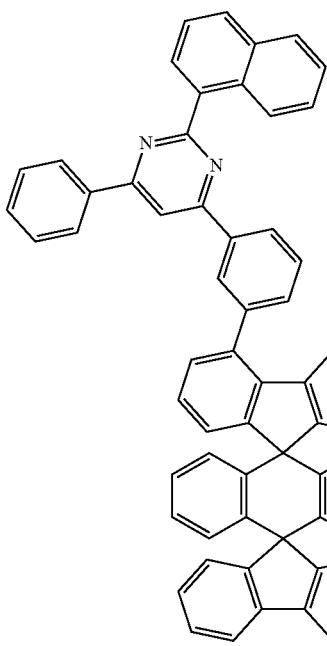

179
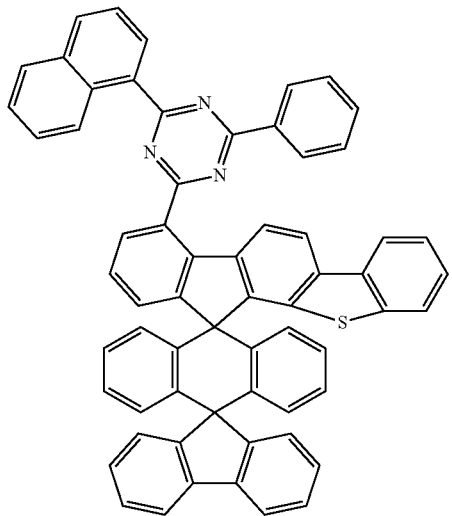
180
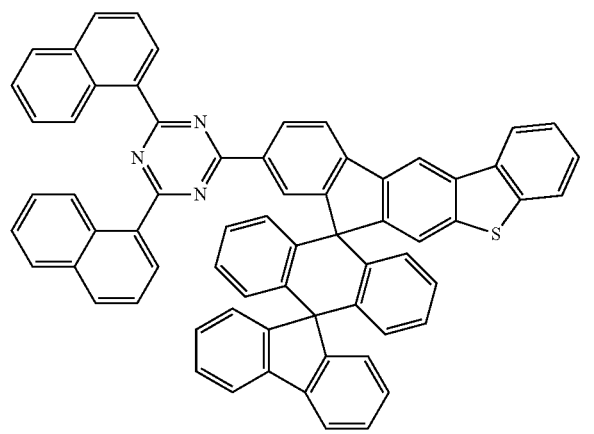
181
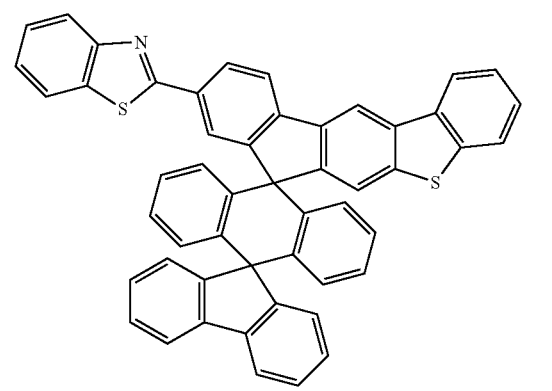
182
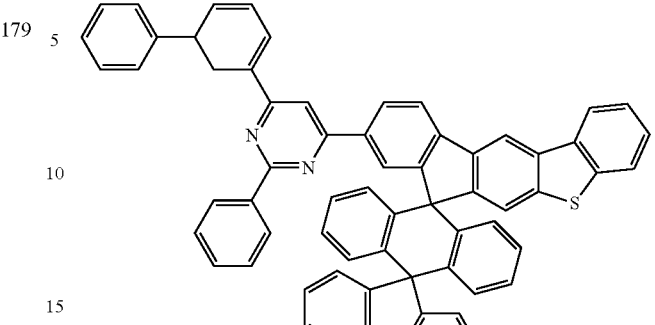
183
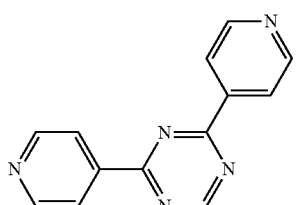
184
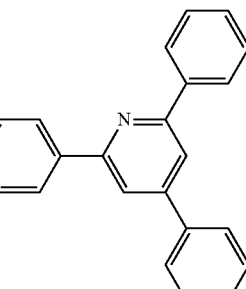

121
-continued
185
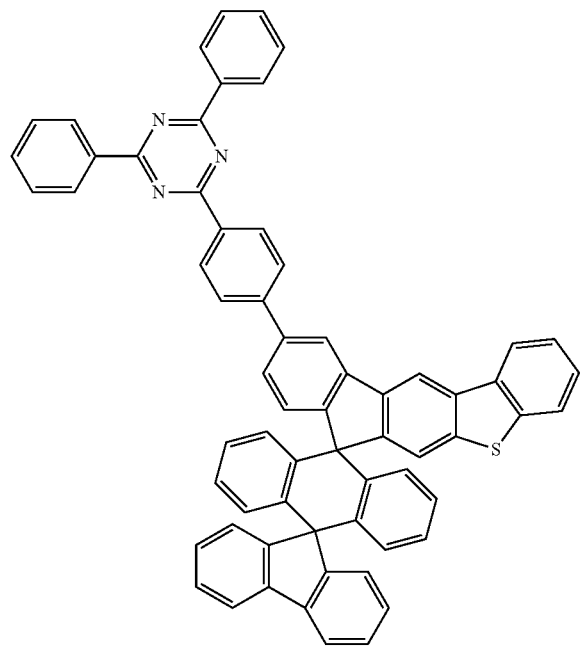
186
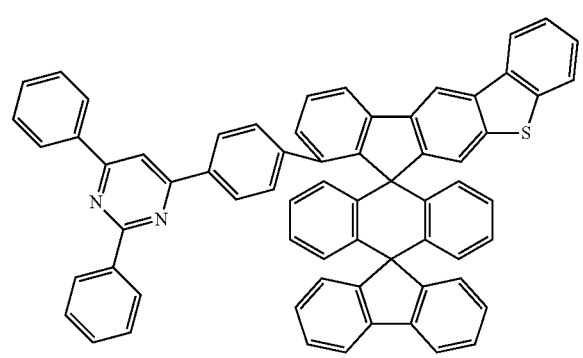
187
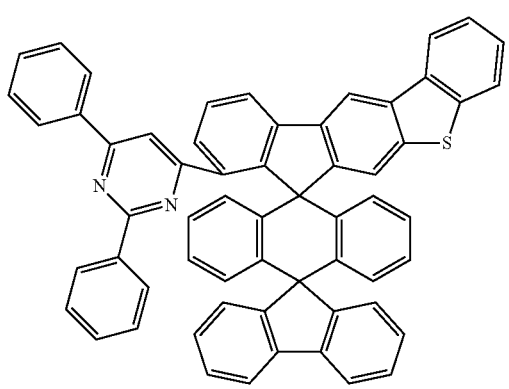
122
-continued
188
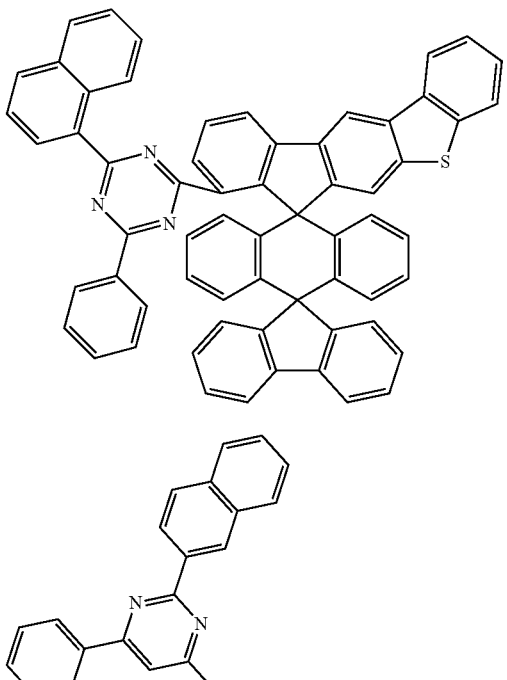
189
190

-continued
191
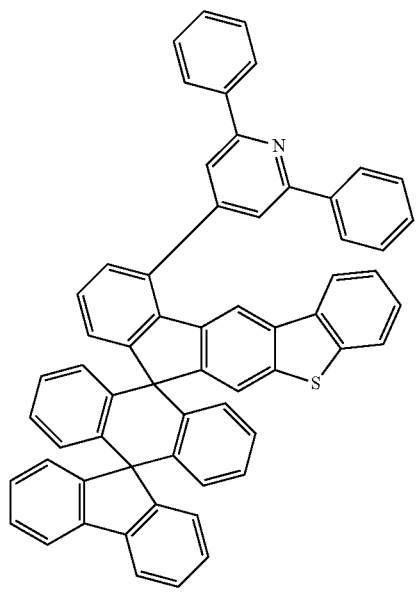
192
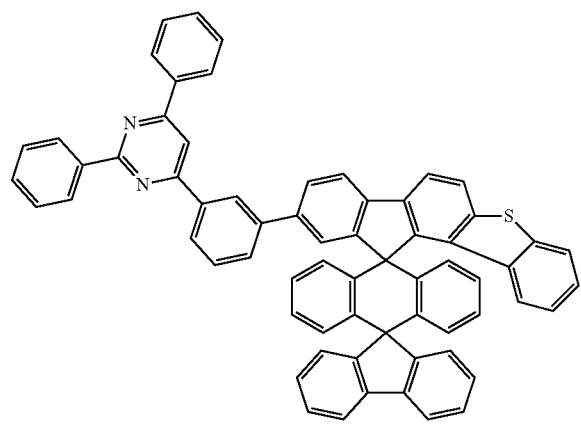
193
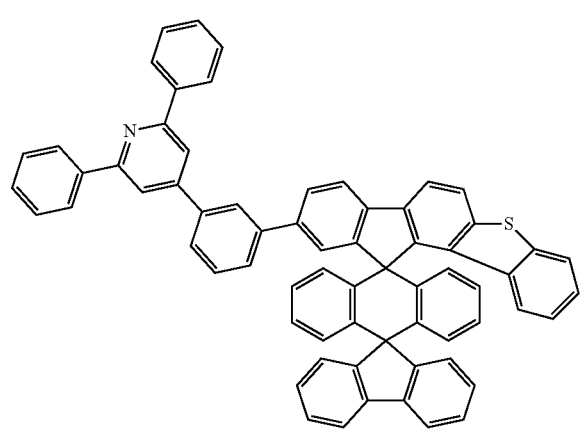
-continued
194
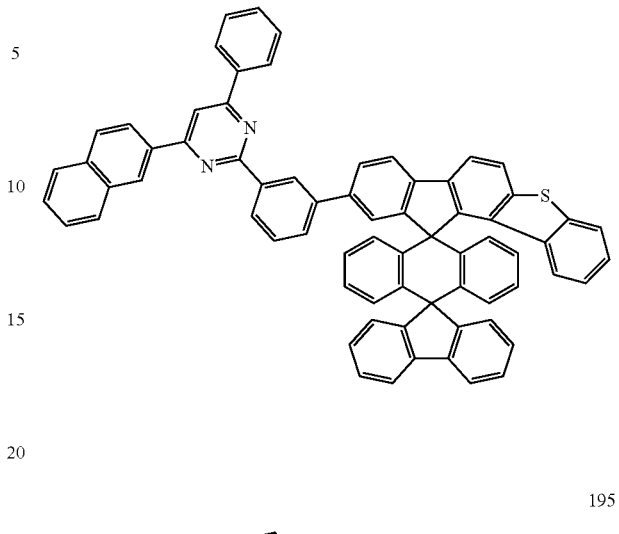
195
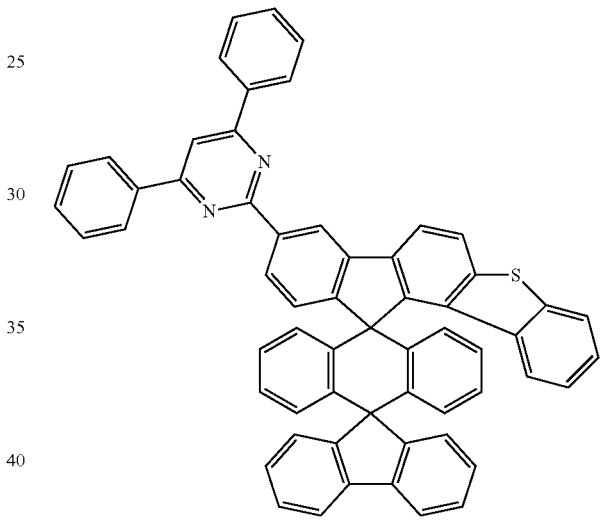
196
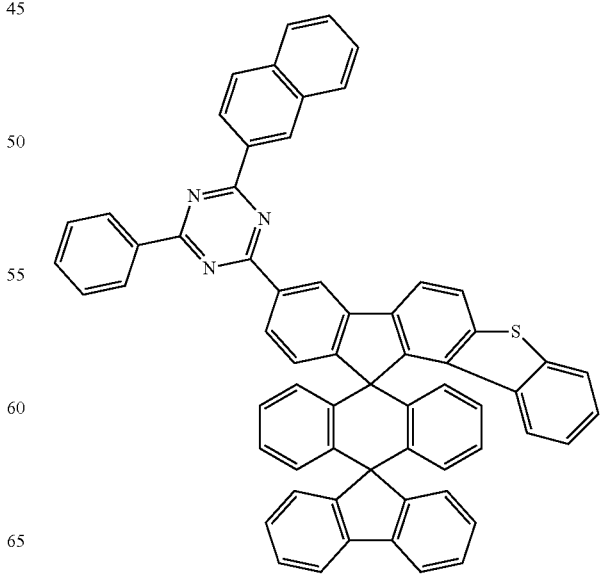

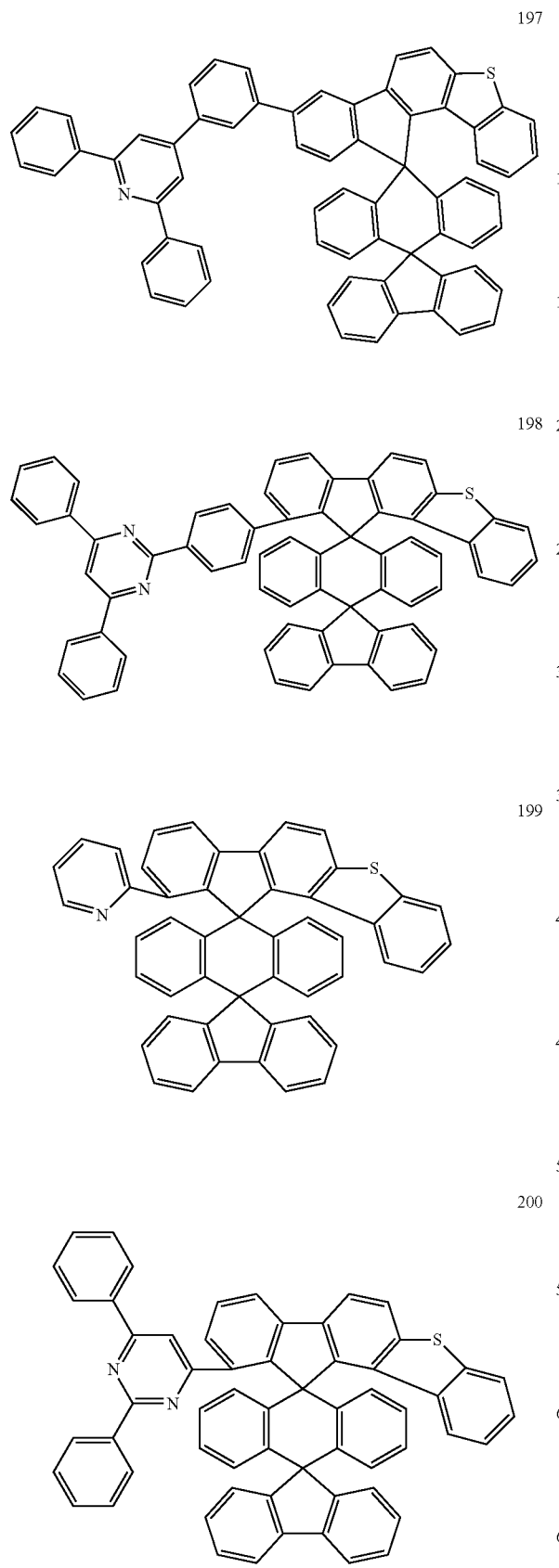
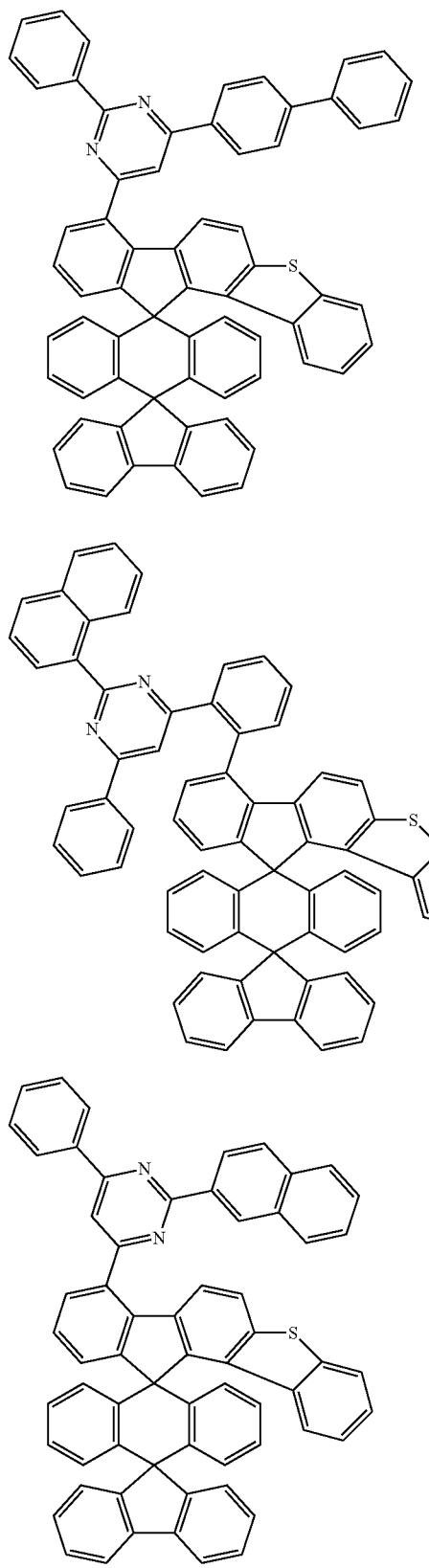
A conjugation length and an energy bandgap of a compound are closely associated with each other. Specifically, the longer the conjugation length of a compound is, the smaller the bandgap thereof is. As described above, the core of the compound of Chemical Formula 1 includes a limited conjugation length and thus has a large energy bandgap property.

In the present specification, various substituents may be introduced into the core structure having a large energy bandgap as described above to synthesize compounds having various energy bandgaps. A substituent is usually introduced into a core structure having a large energy bandgap to easily adjust an energy bandgap, but when a core structure has a small energy bandgap, it is difficult to significantly adjust the energy bandgap by introducing a substituent. In addition, the present invention may also adjust the HOMO and LUMO energy levels of the compound depending on the position of the substituent in the core structure having the structure described above, a material satisfying conditions required by each organic material layer may be synthesized by introducing a substituent usually used in an electron transport layer material into the core structure, and an organic light emitting device having low driving voltage and high light efficiency may be implemented by using the material in the device.

Various substituents, particularly, hydrogen or deuterium may be introduced into the core structure to finely adjust an energy bandgap, and meanwhile, characteristics at the interface between organic materials may be improved, and the use of the material may be diversified.

Meanwhile, the compound of Chemical Formula 1 has a high glass transition temperature (Tg) due to the characteristics of the spiro structure, and thus has excellent thermal stability. The increase in thermal stability becomes an important factor which provides driving stability to a device.

Further, an organic light emitting device according to the present invention is an organic light emitting device including: an anode; a cathode provided to face the anode; and an organic material layer including a light emitting layer provided between the anode and the cathode, in which the organic material layer further includes an organic material layer provided between the light emitting layer and the cathode and including the compound represented by Chemical Formula 1.

The organic light emitting device of the present invention may be manufactured by typical preparation methods and materials of an organic light emitting device, except that the above-described compound is used to form one or more organic material layers.

The organic material layer of the organic light emitting device of the present invention may also be composed of a single-layered structure, but may be composed of a multi-layered structure in which two or more organic material layers are stacked. For example, the organic light emitting device of the present invention may have a structure including a hole injection layer, a hole transport layer, a light emitting layer, an electron transport layer, an electron injection layer, and the like as organic material layers. However, the structure of the organic light emitting device is not limited thereto, and may include a fewer number of organic material layers. Further, the organic material layer may include one or more layers of an electron transport layer, an electron injection layer, and a layer which transports and injects electrons simultaneously, and one or more layers of the layers may include the compound.

The organic material layer including the compound of Chemical Formula 1 may have a multi-layered structure including a hole injection layer, a hole transport layer, a light emitting layer, and an electron transport layer, and the like, but is not limited thereto and may have a single-layered structure. Further, the organic material layer may be manufactured with a fewer number of layers by a method such as a solvent process, for example, spin coating, dip coating, doctor blading, a screen printing, inkjet printing, or a thermal transfer method, by using various polymers, instead of a deposition method.

For example, the structure of the organic light emitting device of the present invention may have a structure as illustrated in FIGS. 1 and 2, but is not limited thereto.

FIG. 1 illustrates the structure of an organic light emitting device in which a positive electrode 2, a light emitting layer 3, an organic material layer 9 including the compound of Chemical Formula 1, and a negative electrode 4 are sequentially stacked on a substrate 1.

FIG. 2 illustrates the structure of an organic light emitting device in which a positive electrode 2, a hole injection layer 5, a hole transport layer 6, a light emitting layer 3, an electron transport layer 8, and a negative electrode 4 are sequentially stacked on a substrate 1. In the structure as described above, the compound may be included in the organic material layer 9 including the compound of Chemical Formula 1 or the electron transport layer 8.

In an exemplary embodiment of the present invention, the organic material layer including the compound of Chemical Formula 1 includes at least one layer of an electron injection layer, an electron transport layer, and a layer which injects and transports electrons simultaneously, and at least one layer of the layers may include the compound of Chemical Formula 1.

According to an exemplary embodiment of the present specification, the organic material layer includes a light emitting layer, and the light emitting layer includes a compound represented by the following Chemical Formula 1-A.

[Chemical Formula 1-A]

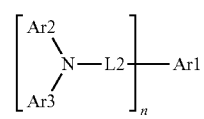

In Chemical Formula 1-A, n is an integer of 1 or more,

Ar1 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L2 is a direct bond; a substituted or unsubstituted arylene group; or a substituted or unsubstituted heteroarylene group, Ar2 and Ar3 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may combine with each other to form a substituted or unsubstituted ring, and when n is 2 or more, two or more structures in the parenthesis are the same as or different from each other.

According to an exemplary embodiment of the present specification, the organic material layer includes a light emitting layer, and the light emitting layer includes the compound represented by Chemical Formula 1-A as a dopant of the light emitting layer.

According to an exemplary embodiment of the present specification, L2 is a direct bond.

According to an exemplary embodiment of the present specification, n is 2.

In an exemplary embodiment of the present specification, Ar1 is a divalent pyrene group which is unsubstituted or substituted with deuterium, a methyl group, an ethyl group, or a tert-butyl group.

According to an exemplary embodiment of the present specification, Ar2 and Ar3 are the same as or different from each other, and are each independently a substituted or unsubstituted aryl group having 6 to 30 carbon atoms.

According to an exemplary embodiment of the present specification, Ar2 and Ar3 are the same as or different from each other, and are each independently an aryl group which is unsubstituted or substituted with a germanium group substituted with an alkyl group.

According to an exemplary embodiment of the present specification, Ar2 and Ar3 are the same as or different from each other, and are each independently an aryl group which is unsubstituted or substituted with a trimethylgermanium group.

According to an exemplary embodiment of the present specification, Ar2 and Ar3 are the same as or different from each other, and are each independently a substituted or unsubstituted phenyl group.

According to an exemplary embodiment of the present specification, Ar2 and Ar3 are a phenyl group which is unsubstituted or substituted with a trimethylgermanium group.

According to an exemplary embodiment of the present specification, Chemical Formula 1-A is represented by the following compound.

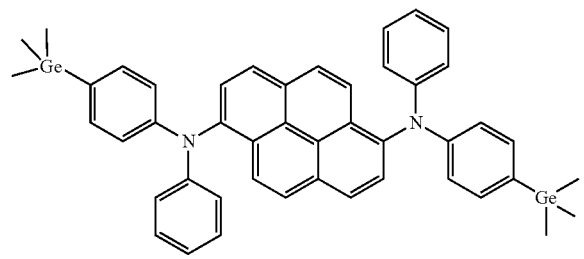

According to an exemplary embodiment of the present specification, the organic material layer includes a light emitting layer, and the light emitting layer includes a compound represented by the following Chemical Formula 2-A.

[Chemical Formula 2-A]

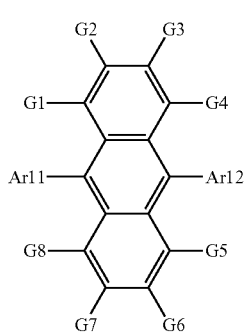

In Chemical Formula 2-A,

Ar11 and Ar12 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

According to an exemplary embodiment of the present specification, the organic material layer includes a light emitting layer, and the light emitting layer includes the compound represented by Chemical Formula 2-A as a host of the light emitting layer.

According to an exemplary embodiment of the present specification, Ar11 and Ar12 are the same as or different from each other, and are each independently a substituted or unsubstituted polycyclic aryl group.

According to an exemplary embodiment of the present specification, Ar11 and Ar12 are the same as or different from each other, and are each independently a substituted or unsubstituted polycyclic aryl group having 10 to 30 carbon atoms.

According to an exemplary embodiment of the present specification, Ar11 and Ar12 are the same as or different from each other, and are each independently a substituted or unsubstituted naphthyl group.

According to an exemplary embodiment of the present specification, Ar11 and Ar12 are the same as or different from each other, and are each independently a substituted or unsubstituted 2-naphthyl group.

According to an exemplary embodiment of the present specification, Ar11 and Ar12 are a 2-naphthyl group.

According to an exemplary embodiment of the present specification, G6 is a substituted or unsubstituted polycyclic aryl group.

According to an exemplary embodiment of the present specification, G6 is a substituted or unsubstituted polycyclic aryl group having 10 to 30 carbon atoms.

According to an exemplary embodiment of the present specification, G6 is a substituted or unsubstituted naphthyl group.

According to an exemplary embodiment of the present specification, G6 is a substituted or unsubstituted 2-naphthyl group.

According to an exemplary embodiment of the present specification, G6 is a 2-naphthyl group substituted with an anthracene group substituted with a phenyl group.

According to an exemplary embodiment of the present specification, G1 to G5, G7, and G8 are hydrogen.

According to an exemplary embodiment of the present specification, Chemical Formula 2-A is selected from the following compound.

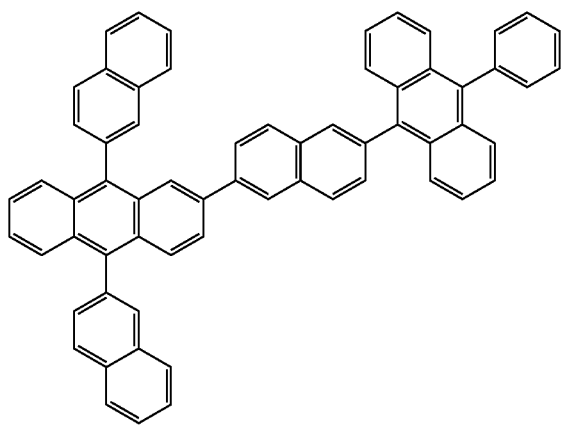 [SMILES: c1ccc(-c2c3ccccc3c(-c3ccc4cc(-c5ccc6c(-c7ccc8ccccc8c7)c7ccccc7c(-c7ccc8ccccc8c7)c6c5)ccc4c3)c3ccccc23)cc1]

For example, the organic light emitting device according to the present invention may be manufactured by depositing a metal or a metal oxide having conductivity, or an alloy thereof on a substrate to form a positive electrode, forming an organic material layer including a hole injection layer, a hole transport layer, a light emitting layer, and an electron transport layer and an organic material layer including the compound of Chemical Formula 1 thereon, and then depositing a material, which may be used as a negative electrode, thereon, by using a physical vapor deposition (PVD) method such as sputtering or e-beam evaporation. In addition to the method as described above, an organic light emitting device may also be made by sequentially depositing a negative electrode material, an organic material layer, and a positive electrode material on a substrate.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection material is a material which may well receive holes injected from a positive electrode at low voltage, and it is preferred that the highest occupied molecular orbital (HOMO) of the hole injection material is between the work function of the positive electrode material and the HOMO of the peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polycompound-based electrically conductive polymer, and the like, but are not limited thereto.

The hole transport material is a material which may receive holes transported from a positive electrode or a hole injection layer and transfer the holes to a light emitting layer, and is suitably a material having a large mobility for holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons transported from a hole transport layer and an electron transport layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The organic material layer including the compound of Chemical Formula 1 may additionally include an n-type dopant. Specifically, the n-type dopant may be one or more selected from the group consisting of an alkali metal; an alkaline earth metal; a halide of an alkali metal; a halide of an alkaline earth metal; an alkali metal oxide; an alkaline earth metal oxide; a carbonate of a metal; and an organic material having a HOMO energy level of 3 eV or less. In an exemplary embodiment, the n-type dopant is LiQ.

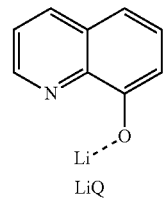

LiQ

The organic light emitting device according to the present invention may be a top emission type, a bottom emission type, or a dual emission type according to the material to be used.

The compound according to the present invention may be operated by a principle which is similar to the principle applied to an organic light emitting device, even in an organic electronic device including an organic solar cell, an organic photoconductor, an organic transistor, and the like.

The preparation method of the compound of Chemical Formula 1 and the manufacture of an organic light emitting device using the same will be specifically described in the following Examples. However, the following Examples are provided for exemplifying the present invention, and the scope of the present invention is not limited thereby.

MODE FOR INVENTION
Preparation Example 1
Preparation of Following 1-1-C to 1-4-C
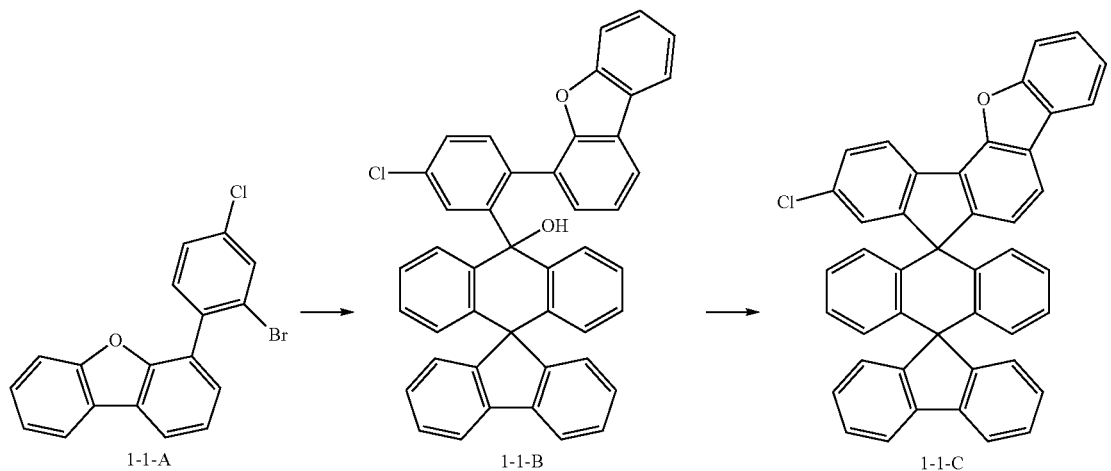
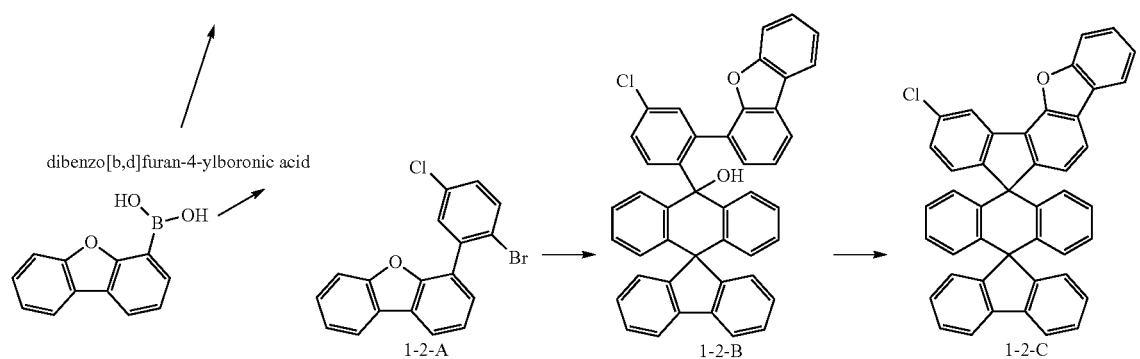
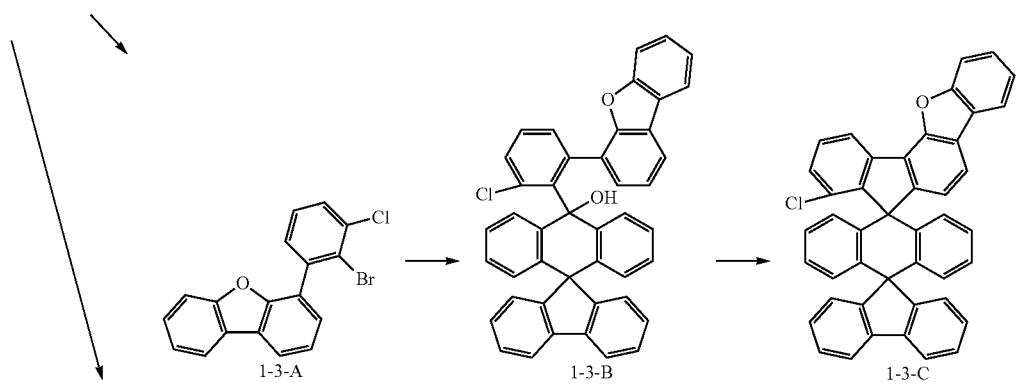

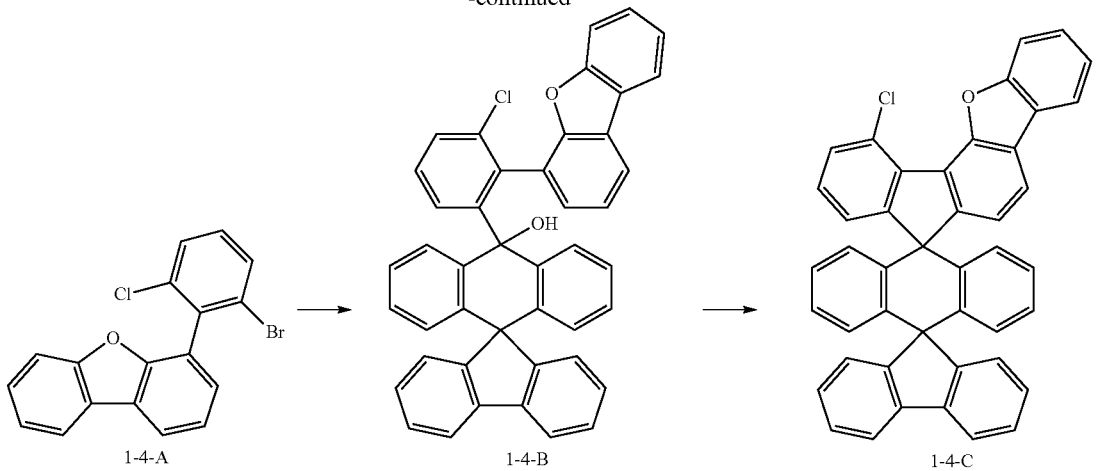

1-4-A    1-4-B    1-4-C

Synthesis of Compound 1-1-A

After dibenzofuran-4-ylboronic acid (10 g, 47.1 mmol) and 2-bromo-4-chloro-1-iodobenzene (15.7 g, 49.5 mmol) were added to THF (300 ml), a 2M aqueous potassium carbonate solution (100 ml) was added thereto, tetrakistriphenyl-phosphinopalladium (1.63 g, 141 mmol) was put thereinto, and then the resulting mixture was heated and stirred for 10 hours. The temperature was lowered to normal temperature, the reaction was terminated, and then the potassium phosphate solution was removed to separate the layers. The solvent was removed, and then a white solid was recrystallized with ethyl acetate and ethanol to prepare Compound 1-1-A (14.31 g, yield 85%).

MS[M+H]$^+$=356.96

Synthesis of Compound 1-2-A

Compound 1-2-A was prepared by performing the synthesis in the same manner as in Synthesis Example 1-1-A, except that 2-bromo-5-chloro-1-iodobenzene was used instead of the compound 2-bromo-4-chloro-1-iodobenzene.

MS[M+H]$^+$=356.96

Synthesis of Compound 1-3-A

Compound 1-3-A was prepared by performing the synthesis in the same manner as in Synthesis Example 1-1-A, except that 2-bromo-3-chloro-1-iodobenzene was used instead of the compound 2-bromo-4-chloro-1-iodobenzene.

MS[M+H]$^+$=356.96

Synthesis of Compound 1-4-A

Compound 1-4-A was prepared by performing the synthesis in the same manner as in Synthesis Example 1-1-A, except that 2-bromo-6-chloro-1-iodobenzene was used instead of the compound 2-bromo-4-chloro-1-iodobenzene.

MS[M+H]$^+$=356.96

Synthesis of Compound 1-1-B

After Compound 1-1-A (14 g, 39.3 mmol) was dissolved in THF (250 ml), the temperature was lowered to −78° C., and then 2.5 M n-BuLi (20.4 ml) was added dropwise thereto, and after 30 minutes, 10H-spiro-[anthracene-9,9'-fluorene]-10-one (13.6 g, 40 mmol) was put thereinto, the temperature was increased to normal temperature, and then the resulting mixture was stirred for 1 hour. After 1 M HCl (300 ml) was put thereinto and the resulting mixture was stirred for 30 minutes, the layers were separated to remove the solvent, and then the residue was purified with ethyl acetate to prepare Compound 1-1-B (19.5 g, 85%).

MS[M+H]$^+$=623.17

Synthesis of Compound 1-2-B

Compound 1-2-B was prepared by performing the synthesis in the same manner as in Synthesis Example 1-1-B, except that Compound 1-2-A was used instead of Compound 1-1-A.

MS[M+H]$^+$=623.17

Synthesis of Compound 1-3-B

Compound 1-3-B was prepared by performing the synthesis in the same manner as in Synthesis Example 1-1-B, except that Compound 1-3-A was used instead of Compound 1-1-A.

MS[M+H]$^+$=623.17

Synthesis of Compound 1-4-B

Compound 1-4-B was prepared by performing the synthesis in the same manner as in Synthesis Example 1-1-B, except that Compound 1-4-A was used instead of Compound 1-1-A.

MS[M+H]$^+$=623.17

Synthesis of Compound 1-1-C

After Compound 1-1-B (10 g, 16.1 mmol) was put into acetic acid (250 ml), 1 ml of sulfuric acid was added dropwise thereto, and the resulting mixture was stirred and refluxed. The temperature was lowered to normal temperature, the resulting product was neutralized with water, and then the filtered solid was recrystallized with tetrahydrofuran and ethyl acetate to prepare Compound 1-1-C (9.24 g, 95%).

MS[M+H]$^+$=605.16

Synthesis of Compound 1-2-C

Compound 1-2-C was prepared by performing the synthesis in the same manner as in Synthesis Example 1-1-C, except that Compound 1-2-B was used instead of Compound 1-1-B.
MS[M+H]$^+$=605.16

Synthesis of Compound 1-3-C

Compound 1-3-C was prepared by performing the synthesis in the same manner as in Synthesis Example 1-1-C, except that Compound 1-3-B was used instead of Compound 1-1-B.
MS[M+H]$^+$=605.16

Synthesis of Compound 1-4-C

Compound 1-4-C was prepared by performing the synthesis in the same manner as in Synthesis Example 1-1-C, except that Compound 1-4-B was used instead of Compound 1-1-B.
MS[M+H]$^+$=605.16

Preparation Example 2

Preparation of Following 2-1-C to 2-4-C

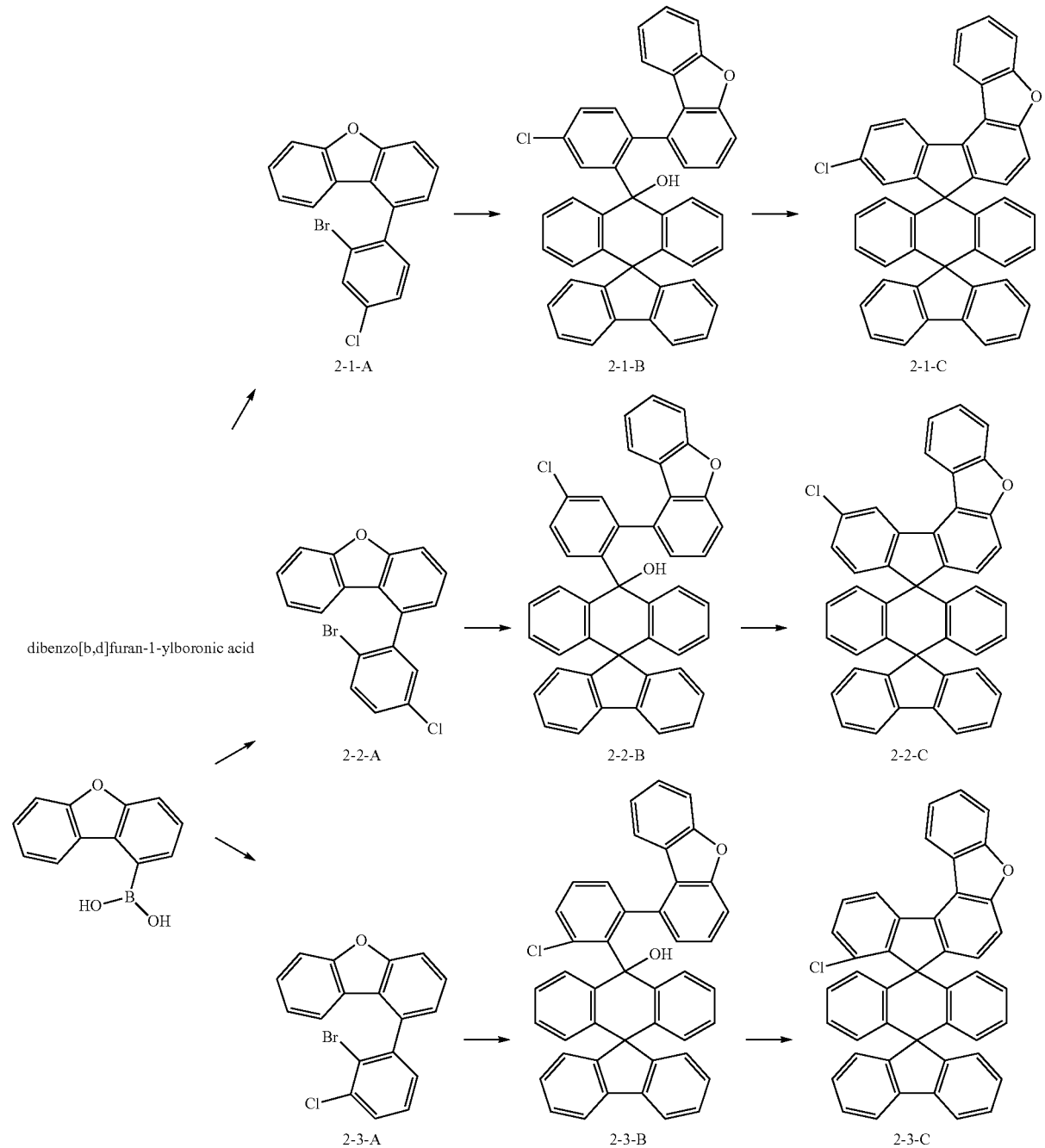

-continued

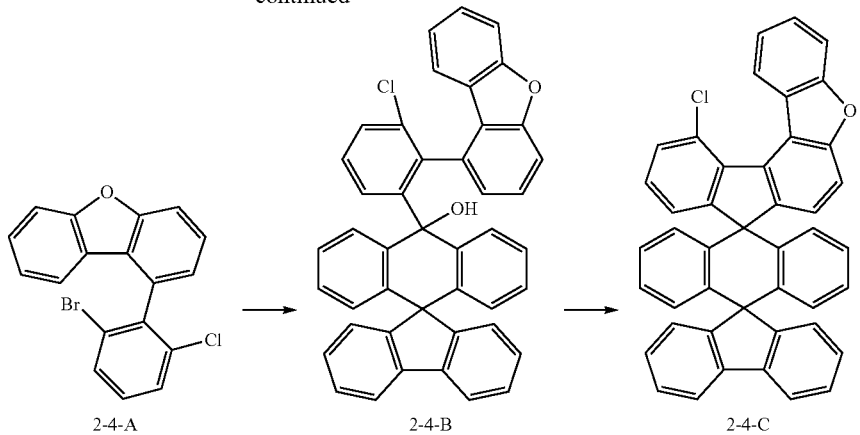

Synthesis of Compound 2-1-A

Compound 2-1-A was prepared by performing the synthesis in the same manner as in Synthesis Example 1-1-A, except that dibenzofuran-1-ylboronic acid was used instead of dibenzofuran-4-ylboronic acid.
MS[M+H]$^+$=356.96

Synthesis of Compound 2-2-A

Compound 2-2-A was prepared by performing the synthesis in the same manner as in Synthesis Example 2-1-A, except that 2-bromo-5-chloro-1-iodobenzene was used instead of the compound 2-bromo-4-chloro-1-iodobenzene.
MS[M+H]$^+$=356.96

Synthesis of Compound 2-3-A

Compound 2-3-A was prepared by performing the synthesis in the same manner as in Synthesis Example 2-1-A, except that 2-bromo-3-chloro-1-iodobenzene was used instead of the compound 2-bromo-4-chloro-1-iodobenzene.
MS[M+H]$^+$=356.96

Synthesis of Compound 2-4-A

Compound 2-4-A was prepared by performing the synthesis in the same manner as in Synthesis Example 2-1-A, except that 2-bromo-6-chloro-1-iodobenzene was used instead of the compound 2-bromo-4-chloro-1-iodobenzene.
MS[M+H]$^+$=356.96

Synthesis of Compound 2-1-B

Compound 2-1-B was prepared by performing the synthesis in the same manner as in Synthesis Example 1-1-B, except that Compound 2-1-A was used instead of Compound 1-1-A.
MS[M+H]$^+$=623.17

Synthesis of Compound 2-2-B

Compound 2-2-B was prepared by performing the synthesis in the same manner as in Synthesis Example 2-1-B, except that Compound 2-2-A was used instead of Compound 2-1-A.
MS[M+H]$^+$=623.17

Synthesis of Compound 2-3-B

Compound 2-3-B was prepared by performing the synthesis in the same manner as in Synthesis Example 2-1-B, except that Compound 2-3-A was used instead of Compound 2-1-A.
MS[M+H]$^+$=623.17

Synthesis of Compound 2-4-B

Compound 2-4-B was prepared by performing the synthesis in the same manner as in Synthesis Example 2-1-B, except that Compound 2-4-A was used instead of Compound 2-1-A.
MS[M+H]$^+$=623.17

Synthesis of Compound 2-1-C

Compound 2-1-C was prepared by performing the synthesis in the same manner as in Synthesis Example 1-1-C, except that Compound 2-1-B was used instead of Compound 1-1-B.
MS[M+H]$^+$=605.16

Synthesis of Compound 2-2-C

Compound 2-2-C was prepared by performing the synthesis in the same manner as in Synthesis Example 2-1-C, except that Compound 2-2-B was used instead of Compound 2-1-B.
MS[M+H]$^+$=605.16

Synthesis of Compound 2-3-C

Compound 2-3-C was prepared by performing the synthesis in the same manner as in Synthesis Example 2-1-C, except that Compound 2-3-B was used instead of Compound 2-1-B.
MS[M+H]$^+$=605.16

Synthesis of Compound 2-4-C

Compound 2-4-C was prepared by performing the synthesis in the same manner as in Synthesis Example 2-1-C, except that Compound 2-4-B was used instead of Compound 2-1-B.
MS[M+H]$^+$=605.16

141
Preparation Example 3
Preparation of Following 3-1-C to 3-4-C and 3-1-D to 3-4-D
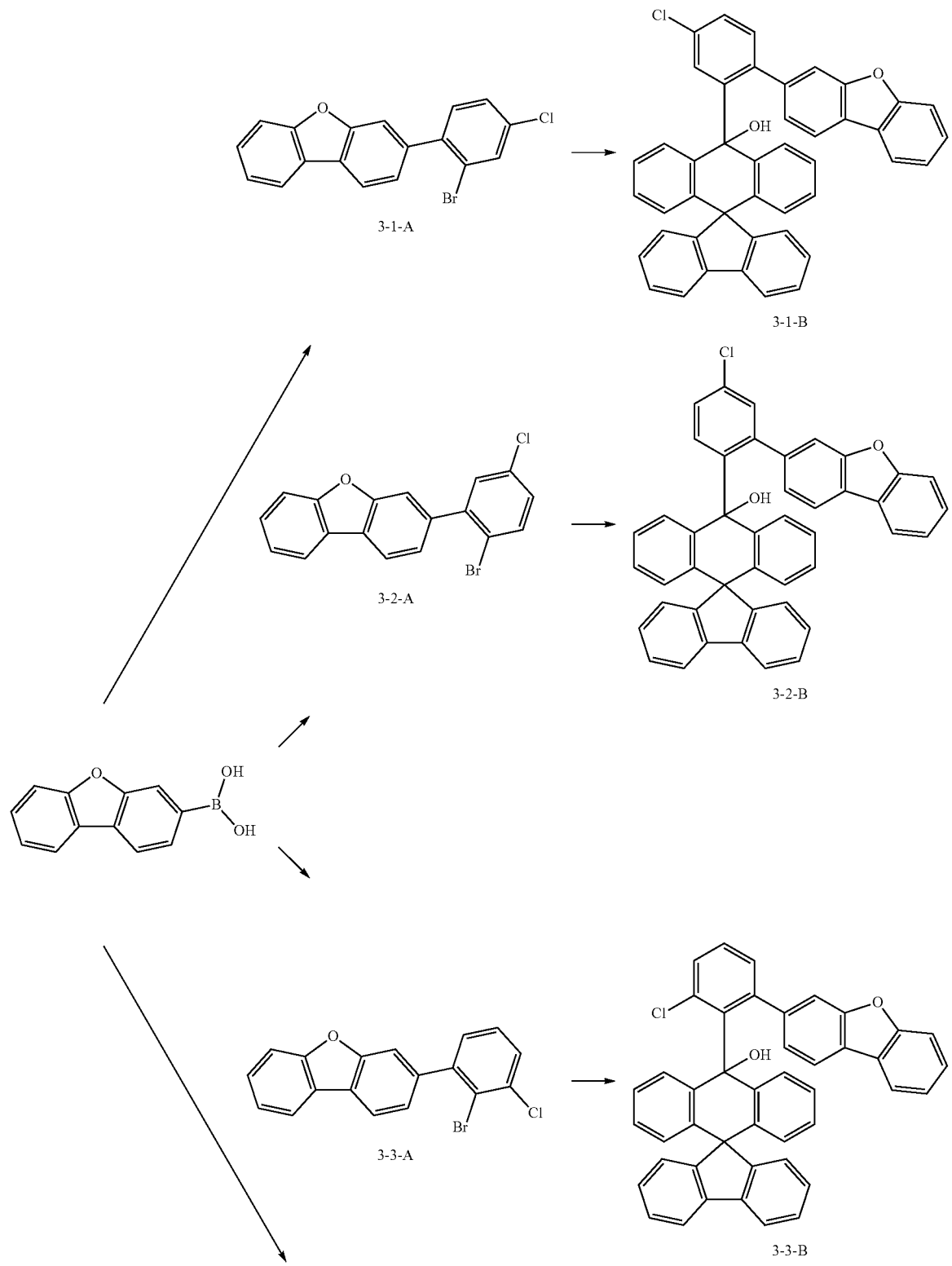

-continued
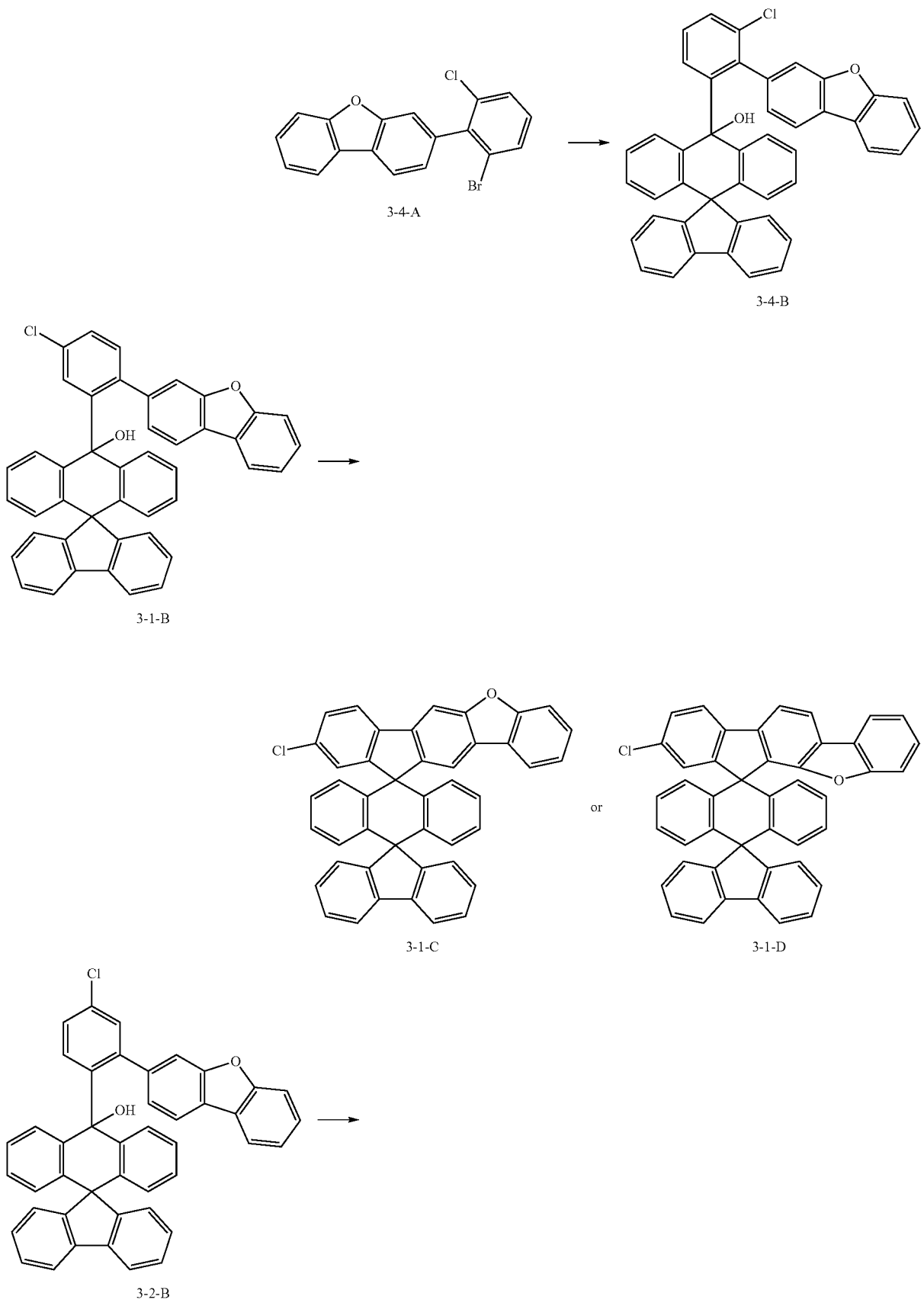

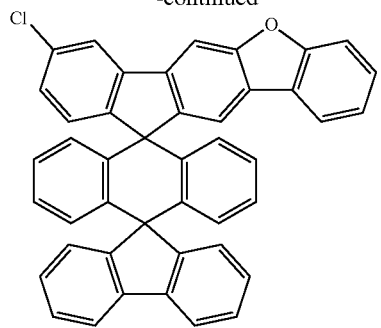
3-2-C
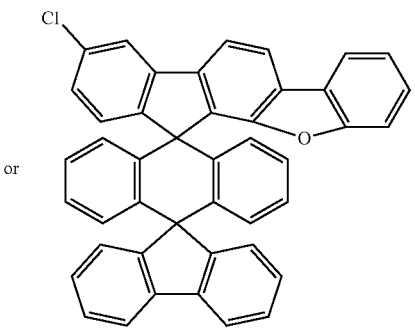
3-2-D
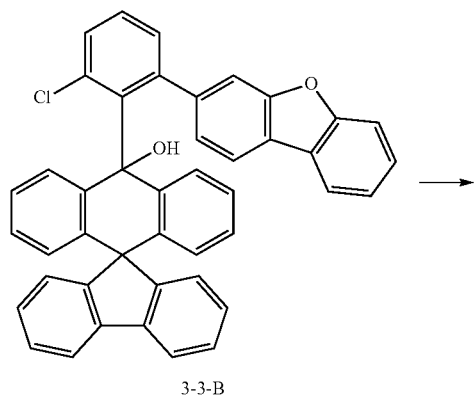
3-3-B
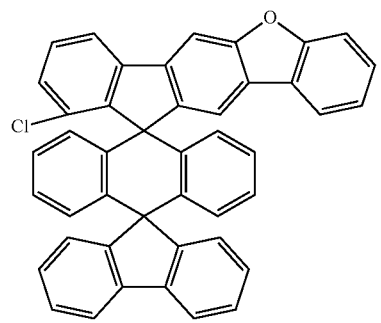
3-3-C
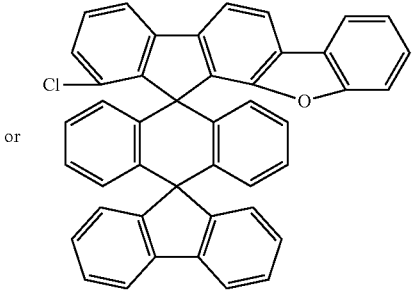
3-3-D
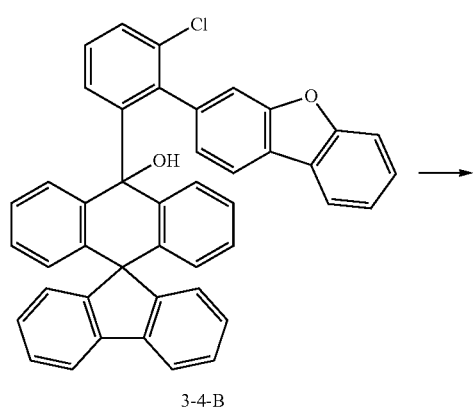
3-4-B

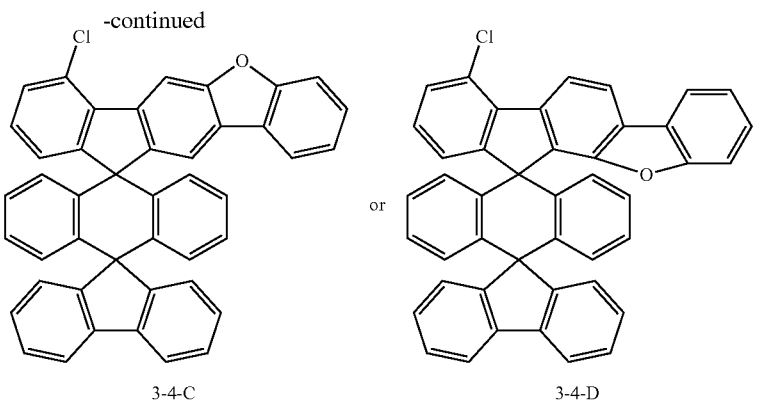

3-4-C    3-4-D

Synthesis of Compound 3-1-A

Compound 3-1-A was prepared by performing the synthesis in the same manner as in Synthesis Example 1-1-A, except that dibenzofuran-3-ylboronic acid was used instead of dibenzofuran-4-ylboronic acid.
MS[M+H]$^+$=356.96

Synthesis of Compound 3-2-A

Compound 3-2-A was prepared by performing the synthesis in the same manner as in Synthesis Example 3-1-A, except that 2-bromo-5-chloro-1-iodobenzene was used instead of the compound 2-bromo-4-chloro-1-iodobenzene.
MS[M+H]$^+$=356.96

Synthesis of Compound 3-3-A

Compound 3-3-A was prepared by performing the synthesis in the same manner as in Synthesis Example 3-1-A, except that 2-bromo-3-chloro-1-iodobenzene was used instead of the compound 2-bromo-4-chloro-1-iodobenzene.
MS[M+H]$^+$=356.96

Synthesis of Compound 3-4-A

Compound 3-4-A was prepared by performing the synthesis in the same manner as in Synthesis Example 3-1-A, except that 2-bromo-6-chloro-1-iodobenzene was used instead of the compound 2-bromo-4-chloro-1-iodobenzene.
MS[M+H]$^+$=356.96

Synthesis of Compound 3-1-B

Compound 3-1-B was prepared by performing the synthesis in the same manner as in Synthesis Example 1-1-B, except that Compound 3-1-A was used instead of Compound 1-1-A.
MS[M+H]$^+$=623.17

Synthesis of Compound 3-2-B

Compound 3-2-B was prepared by performing the synthesis in the same manner as in Synthesis Example 3-1-B, except that Compound 3-2-A was used instead of Compound 3-1-A.
MS[M+H]$^+$=623.17

Synthesis of Compound 3-3-B

Compound 3-3-B was prepared by performing the synthesis in the same manner as in Synthesis Example 3-1-B, except that Compound 3-3-A was used instead of Compound 3-1-A.
MS[M+H]$^+$=623.17

Synthesis of Compound 3-4-B

Compound 3-4-B was prepared by performing the synthesis in the same manner as in Synthesis Example 3-1-B, except that Compound 3-4-A was used instead of Compound 3-1-A.
MS[M+H]$^+$=623.17

Synthesis of Compound 3-1-C

After Compound 3-1-B (10 g, 16.1 mmol) was put into acetic acid (250 ml), 1 ml of sulfuric acid was added dropwise thereto, and the resulting mixture was stirred and refluxed. The temperature was lowered to normal temperature, the resulting product was neutralized with water, and then the filtered solid was purified with a column chromatography and recrystallized with tetrahydrofuran and ethyl acetate to prepare Compound 3-1-C (2.7 g, 30%).
MS[M+H]$^+$=605.16

Synthesis of Compound 3-2-C

Compound 3-2-C was prepared by performing the synthesis in the same manner as in Synthesis Example 3-1-C, except that Compound 3-2-B was used instead of Compound 3-1-B.
MS[M+H]$^+$=605.16

Synthesis of Compound 3-3-C

Compound 3-3-C was prepared by performing the synthesis in the same manner as in Synthesis Example 3-1-C, except that Compound 3-3-B was used instead of Compound 3-1-B.
MS[M+H]$^+$=605.16

Synthesis of Compound 3-4-C

Compound 3-4-C was prepared by performing the synthesis in the same manner as in Synthesis Example 3-1-C, except that Compound 3-4-B was used instead of Compound 3-1-B.
MS[M+H]$^+$=605.16

149

Synthesis of Compound 3-1-D

In Synthesis Example 3-1-C, a column purification was performed, and then a recrystallization was performed to prepare Compound 3-1-D.
MS[M+H]$^+$=605.16

Synthesis of Compound 3-2-D

In Synthesis Example 3-2-C, a column purification was performed, and then a recrystallization was performed to prepare Compound 3-2-D.
MS[M+H]$^+$=605.16

Synthesis of Compound 3-3-D

In Synthesis Example 3-3-C, a column purification was performed, and then a recrystallization was performed to prepare Compound 3-3-D.
MS[M+H]$^+$=605.16

150

Synthesis of Compound 3-4-D

In Synthesis Example 3-4-C, a column purification was performed, and then a recrystallization was performed to prepare Compound 3-4-D.

MS[M+H]$^+$=605.16

Preparation Example 4

Preparation of Following 4-1-C to 4-4-C and 4-1-D to 4-4-D

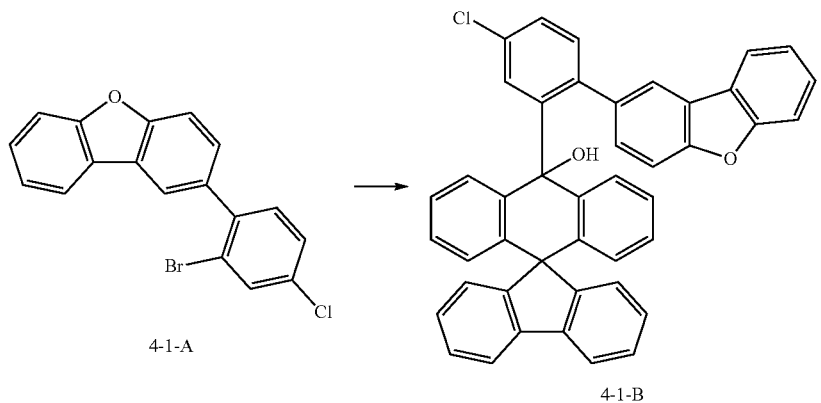

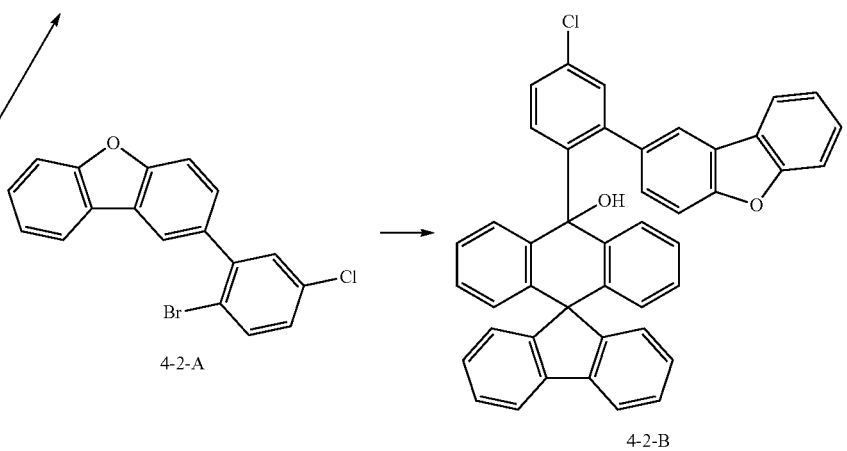

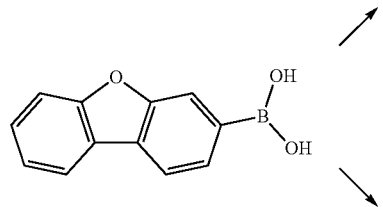

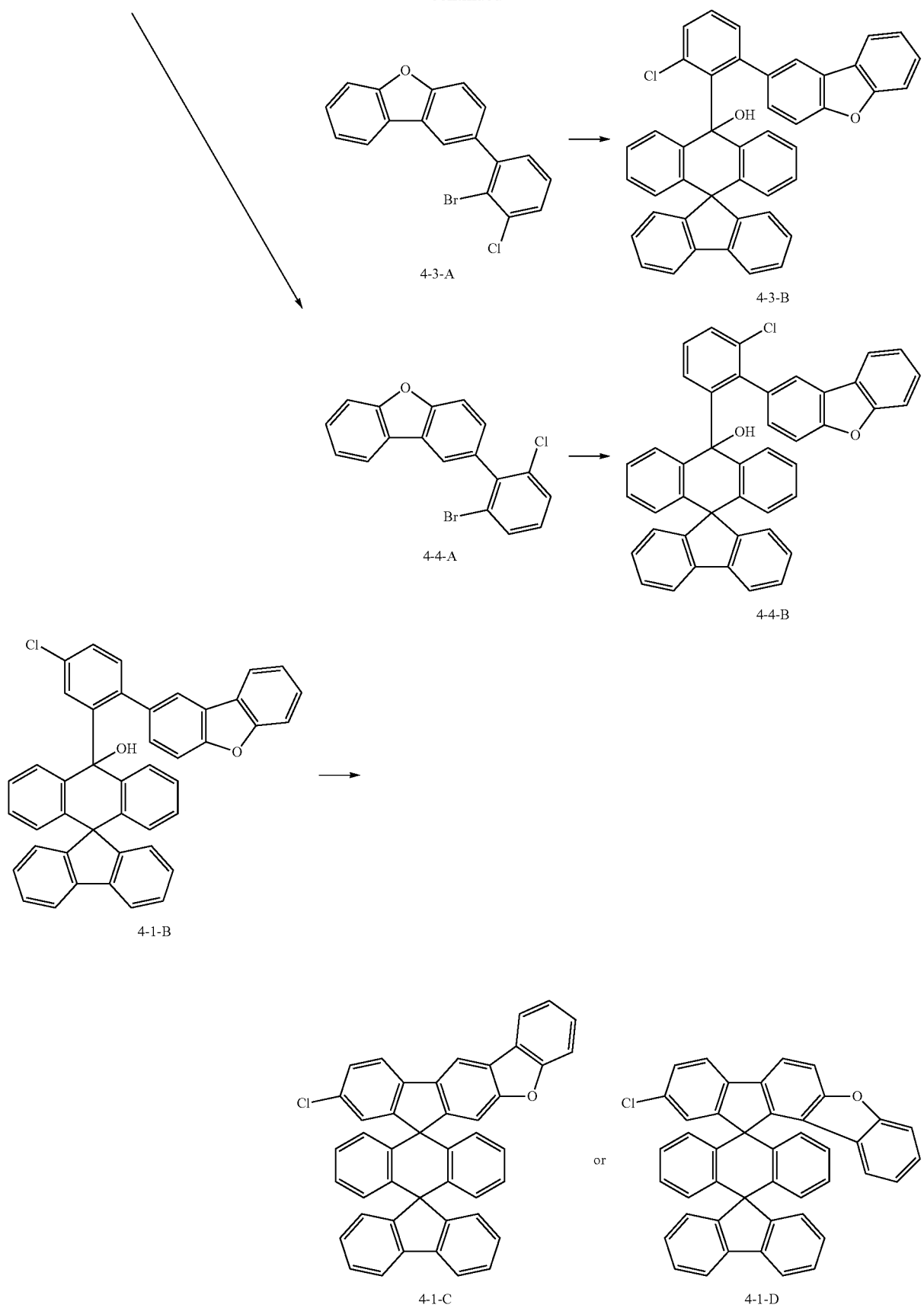

-continued
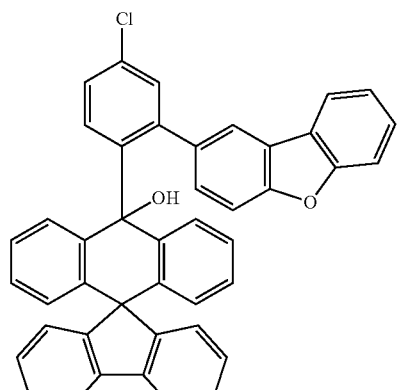
4-2-B
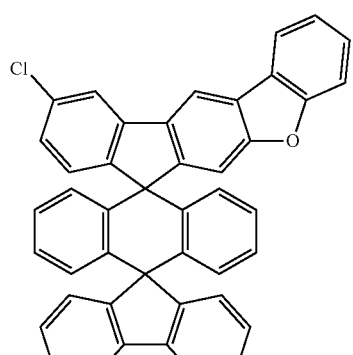
4-2-C
or
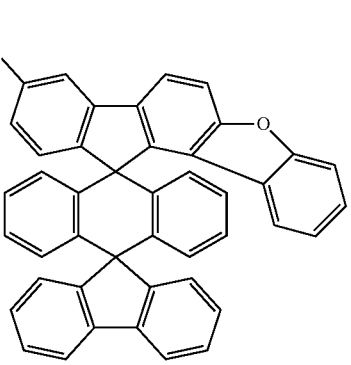
4-2-D
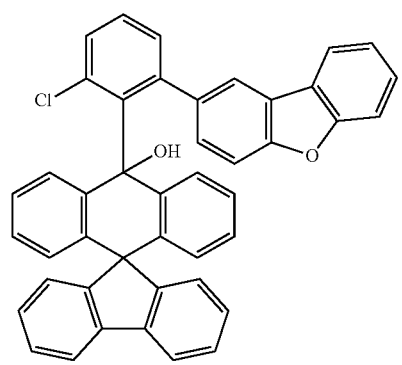
4-3-B
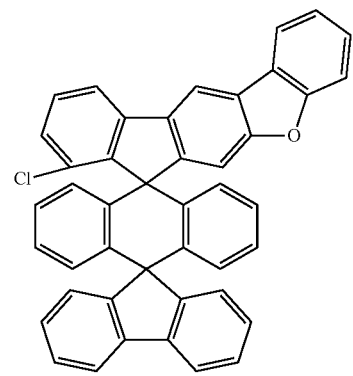
4-3-C
or
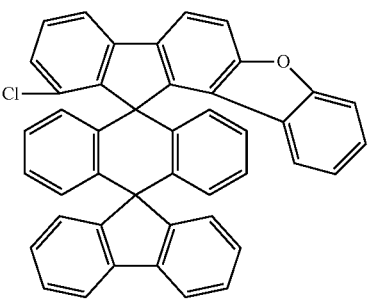
4-3-D -continued

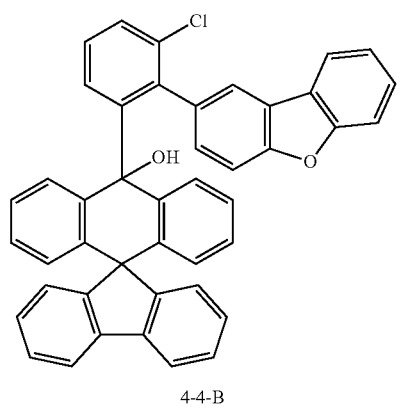

4-4-B

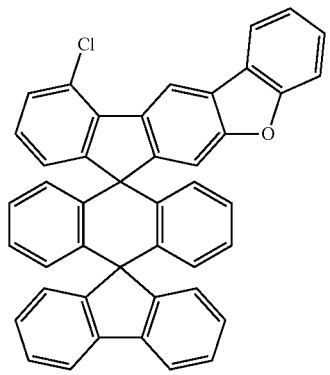

4-4-C or

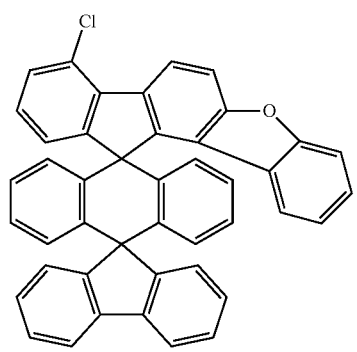

4-4-D

Synthesis of Compound 4-1-A

Compound 4-1-A was prepared by performing the synthesis in the same manner as in Synthesis Example 1-1-A, except that dibenzofuran-2-ylboronic acid was used instead of dibenzofuran-4-ylboronic acid.
MS[M+H]$^+$=356.96

Synthesis of Compound 4-2-A

Compound 4-2-A was prepared by performing the synthesis in the same manner as in Synthesis Example 4-1-A, except that 2-bromo-5-chloro-1-iodobenzene was used instead of the compound 2-bromo-4-chloro-1-iodobenzene.
MS[M+H]$^+$=356.96

Synthesis of Compound 4-3-A

Compound 4-3-A was prepared by performing the synthesis in the same manner as in Synthesis Example 4-1-A, except that 2-bromo-3-chloro-1-iodobenzene was used instead of the compound 2-bromo-4-chloro-1-iodobenzene.
MS[M+H]$^+$=356.96

Synthesis of Compound 4-4-A

Compound 4-4-A was prepared by performing the synthesis in the same manner as in Synthesis Example 3-1-A, except that 2-bromo-6-chloro-1-iodobenzene was used instead of the compound 2-bromo-4-chloro-1-iodobenzene.
MS[M+H]$^+$=356.96

Synthesis of Compound 4-1-B

Compound 4-1-B was prepared by performing the synthesis in the same manner as in Synthesis Example 1-1-B, except that Compound 4-1-A was used instead of Compound 1-1-A.
MS[M+H]$^+$=623.17

Synthesis of Compound 4-2-B

Compound 4-2-B was prepared by performing the synthesis in the same manner as in Synthesis Example 4-1-B, except that Compound 4-2-A was used instead of Compound 4-1-A.
MS[M+H]$^+$=623.17

Synthesis of Compound 4-3-B

Compound 4-3-B was prepared by performing the synthesis in the same manner as in Synthesis Example 4-1-B, except that Compound 4-3-A was used instead of Compound 4-1-A.
MS[M+H]$^+$=623.17

Synthesis of Compound 4-4-B

Compound 4-4-B was prepared by performing the synthesis in the same manner as in Synthesis Example 4-1-B, except that Compound 4-4-A was used instead of Compound 4-1-A.
MS[M+H]$^+$=623.17

Synthesis of Compound 4-1-C

Compound 4-1-C was prepared by performing the synthesis in the same manner as in Synthesis Example 3-1-C, except that Compound 4-1-B was used instead of Compound 3-1-B.

MS[M+H]$^+$=605.16

Synthesis of Compound 4-2-C

Compound 4-2-C was prepared by performing the synthesis in the same manner as in Synthesis Example 4-1-C, except that Compound 4-2-B was used instead of Compound 4-1-B.

MS[M+H]$^+$=605.16

Synthesis of Compound 4-3-C

Compound 4-3-C was prepared by performing the synthesis in the same manner as in Synthesis Example 4-1-C, except that Compound 4-3-B was used instead of Compound 4-1-B.

MS[M+H]$^+$=605.16

Synthesis of Compound 4-4-C

Compound 4-4-C was prepared by performing the synthesis in the same manner as in Synthesis Example 4-1-C, except that Compound 4-4-B was used instead of Compound 4-1-B.

MS[M+H]$^+$=605.16

Synthesis of Compound 4-1-D

In Synthesis Example 4-1-C, a column purification was performed, and then a recrystallization was performed to prepare Compound 4-1-D.

MS[M+H]$^+$=605.16

Synthesis of Compound 4-2-D

In Synthesis Example 4-2-C, a column purification was performed, and then a recrystallization was performed to prepare Compound 4-2-D.

MS[M+H]$^+$=605.16

Synthesis of Compound 4-3-D

In Synthesis Example 4-2-C, a column purification was performed, and then a recrystallization was performed to prepare Compound 4-3-D.

MS[M+H]$^+$=605.16

Synthesis of Compound 4-4-D

In Synthesis Example 4-2-C, a column purification was performed, and then a recrystallization was performed to prepare Compound 4-4-D.

MS[M+H]$^+$=605.16

Preparation Example 5

Preparation of Following 5-1-C to 5-4-C

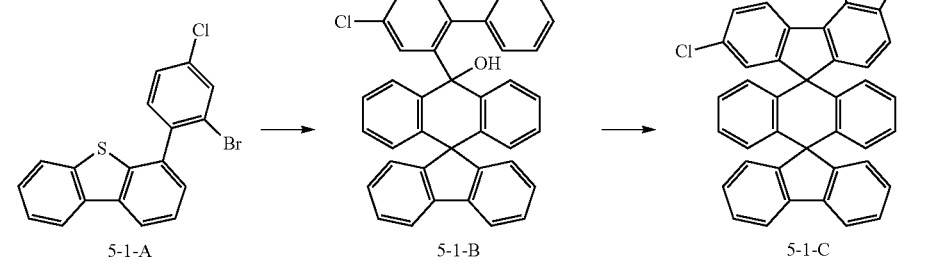

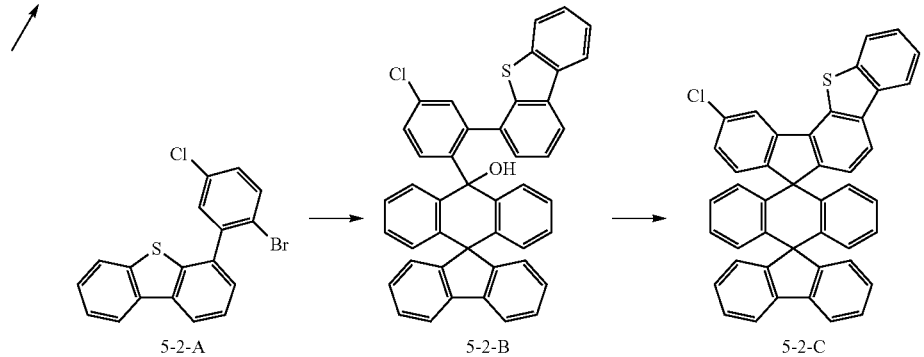

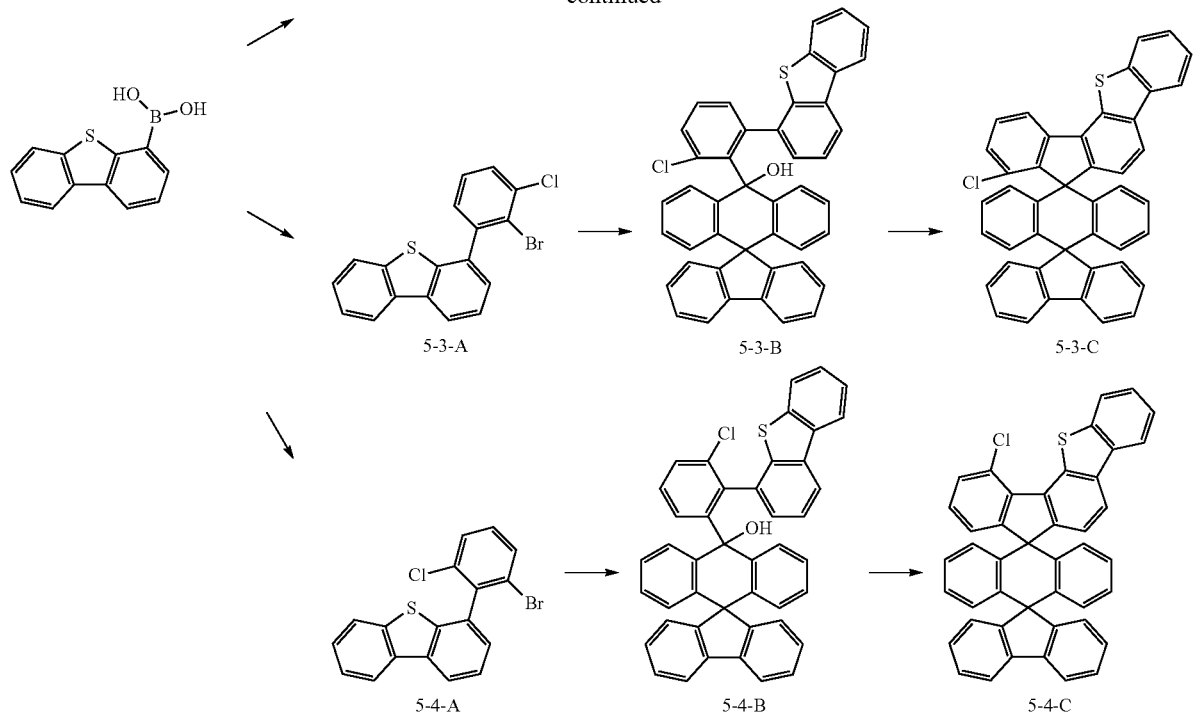

Synthesis of Compound 5-1-A

Compound 5-1-A was prepared by performing the synthesis in the same manner as in Synthesis Example 1-1-A, except that dibenzothiophene-4-ylboronic acid was used instead of dibenzofuran-4-ylboronic acid.

MS[M+H]$^+$=372.94

Synthesis of Compound 5-2-A

Compound 5-2-A was prepared by performing the synthesis in the same manner as in Synthesis Example 5-1-A, except that 2-bromo-5-chloro-1-iodobenzene was used instead of the compound 2-bromo-4-chloro-1-iodobenzene.

MS[M+H]$^+$=372.94

Synthesis of Compound 5-3-A

Compound 5-3-A was prepared by performing the synthesis in the same manner as in Synthesis Example 5-1-A, except that 2-bromo-3-chloro-1-iodobenzene was used instead of the compound 2-bromo-4-chloro-1-iodobenzene.

MS[M+H]$^+$=372.94

Synthesis of Compound 5-4-A

Compound 5-4-A was prepared by performing the synthesis in the same manner as in Synthesis Example 5-1-A, except that 2-bromo-6-chloro-1-iodobenzene was used instead of the compound 2-bromo-4-chloro-1-iodobenzene.

MS[M+H]$^+$=372.94

Synthesis of Compound 5-1-B

Compound 5-1-B was prepared by performing the synthesis in the same manner as in Synthesis Example 1-1-B, except that Compound 5-1-A was used instead of Compound 1-1-A.

MS[M+H]$^+$=640.15

Synthesis of Compound 5-2-B

Compound 5-2-B was prepared by performing the synthesis in the same manner as in Synthesis Example 5-1-B, except that Compound 5-2-A was used instead of Compound 1-1-A.

MS[M+H]$^+$=640.15

Synthesis of Compound 5-3-B

Compound 5-3-B was prepared by performing the synthesis in the same manner as in Synthesis Example 5-1-B, except that Compound 5-3-A was used instead of Compound 1-1-A.

MS[M+H]$^+$=640.15

Synthesis of Compound 5-4-B

Compound 5-4-B was prepared by performing the synthesis in the same manner as in Synthesis Example 5-1-B, except that Compound 5-4-A was used instead of Compound 1-1-A.

MS[M+H]$^+$=640.15

Synthesis of Compound 5-1-C

Compound 5-1-C was prepared by performing the synthesis in the same manner as in Synthesis Example 1-1-C, except that Compound 5-1-B was used instead of Compound 1-1-B.

MS[M+H]$^+$=621.14

Synthesis of Compound 5-2-C

Compound 5-2-C was prepared by performing the synthesis in the same manner as in Synthesis Example 5-1-C, except that Compound 5-2-B was used instead of Compound 5-1-B.

MS[M+H]$^+$=621.14

Synthesis of Compound 5-3-C

Compound 5-3-C was prepared by performing the synthesis in the same manner as in Synthesis Example 5-1-C, except that Compound 5-3-B was used instead of Compound 5-1-B.

MS[M+H]$^+$=621.14

Synthesis of Compound 5-4-C

Compound 5-4-C was prepared by performing the synthesis in the same manner as in Synthesis Example 5-1-C, except that Compound 5-4-B was used instead of Compound 5-1-B.

MS[M+H]$^+$=621.14

Preparation Example 6

Preparation of Following 6-1-C to 6-4-C

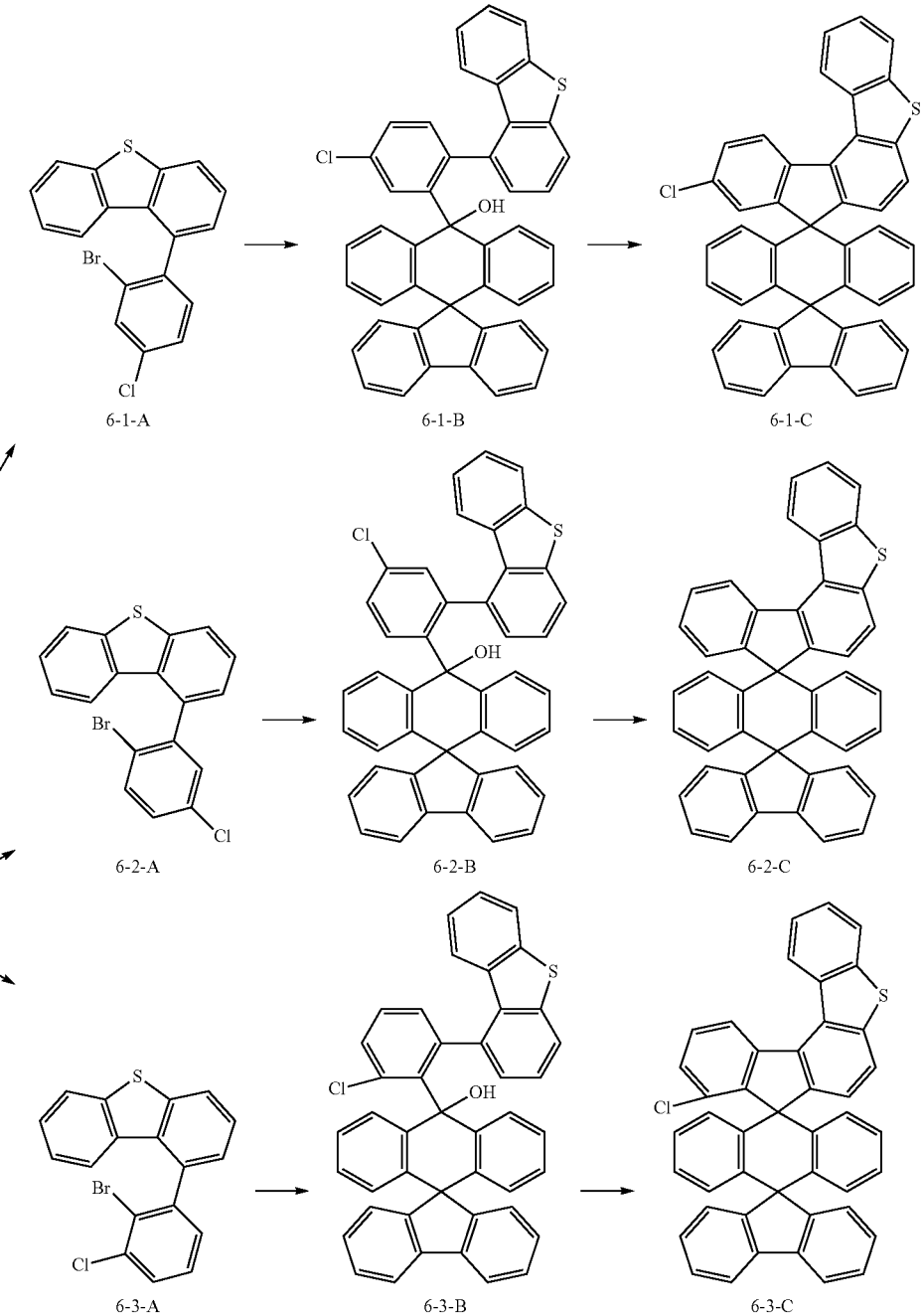

-continued 6-4-A 6-4-B 6-4-C

Synthesis of Compound 6-1-A

Compound 6-1-A was prepared by performing the synthesis in the same manner as in Synthesis Example 5-1-A, except that dibenzothiophene-1-ylboronic acid was used instead of dibenzothiophene-4-ylboronic acid.
MS[M+H]$^+$=372.94

Synthesis of Compound 6-2-A

Compound 6-2-A was prepared by performing the synthesis in the same manner as in Synthesis Example 6-1-A, except that 2-bromo-5-chloro-1-iodobenzene was used instead of the compound 2-bromo-4-chloro-1-iodobenzene.
MS[M+H]$^+$=372.94

Synthesis of Compound 6-3-A

Compound 6-3-A was prepared by performing the synthesis in the same manner as in Synthesis Example 6-1-A, except that 2-bromo-3-chloro-1-iodobenzene was used instead of the compound 2-bromo-4-chloro-1-iodobenzene.
MS[M+H]$^+$=372.94

Synthesis of Compound 6-4-A

Compound 6-4-A was prepared by performing the synthesis in the same manner as in Synthesis Example 6-1-A, except that 2-bromo-6-chloro-1-iodobenzene was used instead of the compound 2-bromo-4-chloro-1-iodobenzene.
MS[M+H]$^+$=372.94

Synthesis of Compound 6-1-B

Compound 6-1-B was prepared by performing the synthesis in the same manner as in Synthesis Example 1-1-B, except that Compound 6-1-A was used instead of Compound 1-1-A.
MS[M+H]$^+$=639.15

Synthesis of Compound 6-2-B

Compound 6-2-B was prepared by performing the synthesis in the same manner as in Synthesis Example 6-1-B, except that Compound 6-2-A was used instead of Compound 6-1-A.
MS[M+H]+=639.15

Synthesis of Compound 6-3-B

Compound 6-3-B was prepared by performing the synthesis in the same manner as in Synthesis Example 6-1-B, except that Compound 6-3-A was used instead of Compound 6-1-A.
MS[M+H]$^+$=639.15

Synthesis of Compound 6-4-B

Compound 6-4-B was prepared by performing the synthesis in the same manner as in Synthesis Example 6-1-B, except that Compound 6-4-A was used instead of Compound 6-1-A.
MS[M+H]$^+$=621.14

Synthesis of Compound 6-1-C

Compound 6-1-C was prepared by performing the synthesis in the same manner as in Synthesis Example 1-1-C, except that Compound 6-1-B was used instead of Compound 1-1-B.
MS[M+H]$^+$=621.14

Synthesis of Compound 6-2-C

Compound 6-2-C was prepared by performing the synthesis in the same manner as in Synthesis Example 6-1-C, except that Compound 6-2-B was used instead of Compound 6-1-B.
MS[M+H]$^+$=621.14

Synthesis of Compound 6-3-C

Compound 6-3-C was prepared by performing the synthesis in the same manner as in Synthesis Example 6-1-C, except that Compound 6-3-B was used instead of Compound 6-1-B.
MS[M+H]$^+$=621.14

Synthesis of Compound 6-4-C

Compound 6-4-C was prepared by performing the synthesis in the same manner as in Synthesis Example 6-1-C, except that Compound 6-4-B was used instead of Compound 6-1-B.
MS[M+H]$^+$=621.14

Preparation Example 7
Preparation of Following 7-1-C to 7-4-C and 7-1-D to 7-4-D
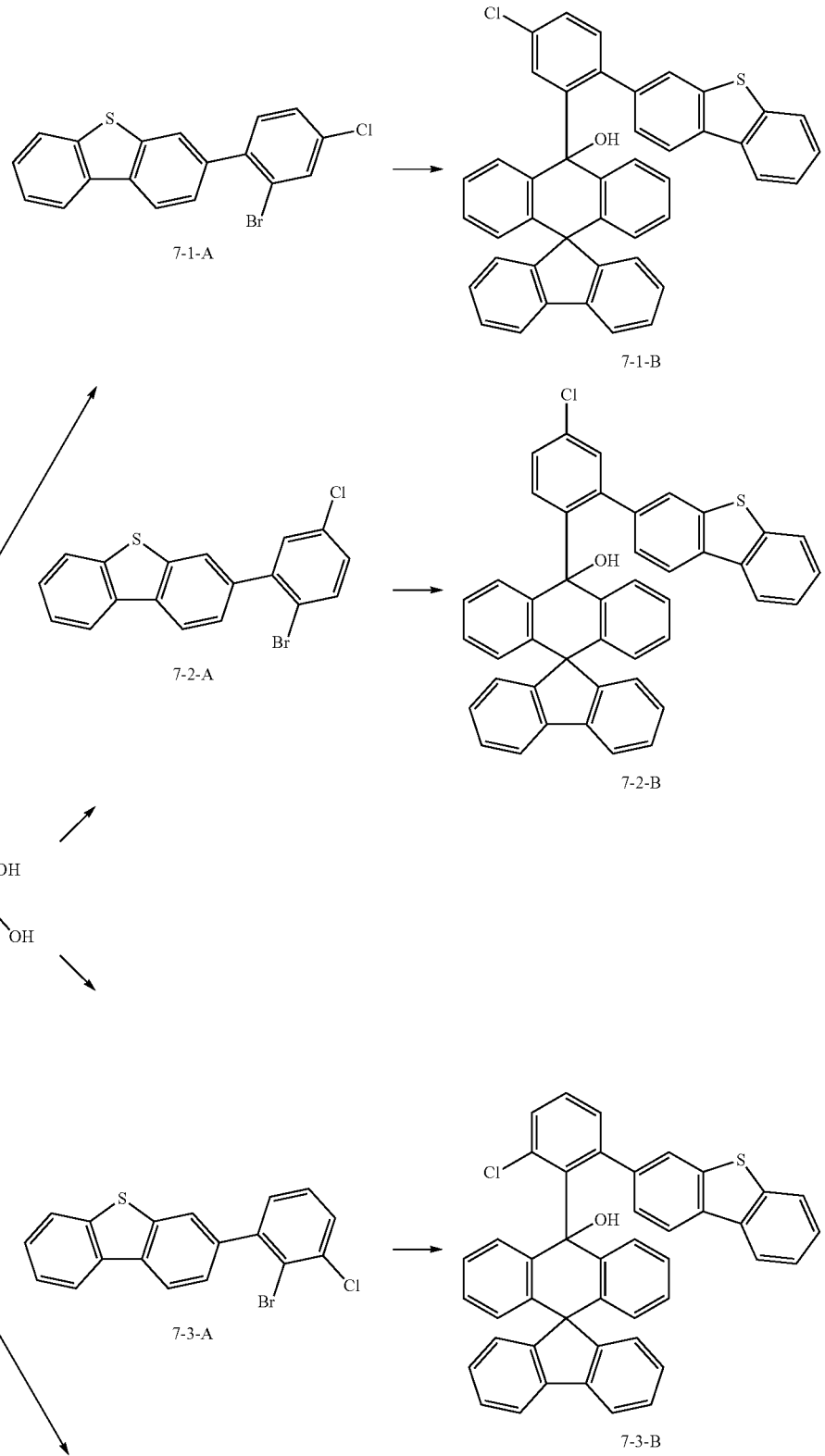

-continued
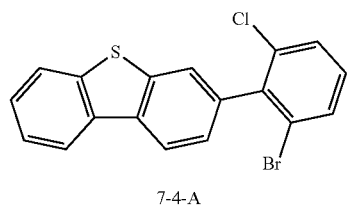
7-4-A
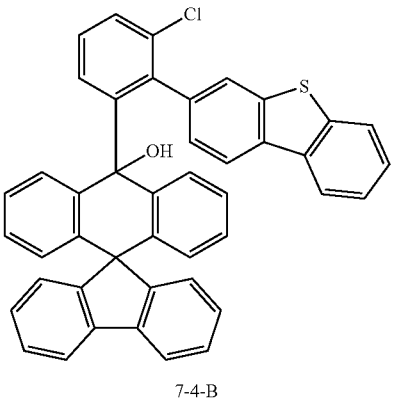
7-4-B
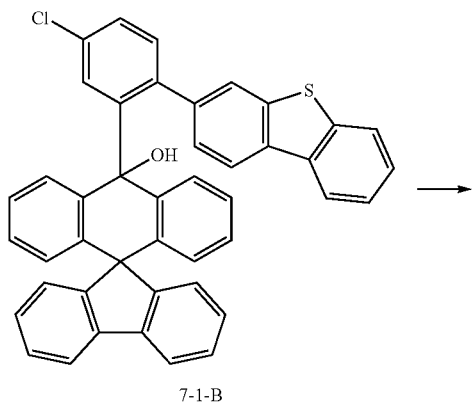
7-1-B
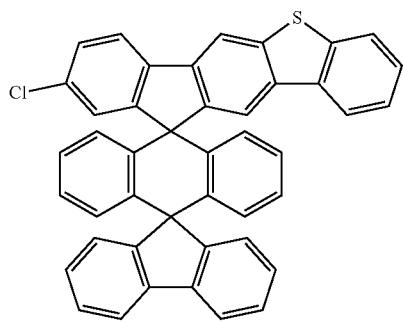
7-1-C
or
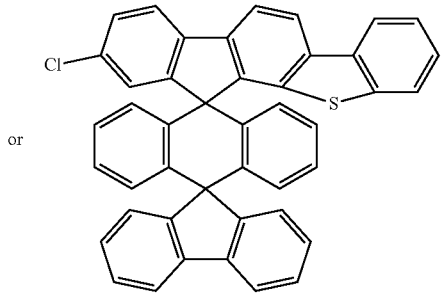
7-1-D
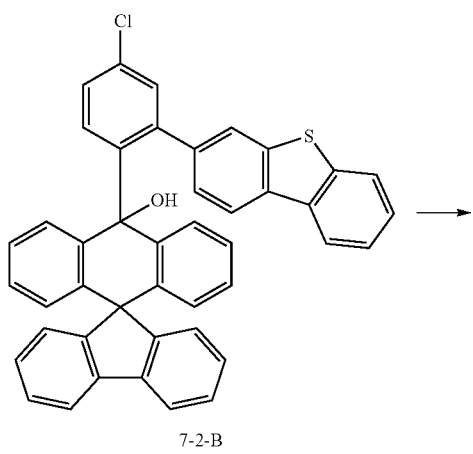
7-2-B -continued
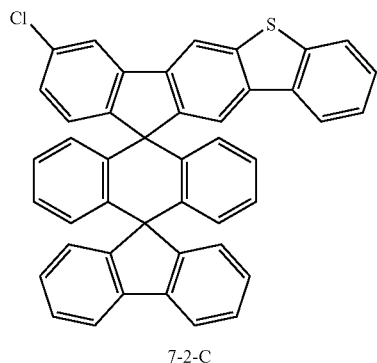
7-2-C
or
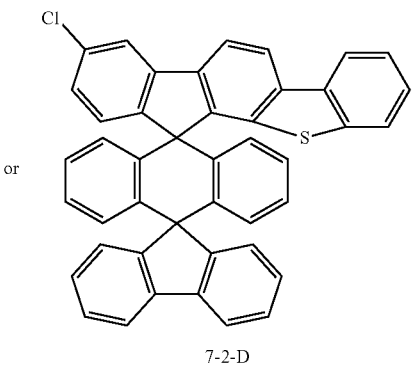
7-2-D
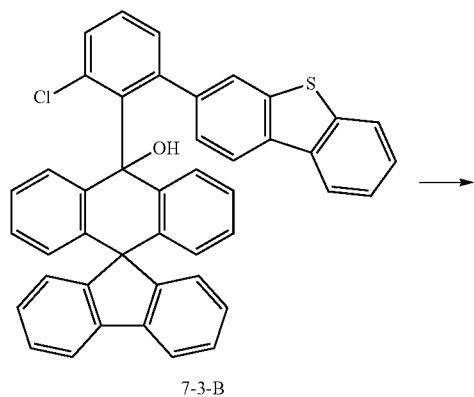
7-3-B
→
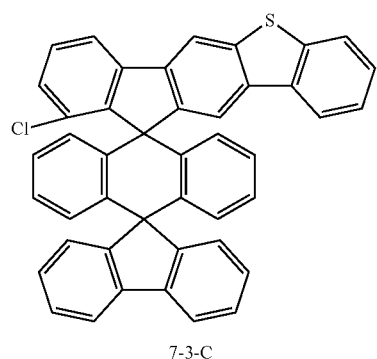
7-3-C
or
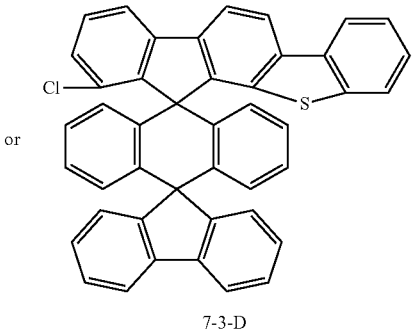
7-3-D
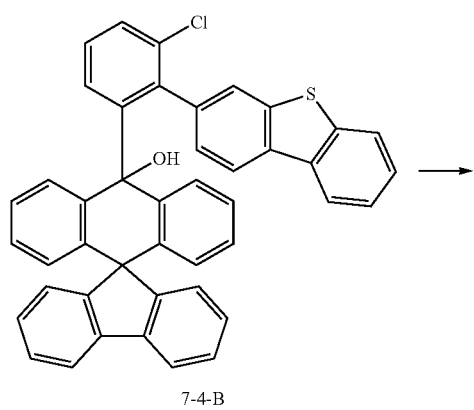
7-4-B
→

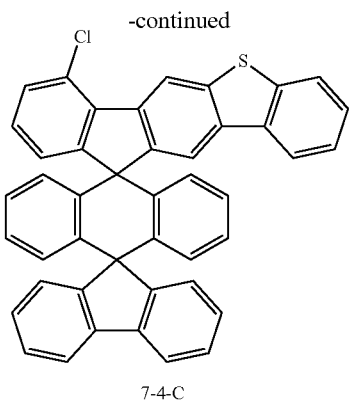

7-4-C

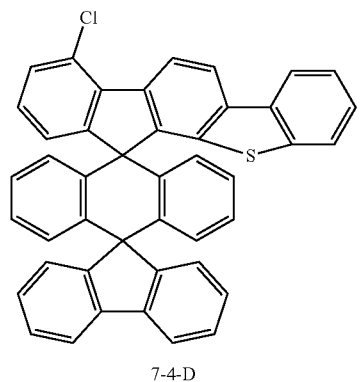

7-4-D

Synthesis of Compound 7-1-A

Compound 7-1-A was prepared by performing the synthesis in the same manner as in Synthesis Example 5-1-A, except that dibenzothiophene-3-ylboronic acid was used instead of dibenzothiophene-4-ylboronic acid.

MS[M+H]$^+$=372.94

Synthesis of Compound 7-2-A

Compound 7-2-A was prepared by performing the synthesis in the same manner as in Synthesis Example 7-1-A, except that 2-bromo-5-chloro-1-iodobenzene was used instead of the compound 2-bromo-4-chloro-1-iodobenzene.

MS[M+H]$^+$=372.94

Synthesis of Compound 7-3-A

Compound 7-3-A was prepared by performing the synthesis in the same manner as in Synthesis Example 7-1-A, except that 2-bromo-3-chloro-1-iodobenzene was used instead of the compound 2-bromo-4-chloro-1-iodobenzene.

MS[M+H]$^+$=372.94

Synthesis of Compound 7-4-A

Compound 7-4-A was prepared by performing the synthesis in the same manner as in Synthesis Example 7-1, except that 2-bromo-6-chloro-1-iodobenzene was used instead of the compound 2-bromo-4-chloro-1-iodobenzene.

MS[M+H]$^+$=372.94

Synthesis of Compound 7-1-B

Compound 7-1-B was prepared by performing the synthesis in the same manner as in Synthesis Example 1-1-B, except that Compound 7-1-A was used instead of Compound 1-1-A.

MS[M+H]$^+$=639.15

Synthesis of Compound 7-2-B

Compound 7-2-B was prepared by performing the synthesis in the same manner as in Synthesis Example 7-1-B, except that Compound 7-2-A was used instead of Compound 7-1-A.

MS[M+H]$^+$=639.15

Synthesis of Compound 7-3-B

Compound 7-3-B was prepared by performing the synthesis in the same manner as in Synthesis Example 7-1-B, except that Compound 7-3-A was used instead of Compound 7-1-A.

MS[M+H]$^+$=639.15

Synthesis of Compound 7-4-B

Compound 7-4-B was prepared by performing the synthesis in the same manner as in Synthesis Example 7-1-B, except that Compound 7-4-A was used instead of Compound 7-1-A.

MS[M+H]$^+$=639.15

Synthesis of Compound 7-1-C

After Compound 7-1-B (10 g, 16.1 mmol) was put into acetic acid (250 ml), 1 ml of sulfuric acid was added dropwise thereto, and the resulting mixture was stirred and refluxed. The temperature was lowered to normal temperature, the resulting product was neutralized with water, and then the filtered solid was purified with a column chromatography and recrystallized with tetrahydrofuran and ethyl acetate to prepare Compound 7-1-C (2.7 g, 30%).

MS[M+H]$^+$=621.14

Synthesis of Compound 7-2-C

Compound 7-2-C was prepared by performing the synthesis in the same manner as in Synthesis Example 7-1-C, except that Compound 7-2-B was used instead of Compound 7-1-B.

MS[M+H]$^+$=621.14

Synthesis of Compound 7-3-C

Compound 7-3-C was prepared by performing the synthesis in the same manner as in Synthesis Example 7-1-C,

173 except that Compound 7-3-B was used instead of Compound 7-1-B.
MS[M+H]⁺=621.14

Synthesis of Compound 7-4-C

Compound 7-4-C was prepared by performing the synthesis in the same manner as in Synthesis Example 7-1-C, except that Compound 7-4-B was used instead of Compound 7-1-B.
MS[M+H]⁺=621.14

Synthesis of Compound 7-1-D

In Synthesis Example 7-1-C, a column purification was performed, and then a recrystallization was performed to prepare Compound 7-1-D.
MS[M+H]⁺=621.14

Synthesis of Compound 7-2-D

In Synthesis Example 7-1-C, a column purification was performed, and then a recrystallization was performed to prepare Compound 7-2-D.
MS[M+H]⁺=621.14

Synthesis of Compound 7-3-D

In Synthesis Example 7-1-C, a column purification was performed, and then a recrystallization was performed to prepare Compound 7-3-D.
MS[M+H]⁺=621.14

Synthesis of Compound 7-4-D

In Synthesis Example 7-1-C, a column purification was performed, and then a recrystallization was performed to prepare Compound 7-4-D.
MS[M+H]⁺=621.14

Preparation Example 8

Preparation of Following 8-1-C to 8-4-C and 8-1-D to 8-4-D

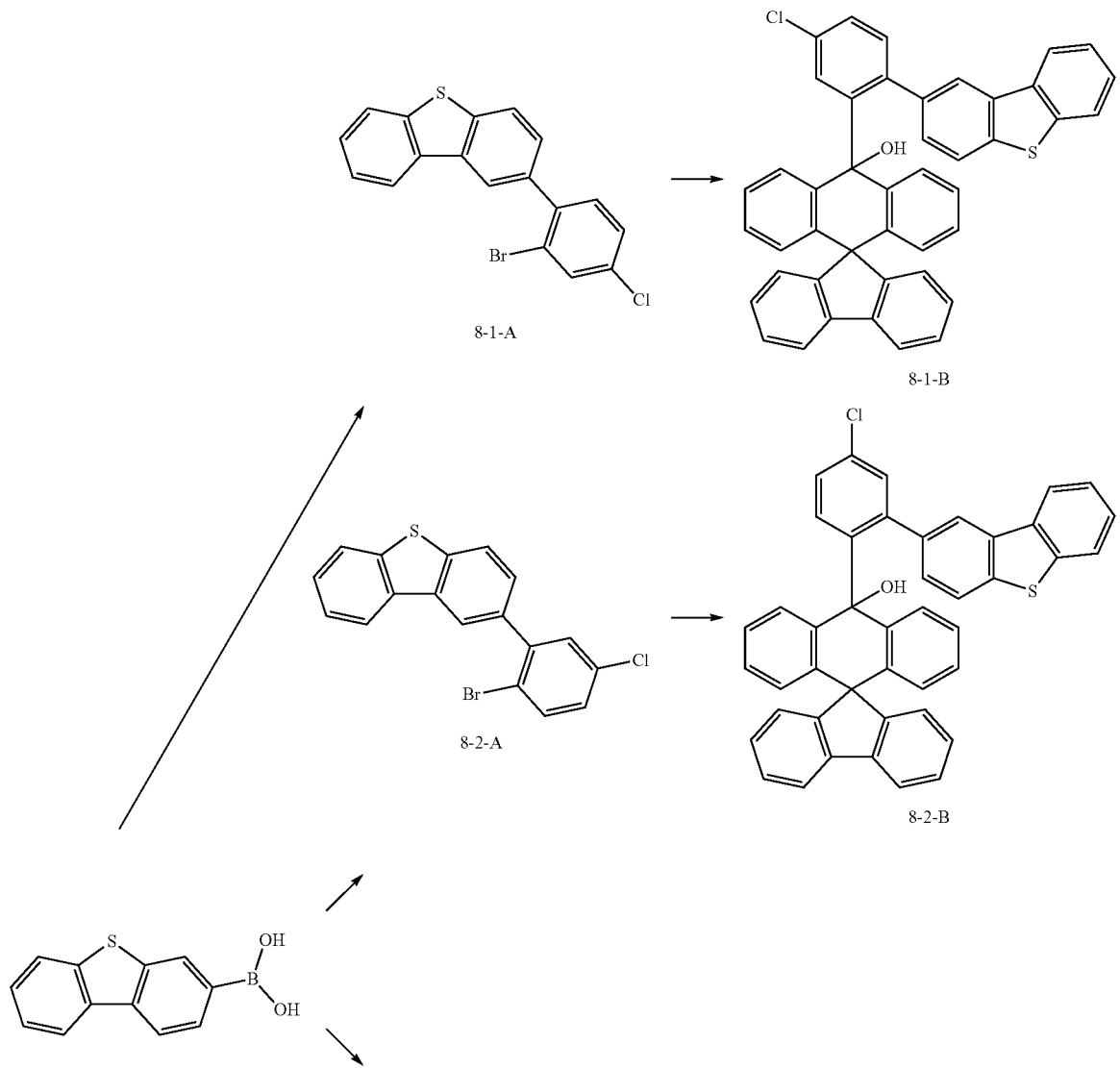

-continued
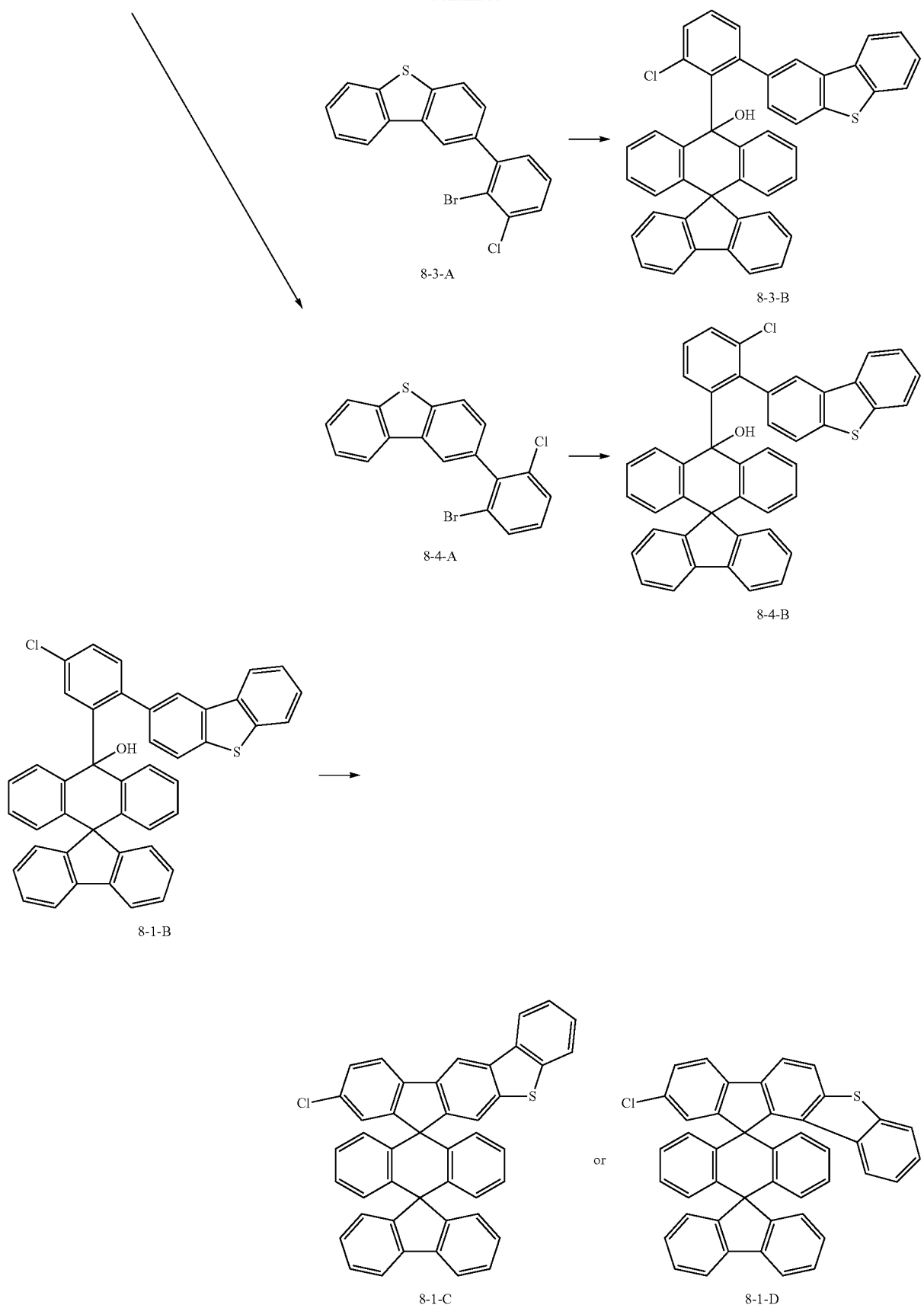

-continued
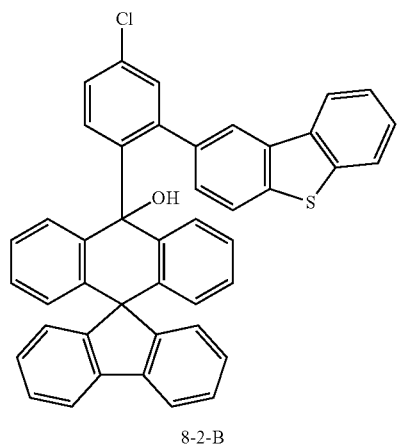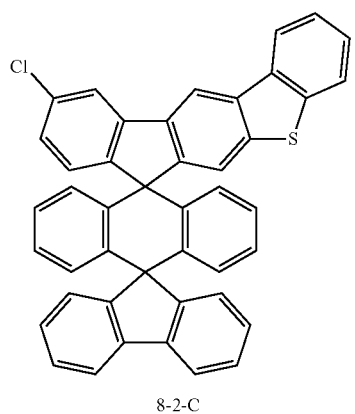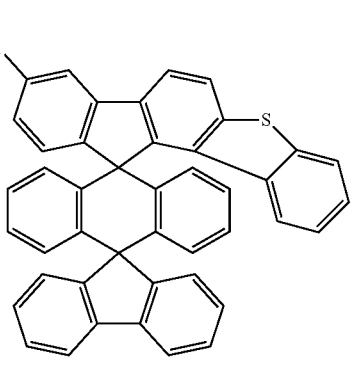
8-2-B
8-2-C or 8-2-D
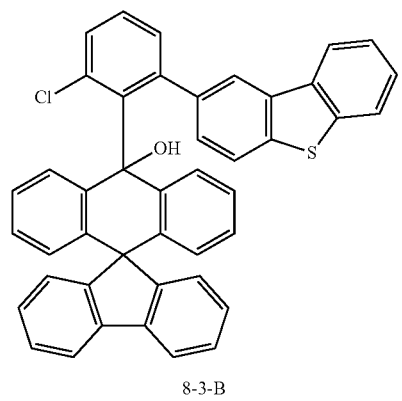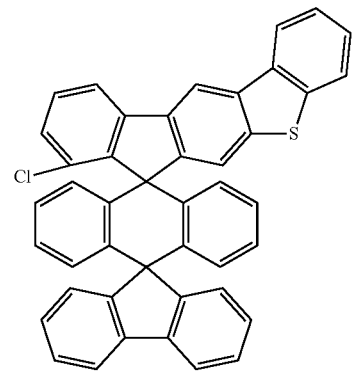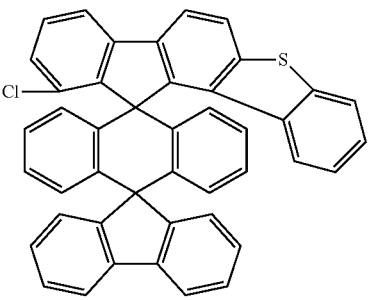
8-3-B
8-3-C or 8-3-D -continued

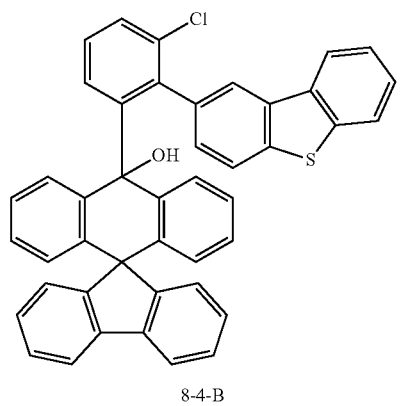
8-4-B

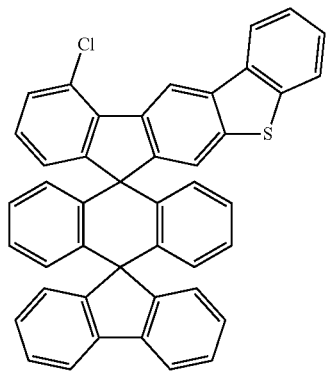
8-4-C or

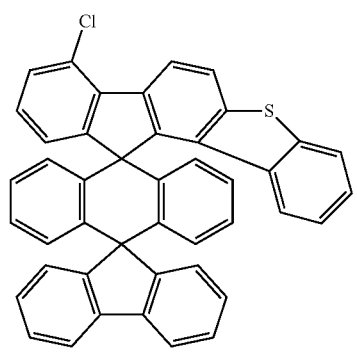
8-4-D

Synthesis of Compound 8-1-A

Compound 8-1-A was prepared by performing the synthesis in the same manner as in Synthesis Example 5-1-A, except that dibenzothiophene-2-ylboronic acid was used instead of dibenzothiophene-4-ylboronic acid.
MS[M+H]$^+$=372.94

Synthesis of Compound 8-2-A

Compound 8-2-A was prepared by performing the synthesis in the same manner as in Synthesis Example 8-1-A, except that 2-bromo-5-chloro-1-iodobenzene was used instead of the compound 2-bromo-4-chloro-1-iodobenzene.
MS [M+H]$^+$=372.94

Synthesis of Compound 8-3-A

Compound 8-3-A was prepared by performing the synthesis in the same manner as in Synthesis Example 8-1-A, except that 2-bromo-3-chloro-1-iodobenzene was used instead of the compound 2-bromo-4-chloro-1-iodobenzene.
MS[M+H]$^+$=372.94

Synthesis of Compound 8-4-A

Compound 8-4-A was prepared by performing the synthesis in the same manner as in Synthesis Example 8-1-A, except that 2-bromo-6-chloro-1-iodobenzene was used instead of the compound 2-bromo-4-chloro-1-iodobenzene.
MS[M+H]$^+$=372.94

Synthesis of Compound 8-1-B

Compound 8-1-B was prepared by performing the synthesis in the same manner as in Synthesis Example 1-1-B, except that Compound 8-1-A was used instead of Compound 1-1-A.
MS[M+H]$^+$=639.15

Synthesis of Compound 8-2-B

Compound 8-2-B was prepared by performing the synthesis in the same manner as in Synthesis Example 8-1-B, except that Compound 8-2-A was used instead of Compound 8-1-A.
MS[M+H]$^+$=639.15

Synthesis of Compound 8-3-B

Compound 8-3-B was prepared by performing the synthesis in the same manner as in Synthesis Example 8-1-B, except that Compound 8-3-A was used instead of Compound 8-1-A.
MS[M+H]$^+$=639.15

Synthesis of Compound 8-4-B

Compound 8-4-B was prepared by performing the synthesis in the same manner as in Synthesis Example 8-1-B, except that Compound 8-4-A was used instead of Compound 8-1-A.
MS[M+H]$^+$=639.15

Synthesis of Compound 8-1-C

Compound 8-1-C was prepared by performing the synthesis in the same manner as in Synthesis Example 5-1-C, except that Compound 8-1-B was used instead of Compound 5-1-B.

MS[M+H]$^+$=621.14

Synthesis of Compound 8-2-C

Compound 8-2-C was prepared by performing the synthesis in the same manner as in Synthesis Example 8-1-C, except that Compound 8-2-B was used instead of Compound 8-1-B.

MS[M+H]$^+$=621.14

Synthesis of Compound 8-3-C

Compound 8-3-C was prepared by performing the synthesis in the same manner as in Synthesis Example 8-1-C, except that Compound 8-3-B was used instead of Compound 8-1-B.

MS[M+H]$^+$=621.14

Synthesis of Compound 8-4-C

Compound 8-4-C was prepared by performing the synthesis in the same manner as in Synthesis Example 8-1-C, except that Compound 8-4-B was used instead of Compound 8-1-B.

MS[M+H]$^+$=621.14

Synthesis of Compound 8-1-D

In Synthesis Example 8-1-C, a column purification was performed, and then a recrystallization was performed to prepare Compound 8-1-D.

MS[M+H]$^+$=621.14

Synthesis of Compound 8-2-D

In Synthesis Example 8-1-C, a column purification was performed, and then a recrystallization was performed to prepare Compound 8-2-D.

MS[M+H]$^+$=621.14

Synthesis of Compound 8-3-D

In Synthesis Example 8-1-C, a column purification was performed, and then a recrystallization was performed to prepare Compound 8-3-D.

MS[M+H]$^+$=621.14

Synthesis of Compound 8-4-D

In Synthesis Example 8-1-C, a column purification was performed, and then a recrystallization was performed to prepare Compound 8-4-D.

MS[M+H]$^+$=621.14

Synthesis of Compound 1

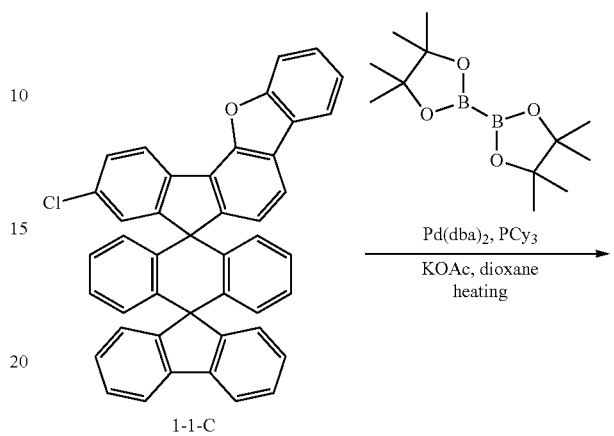

1-1-C

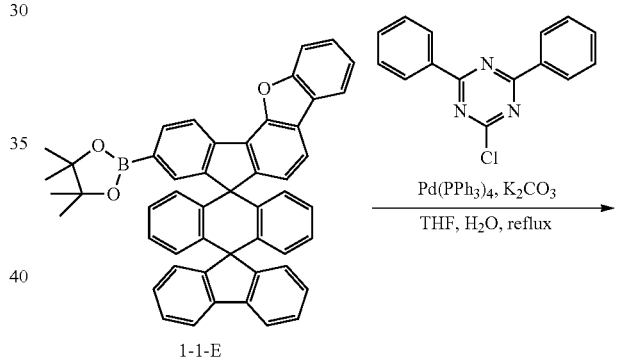

1-1-E

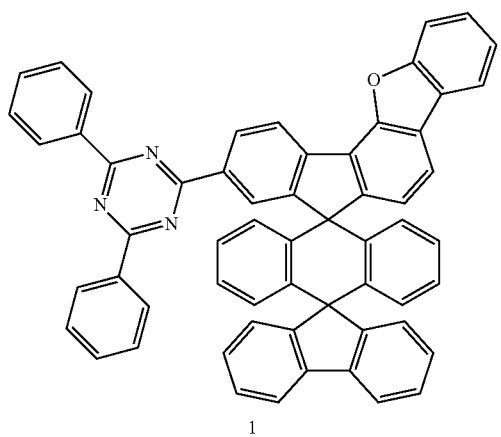

1

Compound 1-1-C (10 g, 16.6 mmol), bis(pinacolato)diboron (4.64 g, 18.2 mmol), and potassium acetate (29.1 g, 296 mmol) were mixed, and the resulting mixture was added to 100 ml of dioxane, and heated and stirred. Bis(dibenzylidineacetone)palladium (0.3 g, 0.55 mol) and tricyclohexylphosphine (1.6 g, 5.9 mmol) were put into the mixture under reflux, and the resulting mixture was heated and stirred for 10 hours. After the reaction was terminated, the temperature was lowered to normal temperature, and then the mixture was filtered. The solvent was removed, and then the residue was poured into water, extraction was performed with chloroform, and the organic layer was dried over anhydrous magnesium sulfate. After the distillation under reduced pressure, recrystallization was performed with ethanol to prepare Compound 1-1-E (9.24 g, yield: 80%).

Compound 1-1-E (9 g, 12.9 mmol) and 2-chloro-4,6-diphenyl-1,3,5-triazine (3.62 g, 13.5 mmol) were added to tetrahydrofuran (250 ml), and then a 2M aqueous potassium carbonate solution (100 ml) was added thereto, tetrakistriphenyl-phosphinopalladium (0.3 g, 0.27 mmol) was put thereinto, and then the resulting mixture was heated and stirred for 5 hours. After the temperature was lowered to normal temperature and the reaction was terminated, the solvent was removed, and then the residue was dissolved in ethyl acetate, the resulting solution was washed with water, and then the layers were separated. After the solvent was removed, the residue was recrystallized with tetrahydrofuran and ethyl acetate to prepare Compound 1 (9.3 g, yield: 90%).

MS[M+H]$^+$=802.28

Synthesis of Compound 6

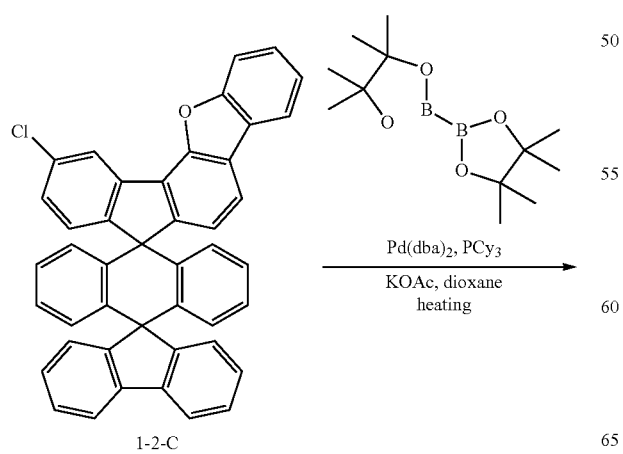

1-2-C

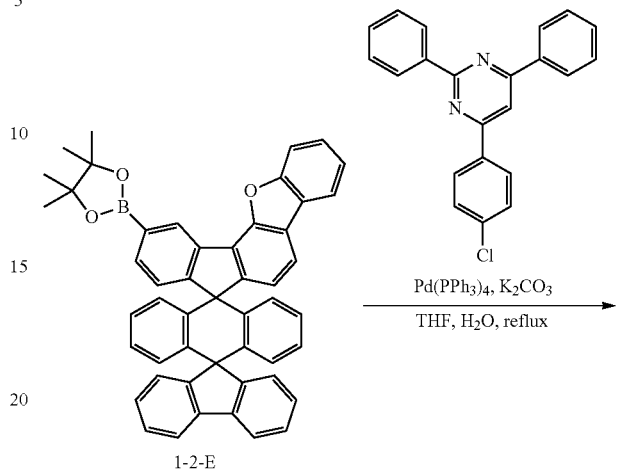

1-2-E

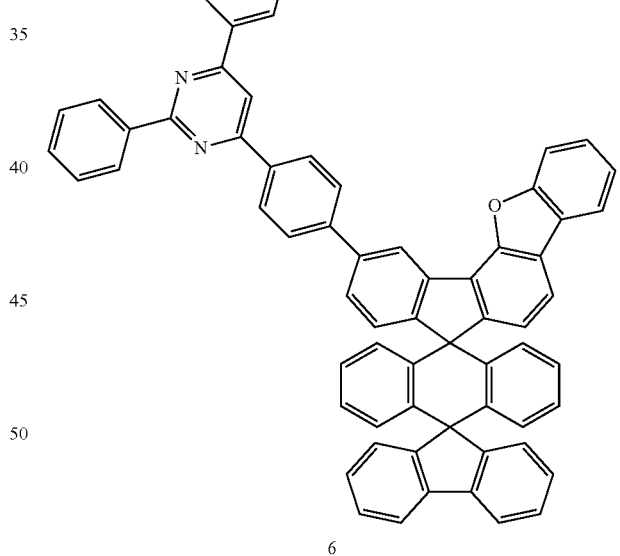

6

Compound 6 was prepared by performing the synthesis in the same manner as in the synthesis of Compound 1, except that 1-2-E was prepared by using Compound 1-2-C instead of Compound 1-1-C, and then 4-(4-chlorophenyl)-2,6-diphenylpyrimidine was used instead of 2-chloro-4,6-diphenyl-1,3,5-triazine.

MS[M+H]$^+$=877.31

Synthesis of Compound 11
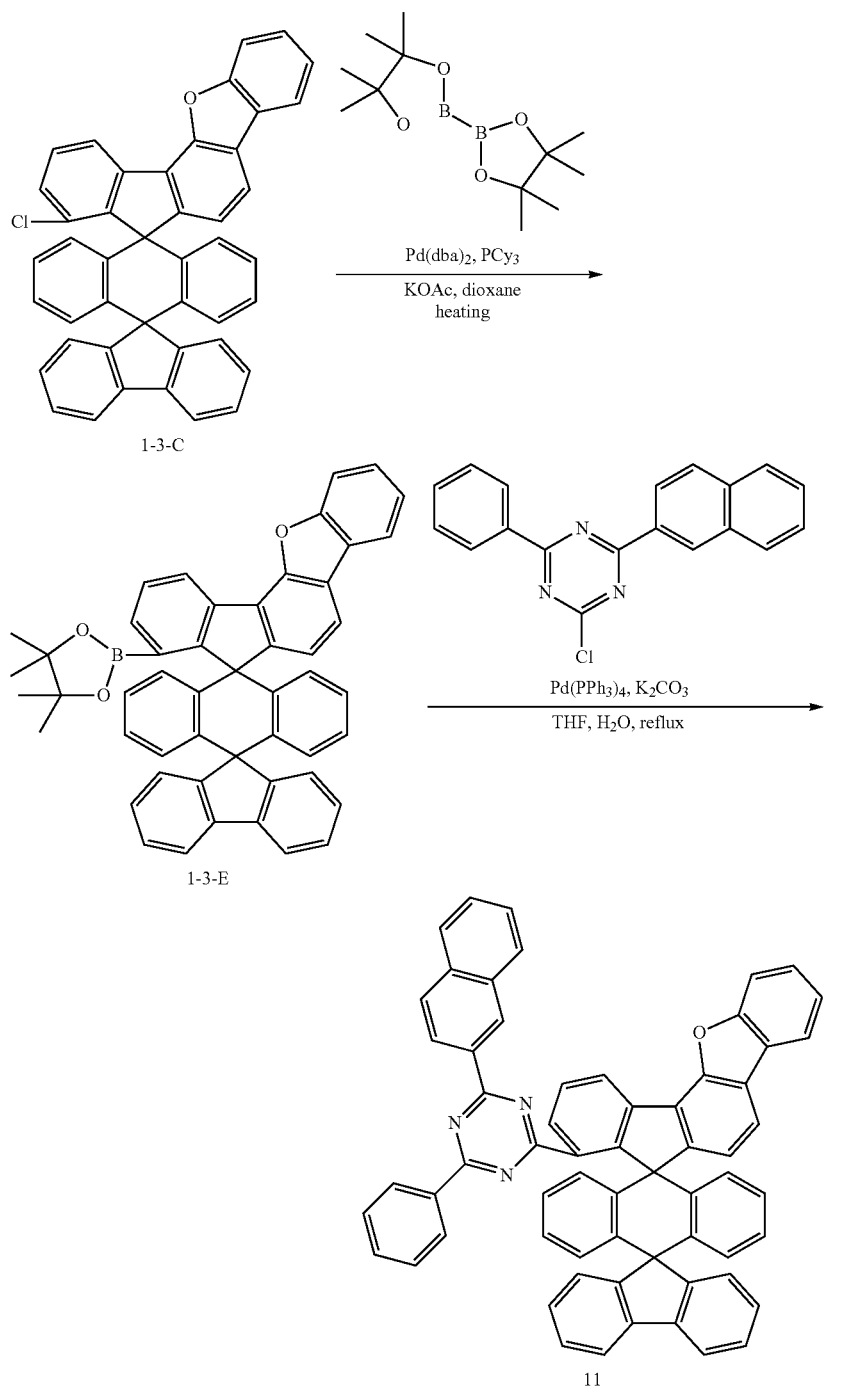
Compound 11 was prepared by performing the synthesis in the same manner as in the synthesis of Compound 1, except that 1-3-E was prepared by using Compound 1-3-C instead of Compound 1-1-C, and then 2-chloro-4-(naphthalen-2-yl)-6-phenyl-1,3,5-triazine was used instead of 2-chloro-4,6-diphenyl-1,3,5-triazine.
MS[M+H]$^+$=852.29

Synthesis of Compound 20
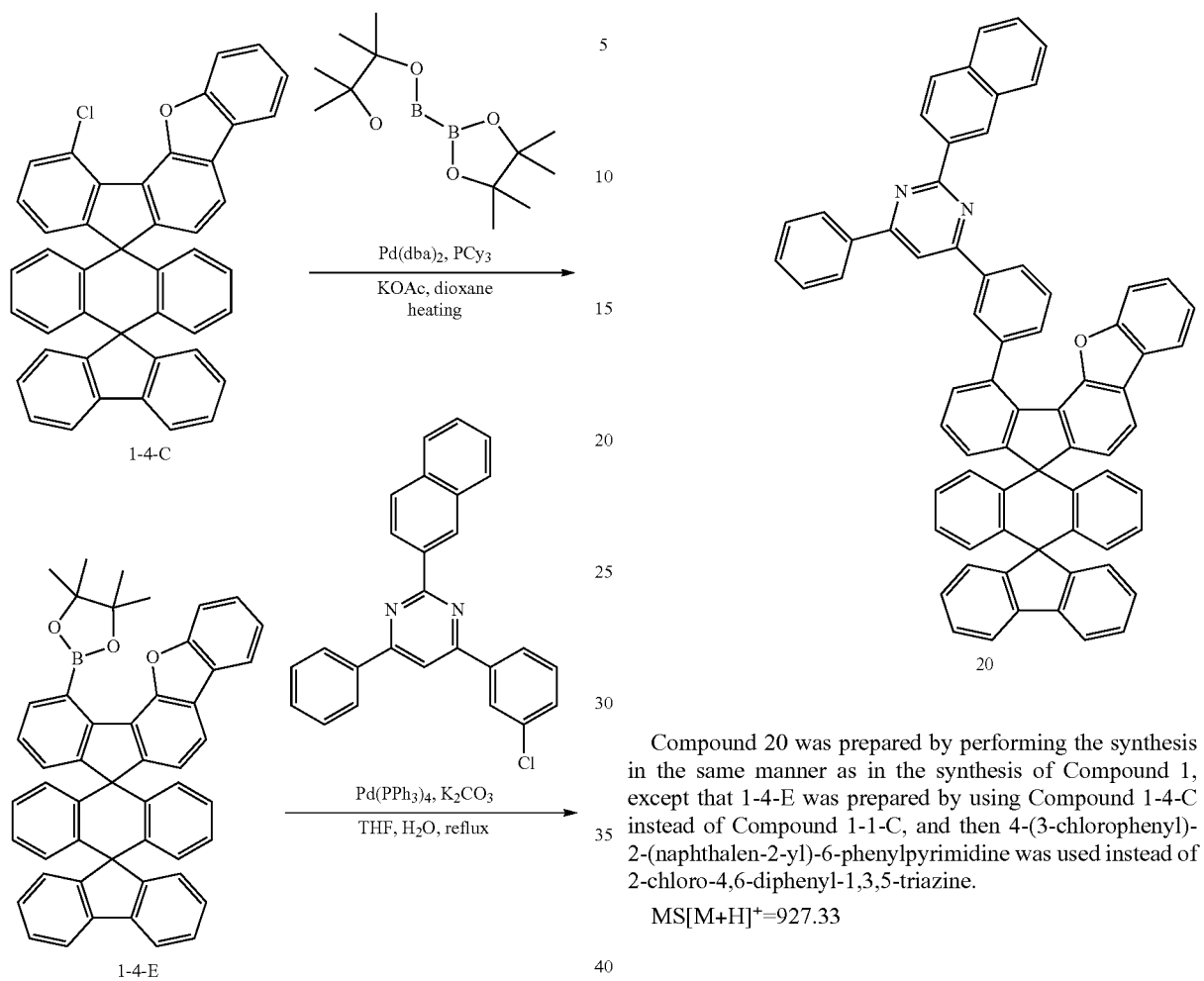
Compound 20 was prepared by performing the synthesis in the same manner as in the synthesis of Compound 1, except that 1-4-E was prepared by using Compound 1-4-C instead of Compound 1-1-C, and then 4-(3-chlorophenyl)-2-(naphthalen-2-yl)-6-phenylpyrimidine was used instead of 2-chloro-4,6-diphenyl-1,3,5-triazine.
MS[M+H]$^+$=927.33
Synthesis of Compound 23
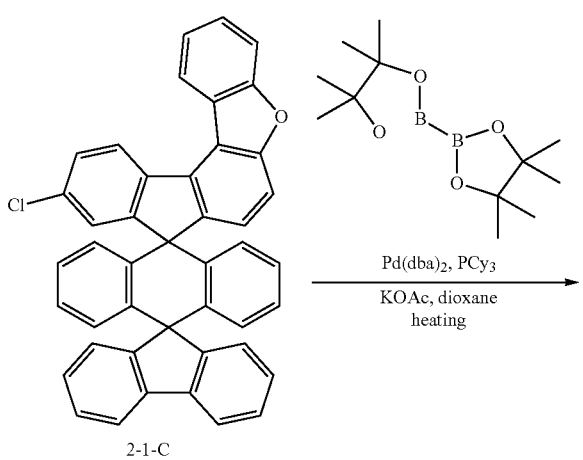

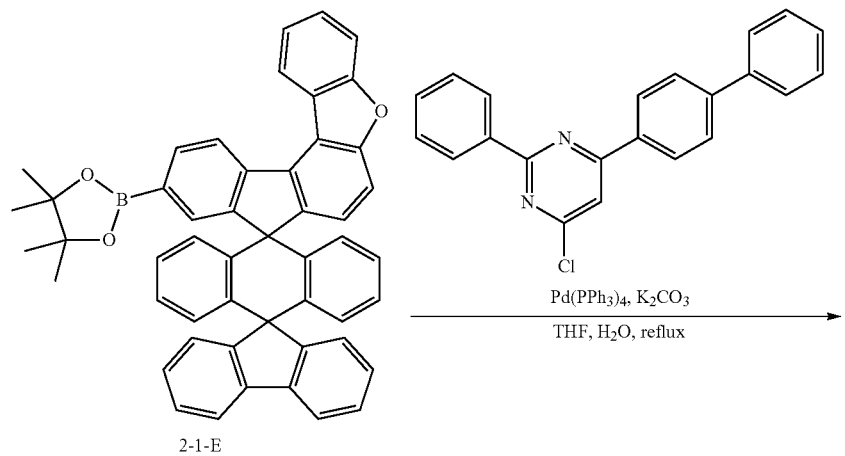
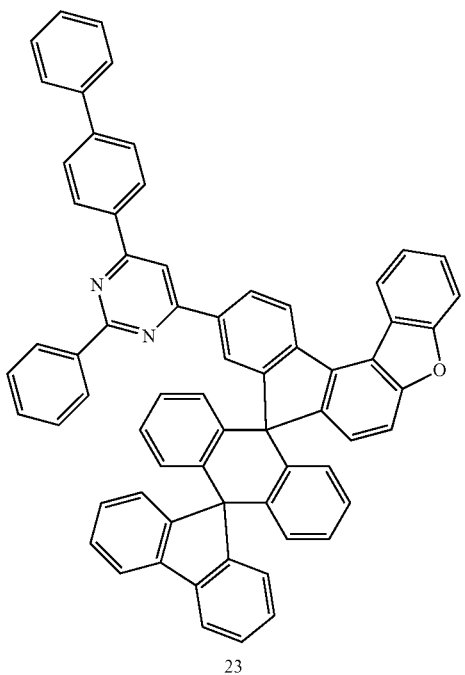
Compound 23 was prepared by performing the synthesis in the same manner as in the synthesis of Compound 1, except that 2-1-E was prepared by using Compound 2-1-C instead of Compound 1-1-C, and then 4-([1,1'-biphenyl]-4-yl-6-chloro-2-phenylpyrimidine was used instead of 2-chloro-4,6-diphenyl-1,3,5-triazine.
MS[M+H]$^+$=877.31

Synthesis of Compound 25

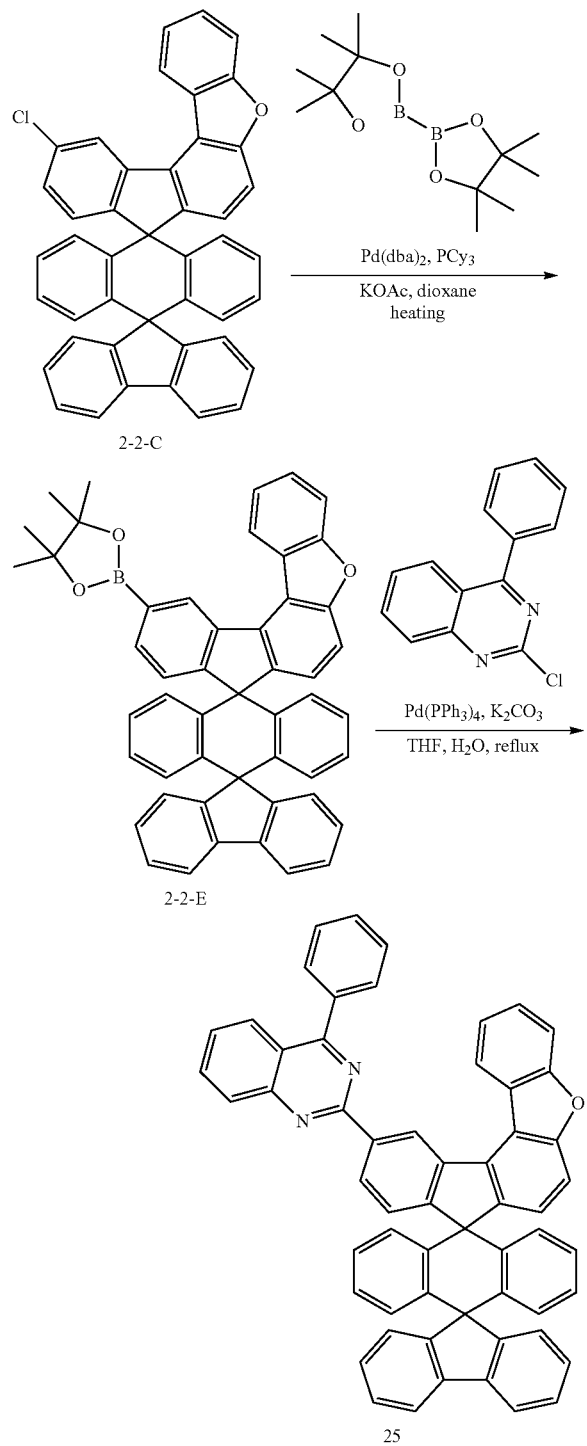

Compound 25 was prepared by performing the synthesis in the same manner as in the synthesis of Compound 1, except that 2-2-E was prepared by using Compound 2-2-C instead of Compound 1-1-C, and then 2-chloro-4-phenylquinazoline was used instead of 2-chloro-4,6-diphenyl-1,3,5-triazine.

MS[M+H]$^+$=775.27

Synthesis of Compound 29

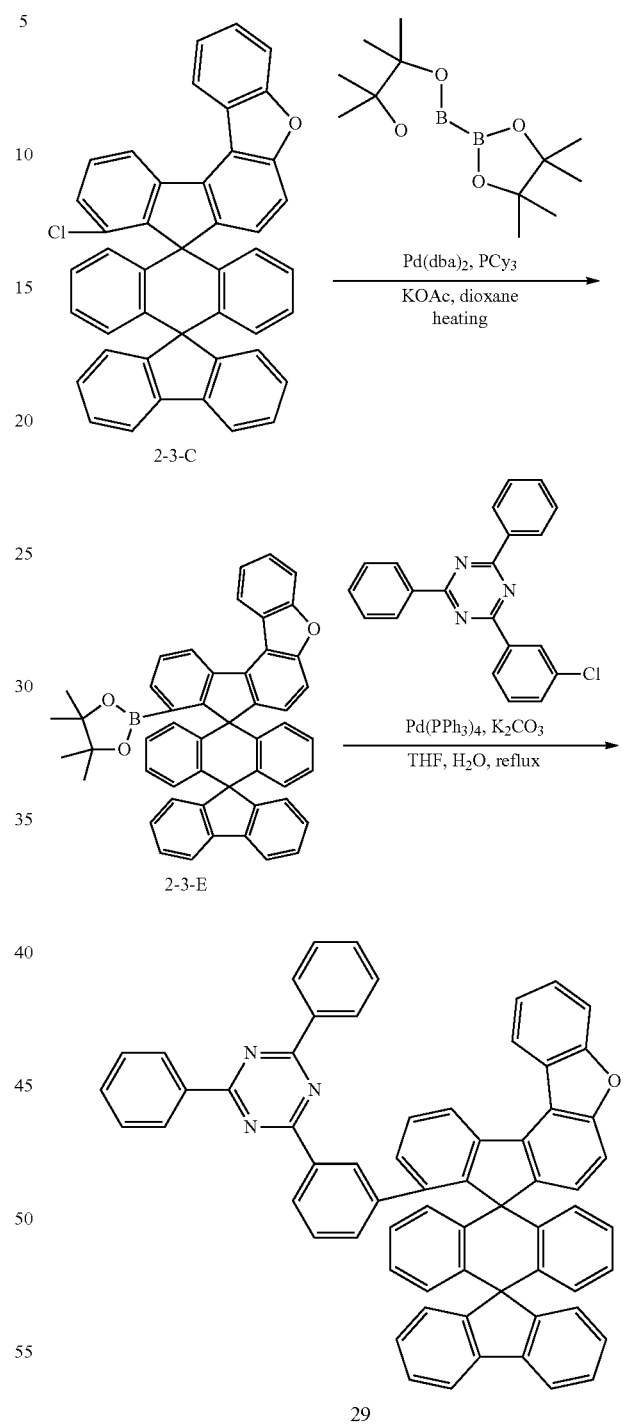

Compound 29 was prepared by performing the synthesis in the same manner as in the synthesis of Compound 1, except that 2-3-E was prepared by using Compound 2-3-C instead of Compound 1-1-C, and then 2-(3-chlorophenyl)-4,6-diphenyl-1,3,5-triazine was used instead of 2-chloro-4,6-diphenyl-1,3,5-triazine.

MS[M+H]$^+$=775.27

Synthesis of Compound 33
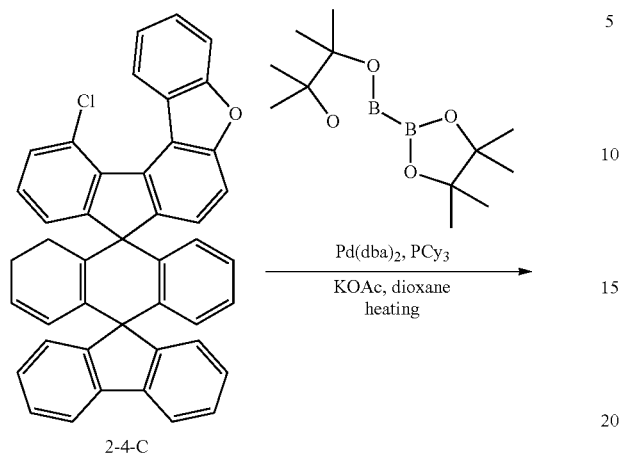
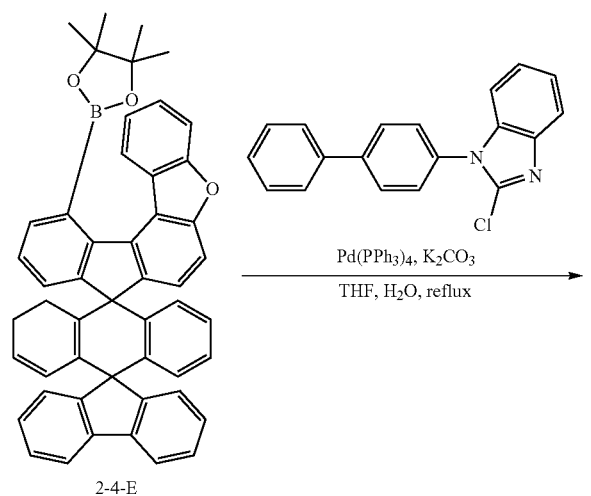
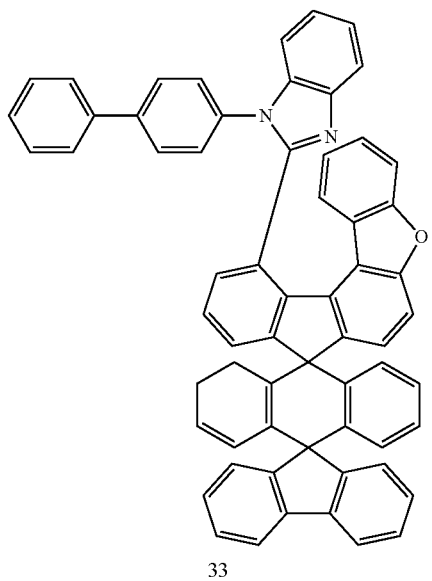
Compound 33 was prepared by performing the synthesis in the same manner as in the synthesis of Compound 1, except that 2-4-E was prepared by using Compound 2-4-C instead of Compound 1-1-C, and then 1-([1,1'-biphenyl]-4-yl)-2-chloro-1H-benzoimidazole was used instead of 2-chloro-4,6-diphenyl-1,3,5-triazine.
MS[M+H]$^+$=841.31
Synthesis of Compound 42
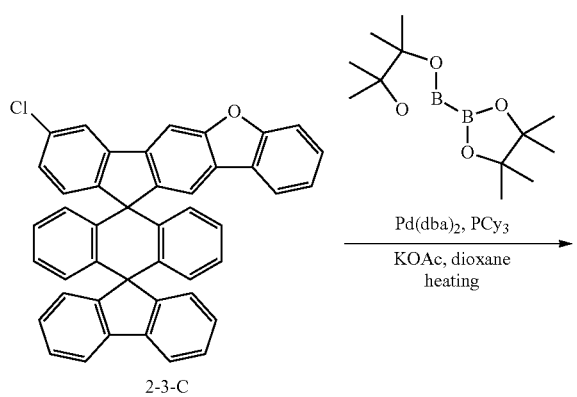

-continued
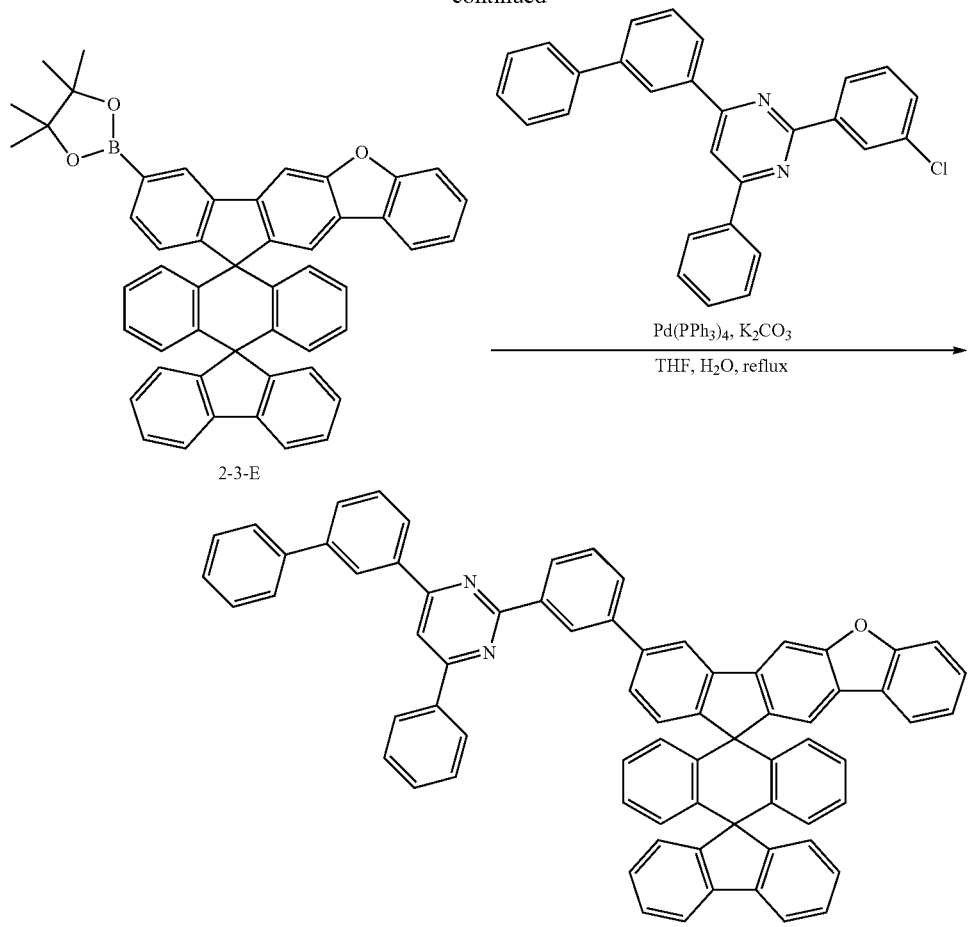
2-3-E
42
Compound 42 was prepared by performing the synthesis in the same manner as in the synthesis of Compound 1, except that 3-2-E was prepared by using Compound 3-2-C instead of Compound 1-1-C, and then 4-([1,1'-biphenyl]-3-yl)-2-(3-chlorophenyl)-6-phenylpyrimidine was used instead of 2-chloro-4,6-diphenyl-1,3,5-triazine.
MS[M+H]$^+$=953.35
Synthesis of Compound 61
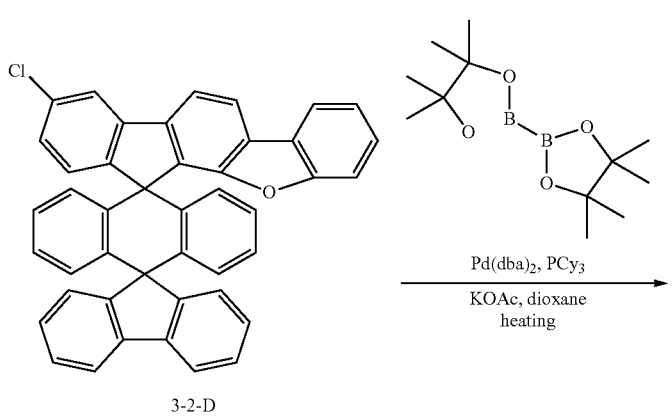
3-2-D -continued

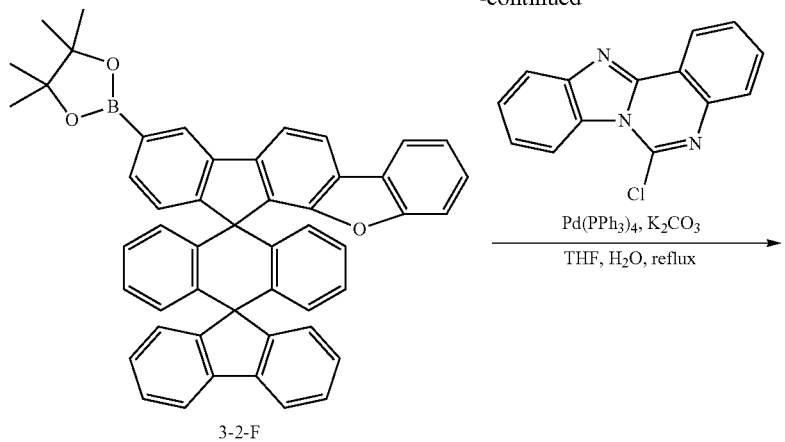

3-2-F

Pd(PPh₃)₄, K₂CO₃
———————————
THF, H₂O, reflux

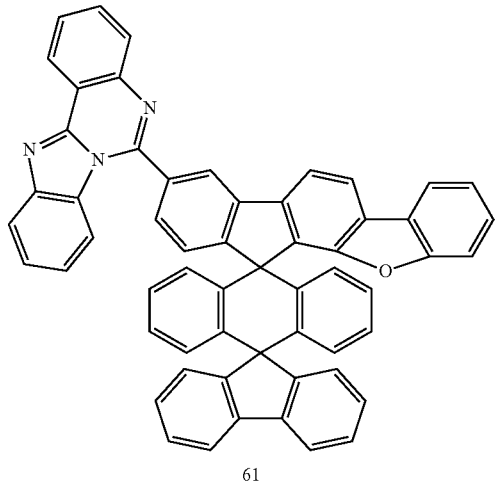

61

Compound 61 was prepared by performing the synthesis in the same manner as in the synthesis of Compound 1, except that 3-2-F was prepared by using Compound 3-2-D instead of Compound 1-1-C, and then 6-chlorobenzo[4,5]imidazo[1,2-c]quinazoline was used instead of 2-chloro-4,6-diphenyl-1,3,5-triazine.

MS[M+H]⁺=788.26

Synthesis of Compound 66

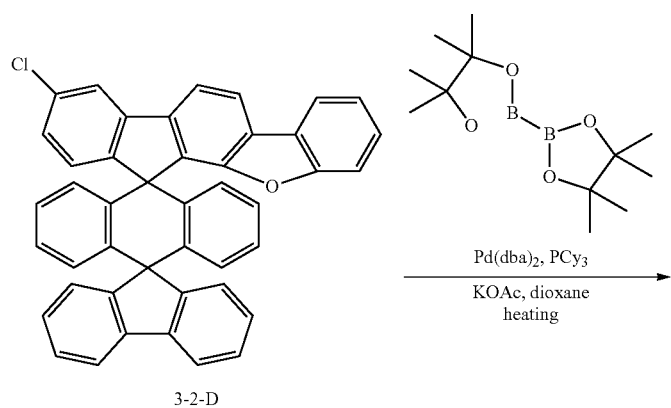

3-2-D

Pd(dba)₂, PCy₃
———————————
KOAc, dioxane
heating

-continued
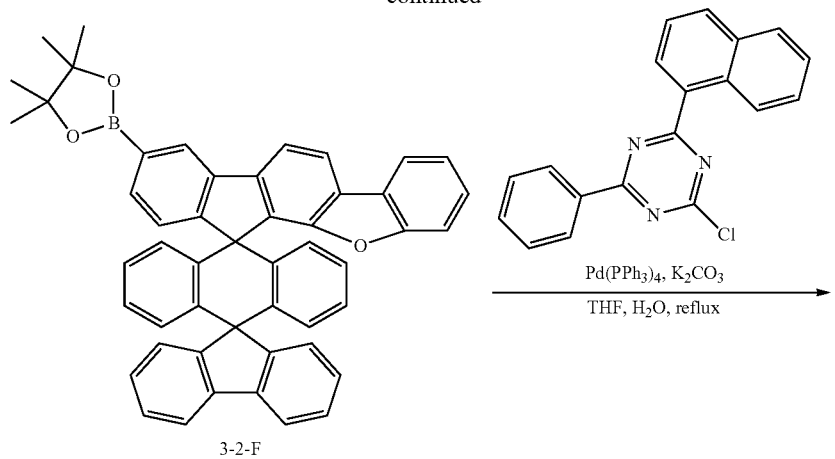
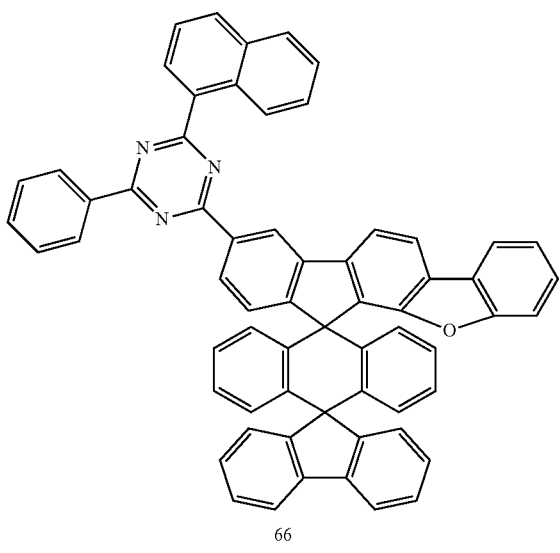
Compound 66 was prepared by performing the synthesis in the same manner as in the synthesis of Compound 1, except that 3-2-F was prepared by using Compound 3-2-D instead of Compound 1-1-C, and then 2-chloro-4-(naphthalen-1-yl)-6-phenyl-1,3,5-triazine was used instead of 2-chloro-4,6-diphenyl-1,3,5-triazine.
MS[M+H]$^+$=852.29
Synthesis of Compound 74
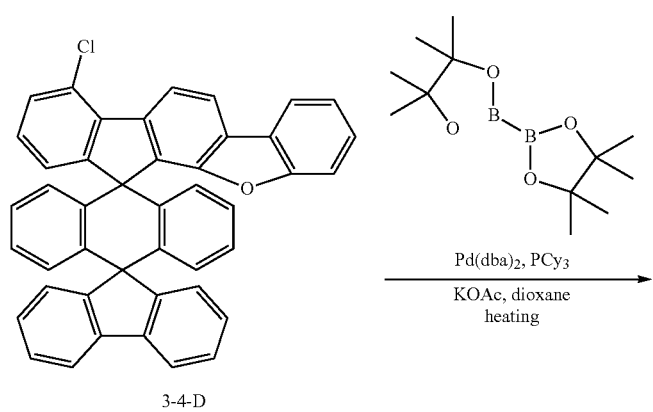

-continued
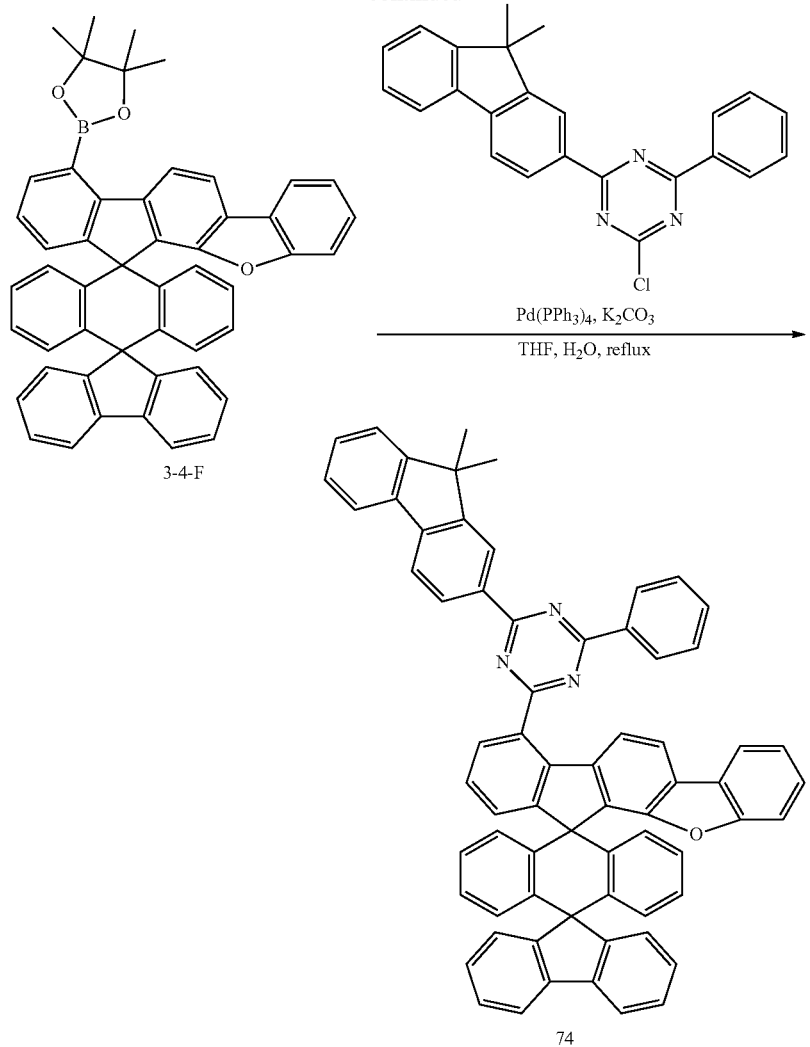
Compound 74 was prepared by performing the synthesis in the same manner as in the synthesis of Compound 1, except that 3-4-F was prepared by using Compound 3-4-D instead of Compound 1-1-C, and then 2-chloro-4-(9,9-dimethyl-9H-fluoren-2-yl)-6-phenyl-1,3,5-triazine was used instead of 2-chloro-4,6-diphenyl-1,3,5-triazine.
MS[M+H]$^+$=918.34
Synthesis of Compound 102
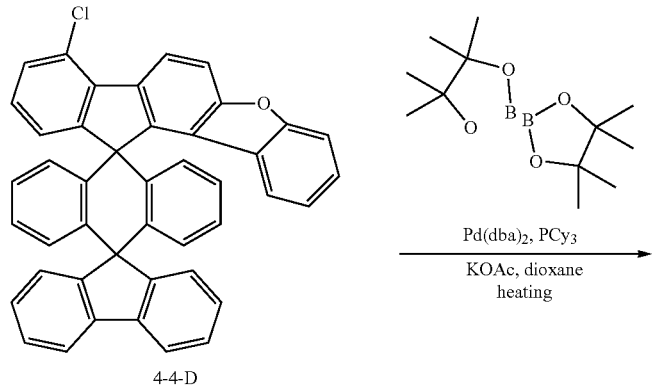

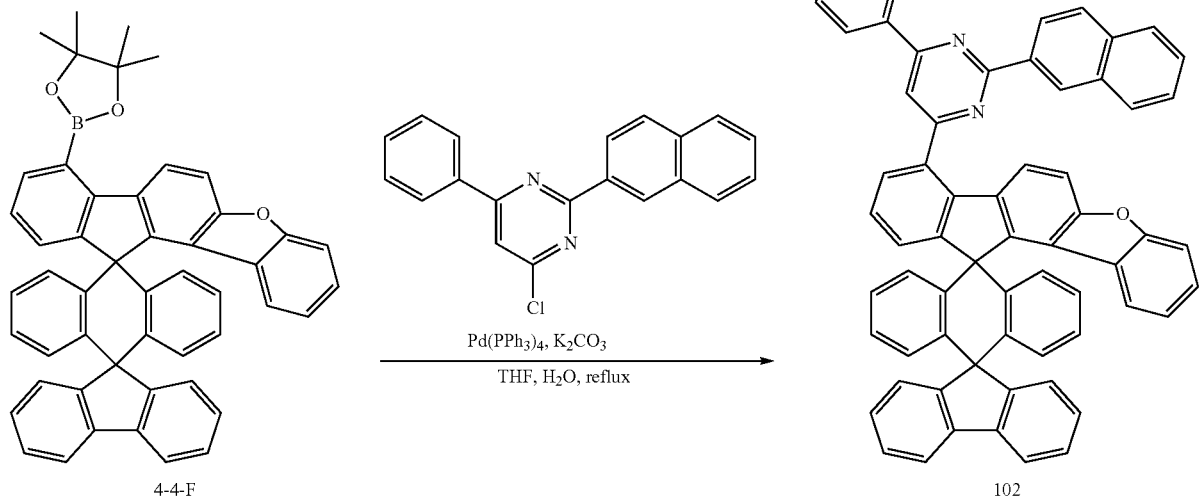
Compound 102 was prepared by performing the synthesis in the same manner as in the synthesis of Compound 1, except that 4-4-F was prepared by using Compound 4-4-D instead of Compound 1-1-C, and then 4-chloro-2-(naphthalen-2-yl)-6-phenylpyrimidine was used instead of 2-chloro-4,6-diphenyl-1,3,5-triazine.
MS[M+H]$^+$=851.30
Synthesis of Compound 106
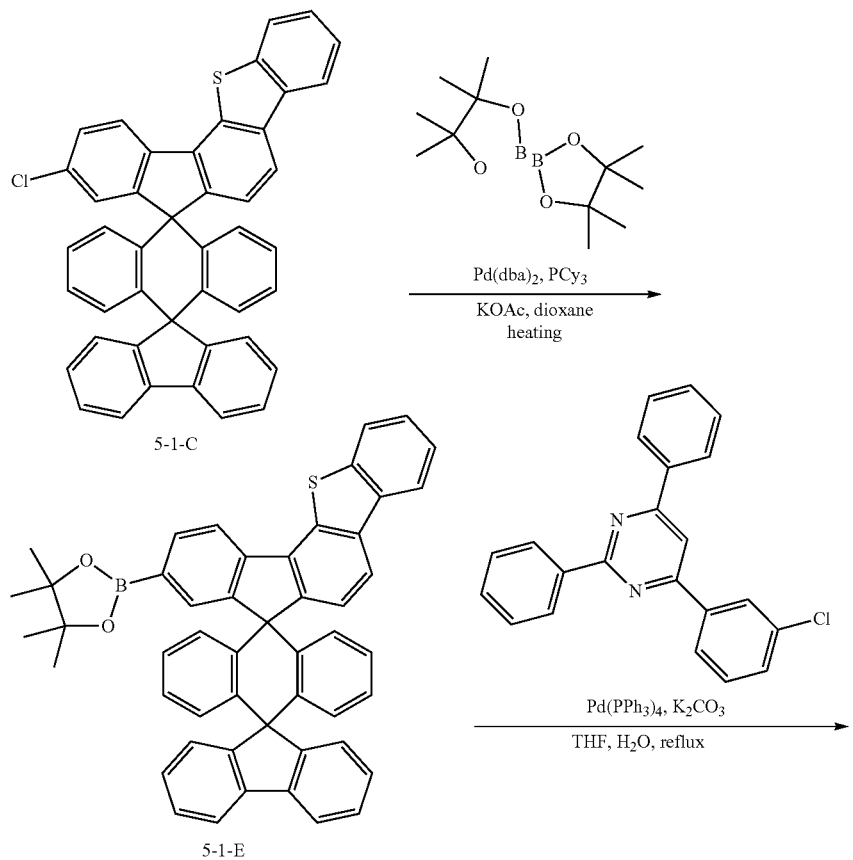

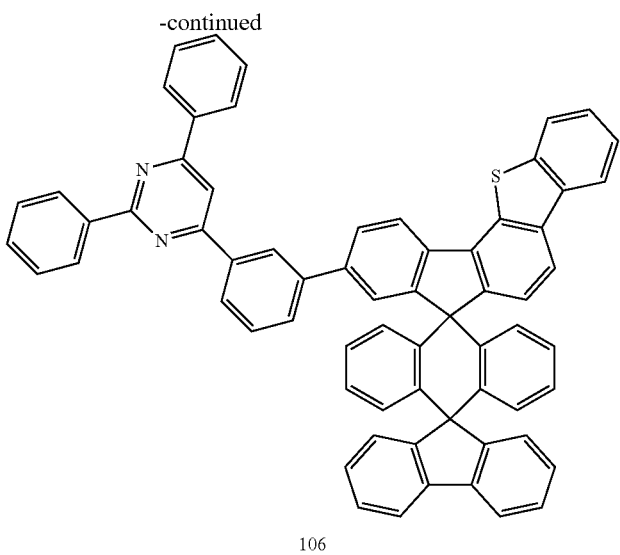

106

Compound 106 was prepared by performing the synthesis in the same manner as in the synthesis of Compound 1, except that 5-1-E was prepared by using Compound 5-1-C instead of Compound 1-1-C, and then 4-(3-chlorophenylyl)-2,6-diphenylpyrimidine was used instead of 2-chloro-4,6-diphenyl-1,3,5-triazine.

MS[M+H]$^+$=894.29

Synthesis of Compound 111

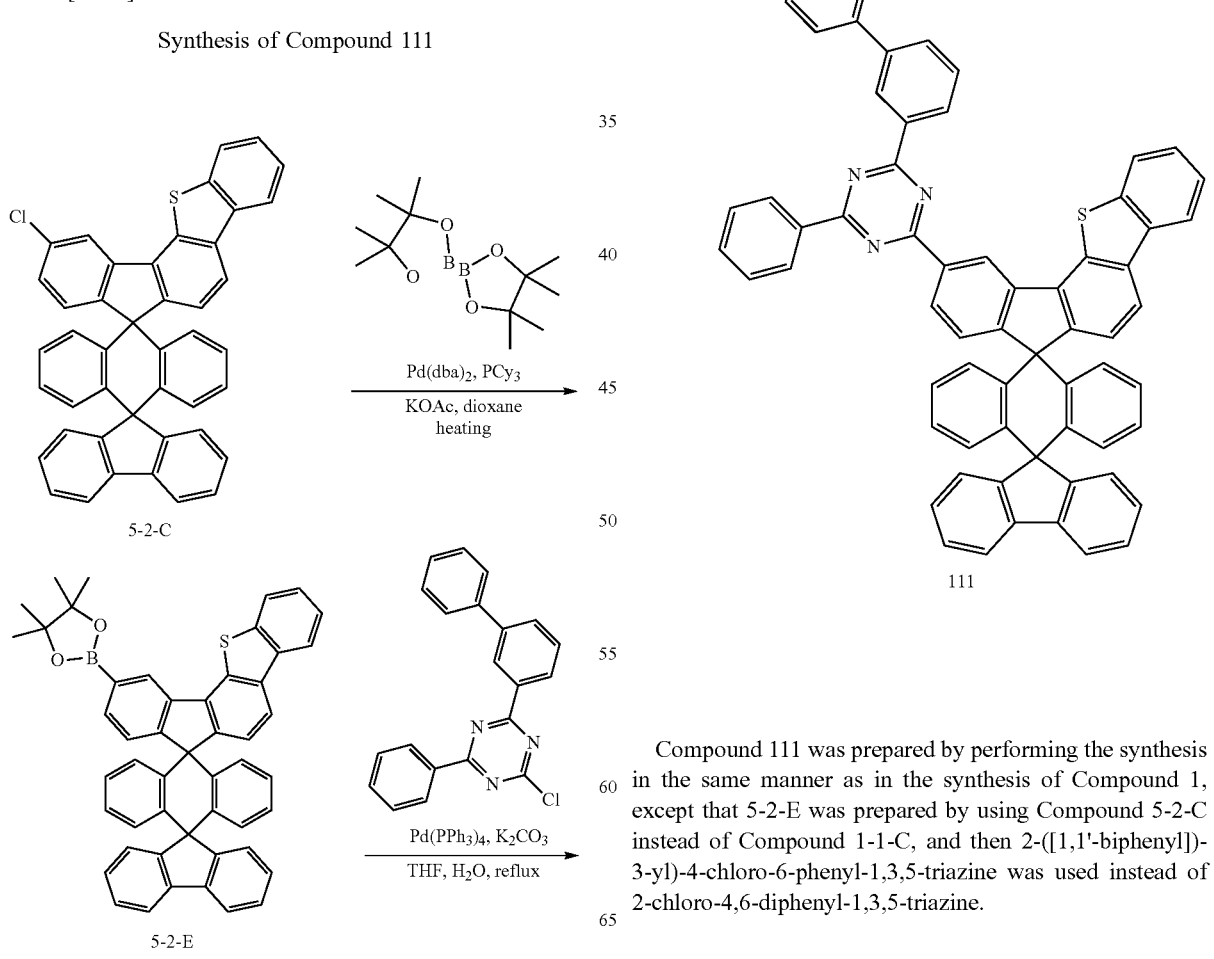

111

Compound 111 was prepared by performing the synthesis in the same manner as in the synthesis of Compound 1, except that 5-2-E was prepared by using Compound 5-2-C instead of Compound 1-1-C, and then 2-([1,1'-biphenyl])-3-yl)-4-chloro-6-phenyl-1,3,5-triazine was used instead of 2-chloro-4,6-diphenyl-1,3,5-triazine.

MS[M+H]$^+$=894.29

Synthesis of Compound 122
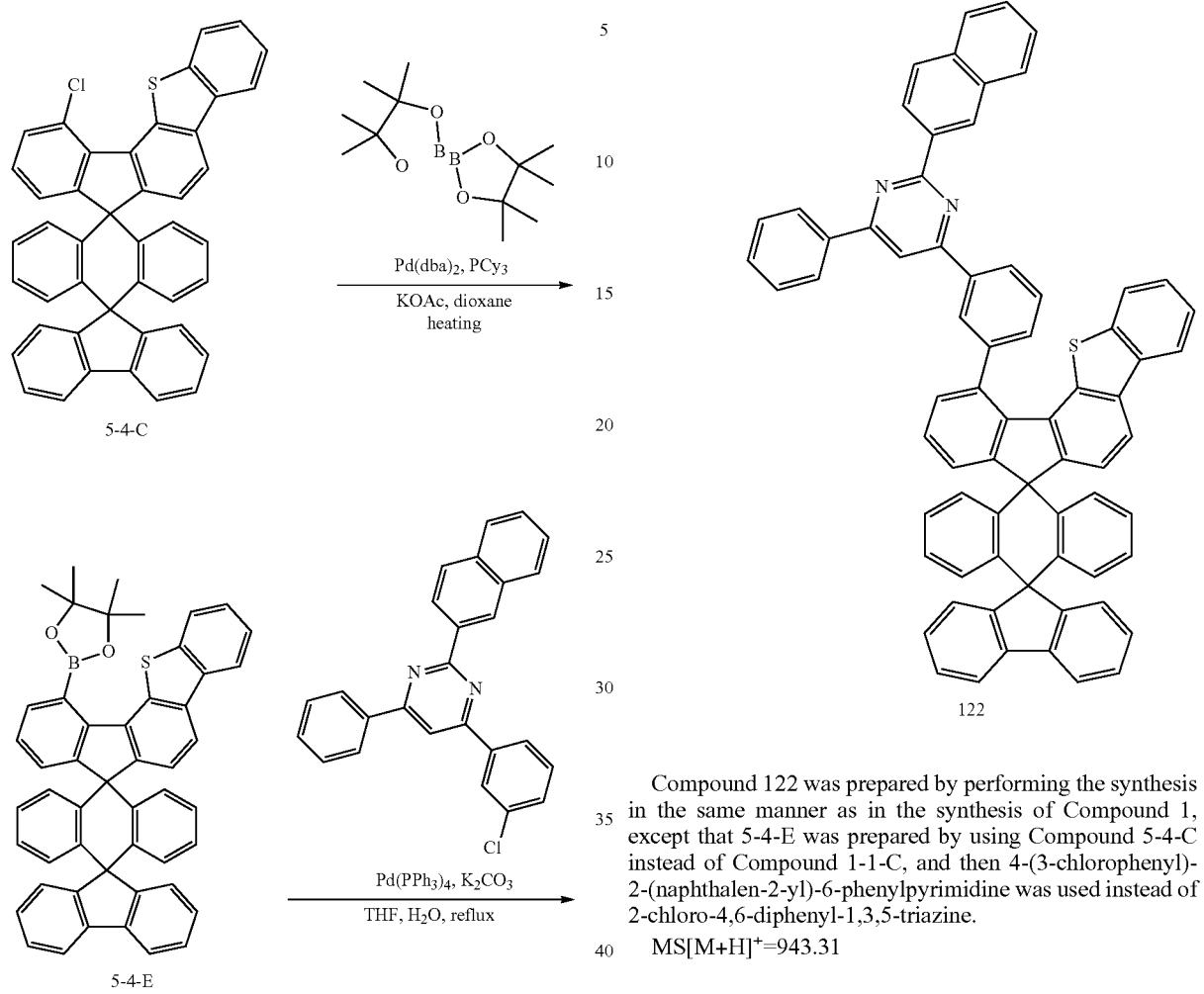
Compound 122 was prepared by performing the synthesis in the same manner as in the synthesis of Compound 1, except that 5-4-E was prepared by using Compound 5-4-C instead of Compound 1-1-C, and then 4-(3-chlorophenyl)-2-(naphthalen-2-yl)-6-phenylpyrimidine was used instead of 2-chloro-4,6-diphenyl-1,3,5-triazine.
MS[M+H]$^+$=943.31
Synthesis of Compound 148
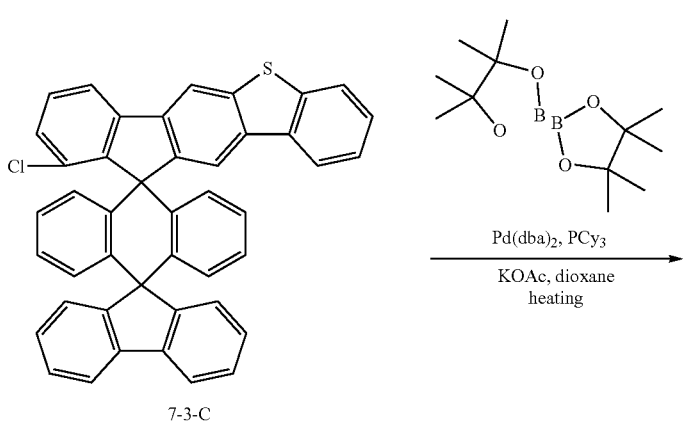

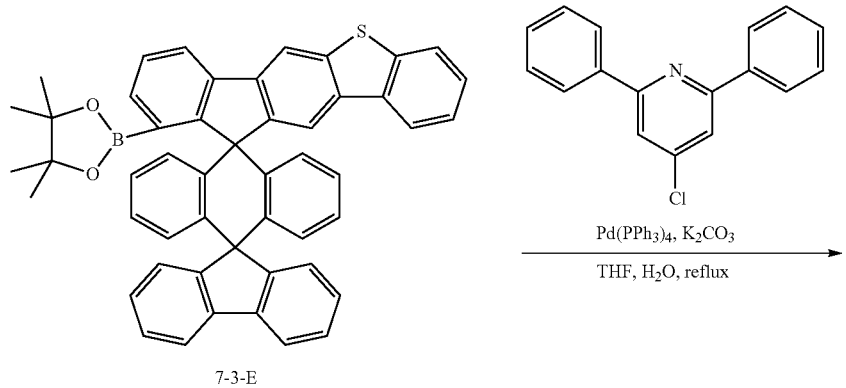
7-3-E
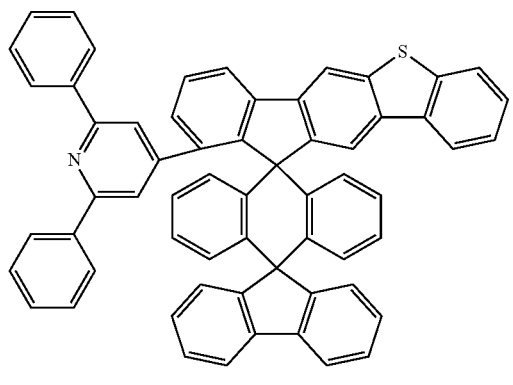
148
Compound 148 was prepared by performing the synthesis in the same manner as in the synthesis of Compound 1, except that 7-3-E was prepared by using Compound 7-3-C instead of Compound 1-1-C, and then 4-chloro-2,6-diphenylpyridine was used instead of 2-chloro-4,6-diphenyl-1,3,5-triazine.
MS[M+H]$^+$=816.26
Synthesis of Compound 152
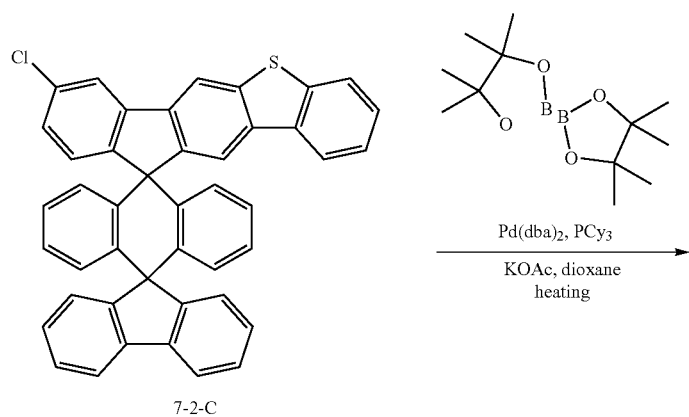
7-2-C -continued
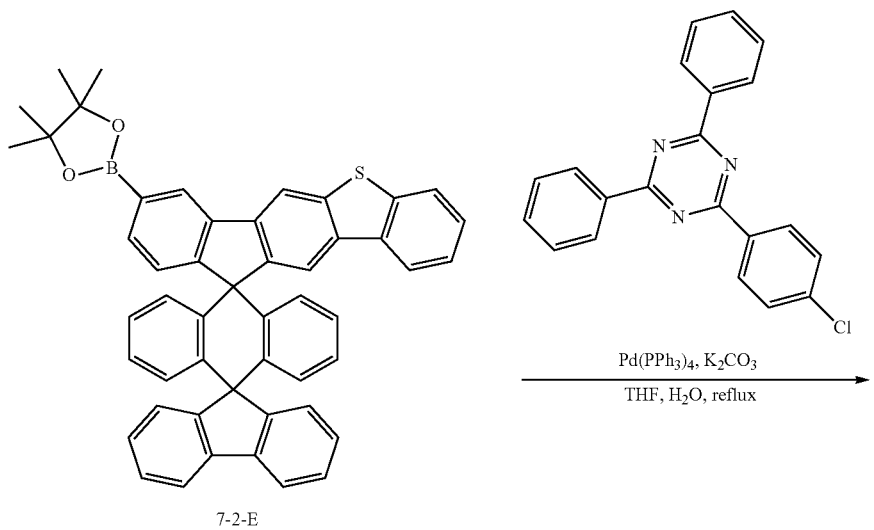
7-2-E
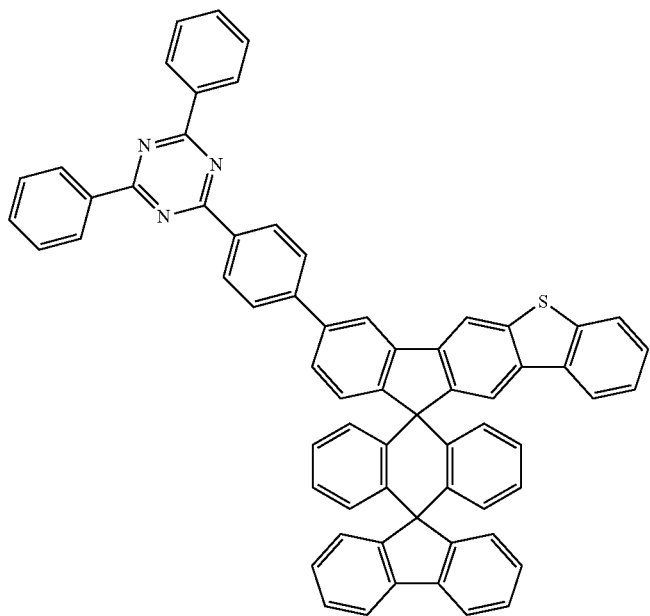
152
Compound 152 was prepared by performing the synthesis in the same manner as in the synthesis of Compound 1, except that 7-2-E was prepared by using Compound 7-2-C instead of Compound 1-1-C, and then 2-(4-chlorophenyl)-4,6-diphenyl-1,3,5-triazine was used instead of 2-chloro-4,6-diphenyl-1,3,5-triazine.
MS[M+H]$^+$=894.29

Synthesis of Compound 179
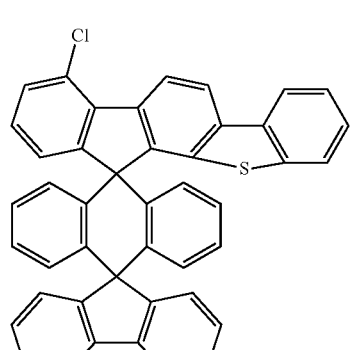
7-4-D
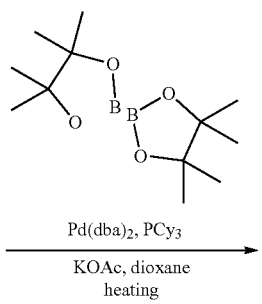
Pd(dba)₂, PCy₃
KOAc, dioxane
heating
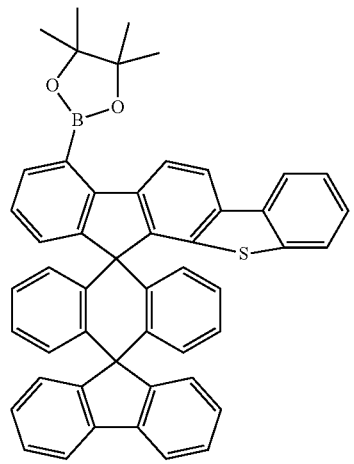
7-4-F
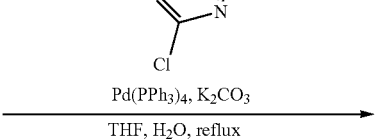
Pd(PPh₃)₄, K₂CO₃
THF, H₂O, reflux
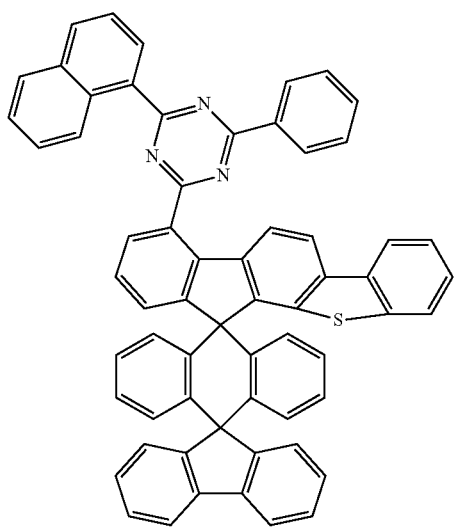
179
Compound 179 was prepared by performing the synthesis in the same manner as in the synthesis of Compound 1, except that 7-4-F was prepared by using Compound 7-4-D instead of Compound 1-1-C, and then 2-chloro-4-(naphthalen-1-yl)-6-phenyl-1,3,5-triazine was used instead of 2-chloro-4,6-diphenyl-1,3,5-triazine.
MS[M+H]⁺=868.27

Synthesis of Compound 180
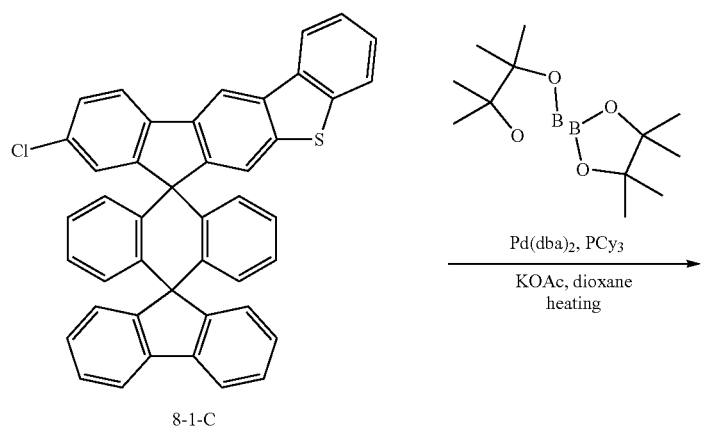
8-1-C
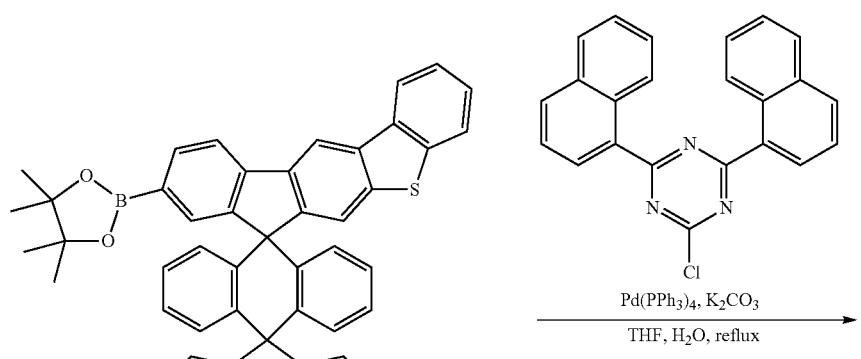
8-1-E
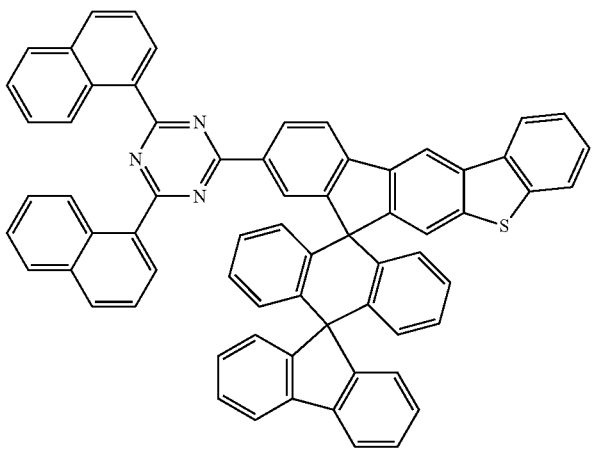
180
Compound 180 was prepared by performing the synthesis in the same manner as in the synthesis of Compound 1, except that 8-1-E was prepared by using Compound 8-1-C instead of Compound 1-1-C, and then 2-chloro-4,6-di(naphthalen-1-yl)-1,3,5-triazine was used instead of 2-chloro-4,6-diphenyl-1,3,5-triazine.
$MS[M+H]^+=918.29$ Synthesis of Compound 195
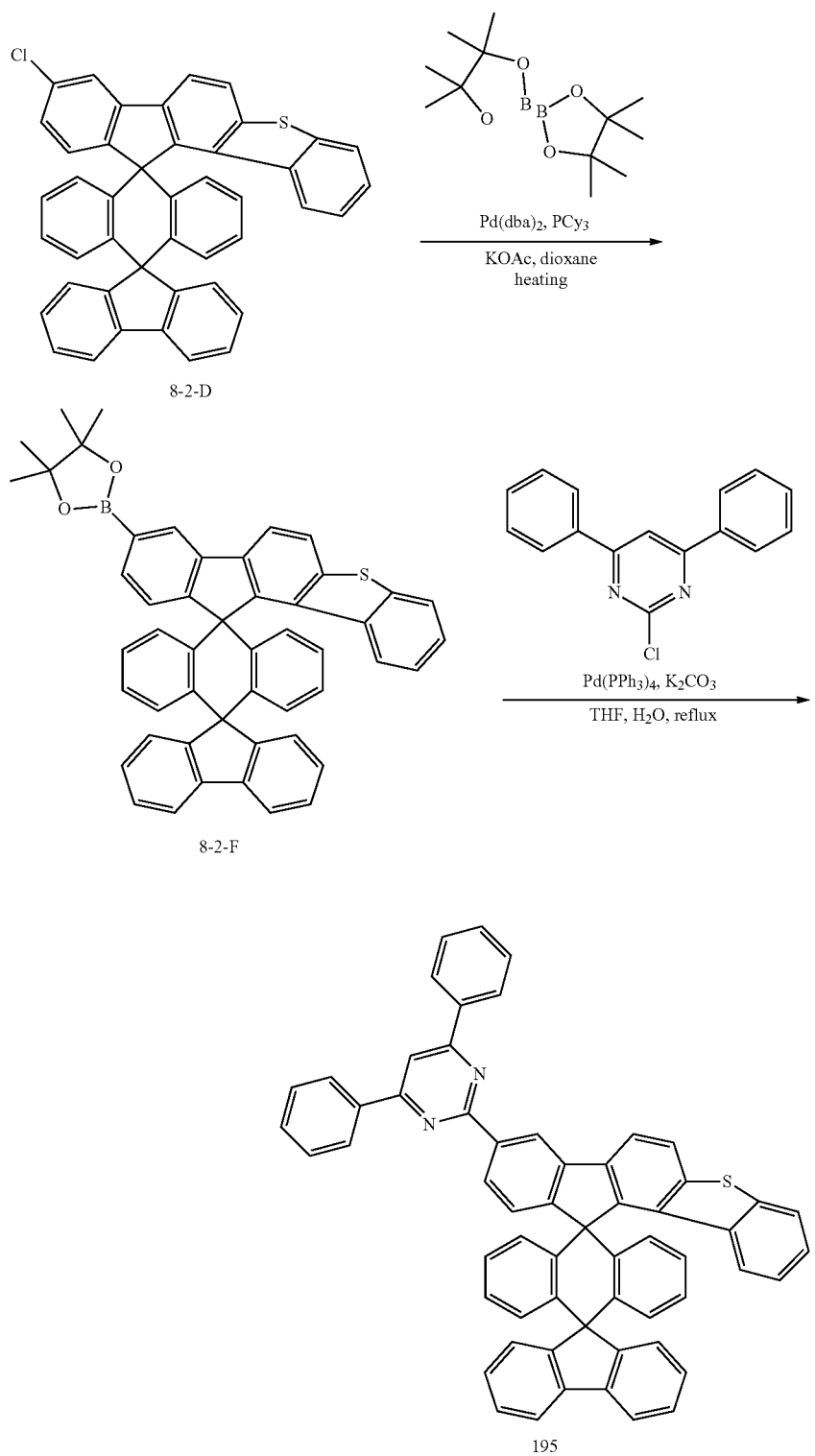
Compound 195 was prepared by performing the synthesis in the same manner as in the synthesis of Compound 1, except that 8-2-F was prepared by using Compound 8-2-D instead of Compound 1-1-C, and then 2-chloro-4,6-diphenylpyrimidine was used instead of 2-chloro-4,6-diphenyl-1,3,5-triazine.
MS[M+H]$^+$=817.26

Synthesis of Compound 201
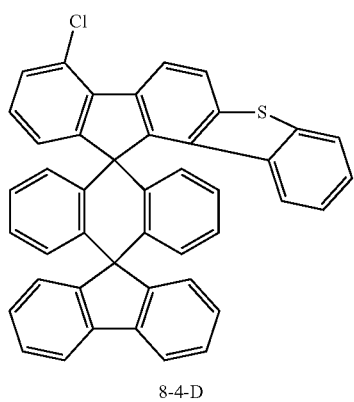
8-4-D
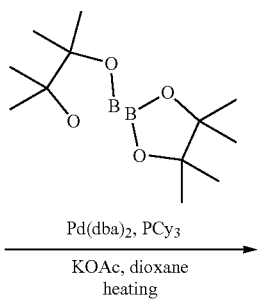
Pd(dba)₂, PCy₃
KOAc, dioxane
heating
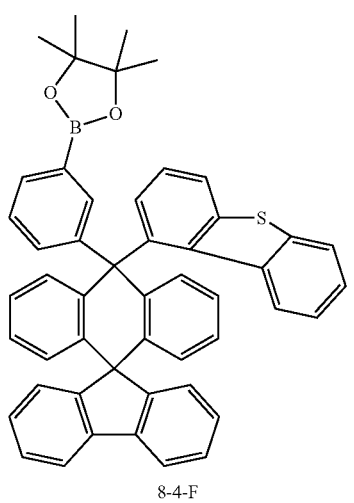
8-4-F
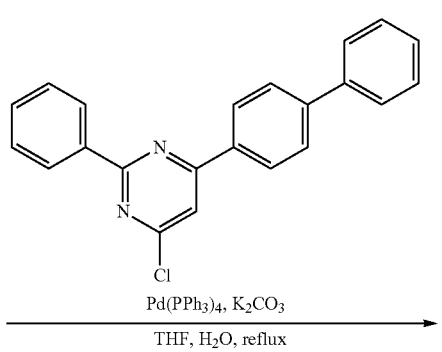
Pd(PPh₃)₄, K₂CO₃
THF, H₂O, reflux
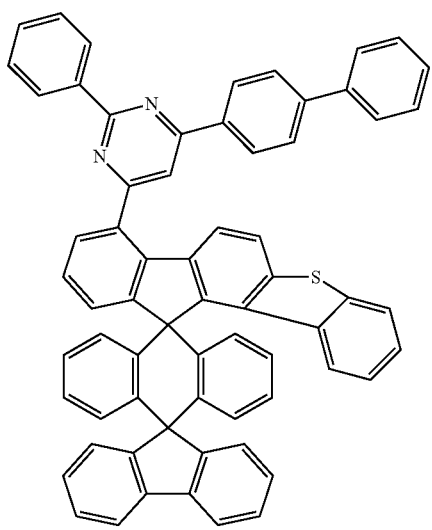
201

Compound 201 was prepared by performing the synthesis in the same manner as in the synthesis of Compound 1, except that 8-4-F was prepared by using Compound 8-4-D instead of Compound 1-1-C, and then 4-([1,1'-biphenyl]-4-yl)-6-chloro-2-phenylpyrimidine was used instead of 2-chloro-4,6-diphenyl-1,3,5-triazine.

MS[M+H]$^+$=893.29

Example 1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

Hexanitrile hexaazatriphenylene (HAT) of the following Chemical Formula was thermally vacuum deposited to have a thickness of 500 Å on the transparent ITO electrode, which was thus prepared, thereby forming a hole injection layer.

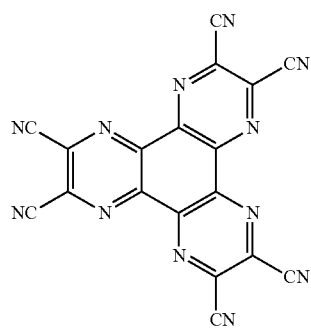

[HAT]

The following compound 4-4'-bis[N-(1-naphthyl)-N-phenylamino]biphenyl (NPB) (400 Å), which is a material for transporting holes, was vacuum deposited on the hole injection layer, thereby forming a hole transport layer.

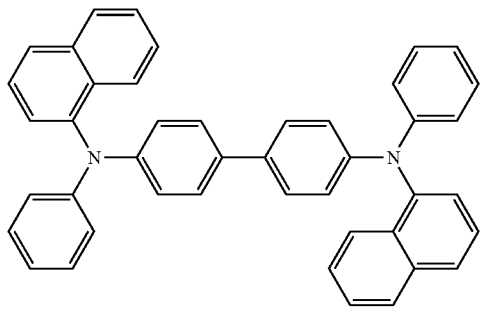

[NPB]

Subsequently, the following BH and BD were vacuum deposited at a weight ratio of 25:1 to have a film thickness of 300 Å on the hole transport layer, thereby forming a light emitting layer.

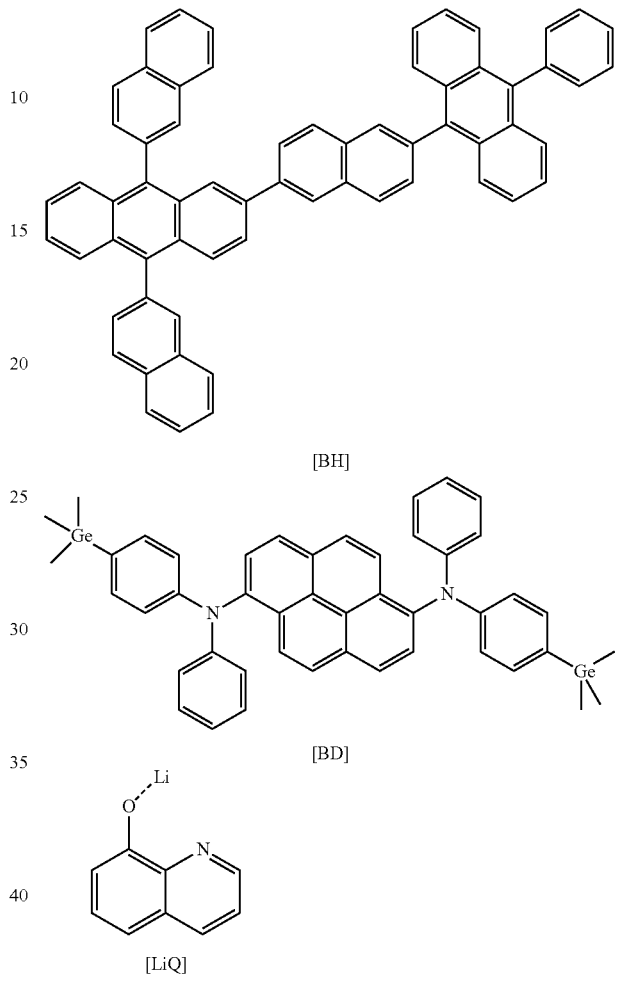

[BH]

[BD]

[LiQ]

Compound 1 prepared in the Preparation Example and Compound LiQ (lithium quinolate) were vacuum deposited at a weight ratio of 1:1 on the light emitting layer, thereby forming an electron injection and transport layer having a thickness of 300 Å. Lithium fluoride (LiF) and aluminum were sequentially deposited to have a thickness of 12 Å and 2,000 Å, respectively, on the electron injection and transport layer, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at 2×10-7 to 5×10-6 torr, thereby manufacturing an organic light emitting device.

Example 2

An organic light emitting device was manufactured in the same manner as in Example 1, except that Compound 6 was used instead of Compound 1 in Example 1.

Example 3

An organic light emitting device was manufactured in the same manner as in Example 1, except that Compound 11 was used instead of Compound 1 in Example 1.

Example 4

An organic light emitting device was manufactured in the same manner as in Example 1, except that Compound 20 was used instead of Compound 1 in Example 1.

Example 5

An organic light emitting device was manufactured in the same manner as in Example 1, except that Compound 23 was used instead of Compound 1 in Example 1.

Example 6

An organic light emitting device was manufactured in the same manner as in Example 1, except that Compound 25 was used instead of Compound 1 in Example 1.

Example 7

An organic light emitting device was manufactured in the same manner as in Example 1, except that Compound 29 was used instead of Compound 1 in Example 1.

Example 8

An organic light emitting device was manufactured in the same manner as in Example 1, except that Compound 33 was used instead of Compound 1 in Example 1.

Example 9

An organic light emitting device was manufactured in the same manner as in Example 1, except that Compound 42 was used instead of Compound 1 in Example 1.

Example 10

An organic light emitting device was manufactured in the same manner as in Example 1, except that Compound 61 was used instead of Compound 1 in Example 1.

Example 11

An organic light emitting device was manufactured in the same manner as in Example 1, except that Compound 66 was used instead of Compound 1 in Example 1.

Example 12

An organic light emitting device was manufactured in the same manner as in Example 1, except that Compound 74 was used instead of Compound 1 in Example 1.

Example 13

An organic light emitting device was manufactured in the same manner as in Example 1, except that Compound 102 was used instead of Compound 1 in Example 1.

Example 14

An organic light emitting device was manufactured in the same manner as in Example 1, except that Compound 106 was used instead of Compound 1 in Example 1.

Example 15

An organic light emitting device was manufactured in the same manner as in Example 1, except that Compound 111 was used instead of Compound 1 in Example 1.

Example 16

An organic light emitting device was manufactured in the same manner as in Example 1, except that Compound 122 was used instead of Compound 1 in Example 1.

Example 17

An organic light emitting device was manufactured in the same manner as in Example 1, except that Compound 148 was used instead of Compound 1 in Example 1.

Example 18

An organic light emitting device was manufactured in the same manner as in Example 1, except that Compound 152 was used instead of Compound 1 in Example 1.

Example 19

An organic light emitting device was manufactured in the same manner as in Example 1, except that Compound 179 was used instead of Compound 1 in Example 1.

Example 20

An organic light emitting device was manufactured in the same manner as in Example 1, except that Compound 180 was used instead of Compound 1 in Example 1.

Example 21

An organic light emitting device was manufactured in the same manner as in Example 1, except that Compound 195 was used instead of Compound 1 in Example 1.

Example 22

An organic light emitting device was manufactured in the same manner as in Example 1, except that Compound 201 was used instead of Compound 1 in Example 1.

Comparative Example 1

An organic light emitting device was manufactured in the same manner as in Example 1, except that a compound of the following ET1 was used instead of Compound 1 in Example 1.

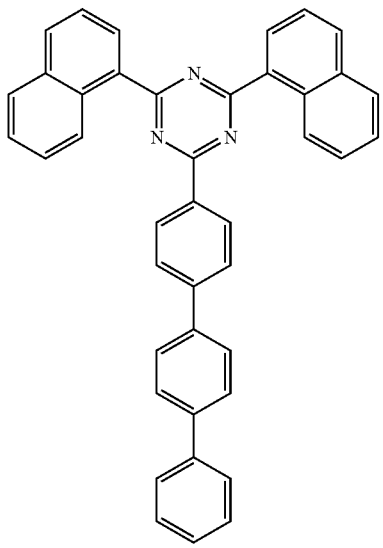

[ET1]

Comparative Example 2

An organic light emitting device was manufactured in the same manner as in Example 1, except that a compound of the following ET2 was used instead of Compound 1 in Example 1.

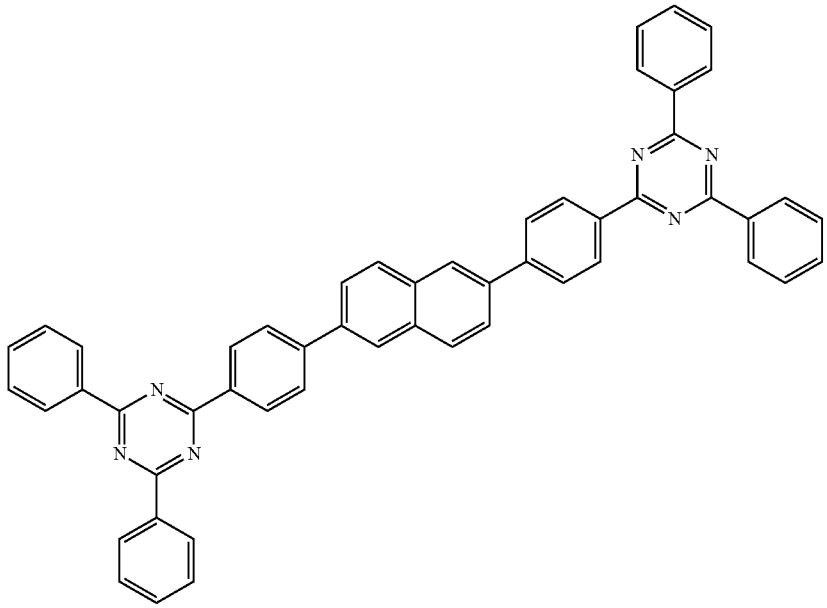

[ET2]

Comparative Example 3

An organic light emitting device was manufactured in the same manner as in Example 1, except that a compound of the following ET3 was used instead of Compound 1 in Example 1.

[ET3]

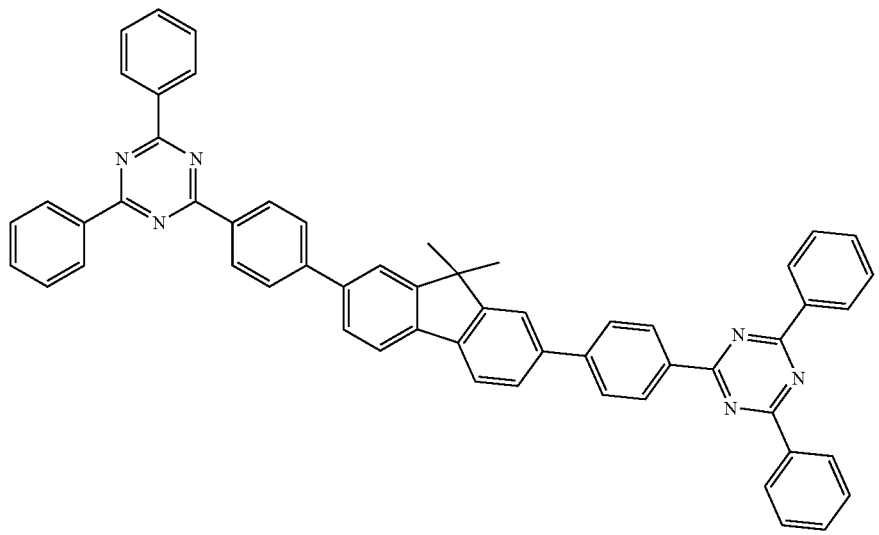

Comparative Example 4

An organic light emitting device was manufactured in the same manner as in Example 1, except that a compound of the following ET4 was used instead of Compound 1 in Example 1.

[ET4]

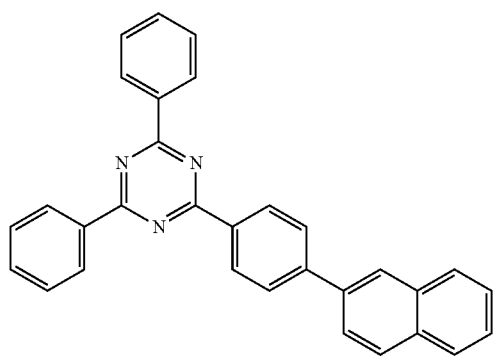

When current was applied to the organic light emitting devices manufactured in Experimental Examples 1 to 22 and Comparative Examples 1 to 4, the results of Table 1 were obtained.

TABLE 1

| | Electron transport layer material | Voltage (V@10 mA/ $cm^2$) | Efficiency (cd/A@10 mA/ $cm^2$) | Color coordinate (x, y) |
|---|---|---|---|---|
| Experimental Example 1 | Compound 1 | 3.98 | 4.23 | (0.138, 0.127) |
| Experimental Example 2 | Compound 6 | 3.75 | 5.15 | (0.139, 0.122) |
| Example 3 | Compound 11 | 3.86 | 5.04 | (0.138, 0.126) |
| Example 4 | Compound 20 | 3.85 | 5.51 | (0.138, 0.127) |
| Example 5 | Compound 23 | 3.77 | 5.22 | (0.137, 0.125) |
| Example 6 | Compound 25 | 3.83 | 5.18 | (0.136, 0.127) |
| Example 7 | Compound 29 | 3.82 | 5.14 | (0.136, 0.127) |
| Example 8 | Compound 33 | 3.84 | 5.27 | (0.136, 0.125) |
| Example 9 | Compound 42 | 3.83 | 5.52 | (0.138, 0.127) |
| Example 10 | Compound 61 | 3.74 | 5.33 | (0.139, 0.122) |
| Example 11 | Compound 66 | 3.85 | 5.12 | (0.138, 0.126) |
| Example 12 | Compound 74 | 3.83 | 5.35 | (0.138, 0.127) |
| Example 13 | Compound 102 | 3.85 | 5.30 | (0.137, 0.125) |
| Example 14 | Compound 106 | 3.83 | 5.52 | (0.136, 0.127) |
| Example 15 | Compound 111 | 3.71 | 5.33 | (0.136, 0.127) |
| Example 16 | Compound 122 | 3.73 | 5.11 | (0.136, 0.125) |
| Example 17 | Compound 148 | 3.84 | 5.22 | (0.138, 0.127) |
| Example 18 | Compound 152 | 3.85 | 5.31 | (0.139, 0.122) |
| Example 19 | Compound 179 | 3.73 | 5.34 | (0.138, 0.126) |

TABLE 1-continued

| | Electron transport layer material | Voltage (V@10 mA/ cm$^2$) | Efficiency (cd/A@10 mA/ cm$^2$) | Color coordinate (x, y) |
|---|---|---|---|---|
| Example 20 | Compound 180 | 3.74 | 5.12 | (0.138, 0.127) |
| Example 21 | Compound 195 | 3.82 | 5.23 | (0.137, 0.125) |
| Example 22 | Compound 201 | 3.81 | 5.31 | (0.136, 0.127) |
| Comparative Example 1 | ET1 | 4.02 | 3.95 | (0.136, 0.127) |
| Comparative Example 2 | ET2 | 4.13 | 3.87 | (0.136, 0.125) |
| Comparative Example 3 | ET3 | 4.05 | 4.01 | (0.135, 0.125) |
| Comparative Example 4 | ET4 | 4.07 | 3.89 | (0.135, 0.130) |

The synthesized compounds may have characteristics suitable to be used as an organic material layer used in an organic light emitting device by employing a spiro structure as a core structure and introducing various substituents as represented in Chemical Formula 1.

The invention claimed is:

1. An organic light emitting device comprising:
an anode;
a cathode provided to face the anode; and
an organic material layer comprising a light emitting layer provided between the anode and the cathode,
wherein the organic material layer further comprises a layer provided between the light emitting layer and the cathode and comprising a compound of the following Chemical Formula 1:

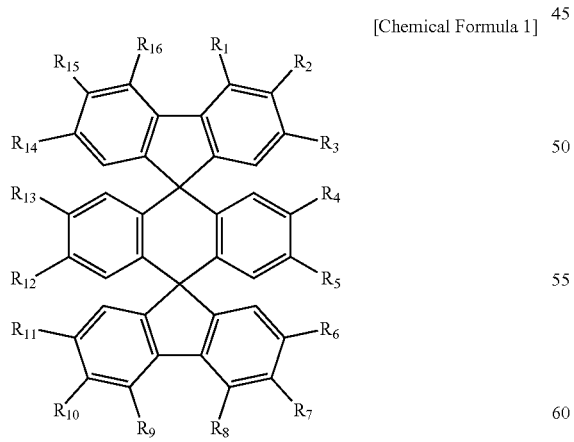

[Chemical Formula 1]

in Chemical Formula 1,
at least one of $R_1$ to $R_3$, $R_6$ to $R_{11}$, or $R_{14}$ to $R16$ combines with an adjacent group to form a ring of Chemical Formula 1-1,

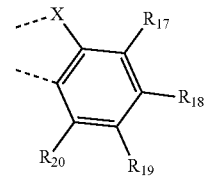

[Chemical Formula 1-1]

X is O or S, and
a group, which does not form the ring among $R_1$ to $R_{16}$, and $R_{17}$ to $R_{20}$ are the same as or different from each other, and are each independently hydrogen; deuterium; a halogen group; a nitrile group; a nitro group; a hydroxy group; a carbonyl group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

2. The organic light emitting device of claim 1, wherein Chemical Formula 1 is represented by any one of Chemical Formulae 2 to 7:

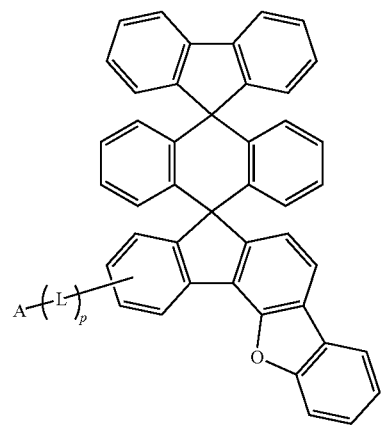

Chemical Formula 2

231
-continued

Chemical Formula 3

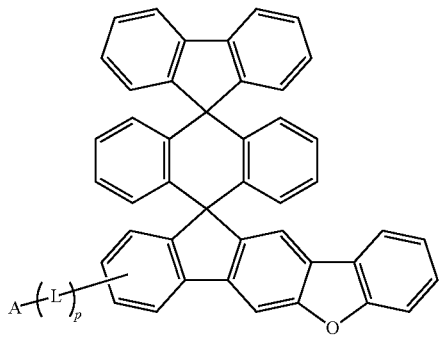

Chemical Formula 4

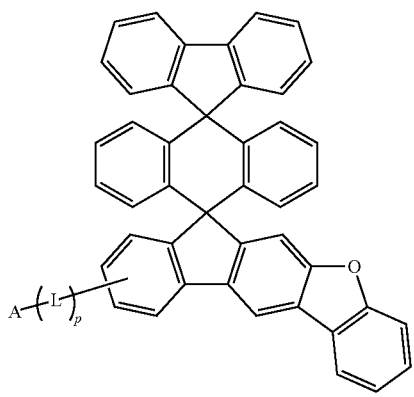

Chemical Formula 5

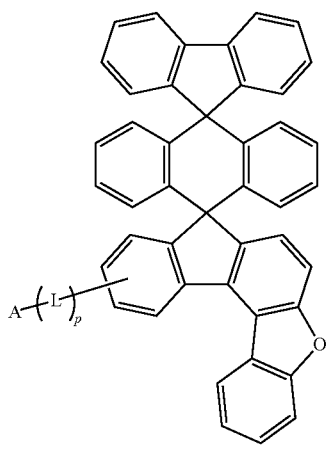

Chemical Formula 6

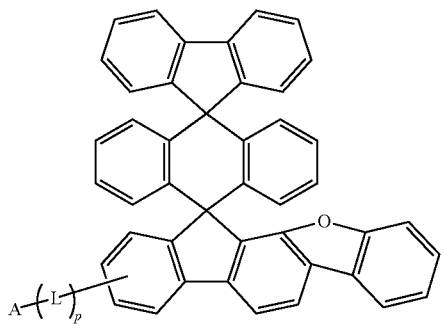

232
-continued

Chemical Formula 7

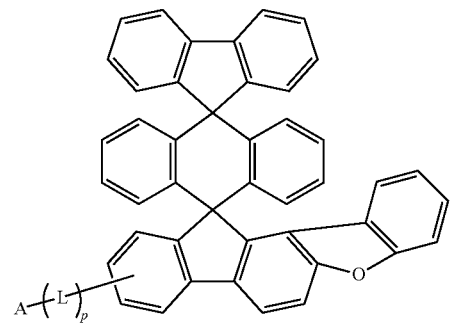

in Chemical Formulae 2 to 7, p is an integer of 0 to 5,

L is a direct bond; a substituted or unsubstituted arylene group; or a substituted or unsubstituted heteroarylene group, and A is hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

3. The organic light emitting device of claim 2, wherein Chemical Formula 1 is represented by any one of Chemical Formulae 2-1 to 2-4, Chemical Formulae 3-1 to 3-4, and Chemical Formulae 4-1 to 4-4:

Chemical Formula 2-1

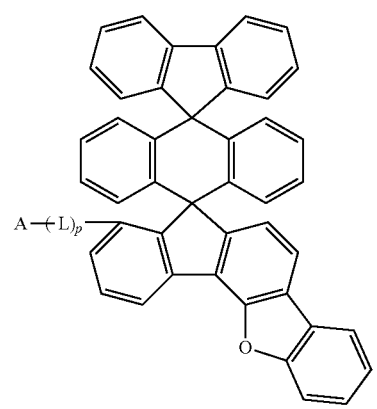

Chemical Formula 2-2
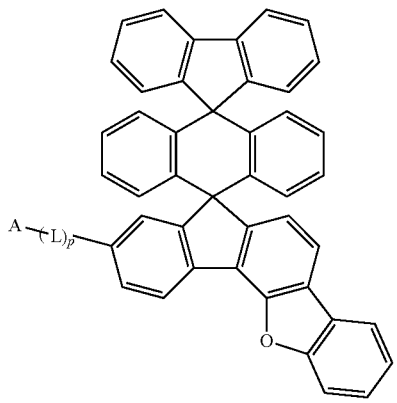
Chemical Formula 2-3
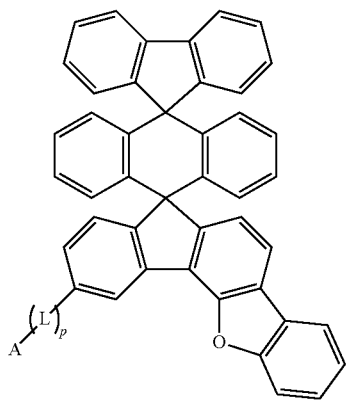
Chemical Formula 2-4
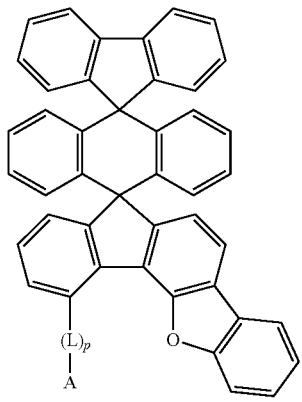
Chemical Formula 3-1
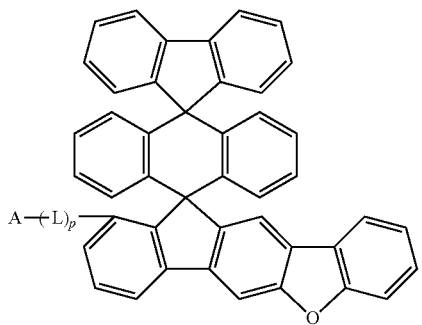
Chemical Formula 3-2
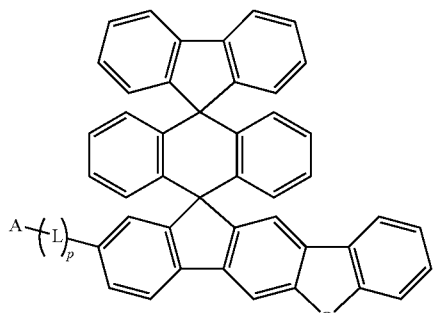
Chemical Formula 3-3
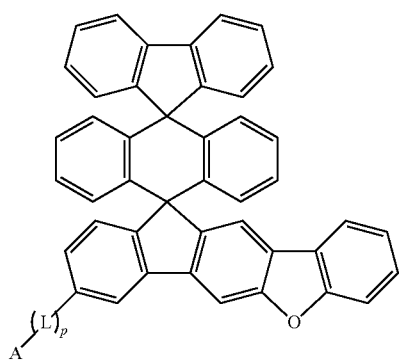
Chemical Formula 3-4
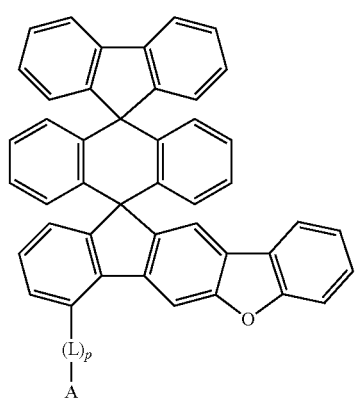
Chemical Formula 4-1
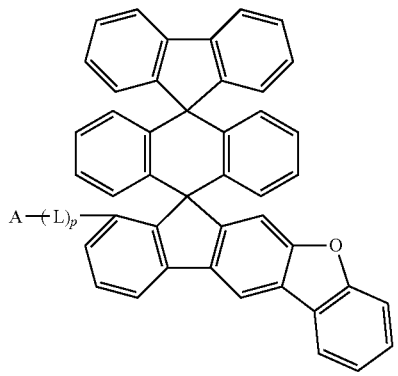

-continued

Chemical Formula 4-2

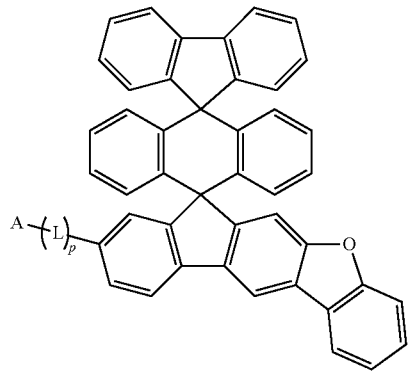

Chemical Formula 4-3

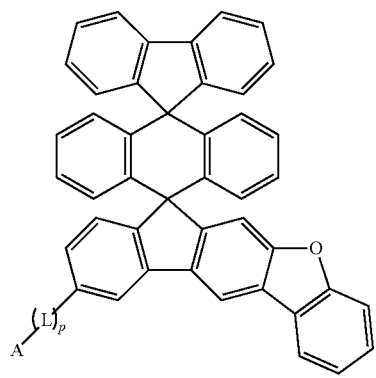

Chemical Formula 4-4

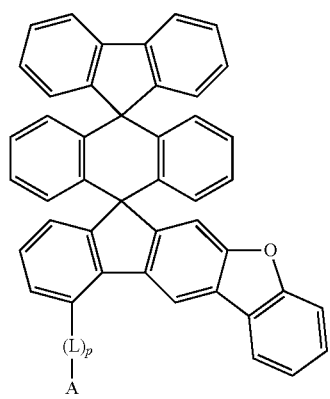

in Chemical Formulae 2-1 to 2-4, Chemical Formulae 3-1 to 3-4, and Chemical Formulae 4-1 to 4-4, p, L, and A are each the same as that defined in Chemical Formulae 2 to 7.

4. The organic light emitting device of claim 2, wherein Chemical Formula 1 is represented by any one of Chemical Formulae 5-1 to 5-4, Chemical Formulae 6-1 to 6-4, and Chemical Formulae 7-1 to 7-4:

Chemical Formula 5-1

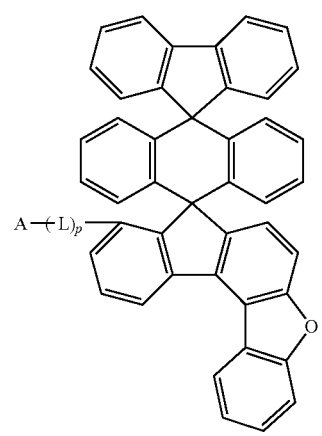

Chemical Formula 5-2

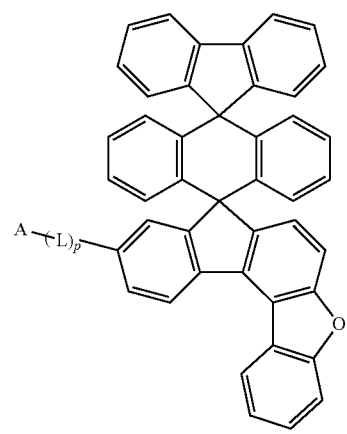

Chemical Formula 5-3

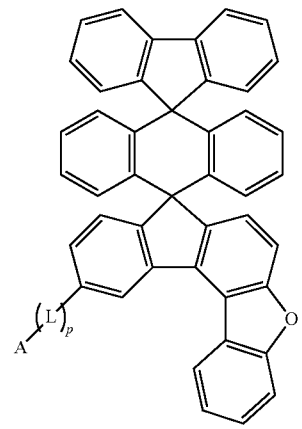

Chemical Formula 5-4
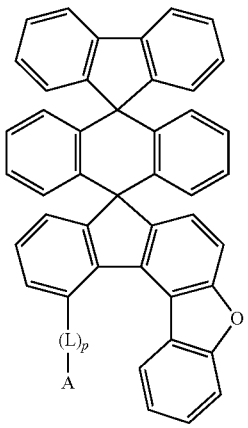
Chemical Formula 6-1
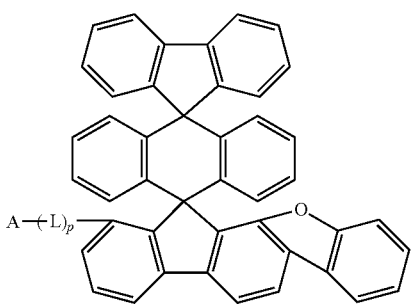
Chemical Formula 6-2
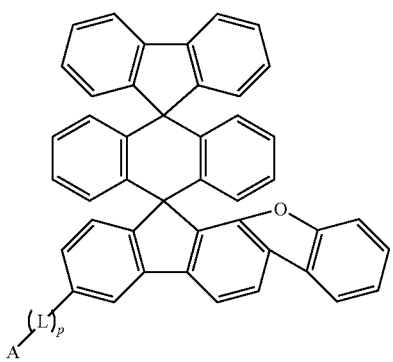
Chemical Formula 6-3
Chemical Formula 6-4
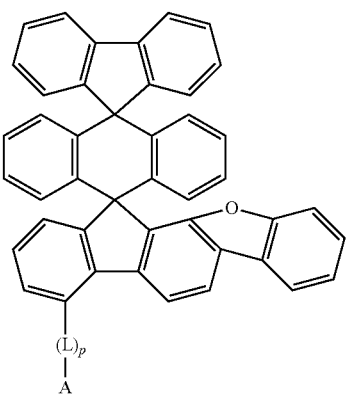
Chemical Formula 7-1
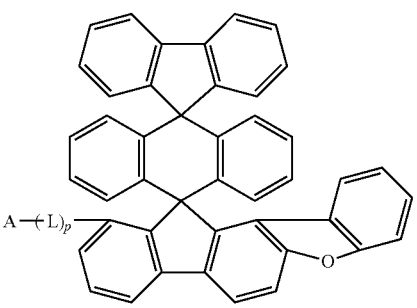
Chemical Formula 7-2
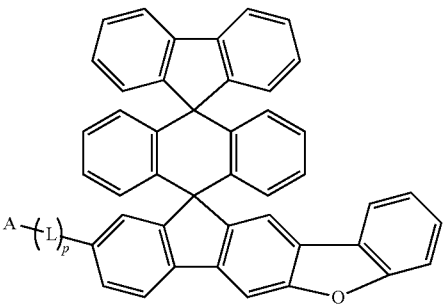
Chemical Formula 7-3
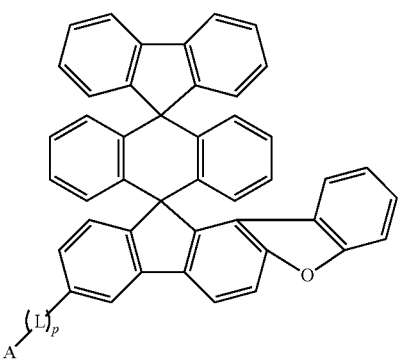

Chemical Formula 7-4

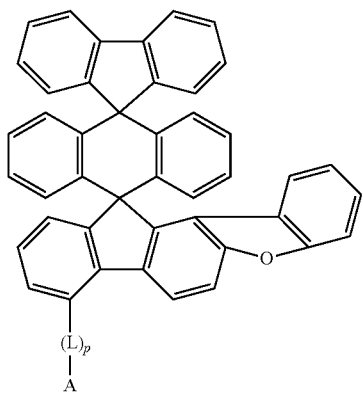

in Chemical Formulae 5-1 to 5-4, Chemical Formulae 6-1 to 6-4, and Chemical Formulae 7-1 to 7-4, p, L, and A are each the same as that defined in Chemical Formulae 2 to 7.

5. The organic light emitting device of claim 2, wherein L is a direct bond or any one selected from the following structures:

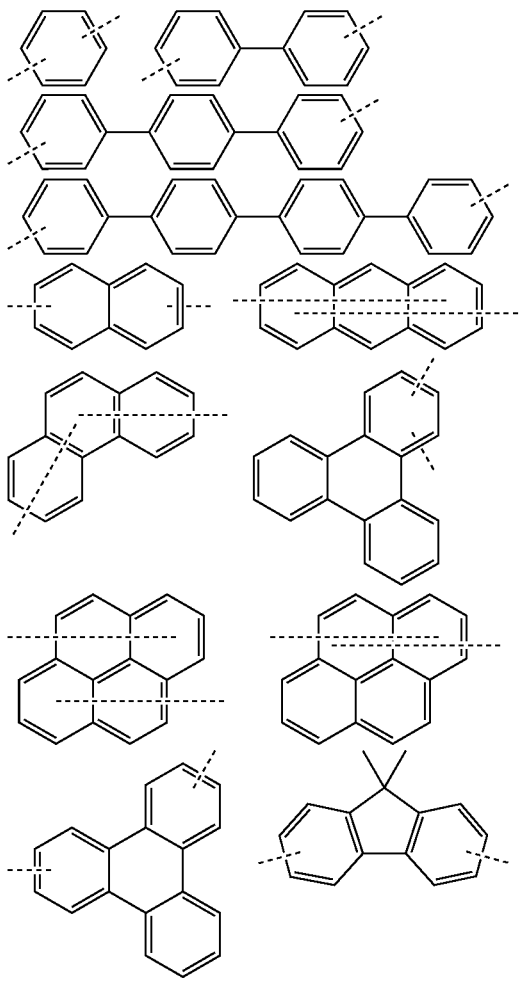

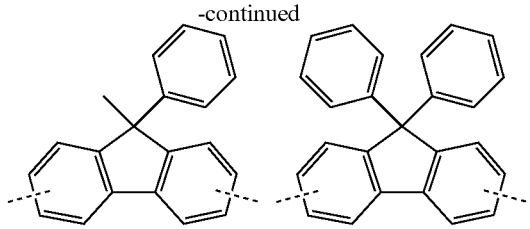

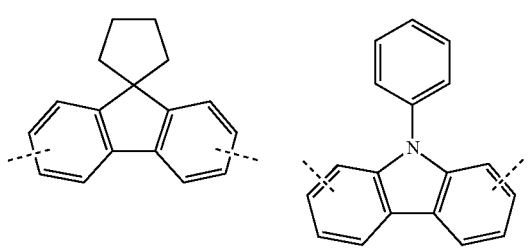

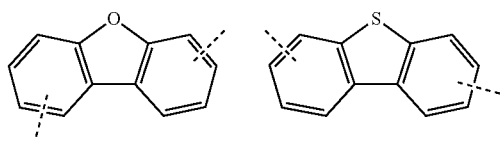

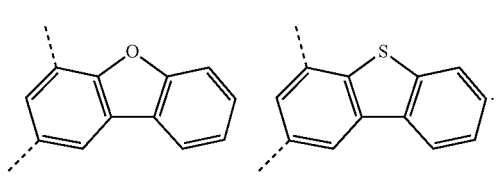

6. The organic light emitting device of claim 2, wherein A is hydrogen; deuterium; or any one selected from the following structures:

B-1

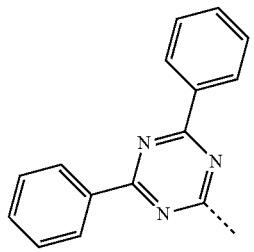

B-2

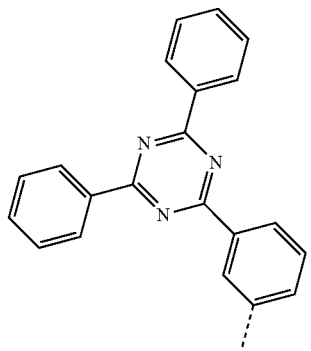

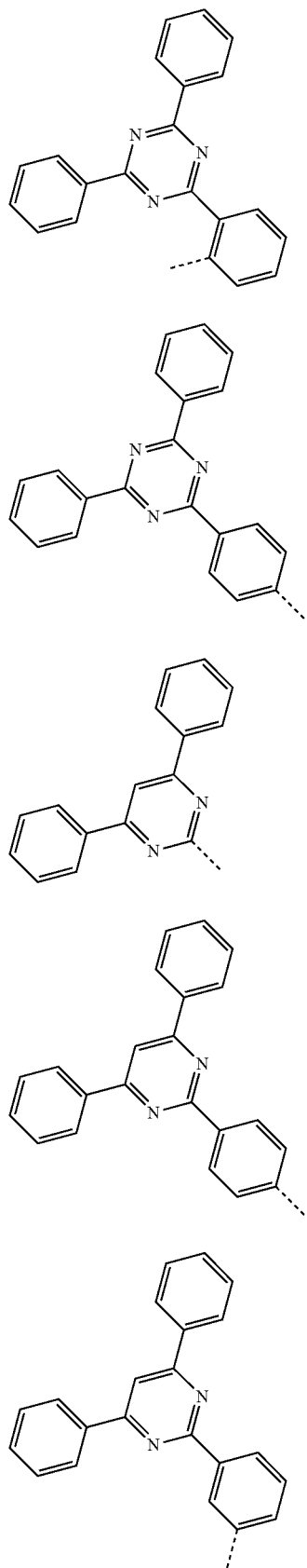
B-3
B-4
B-5
B-6
B-7
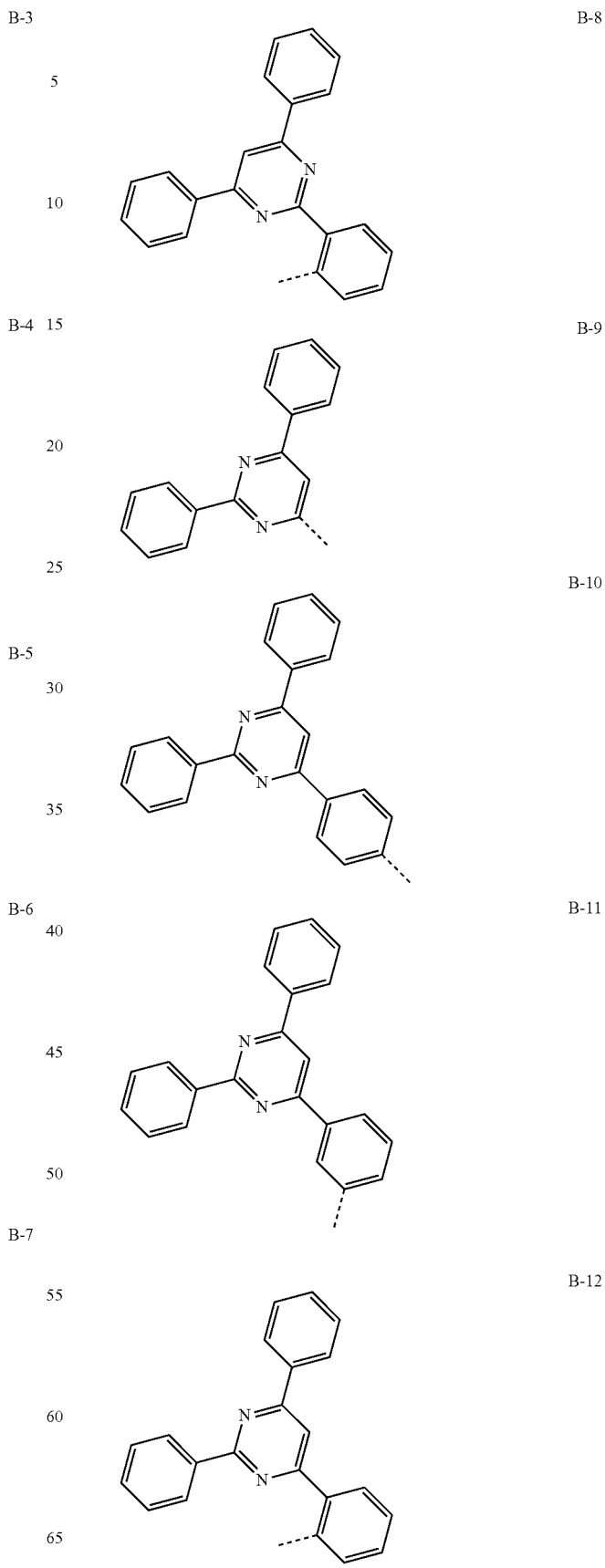
B-8
B-9
B-10
B-11
B-12

B-13 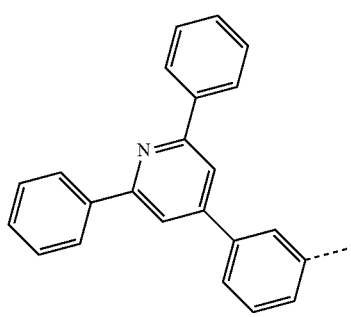
B-14 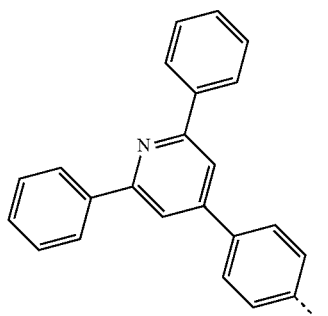
B-15 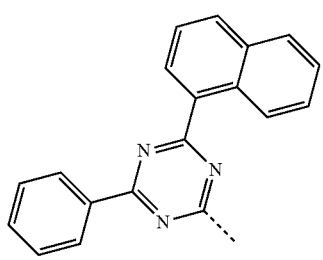
B-16 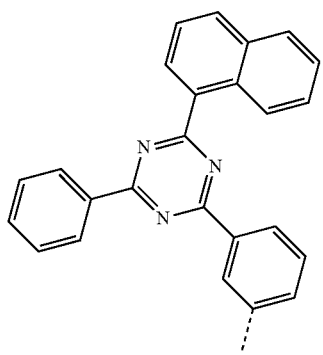
B-17 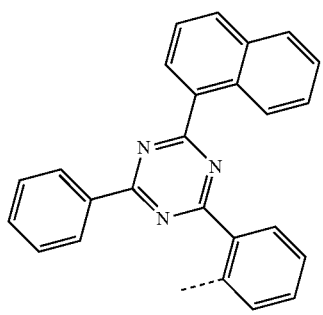
B-18 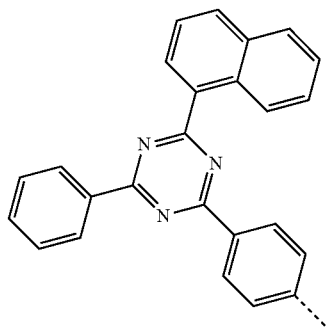
B-19 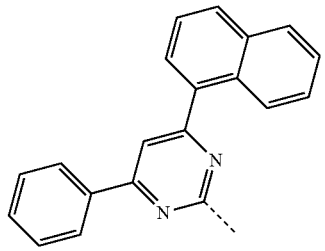
B-20 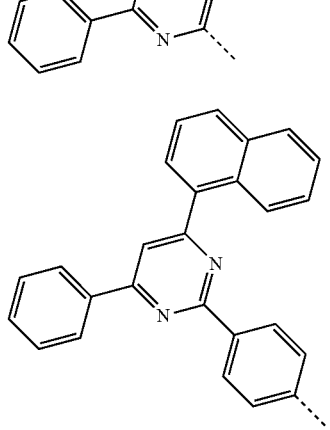
B-21 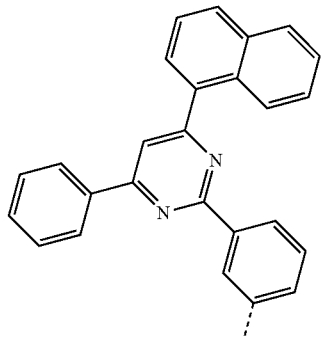
B-22 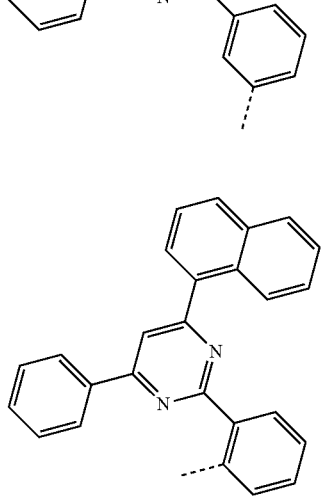

B-23
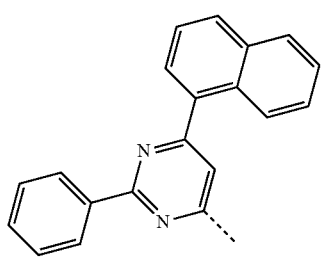
B-24
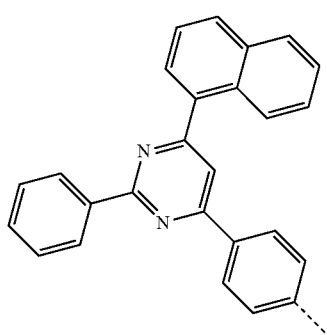
B-25
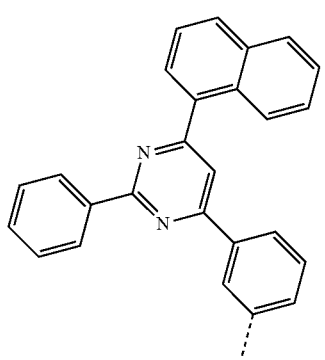
B-26
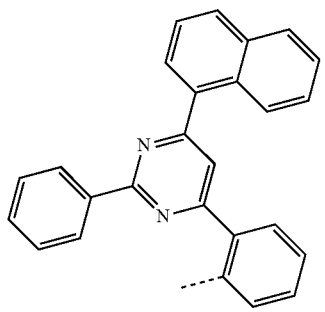
B-27
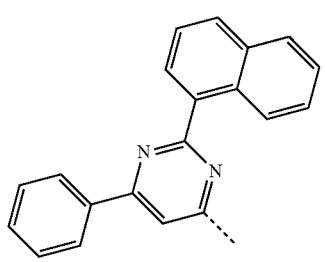
B-28
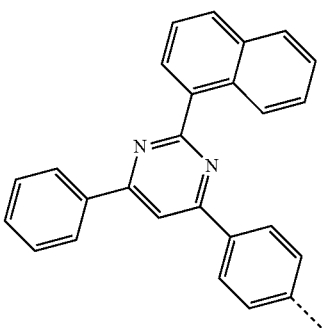
B-29
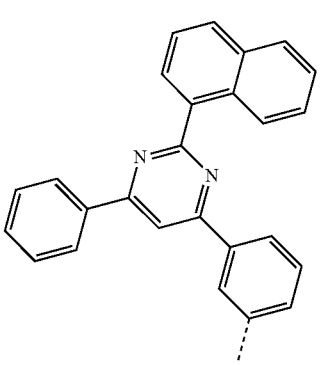
B-30
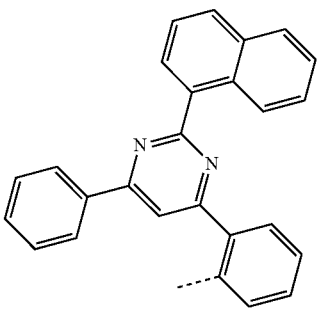
B-31
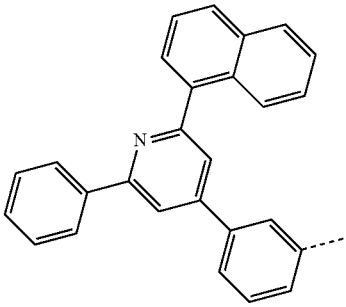
B-32
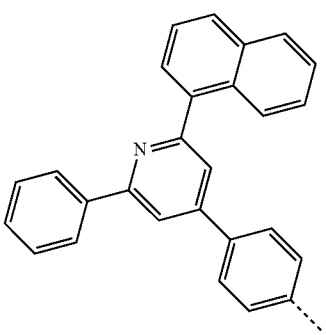

B-33
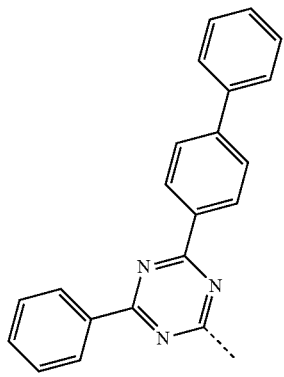
B-34
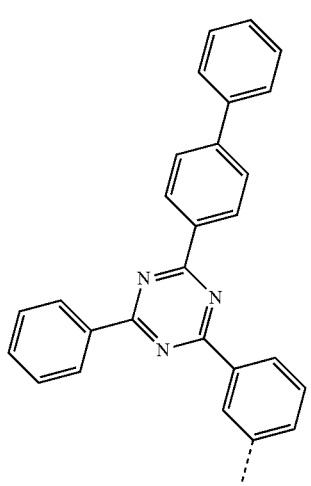
B-35
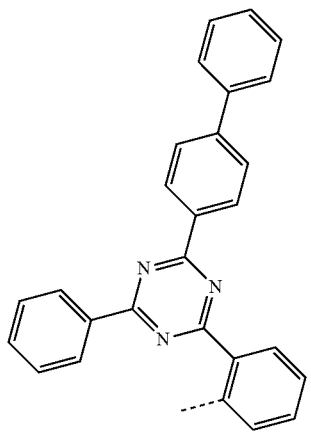
B-36
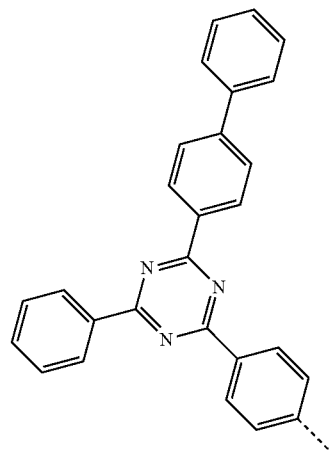
B-37
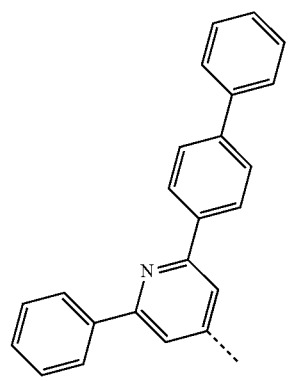
B-38
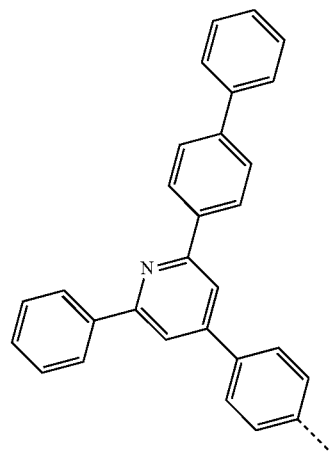

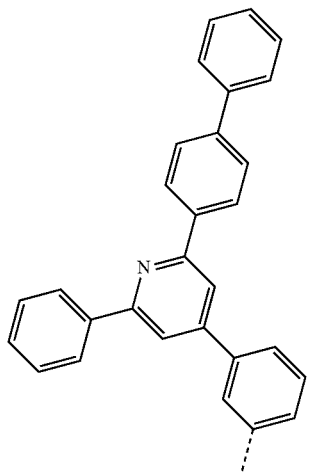
B-39
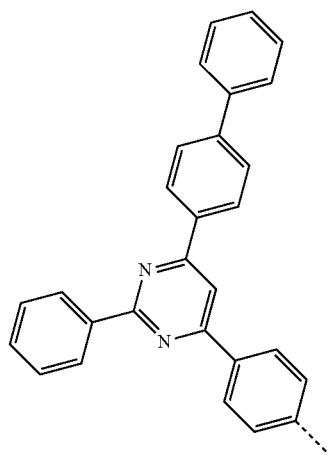
B-40
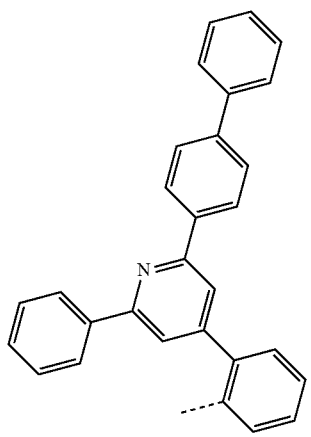
B-42
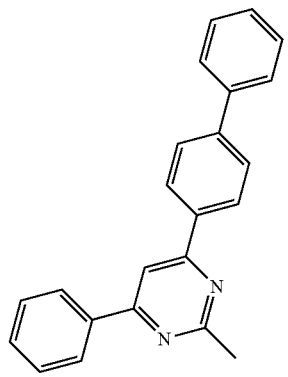
B-43
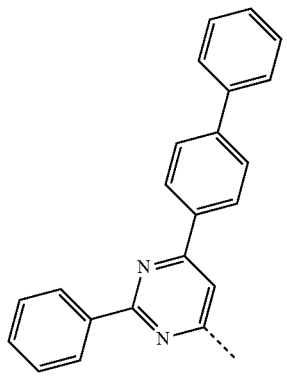
B-41
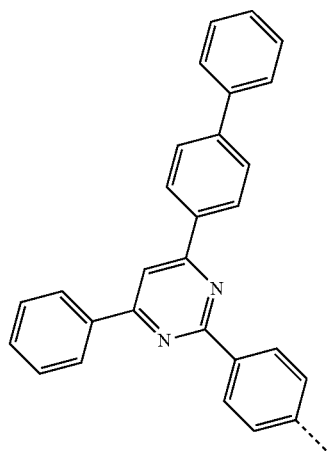
B-44

B-45
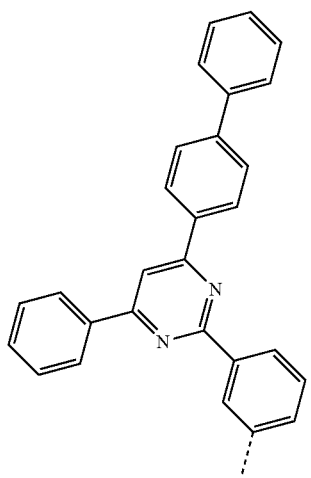
B-46
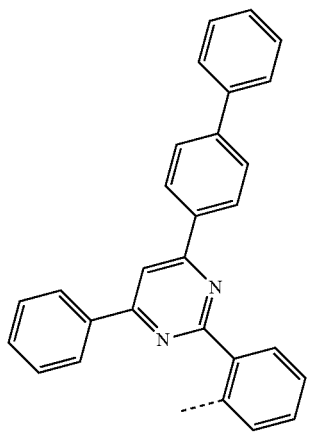
B-47
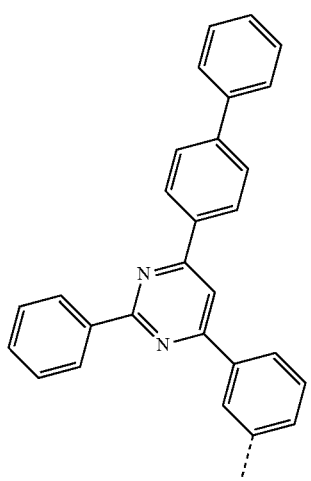
B-48
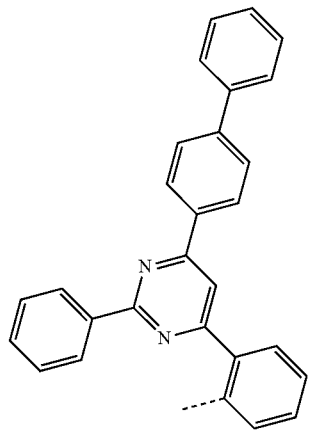
B-49
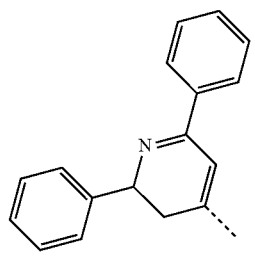
B-50
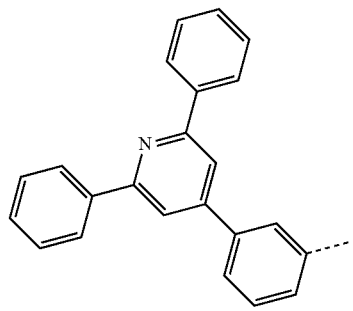
B-51
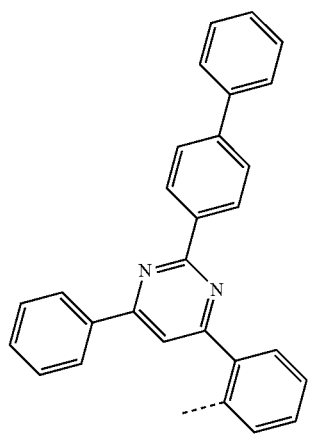

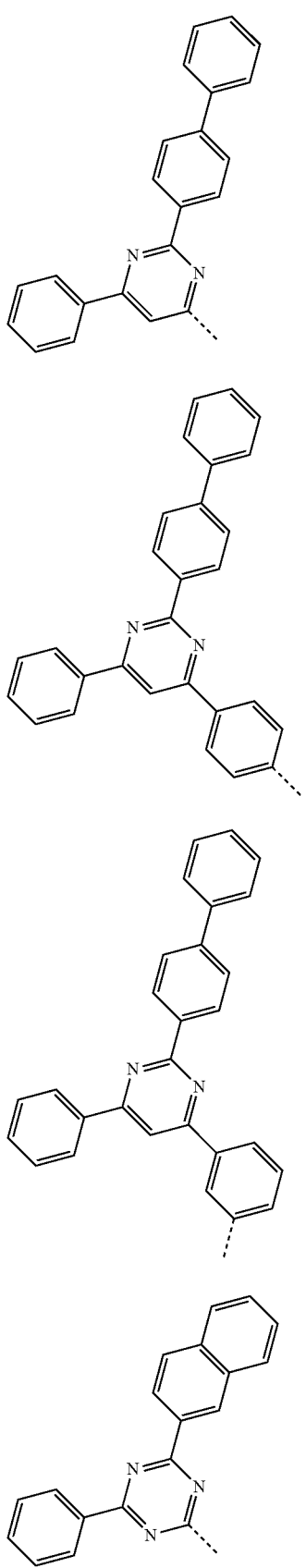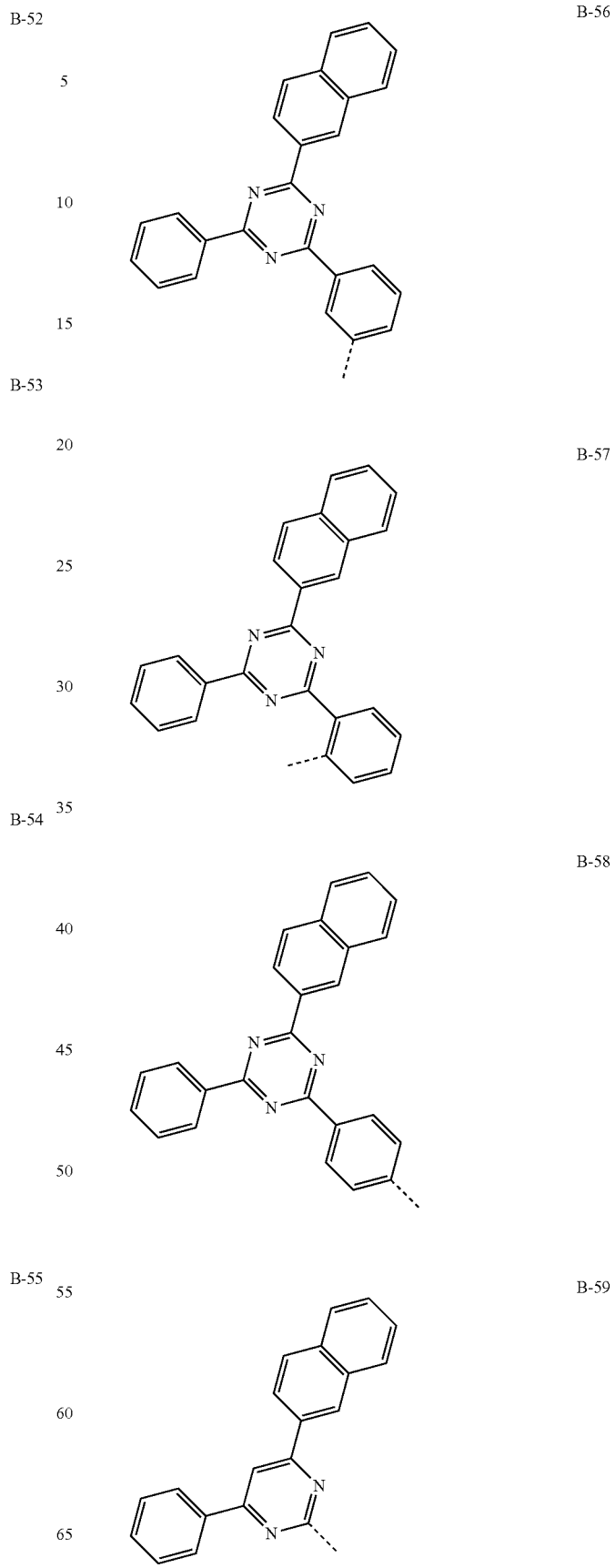

B-60 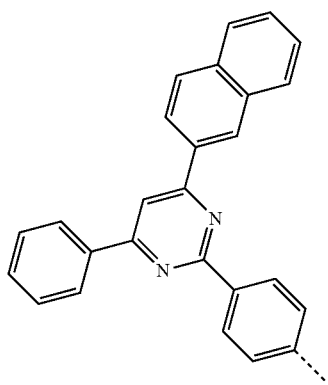
B-61 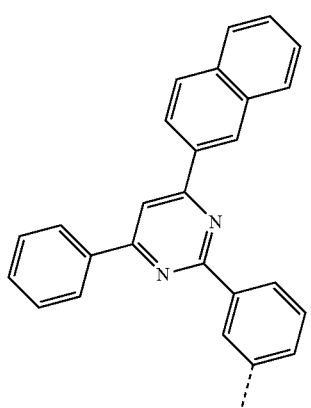
B-62 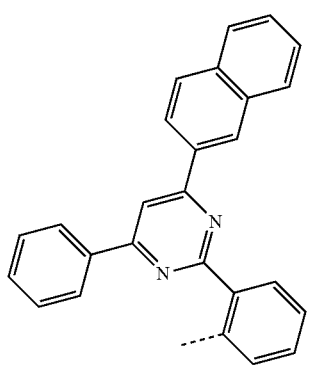
B-63 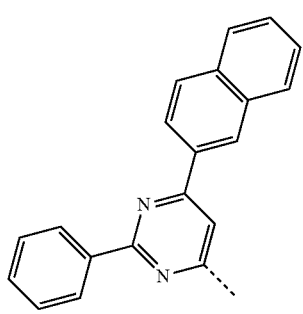
B-64 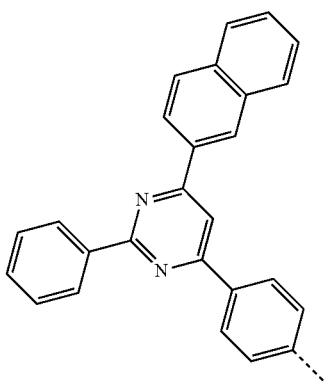
B-65 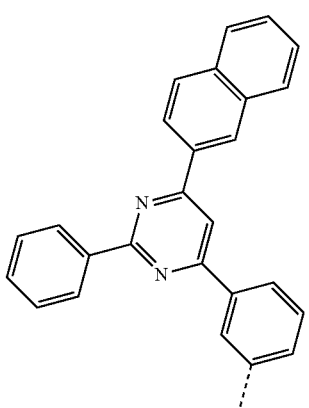
B-66 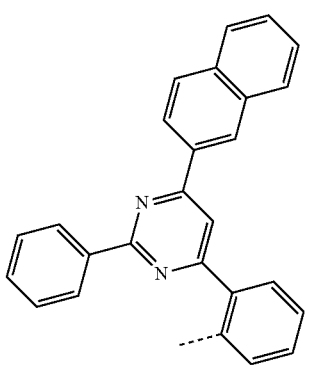
B-67 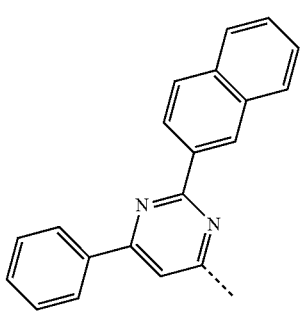

B-68
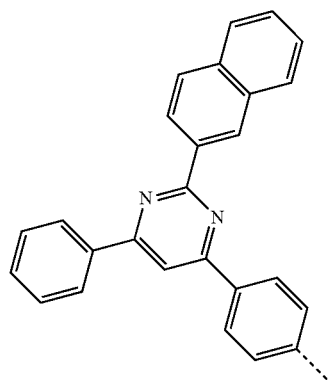
B-69
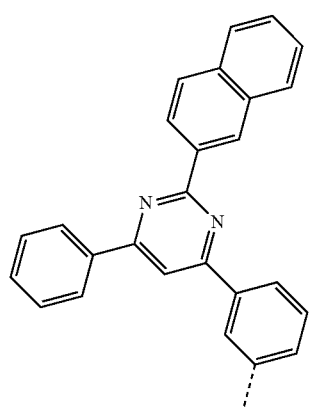
B-70
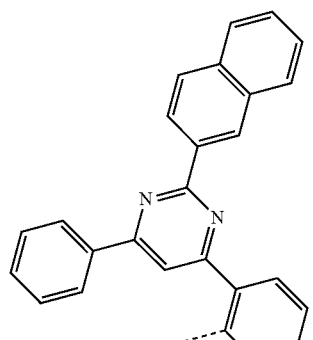
B-71
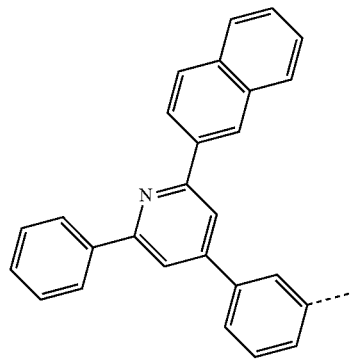
B-72
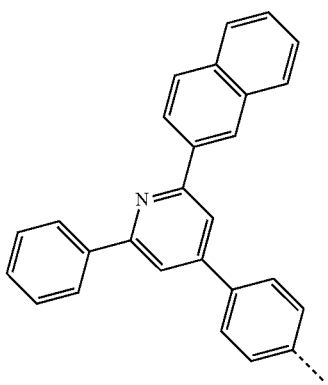
B-73
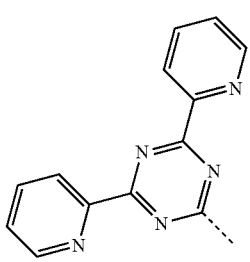
B-74
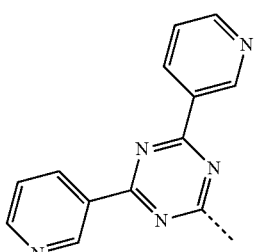
B-75
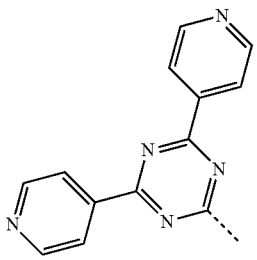
B-76
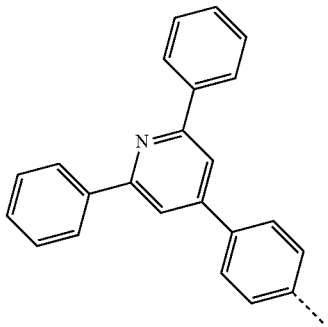

 B-77
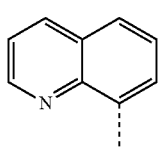 B-78
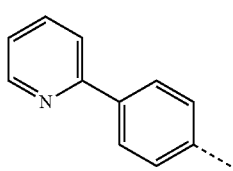 B-79
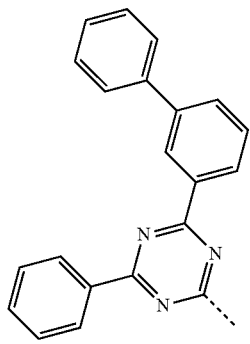 B-80
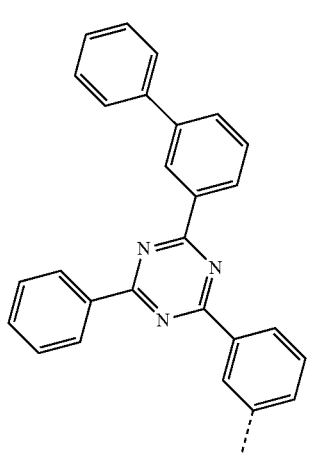 B-81
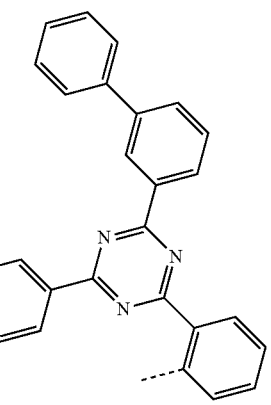 B-82
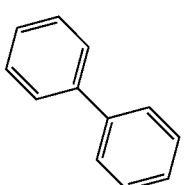 B-83
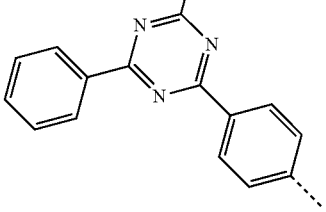 B-84
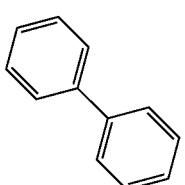 
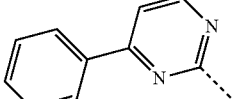 
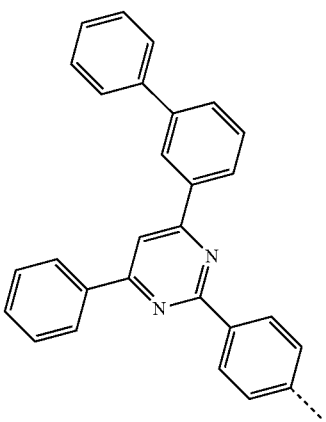 B-85

B-86 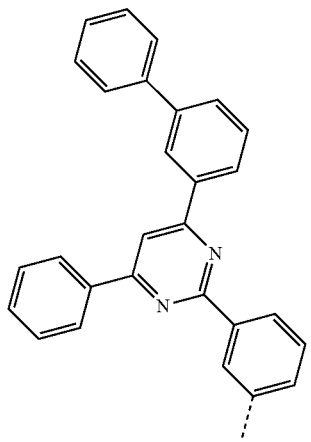
B-87 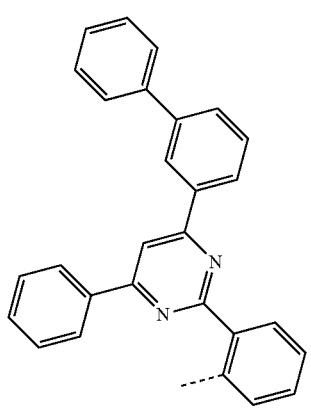
B-88 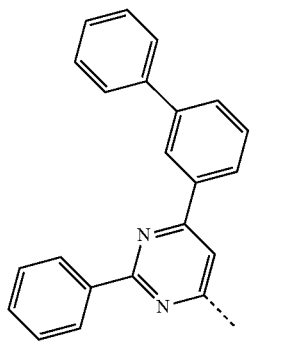
B-89
B-90 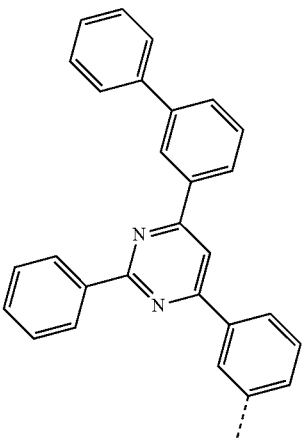
B-91 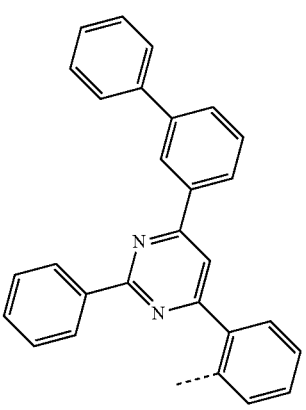
B-92 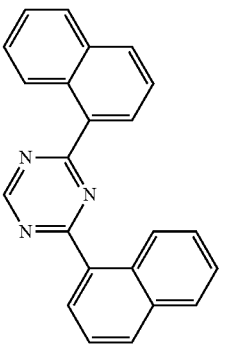
B-93 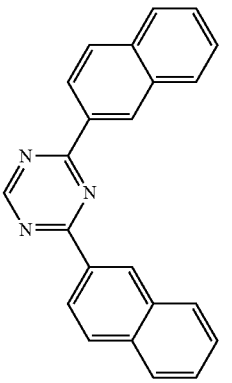

B-94
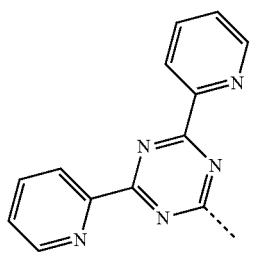
B-95
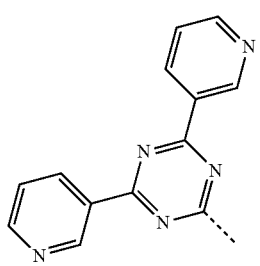
B-96
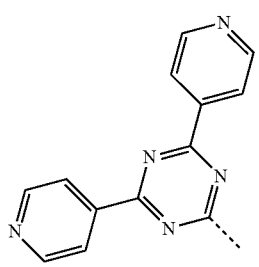
B-97
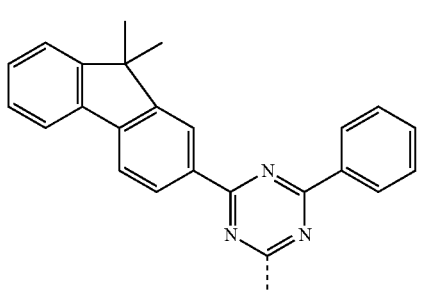
B-98
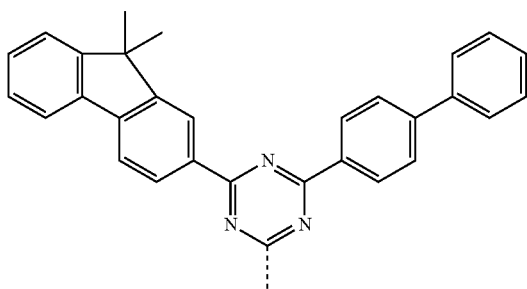
B-99
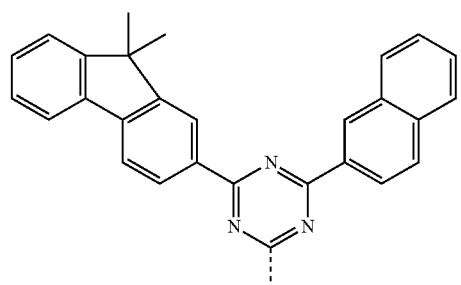
B-100
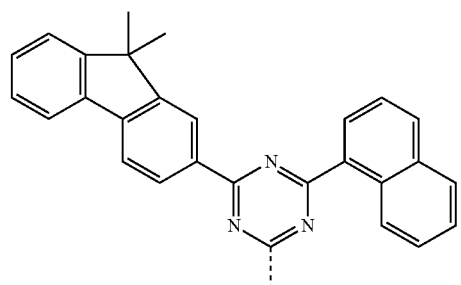
B-101
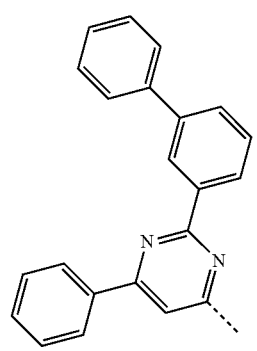
C-1
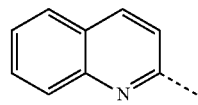
C-2
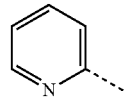
C-3
C-4
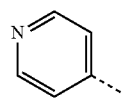
C-5
C-6
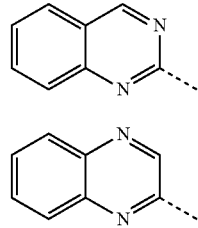

-continued
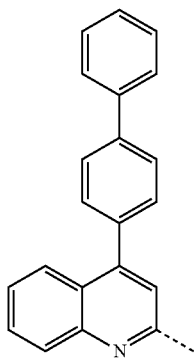
C-7
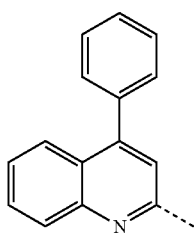
C-8
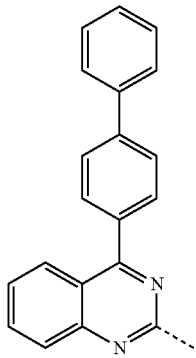
C-9
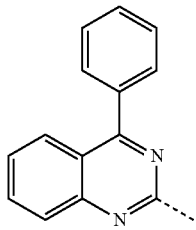
C-10
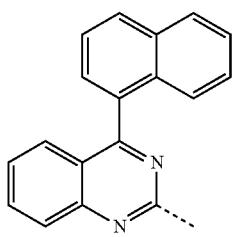
C-11
-continued
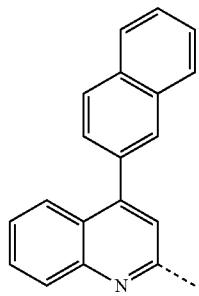
C-12
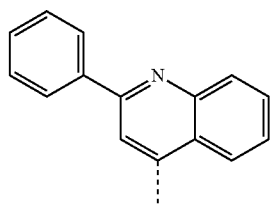
C-13
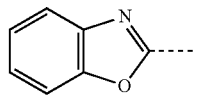
C-14
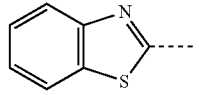
C-15
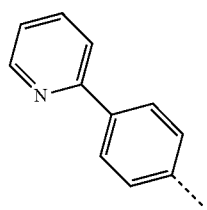
C-16
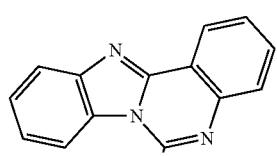
C-17
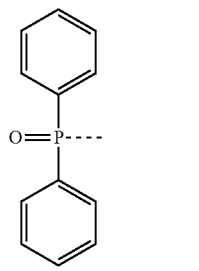
C-18

C-19 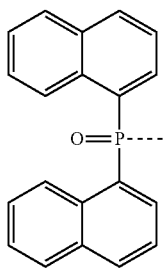
C-20 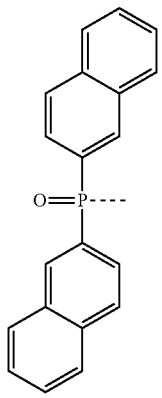
C-21 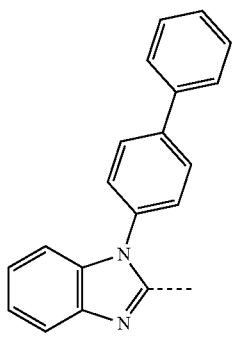
C-22 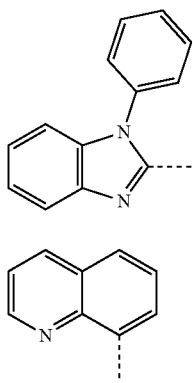
C-23
C-24 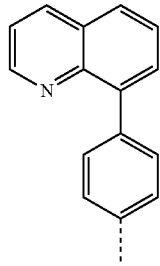
C-25 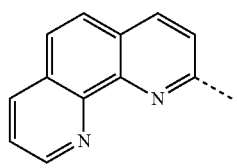
7. The organic light emitting device of claim 1, wherein Chemical Formula 1 is represented by any one of Chemical Formulae 8 to 13:
Chemical Formula 8
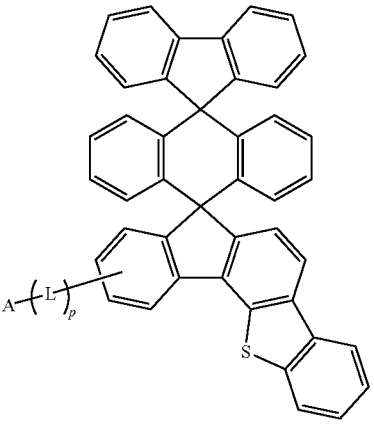
Chemical Formula 9
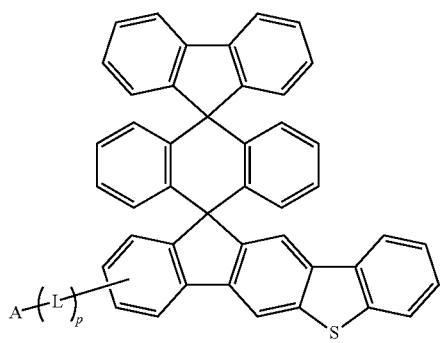

Chemical Formula 10

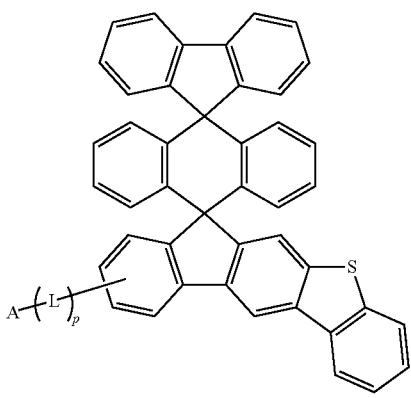

Chemical Formula 11

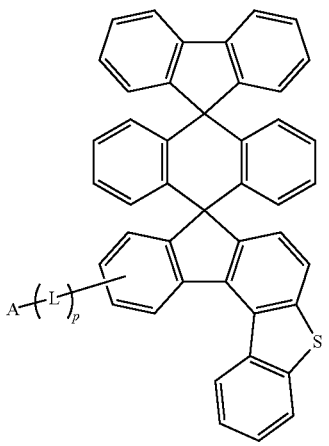

Chemical Formula 12

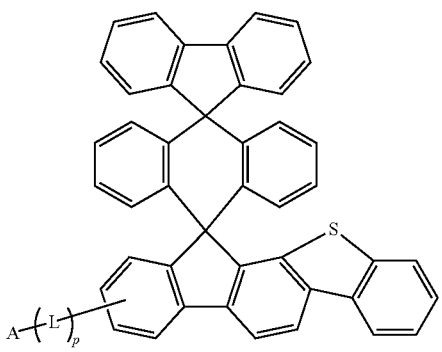

Chemical Formula 13

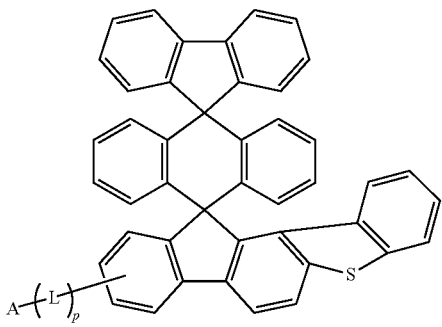

in Chemical Formulae 8 to 13, p is an integer of 0 to 5,

L is a direct bond; a substituted or unsubstituted arylene group; or a substituted or unsubstituted heteroarylene group, and A is hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

8. The organic light emitting device of claim 7, wherein Chemical Formula 1 is represented by any one of Chemical Formulae 8-1 to 8-4, Chemical Formulae 9-1 to 9-4, and Chemical Formulae 10-1 to 10-4:

Chemical Formula 8-1

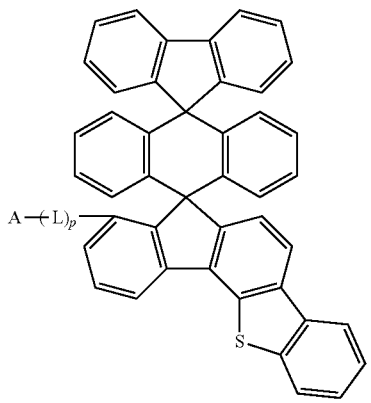

Chemical Formula 8-2

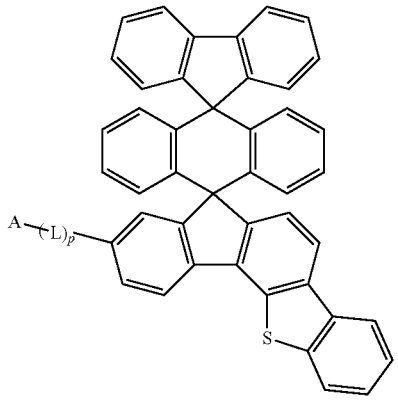

-continued
Chemical Formula 8-3
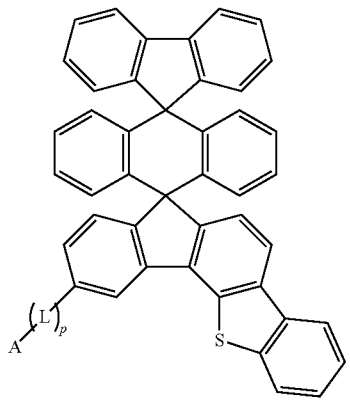
Chemical Formula 8-4
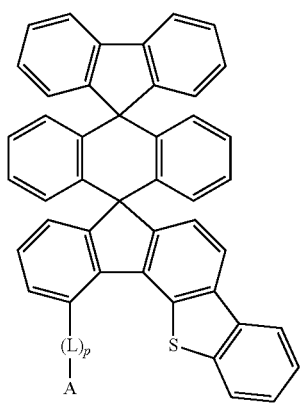
Chemical Formula 9-1
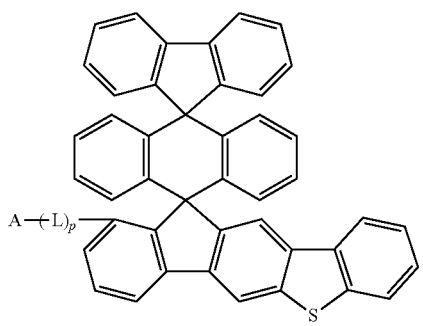
Chemical Formula 9-2
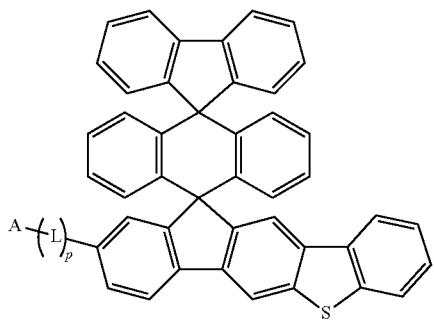
-continued
Chemical Formula 9-3
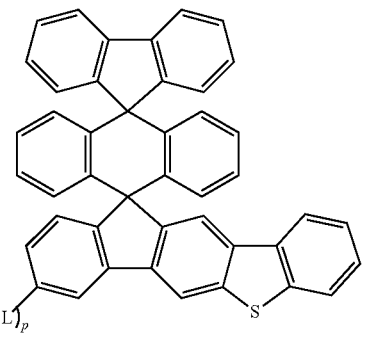
Chemical Formula 9-4
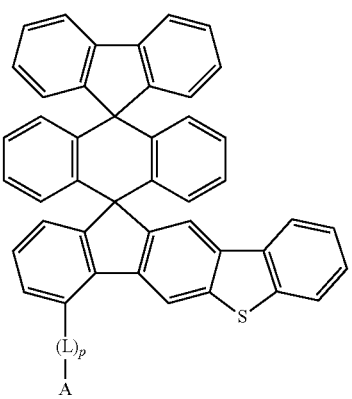
Chemical Formula 10-1
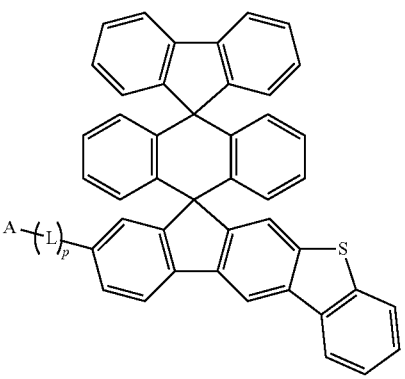
Chemical Formula 10-2

Chemical Formula 10-3

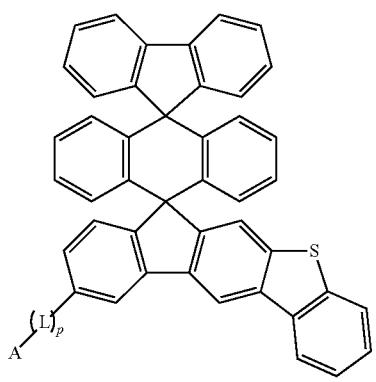

Chemical Formula 10-4

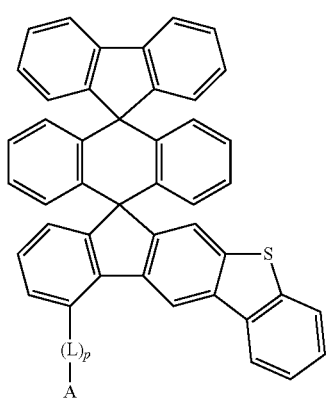

in Chemical Formulae 8-1 to 8-4, Chemical Formulae 9-1 to 9-4, and Chemical Formulae 10-1 to 10-4, p, L, and A are each the same as that defined in Chemical Formulae 8 to 13.

9. The organic light emitting device of claim 7, wherein Chemical Formula 1 is represented by any one of Chemical Formulae 11-1 to 11-4, Chemical Formulae 12-1 to 12-4, and Chemical Formulae 13-1 to 13-4:

Chemical Formula 11-1

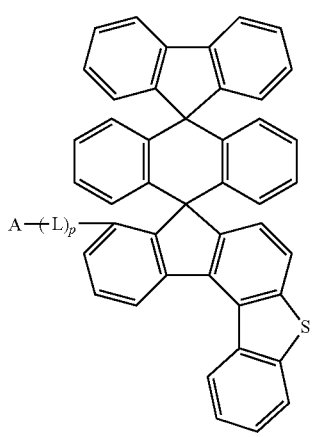

Chemical Formula 11-2

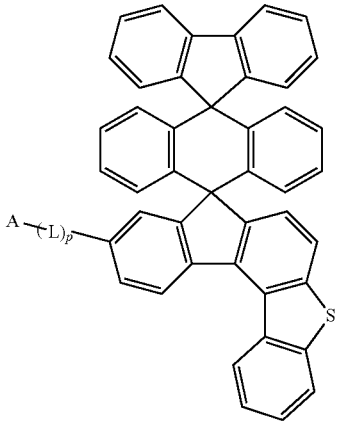

Chemical Formula 11-3

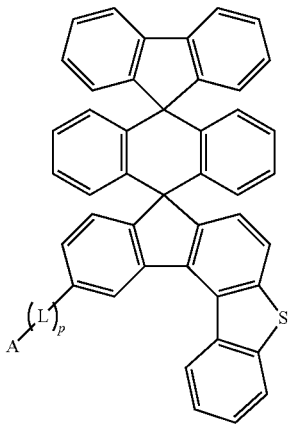

Chemical Formula 11-4

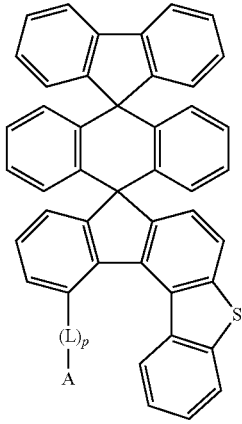

Chemical Formula 12-1

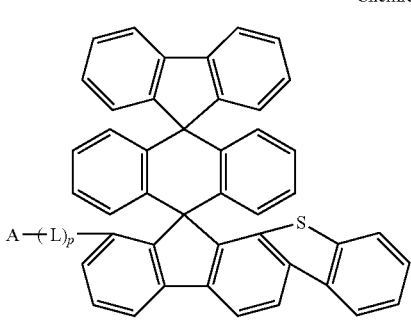

Chemical Formula 12-2

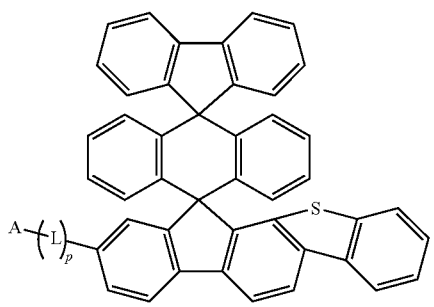

Chemical Formula 12-3

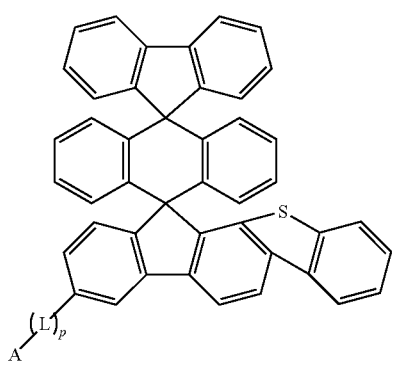

Chemical Formula 12-4

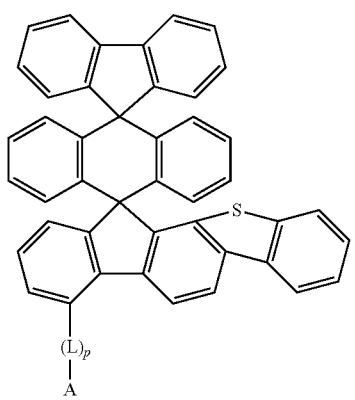

Chemical Formula 13-1

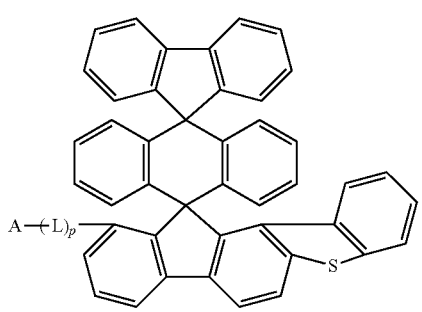

Chemical Formula 13-2

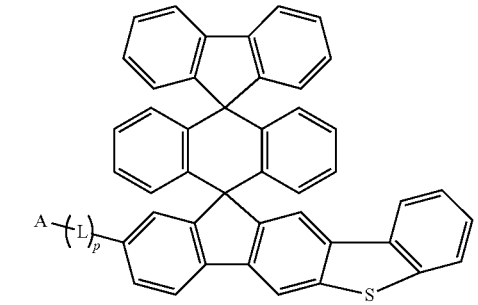

Chemical Formula 13-3

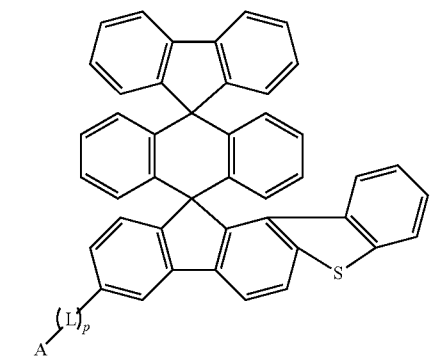

Chemical Formula 13-4

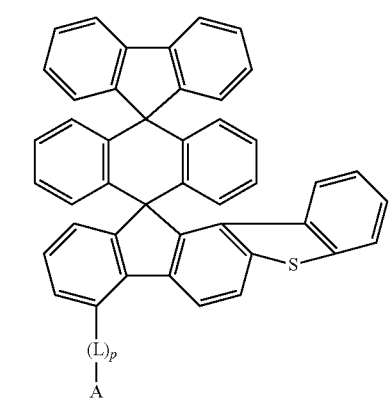

in Chemical Formulae 11-1 to 11-4, Chemical Formulae 12-1 to 12-4, and Chemical Formulae 13-1 to 13-4, p, L, and A are each the same as that defined in Chemical Formulae 8 to 13.

10. The organic light emitting device of claim 7, wherein L is a direct bond or any one selected from the following structures:

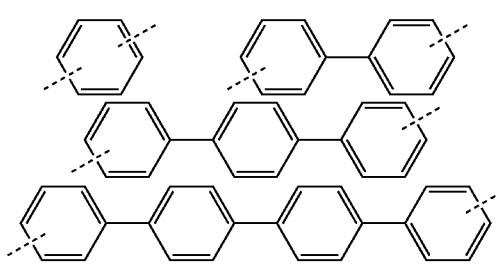

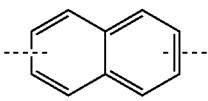
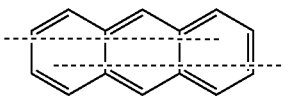
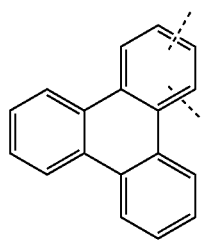
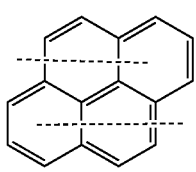
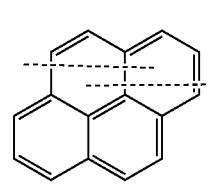
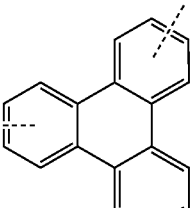
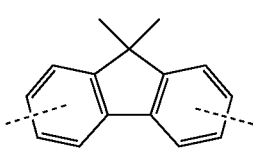
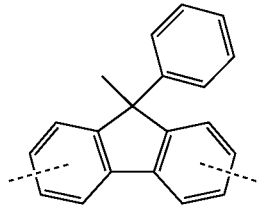
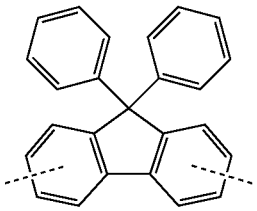
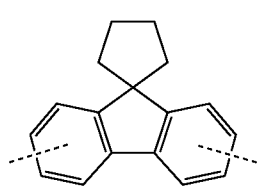
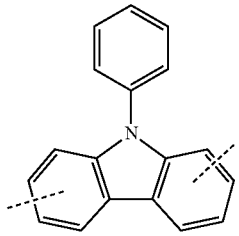
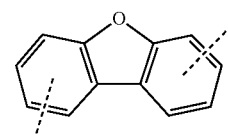
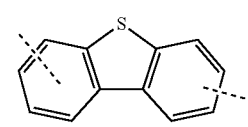
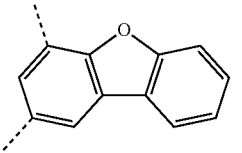
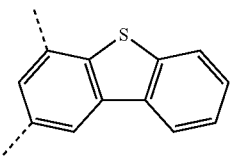
11. The organic light emitting device of claim 7, wherein A is hydrogen; deuterium;
or any one selected from the following structures:
B-1
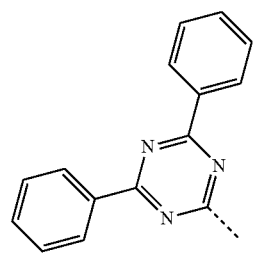
B-2
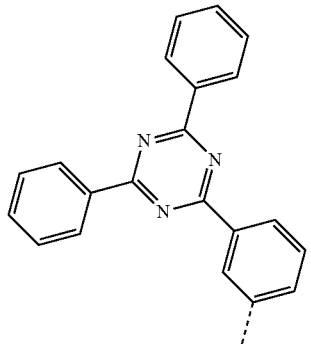
B-3
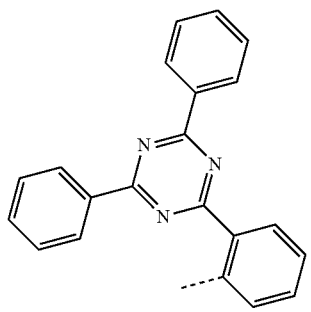
B-4
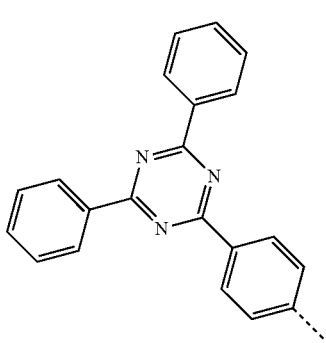

-continued
B-5
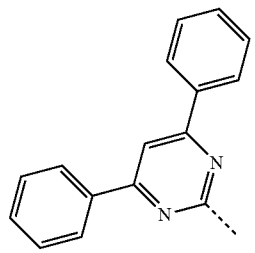
B-6
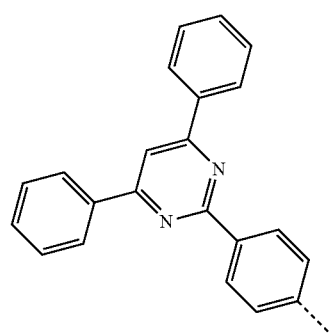
B-7
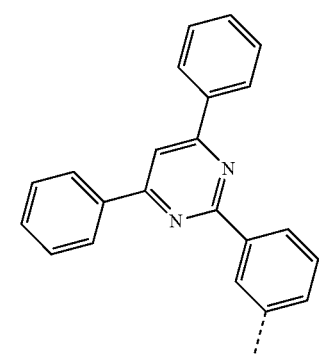
B-8
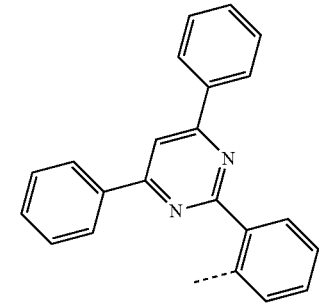
B-9
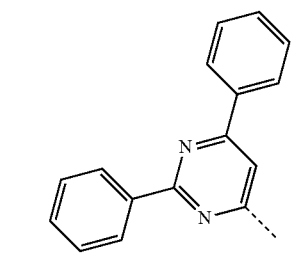
-continued
B-10
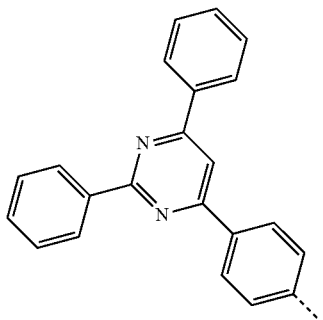
B-11
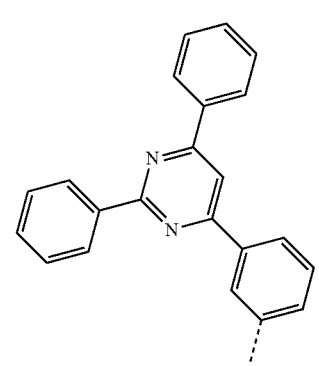
B-12
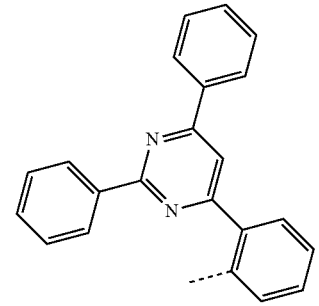
B-13
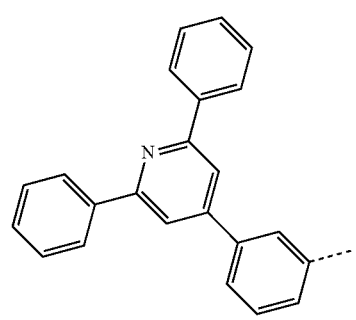
B-14
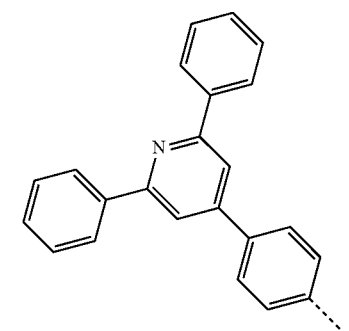

B-15 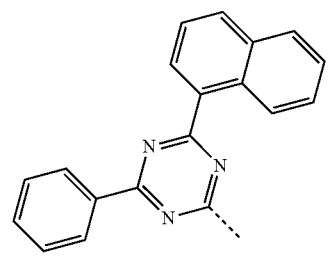
B-16 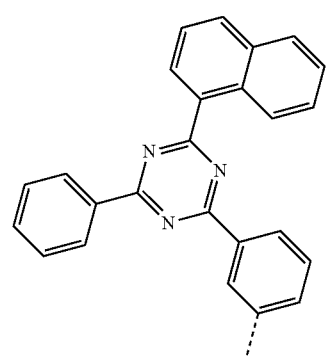
B-17 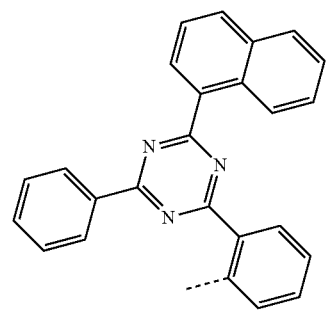
B-18 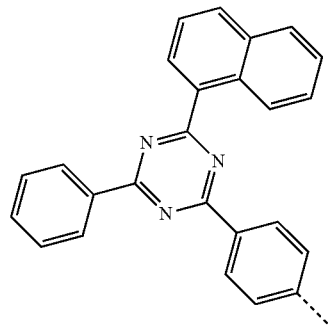
B-19 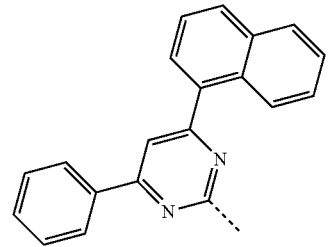
B-20 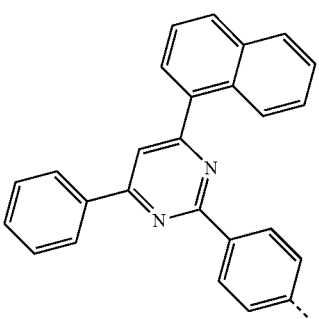
B-21 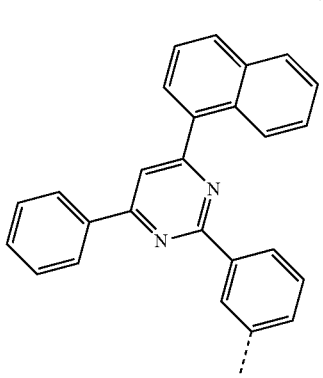
B-22 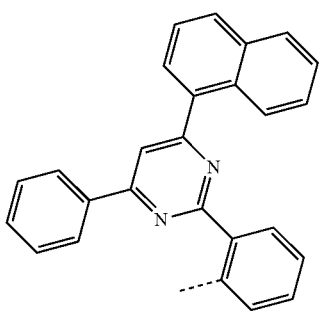
B-23 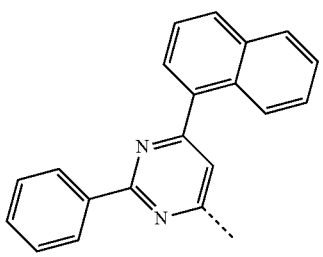
B-24 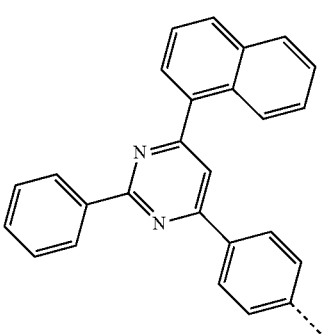

B-25
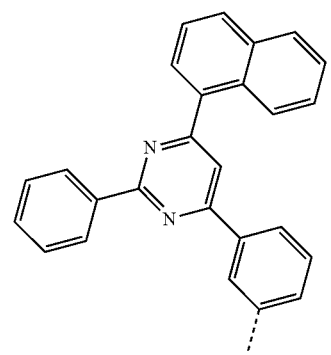
B-26
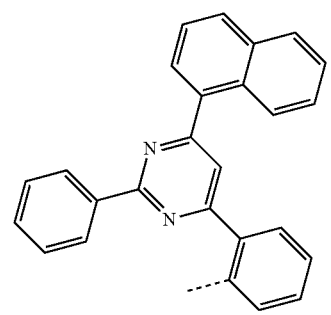
B-27
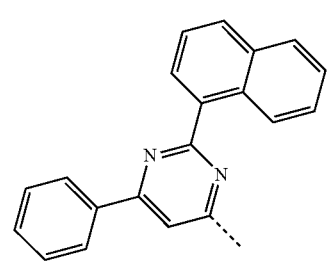
B-28
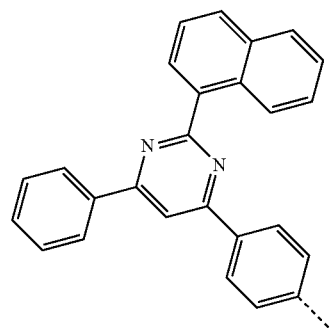
B-29
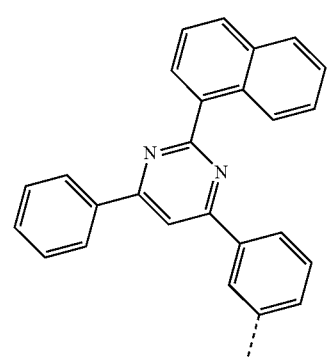
B-30
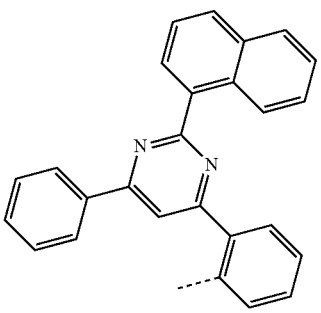
B-31
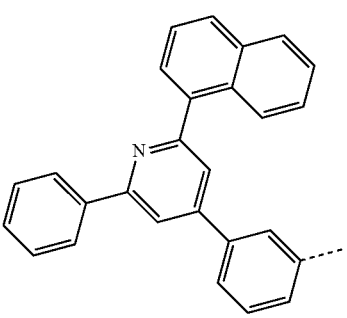
B-32
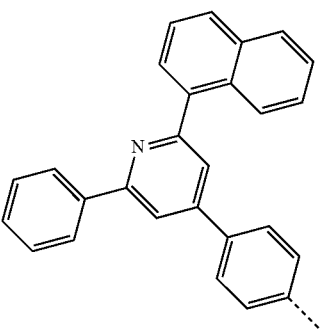
B-33
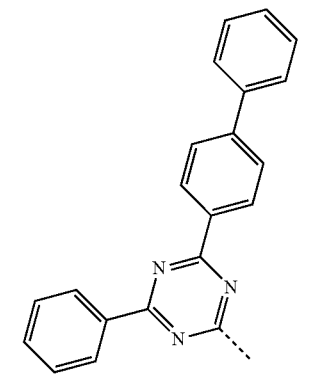

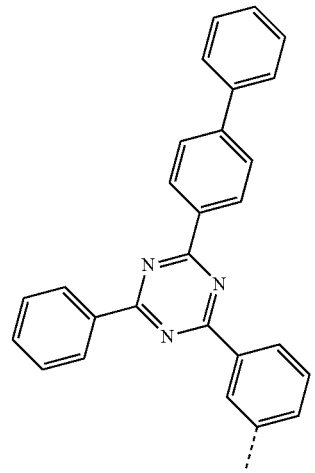
B-34
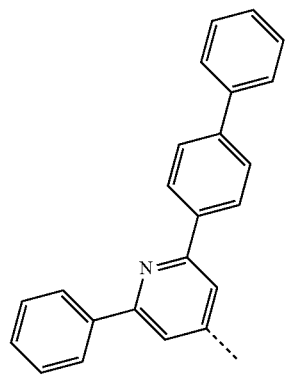
B-37
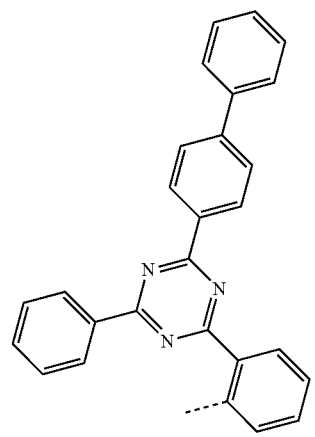
B-35
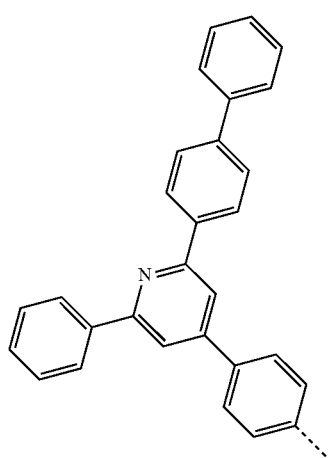
B-38
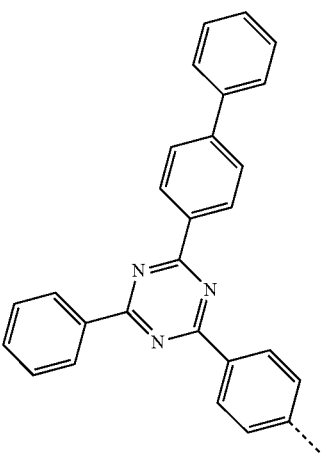
B-36
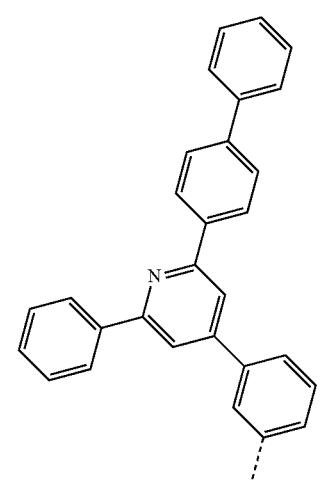
B-39

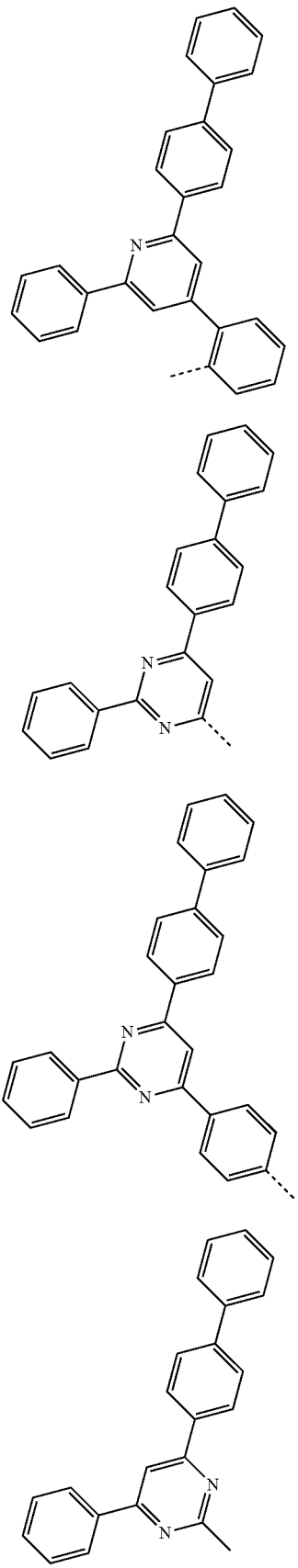
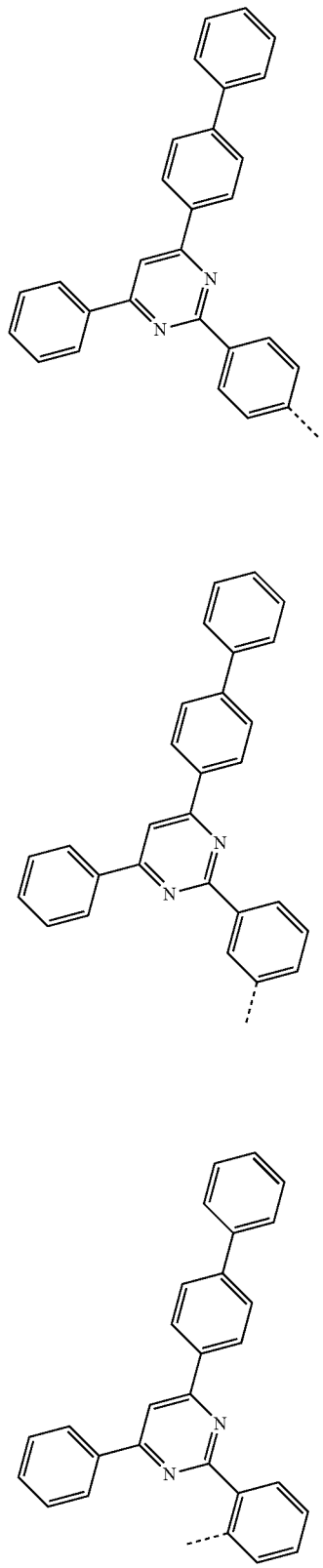

B-47
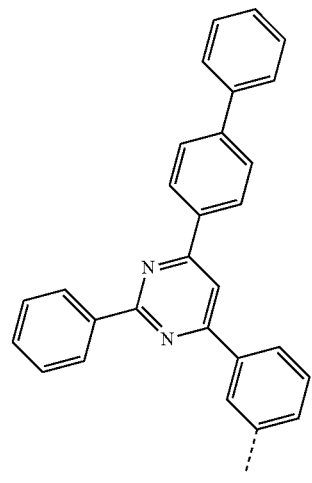
B-48
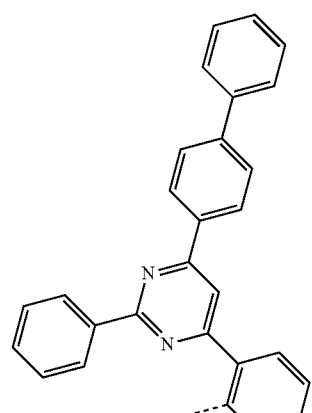
B-49
B-50
B-51
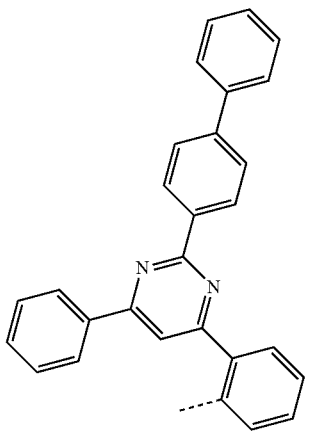
B-52
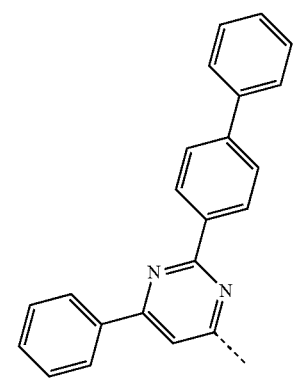
B-53
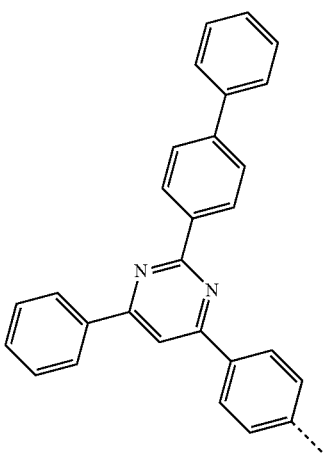

-continued
B-54
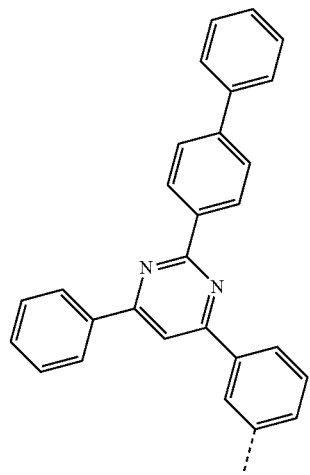
B-55
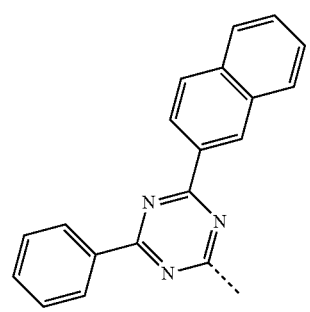
B-56
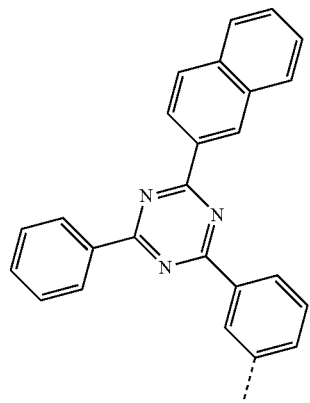
B-57
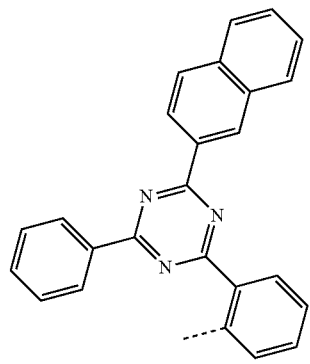
-continued
B-58
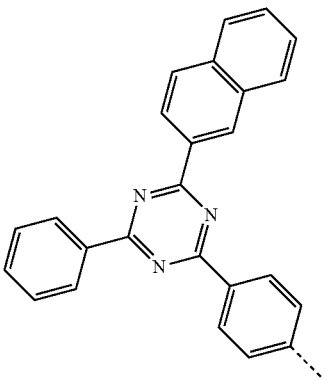
B-59
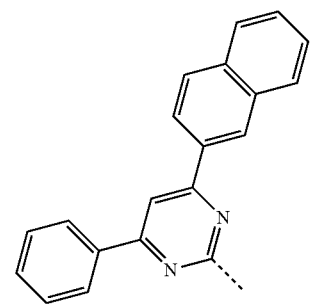
B-60
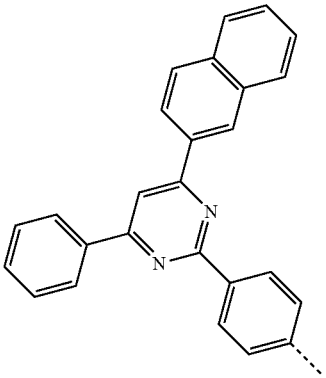
B-61
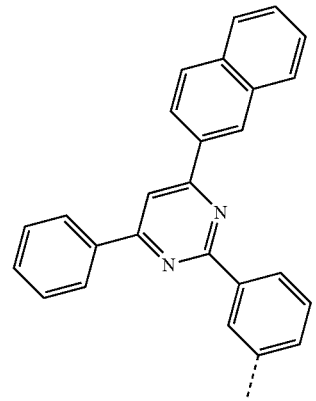

B-62
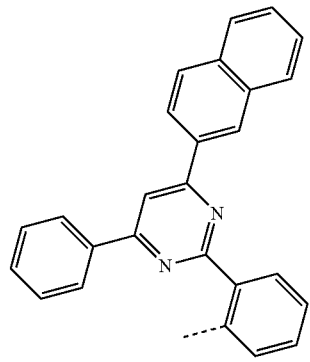
B-63
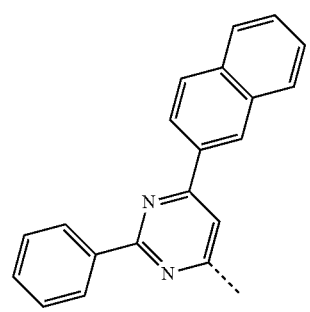
B-64
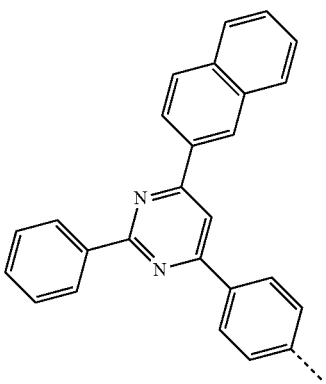
B-65
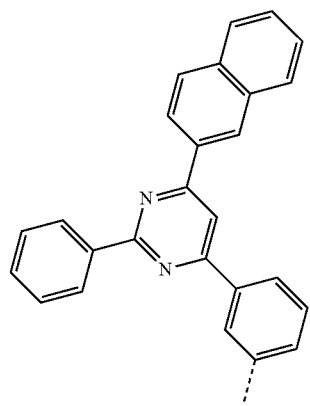
B-66
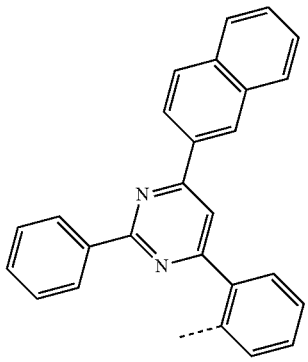
B-67
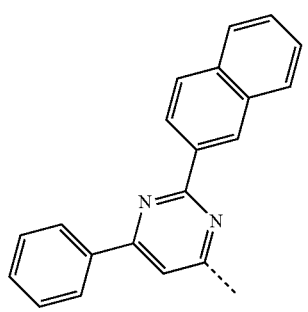
B-68
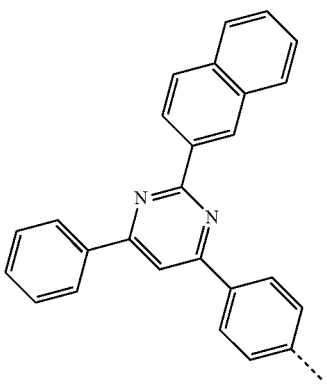
B-69
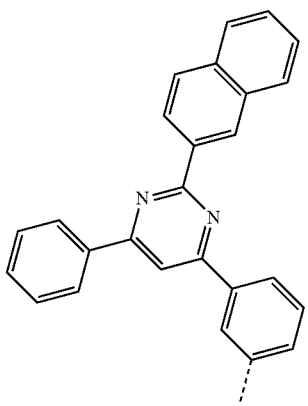

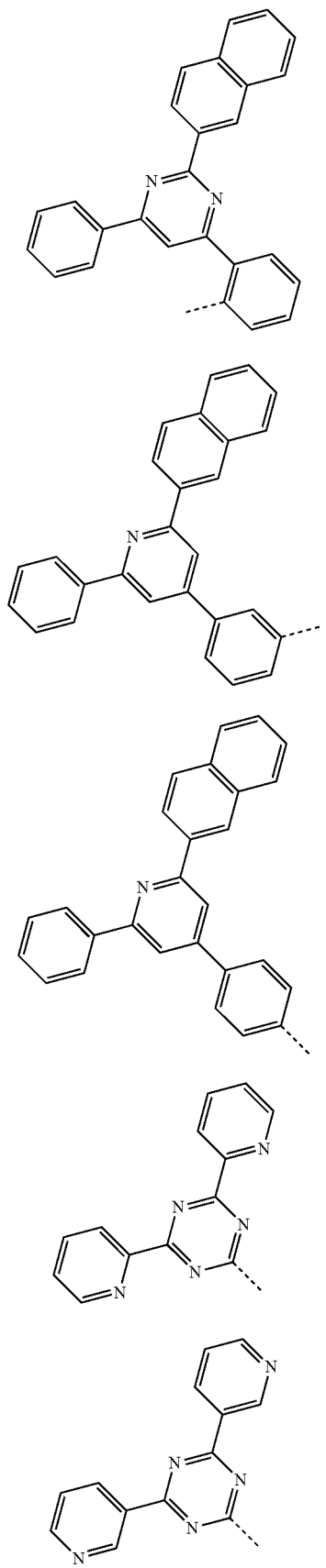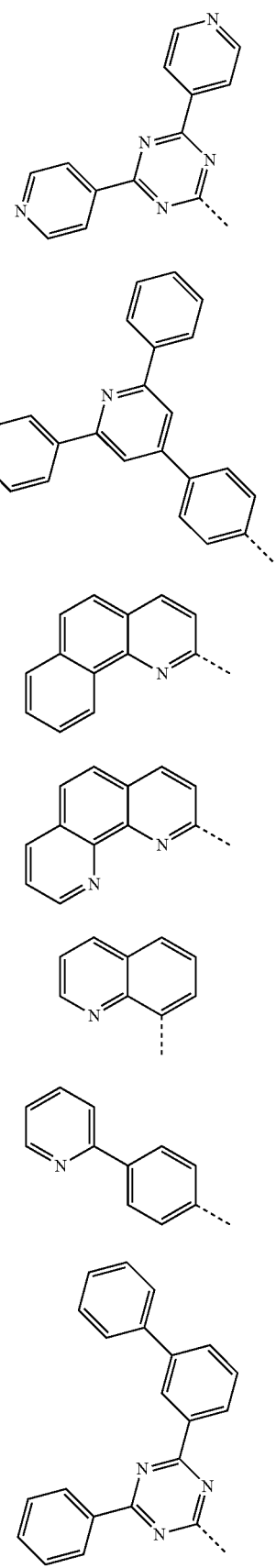

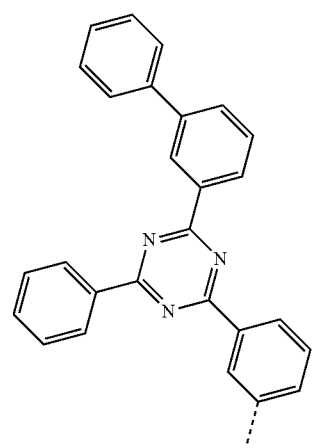
B-81
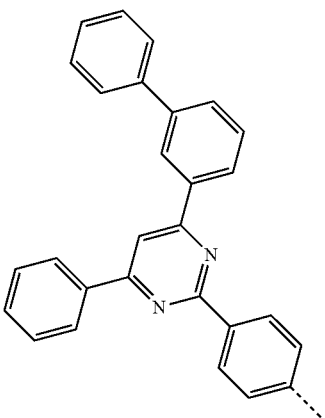
B-85
B-82
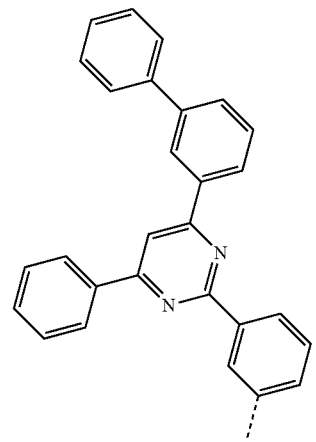
B-86
B-83
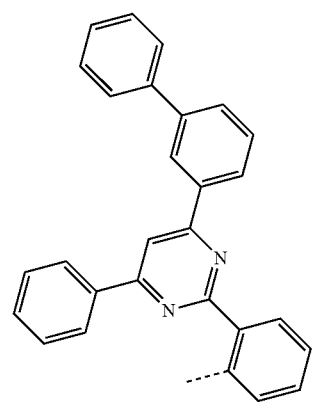
B-87
B-84
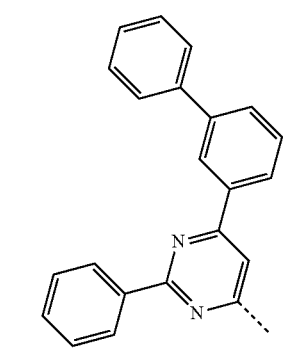
B-88

B-89
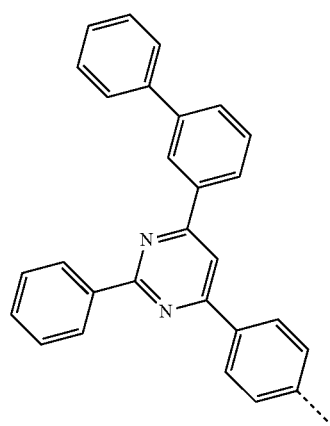
B-90
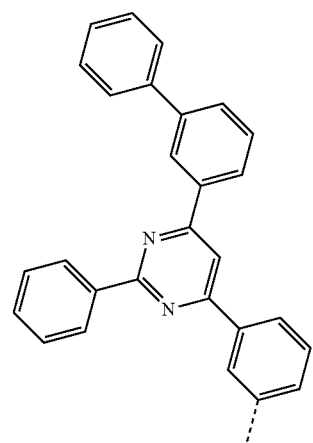
B-91
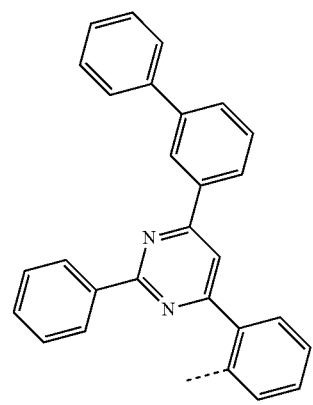
B-92
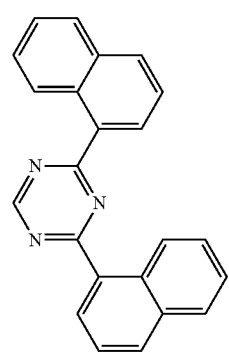
B-93
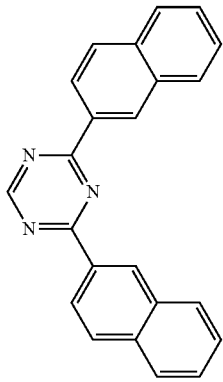
B-94
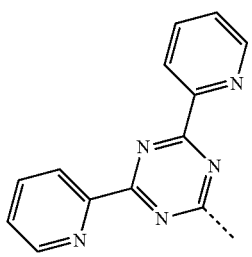
B-95
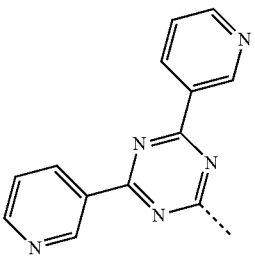
B-96
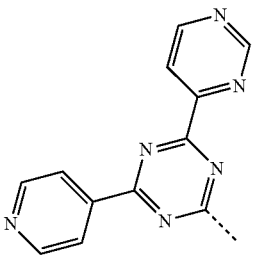
B-97
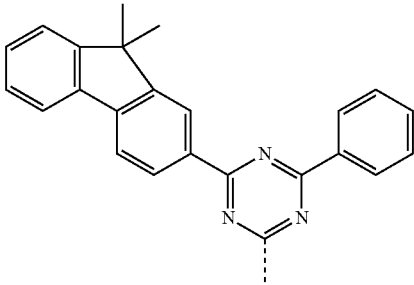

B-98
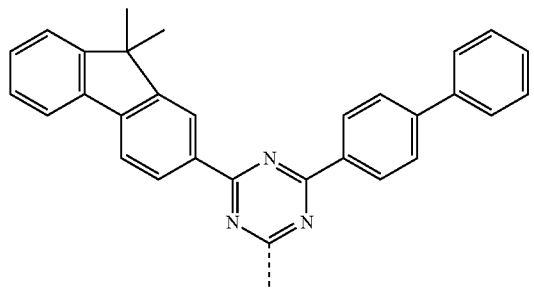
B-99
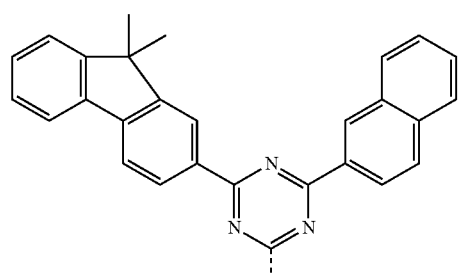
B-100
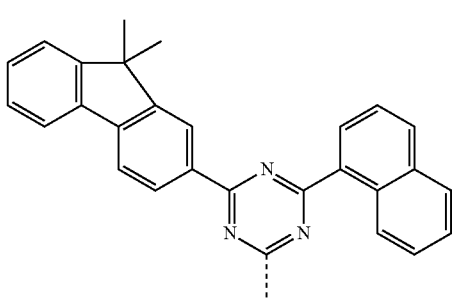
B-101
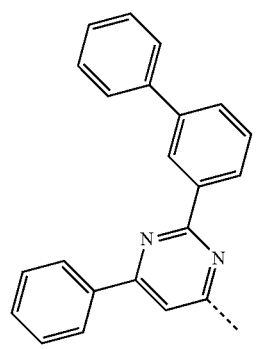
C-1
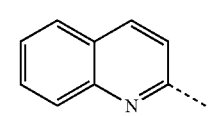
C-2
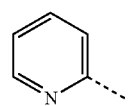
C-3
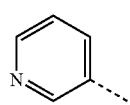
C-4
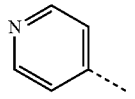
C-5
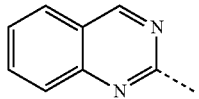
C-6
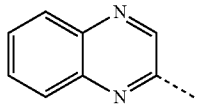
C-7
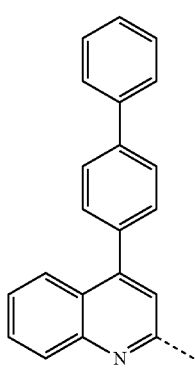
C-8
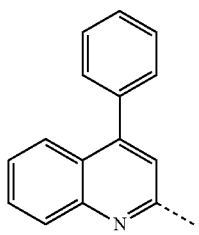
C-9
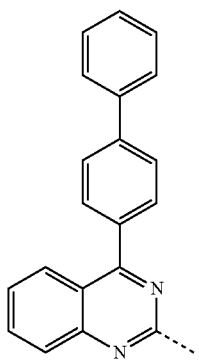
C-10
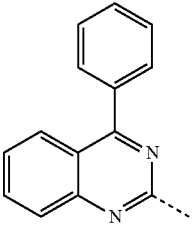

303
-continued
C-11
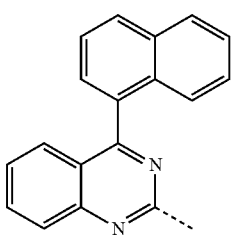
C-12
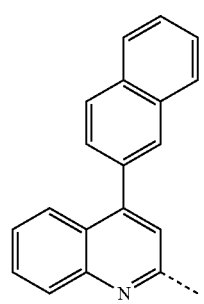
C-13
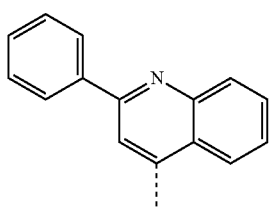
C-14
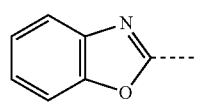
C-15
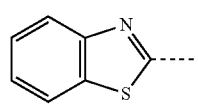
C-16
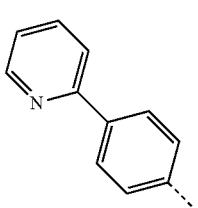
C-17
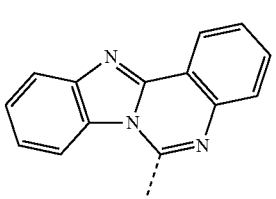
304
-continued
C-18
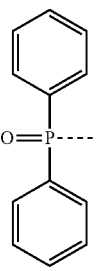
C-19
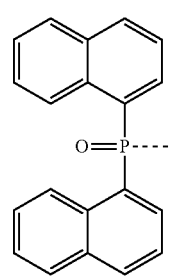
C-20
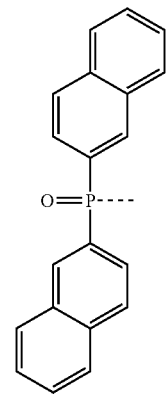
C-21
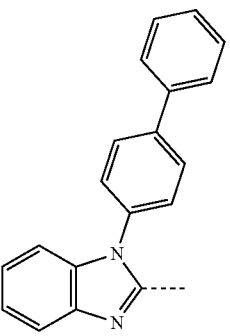
C-22
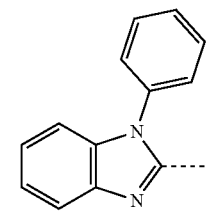

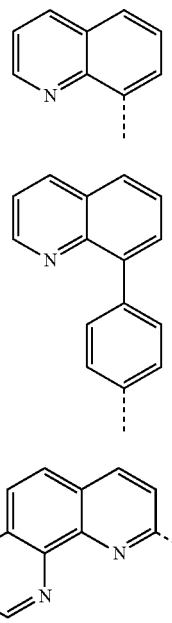
C-23
C-24
C-25
12. The organic light emitting device of claim 1, wherein the compound of Chemical Formula 1 is any one selected from the following compounds:
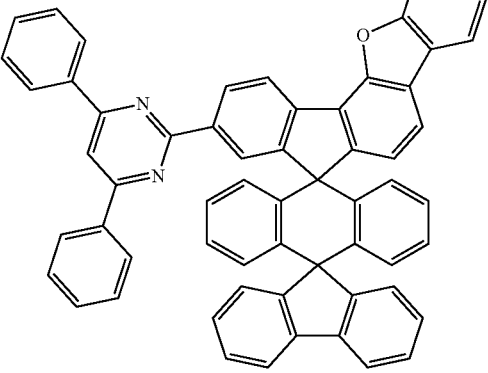
3
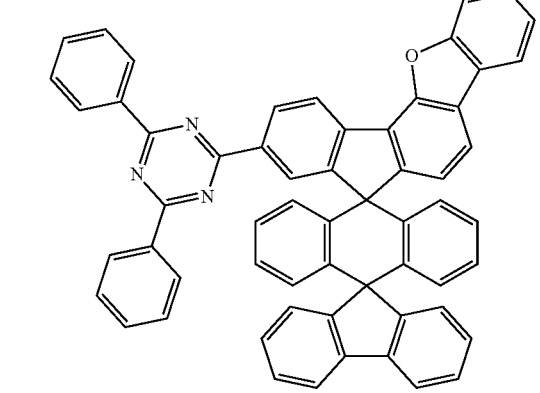
1
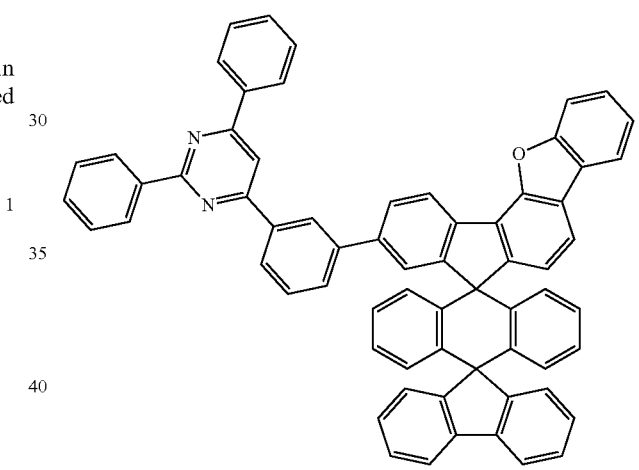
4
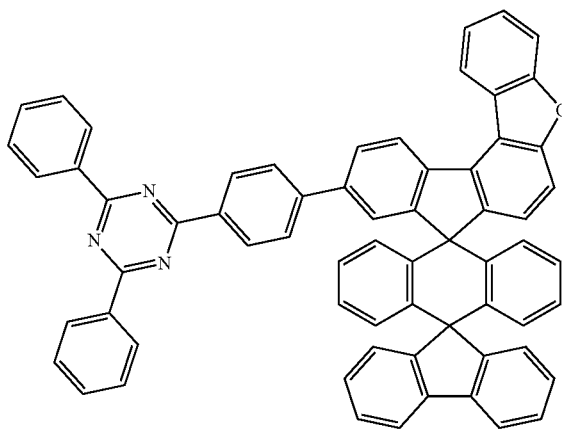
2
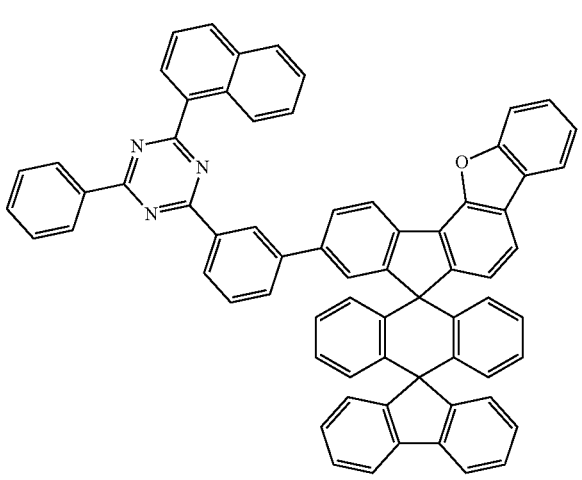
5

307
-continued
6
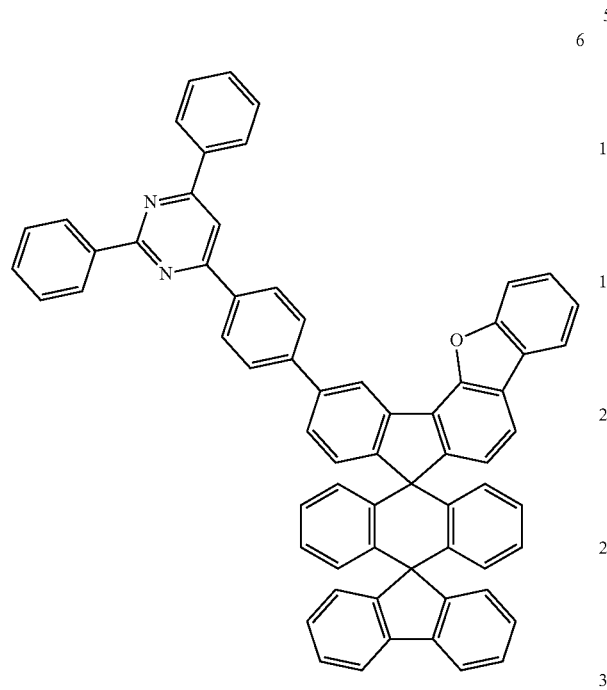
7
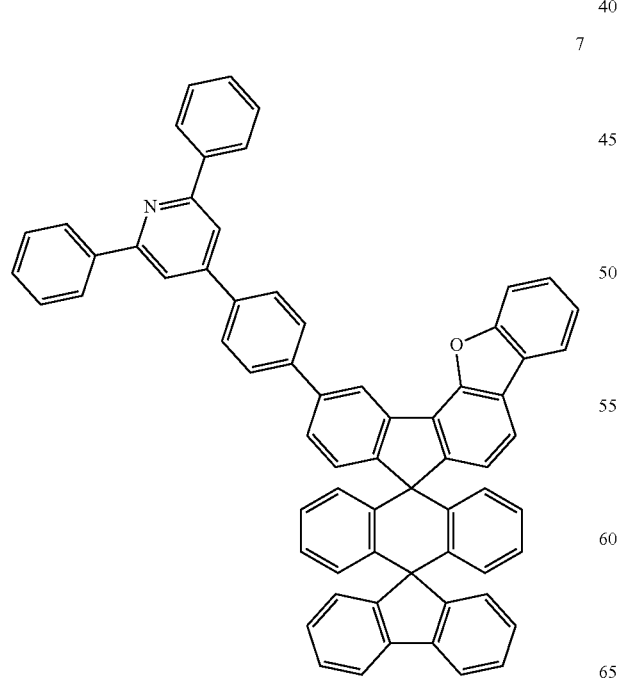
308
-continued
8
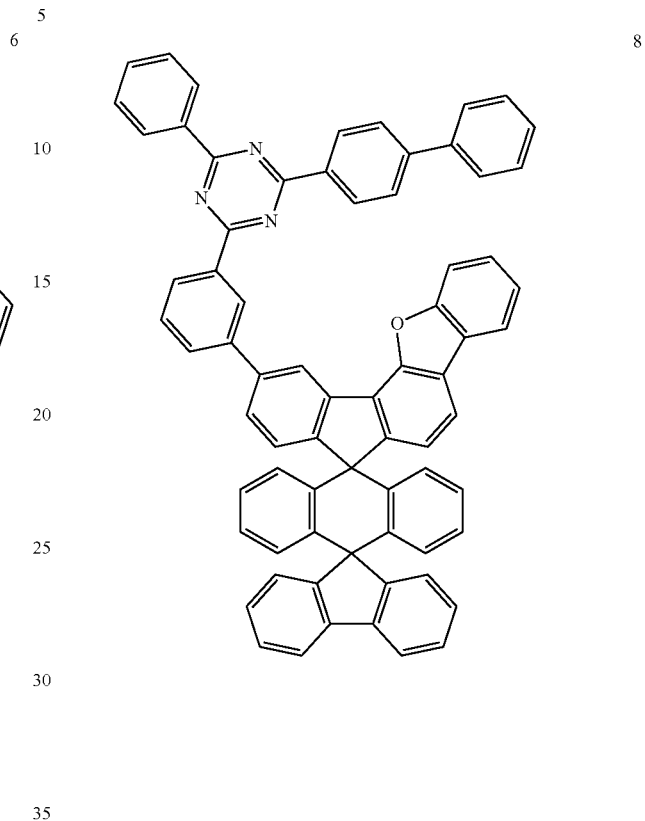
9
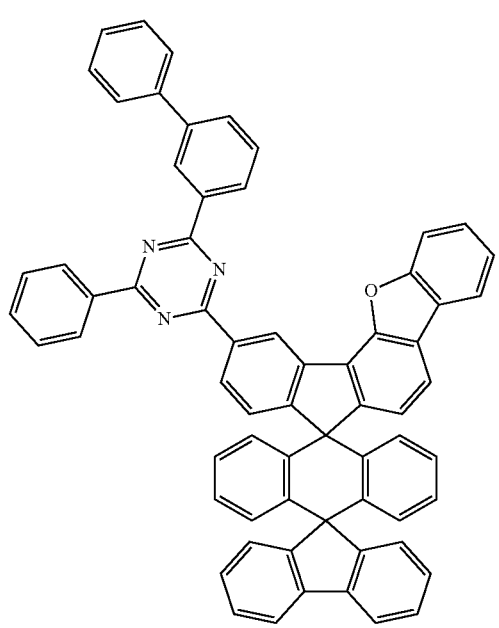

309
-continued
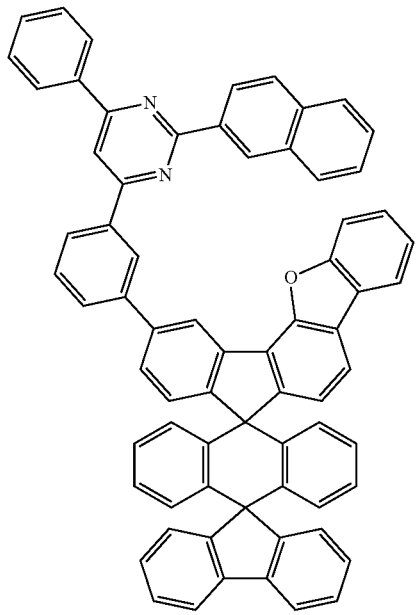
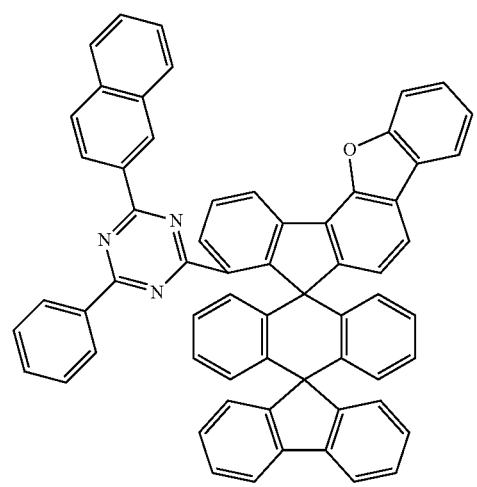
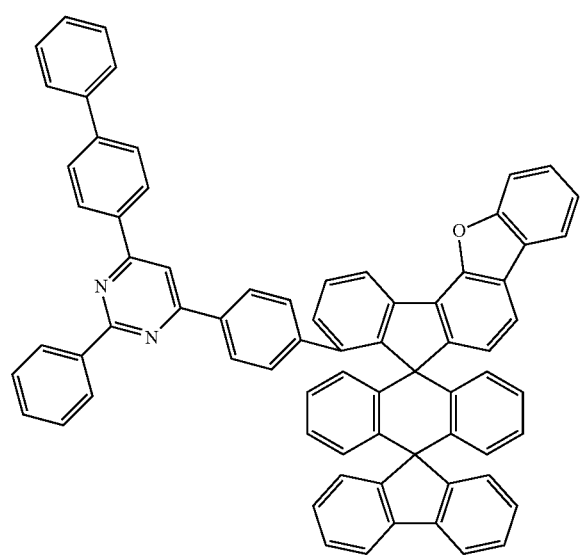
310
-continued
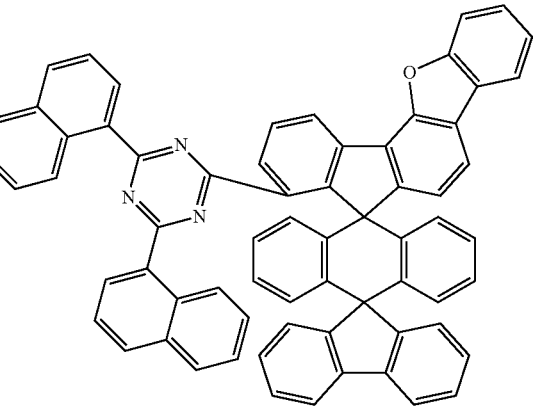
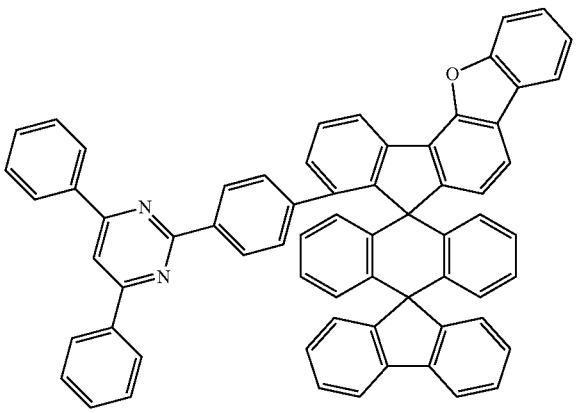

311
-continued
16
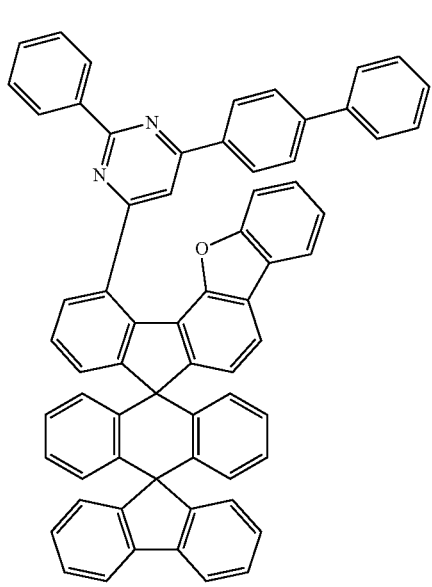
17
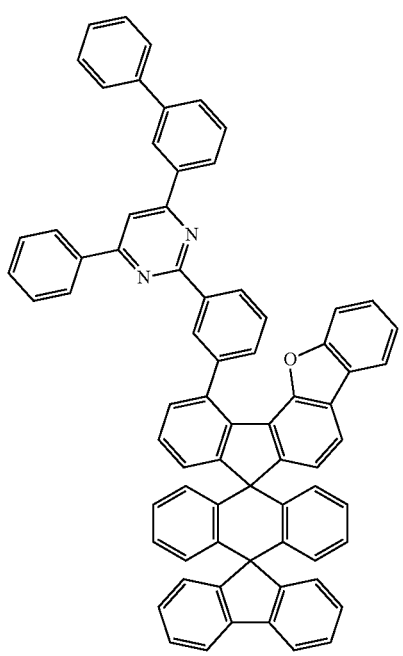
312
-continued
18
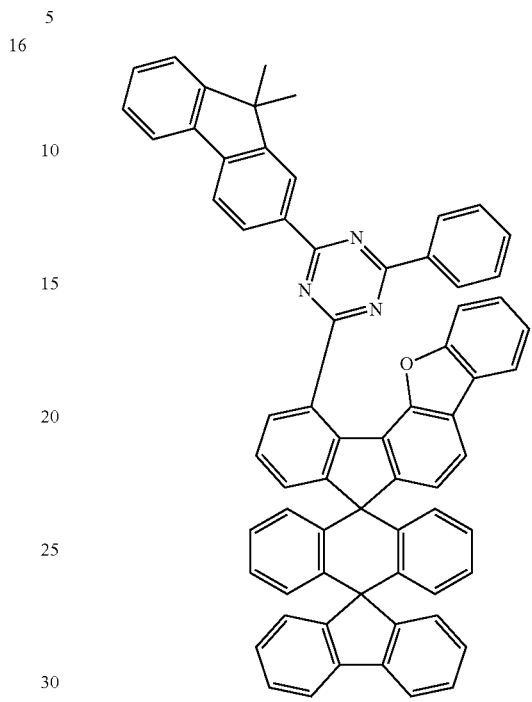
19
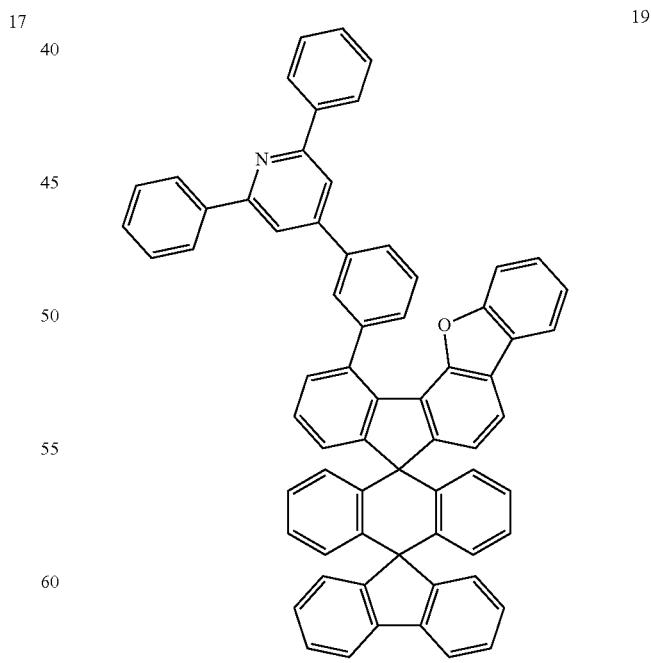

313
-continued
20
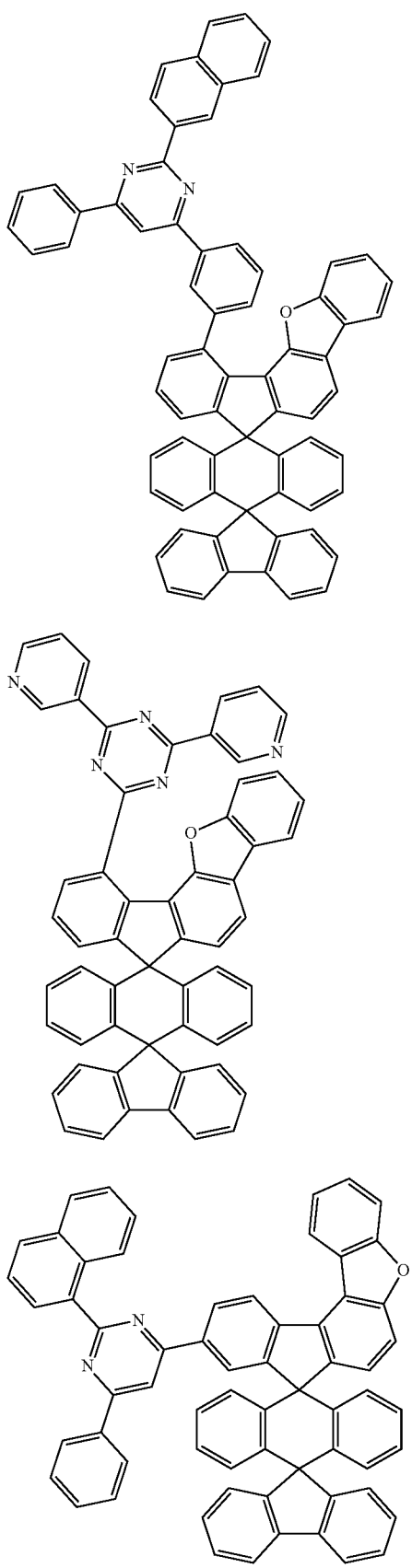
314
-continued
23
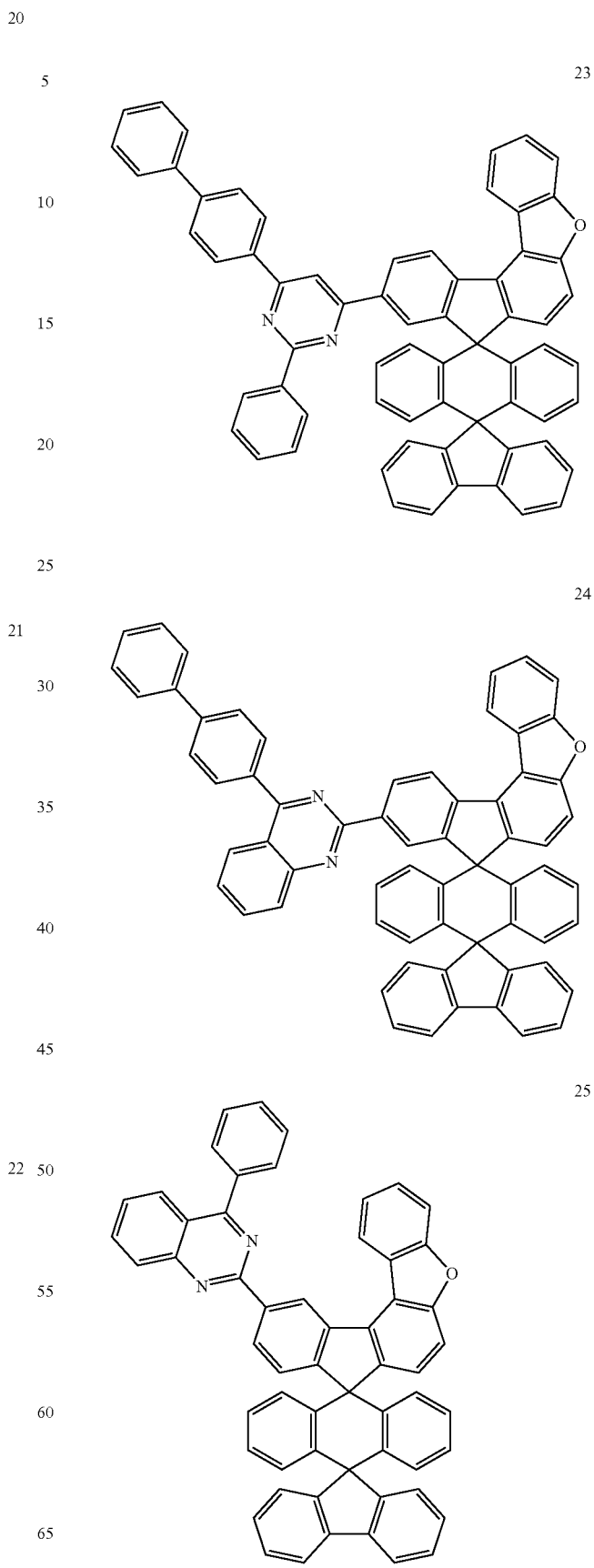
21
22
24
25

315
-continued
316
-continued
26
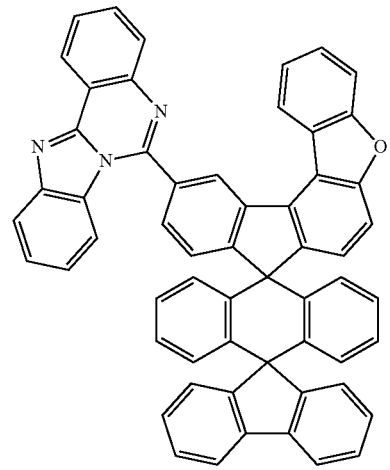
29
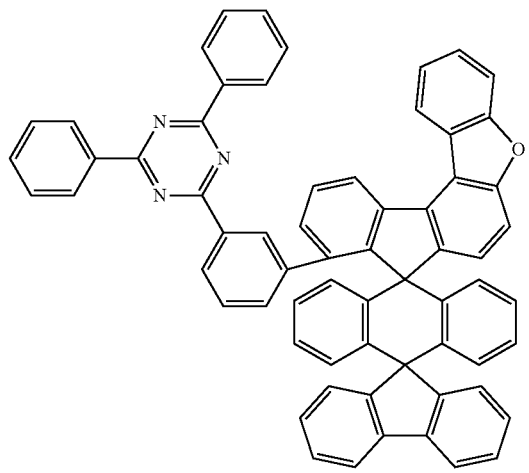
27
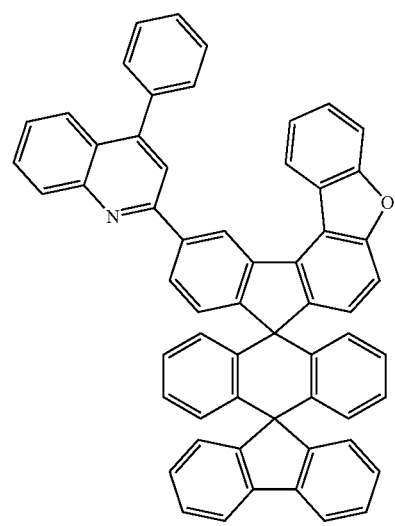
30
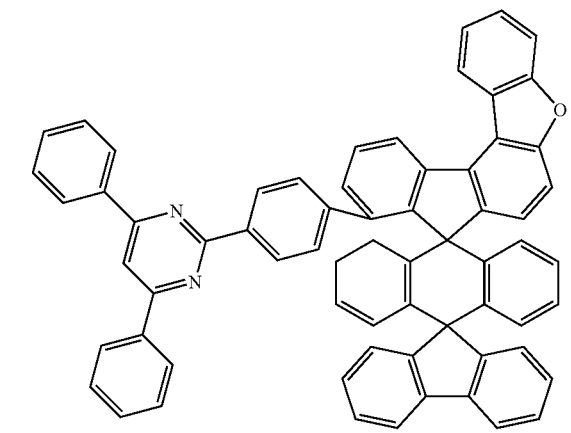
28
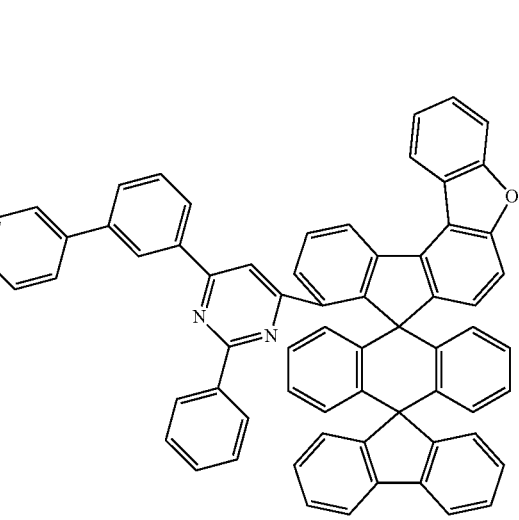
31
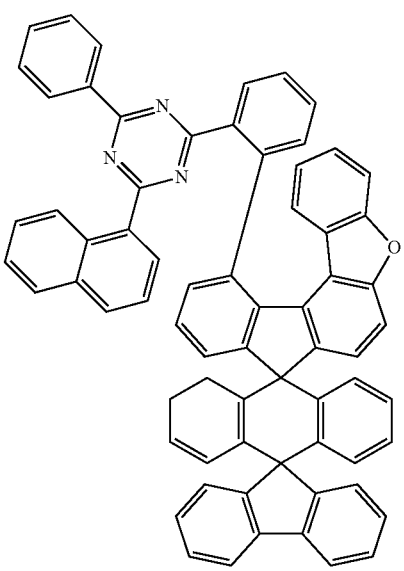

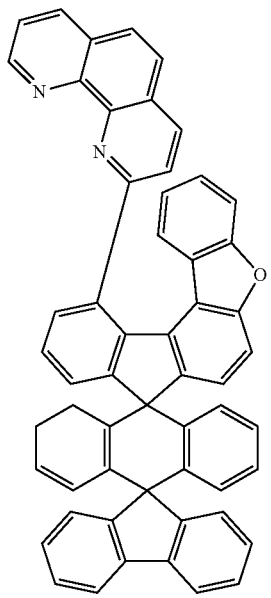
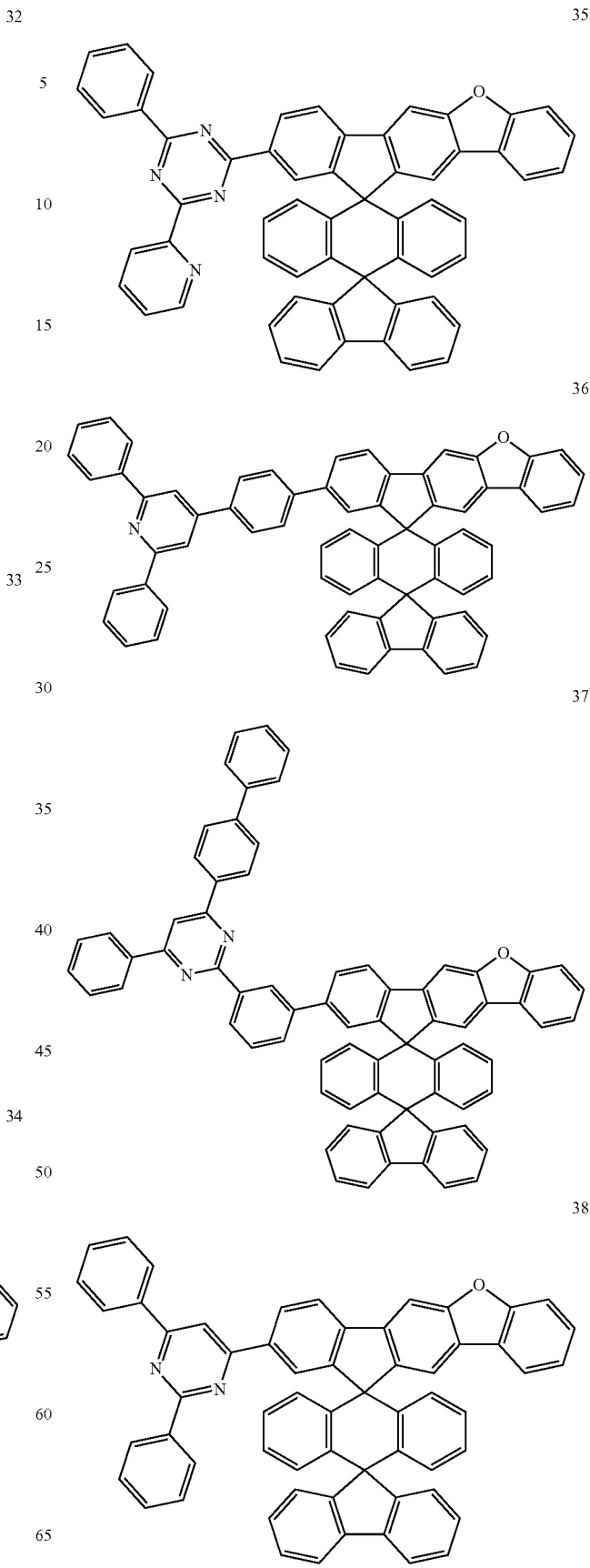

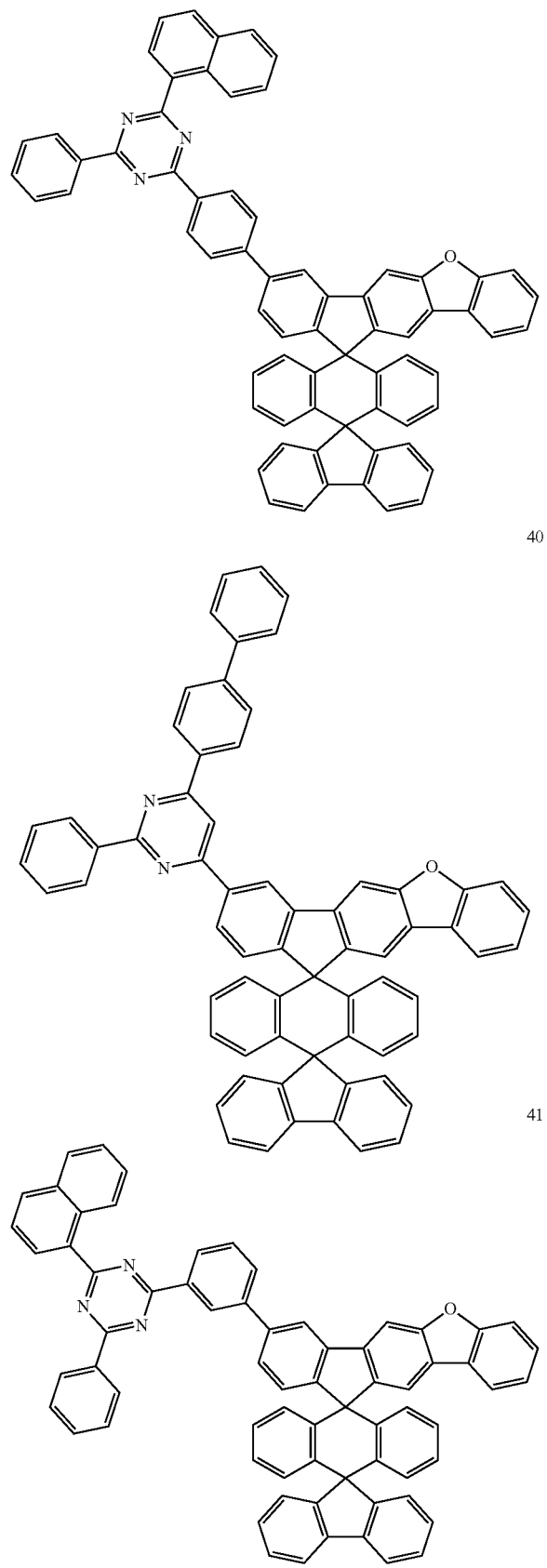
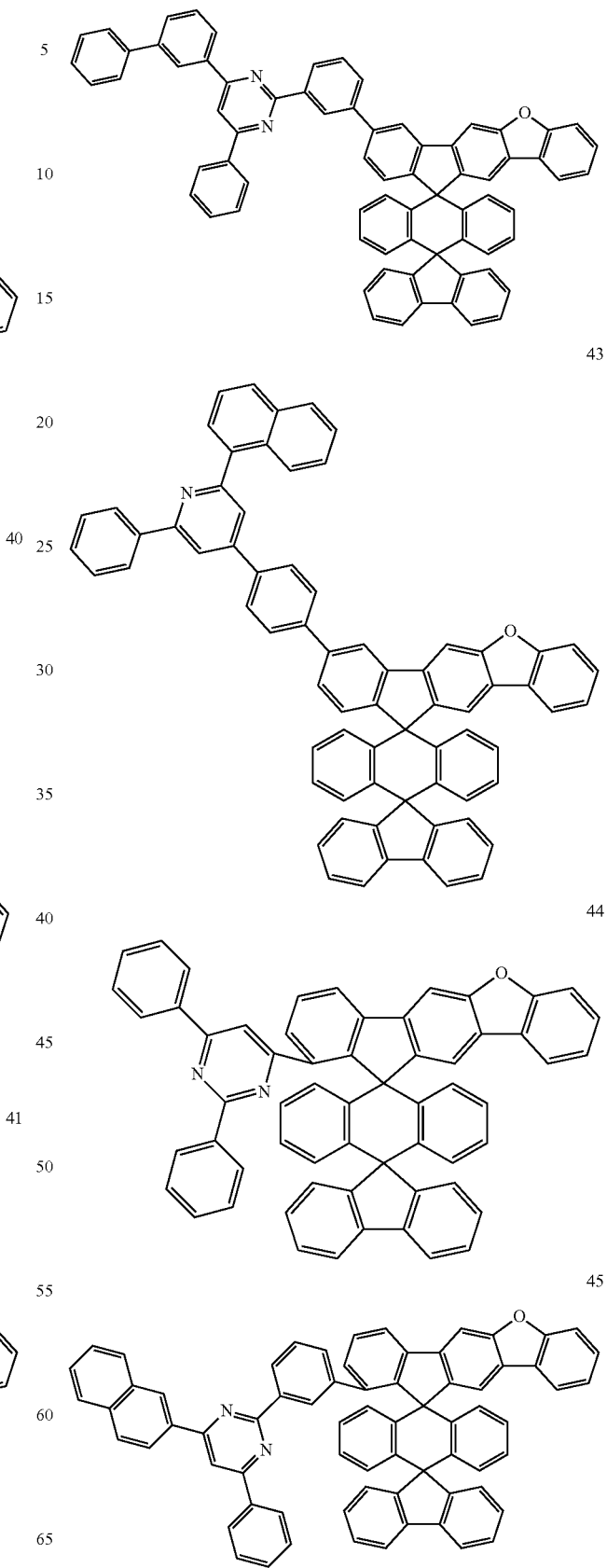

321
-continued
46
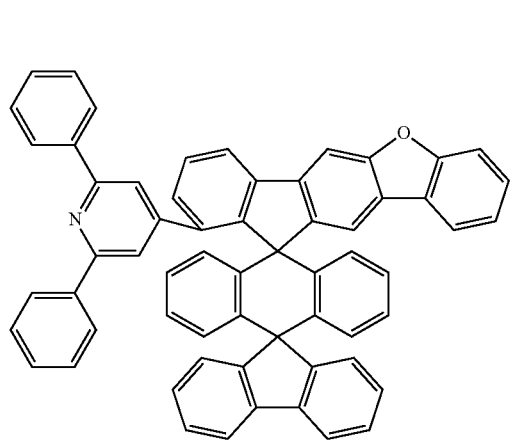
47
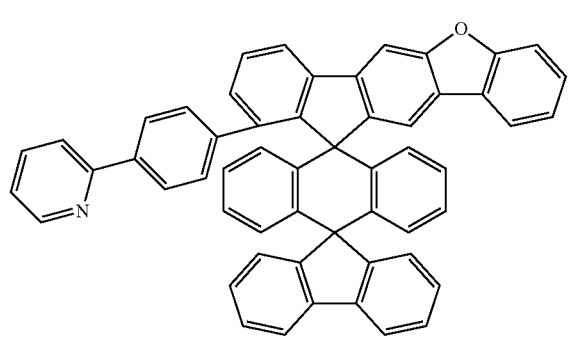
48
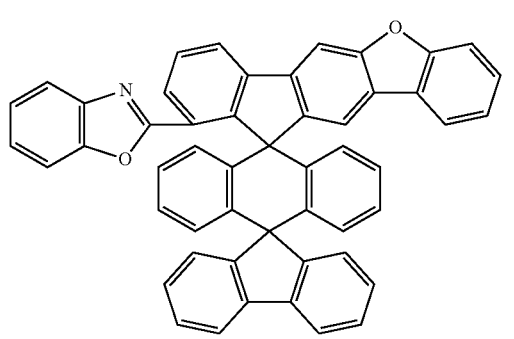
322
-continued
49
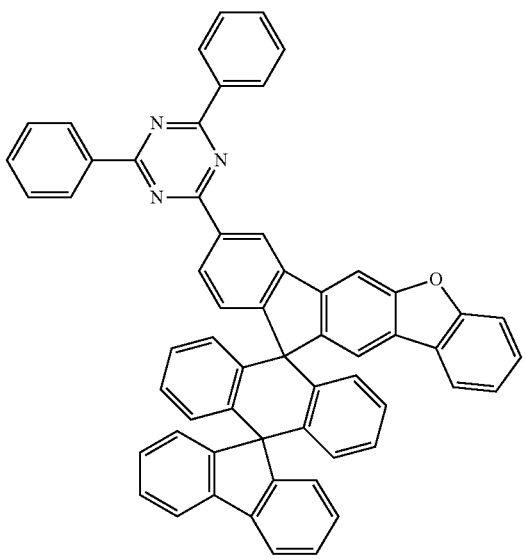
50
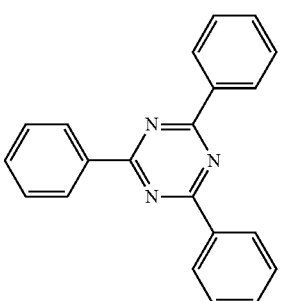
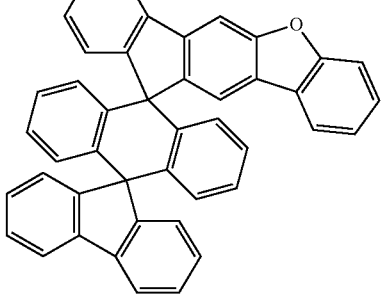

51
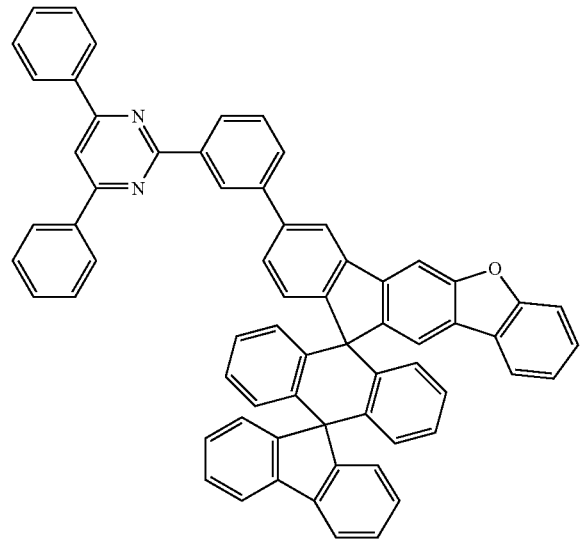
52
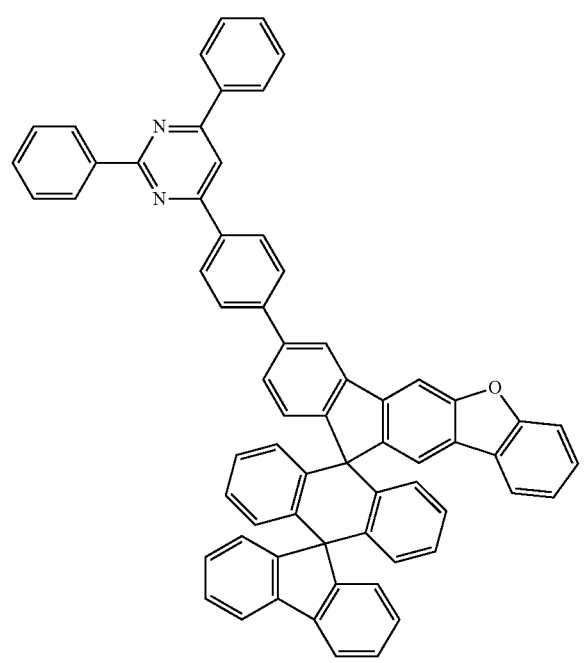
53
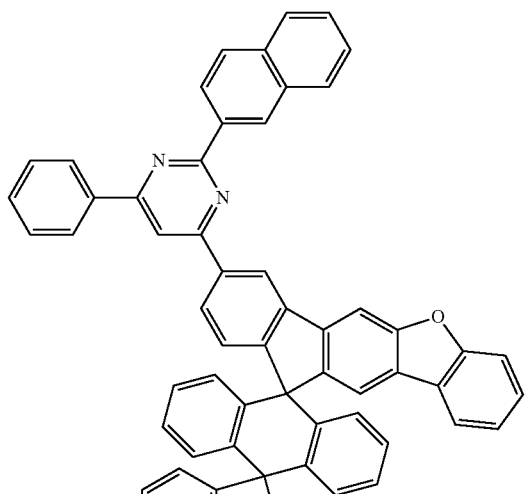
54
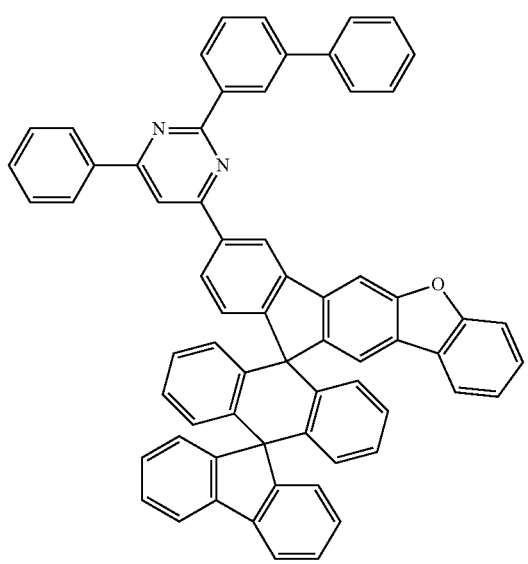
55
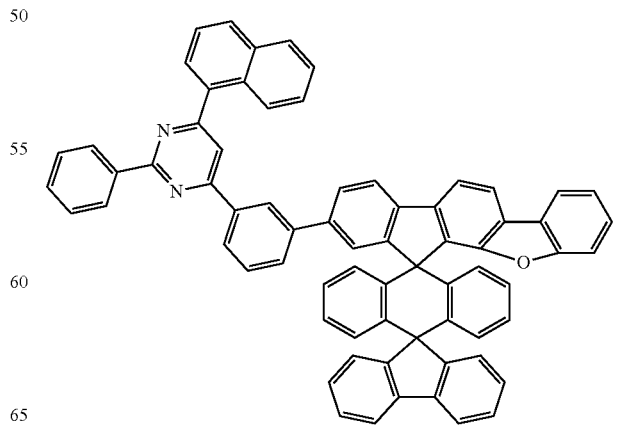

-continued
56
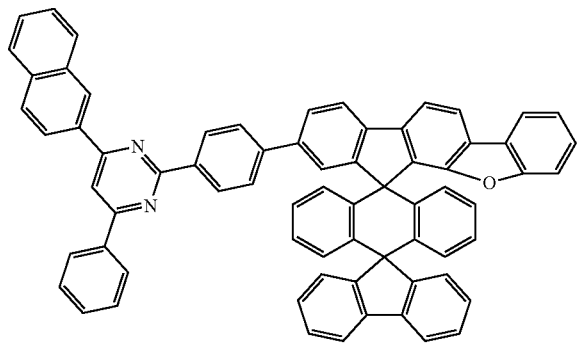
57
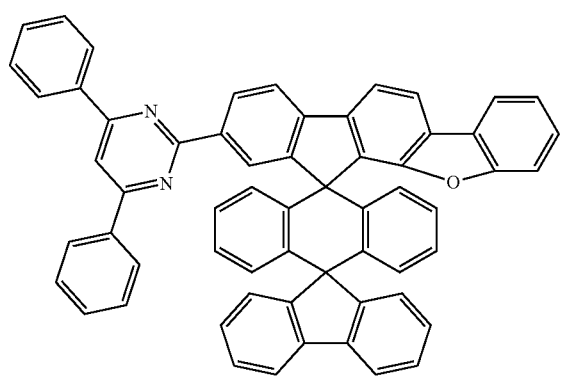
58
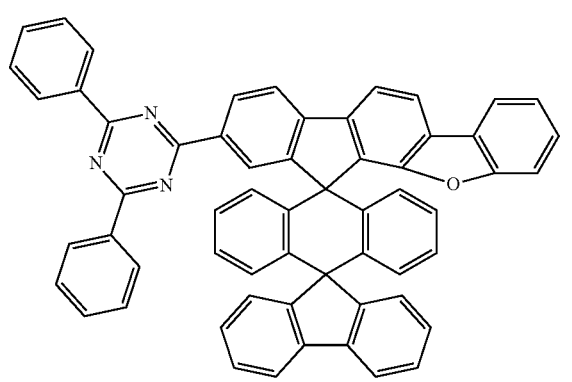
59
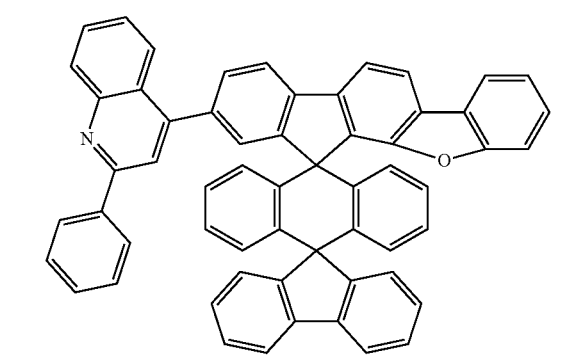
-continued
60
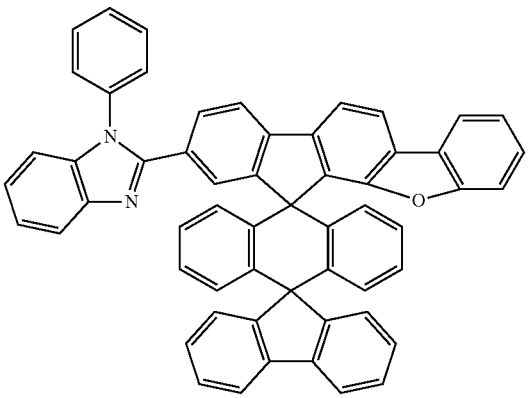
61
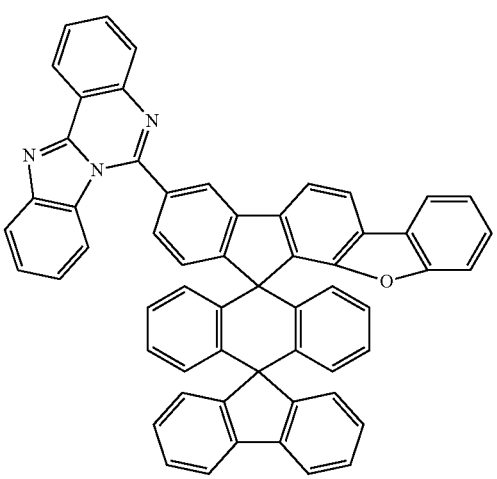
62
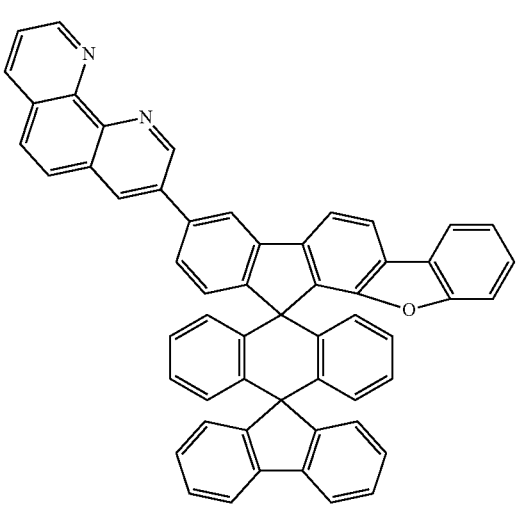

327
-continued
63
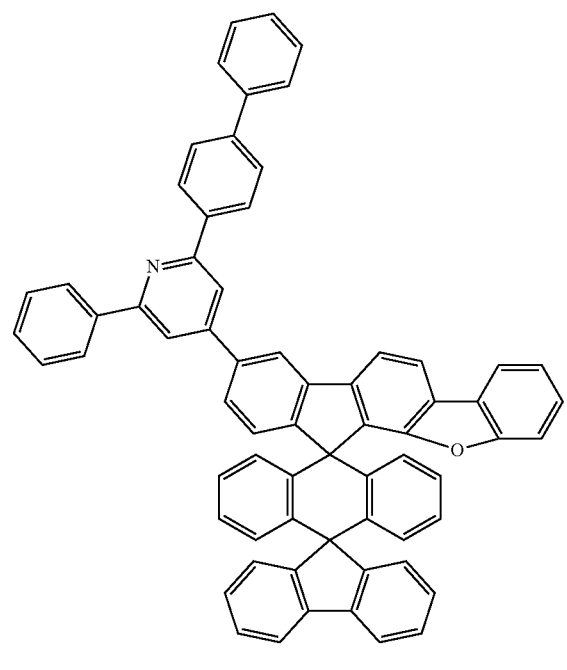
64
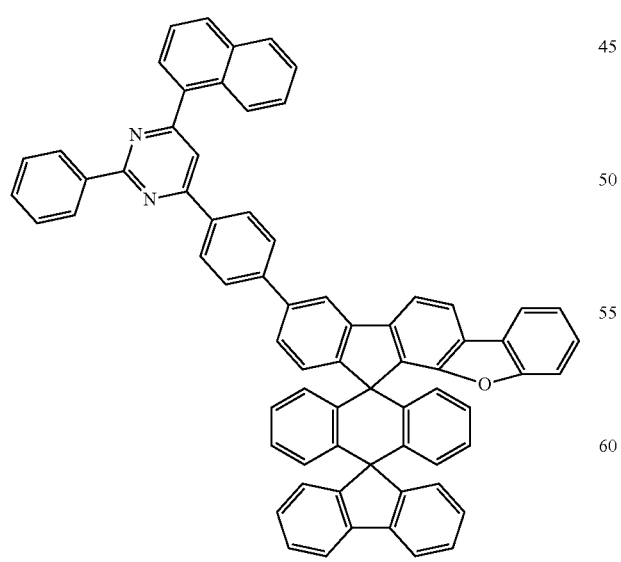
328
-continued
65
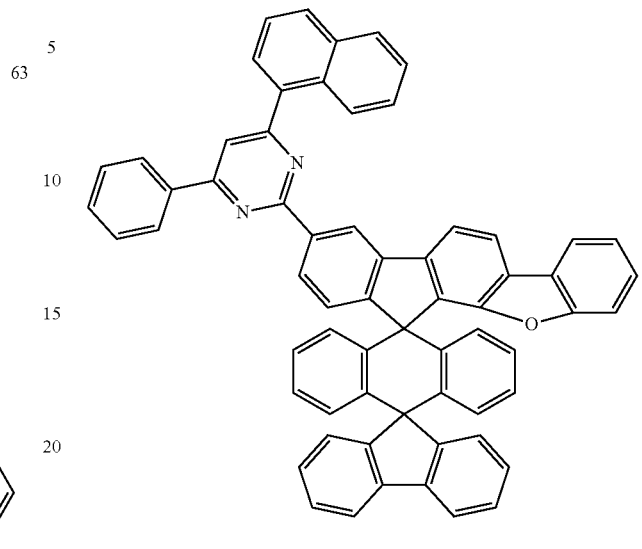
66
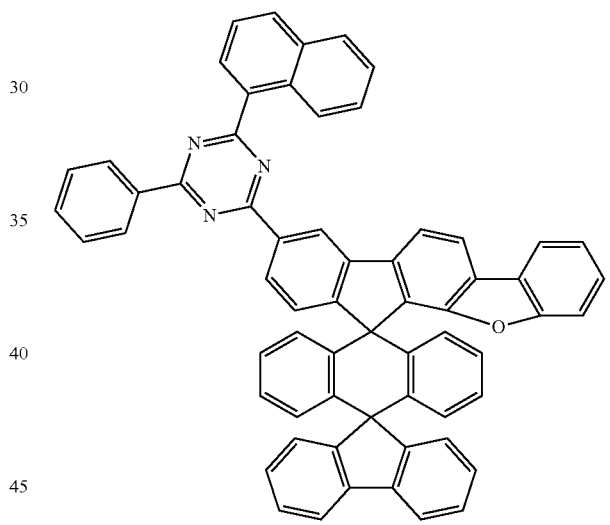
67
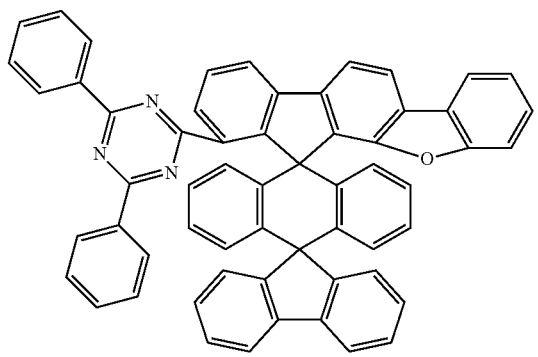

329
-continued
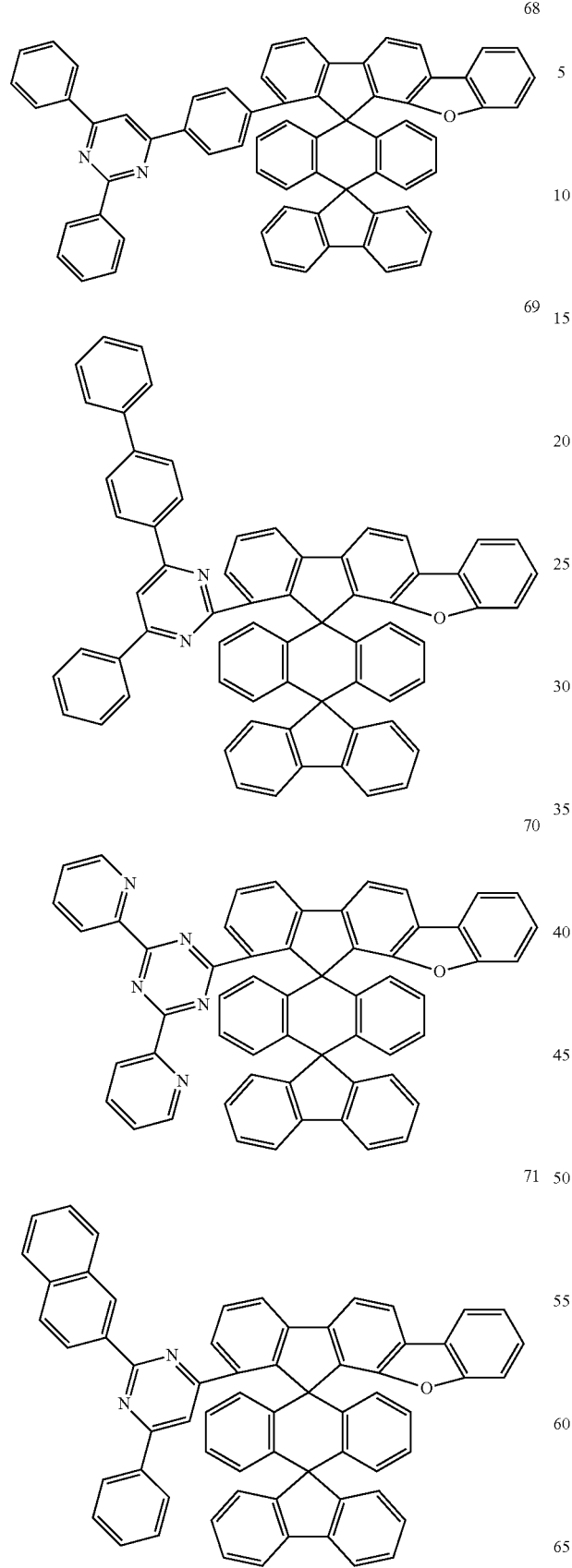
330
-continued
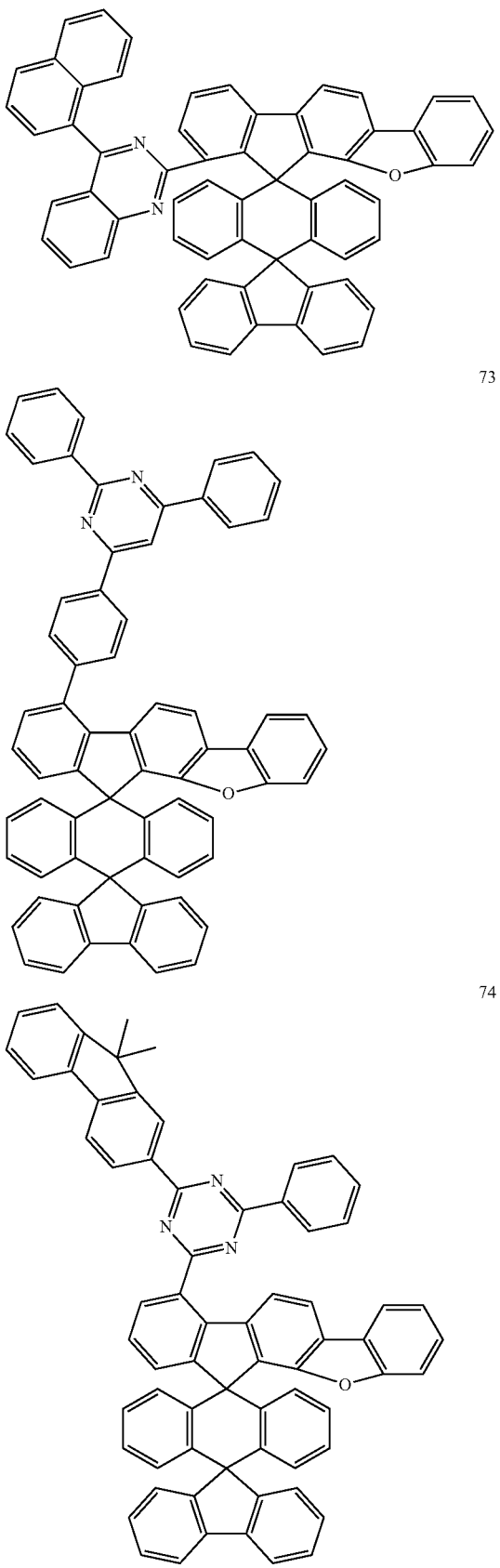

331
-continued
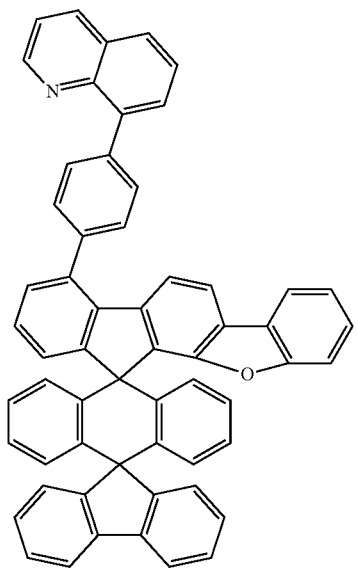
76
332
-continued
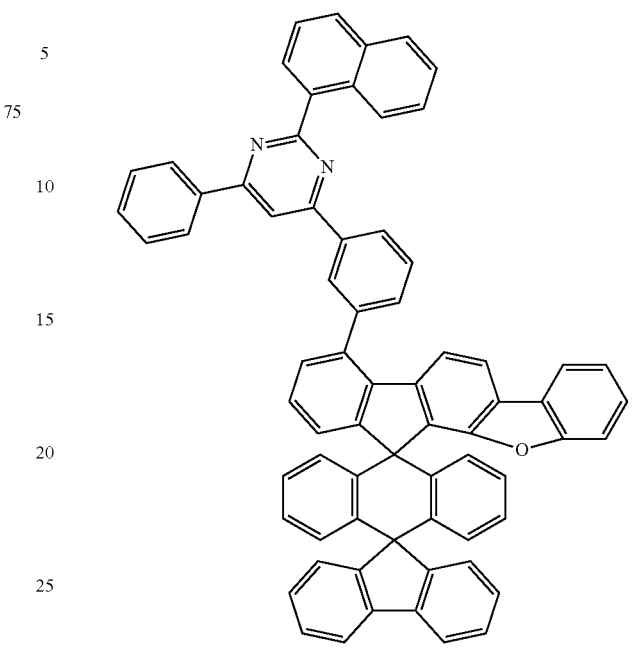
77
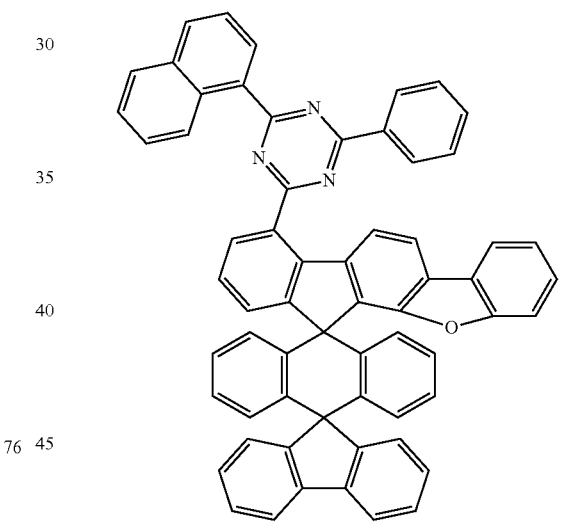
78
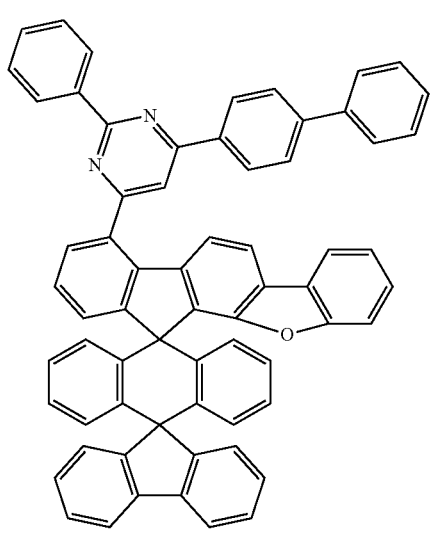
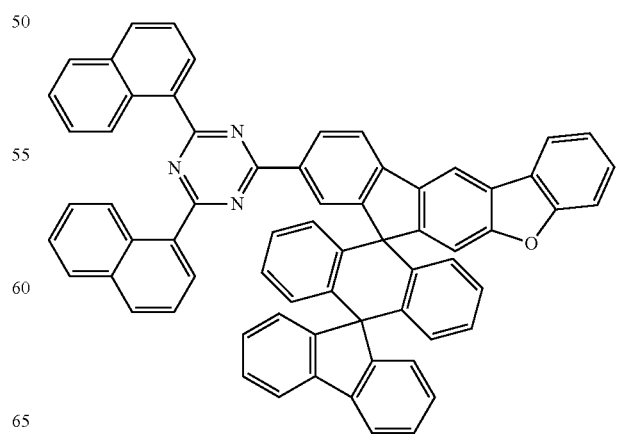
79

333
-continued
334
-continued
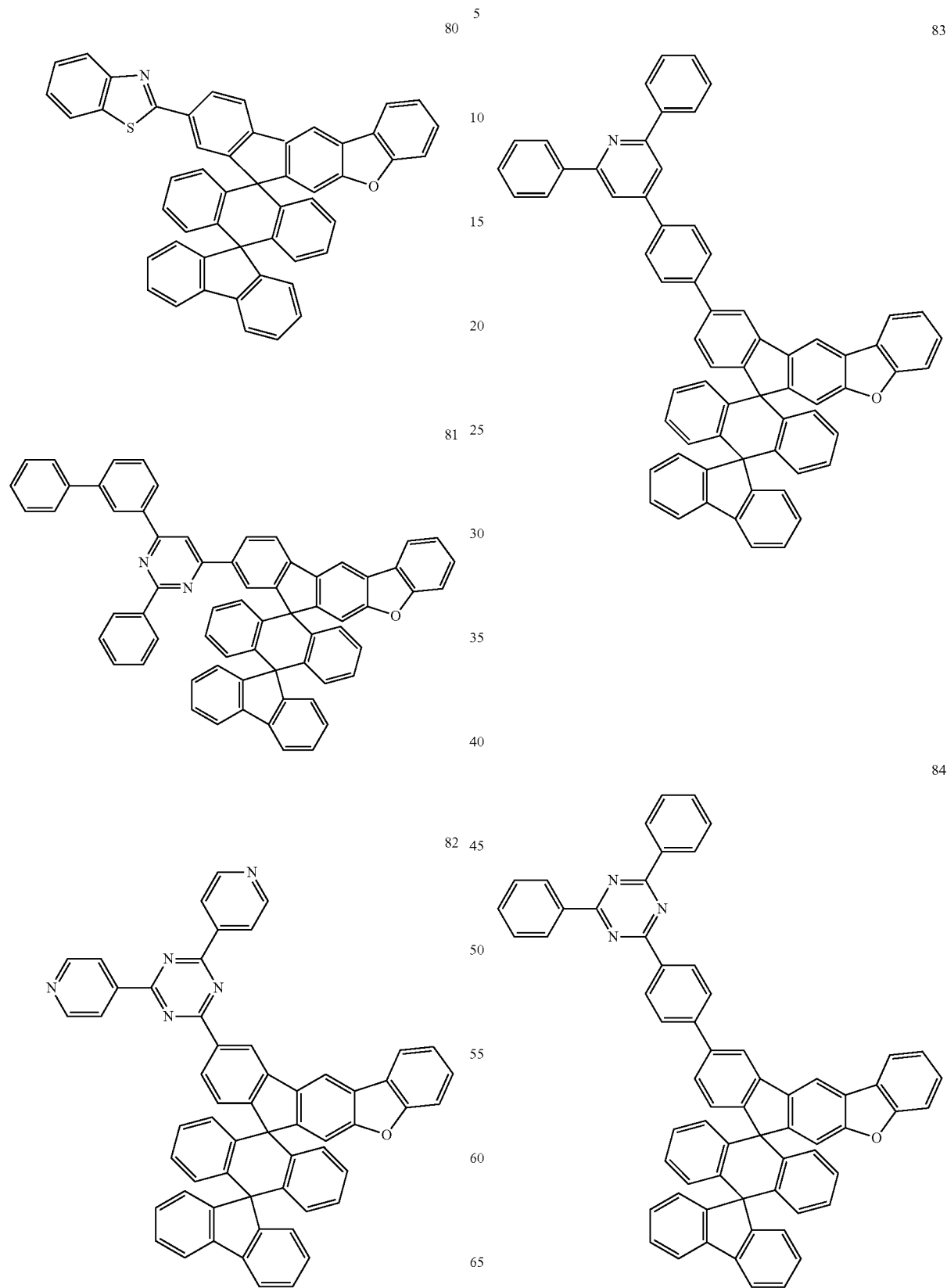

335
-continued
85
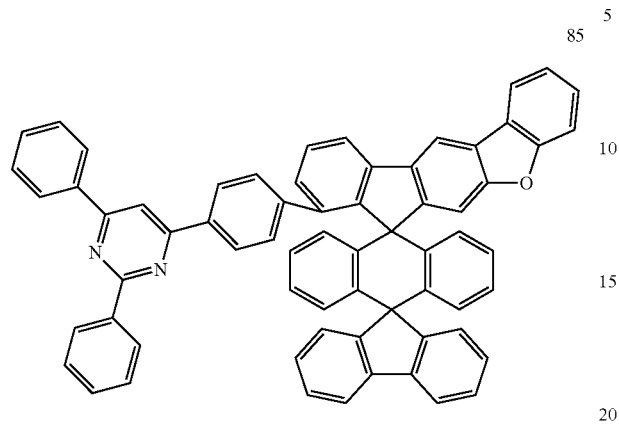
86
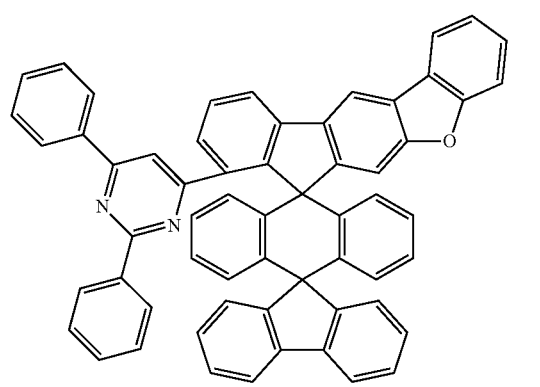
87
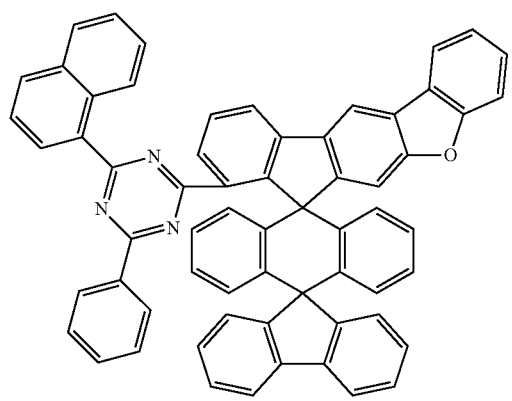
336
-continued
88
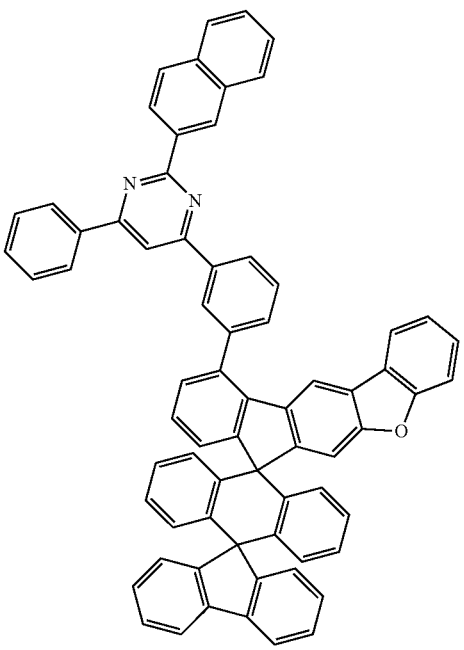
89
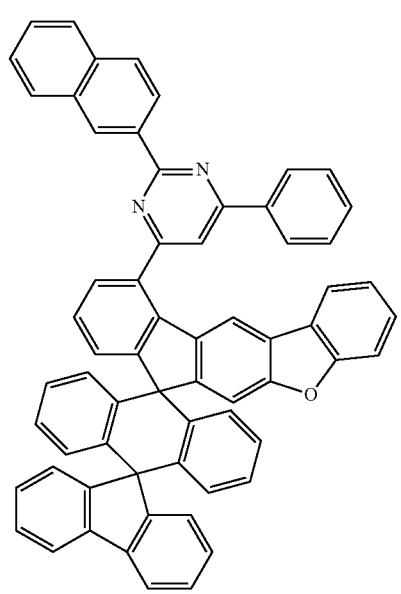

337
-continued
338
-continued
90
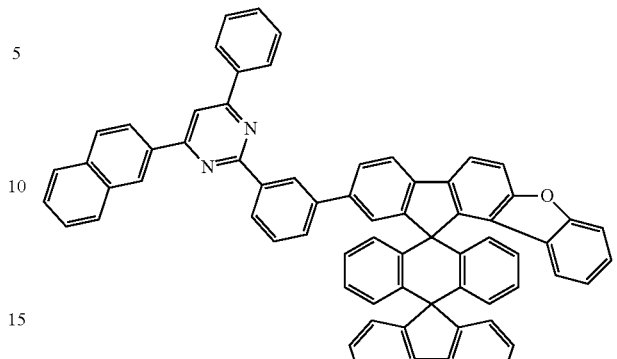
93
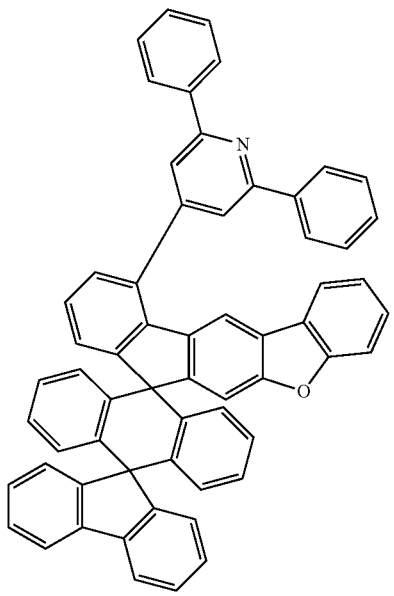
94
91
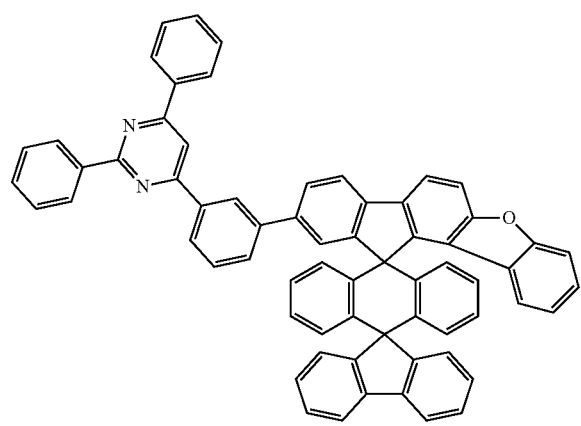
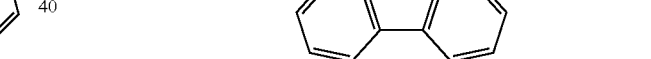
95
92
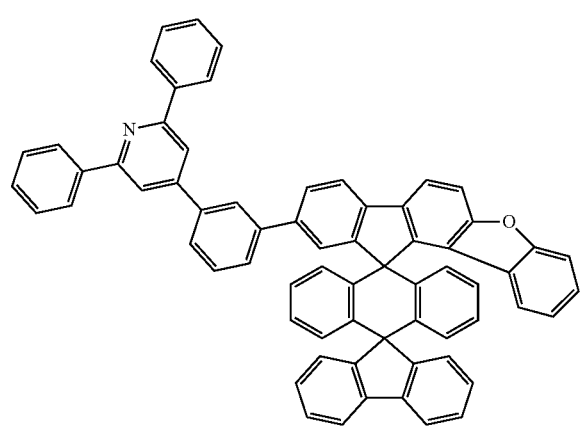
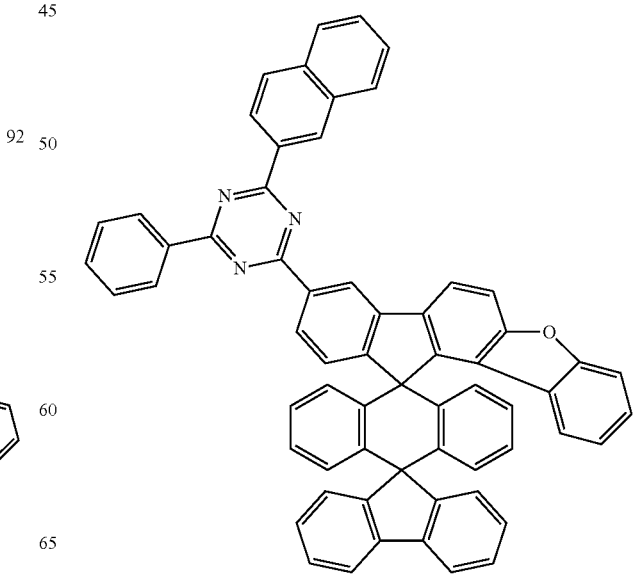

96
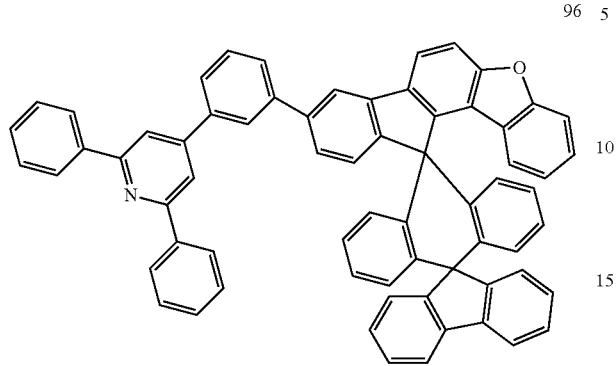
97
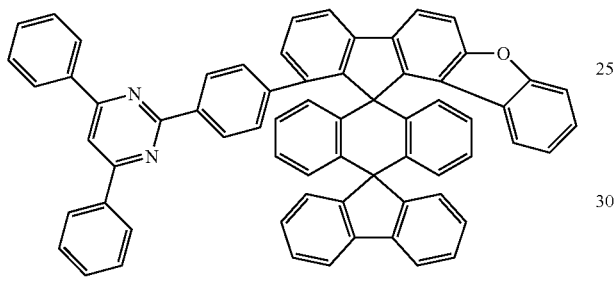
98
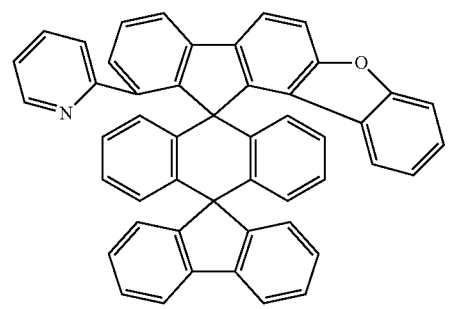
99
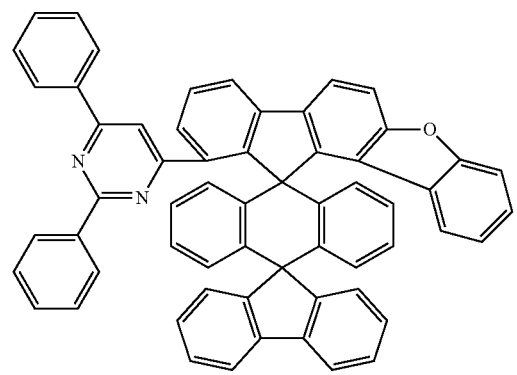
100
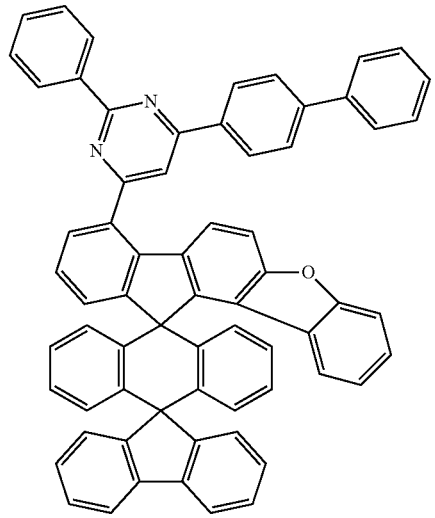
101
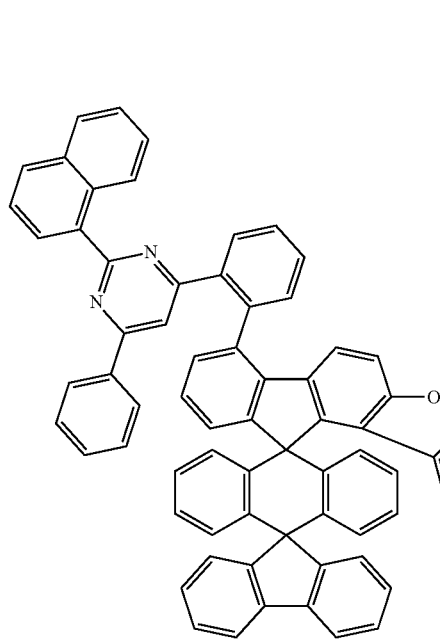
102
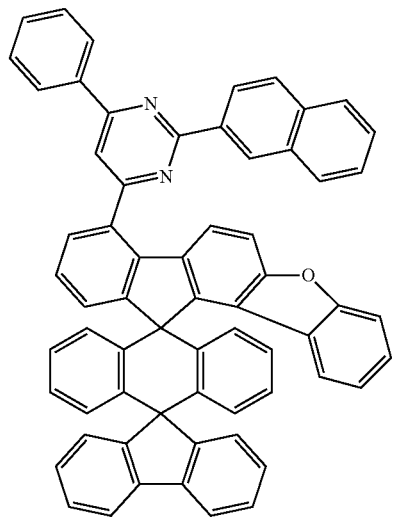

341
-continued
103
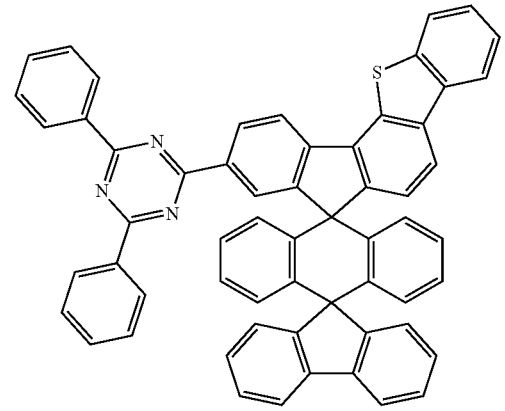
104
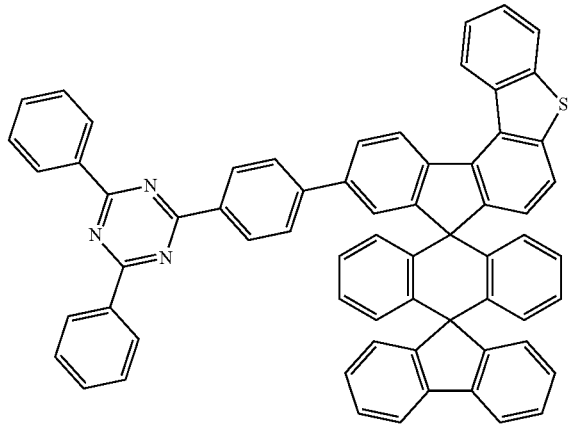
105
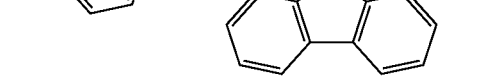
342
-continued
106
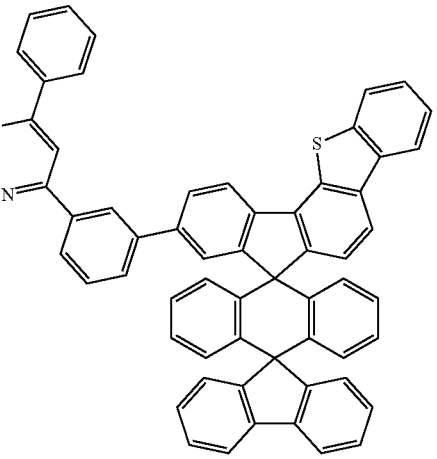
107
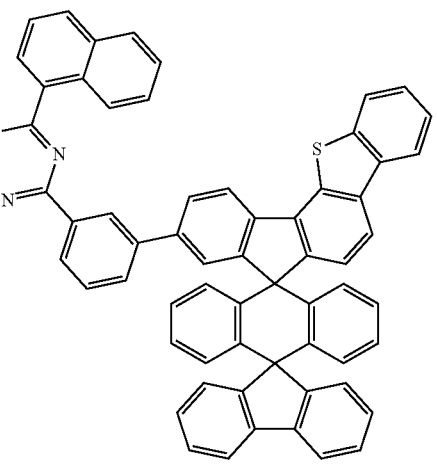
108
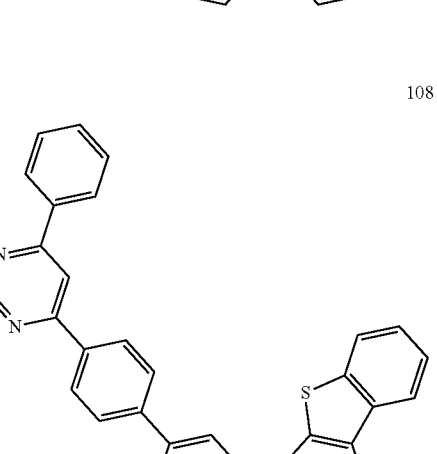

343
-continued
109
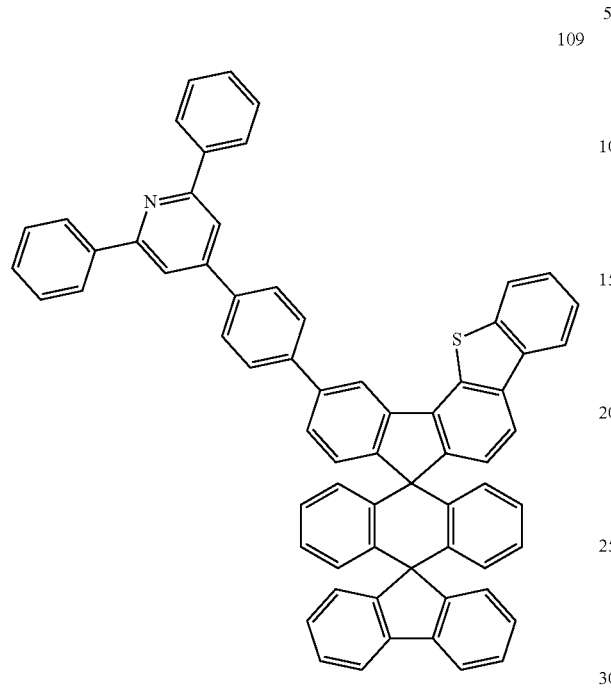
110
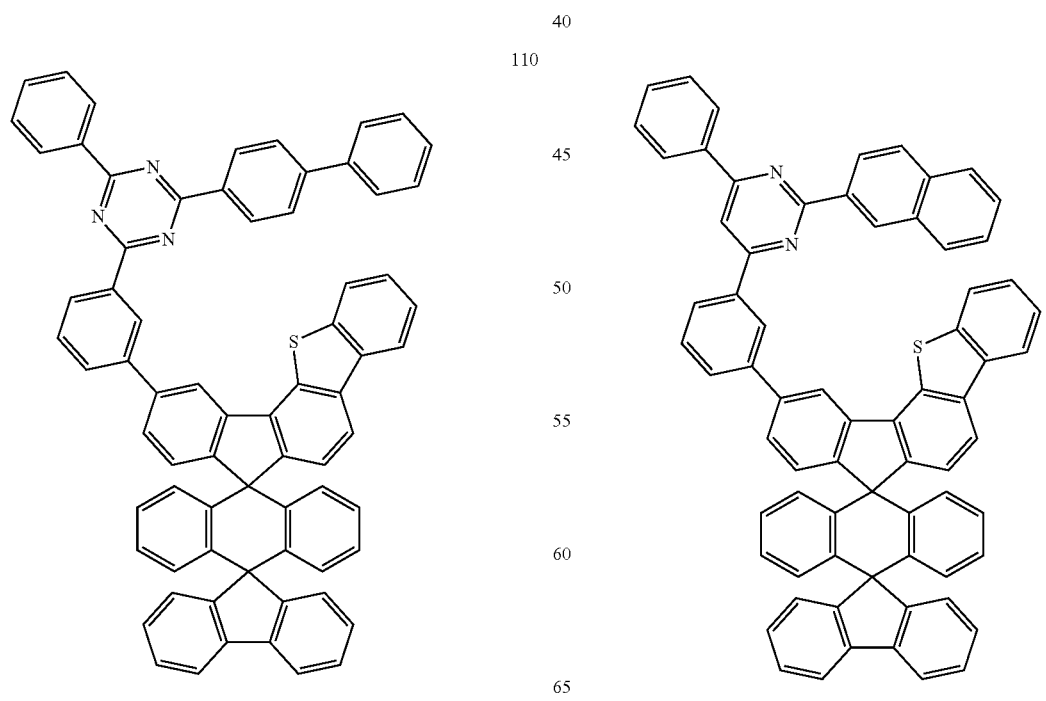
344
-continued
111
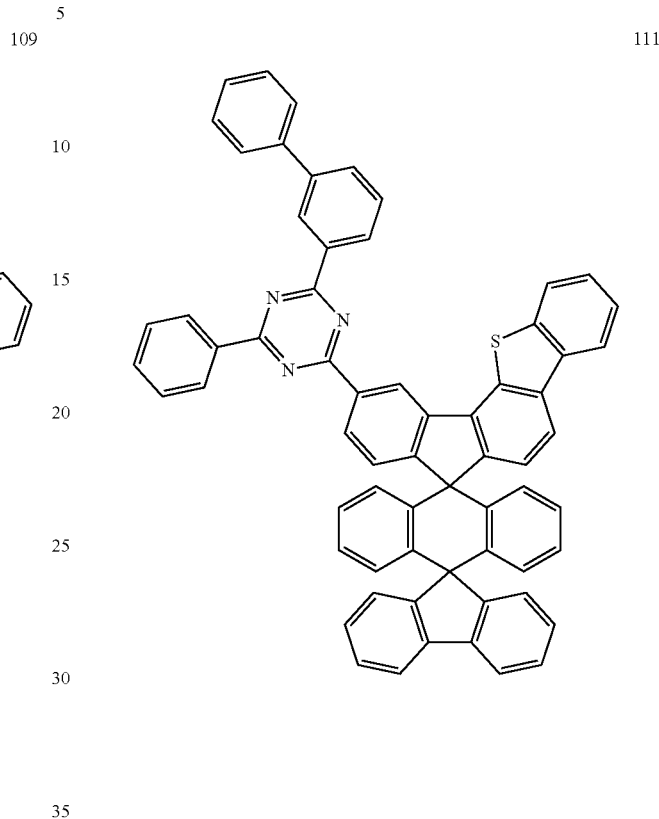
112

-continued
113
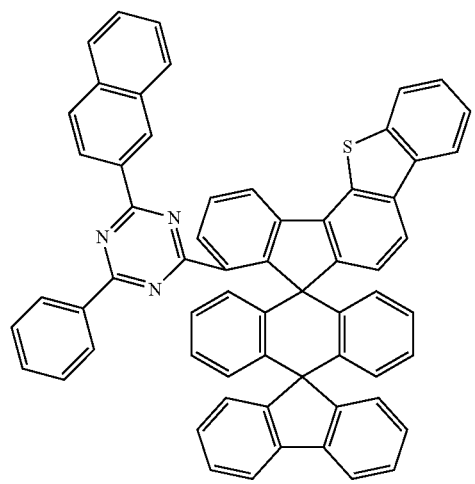
114
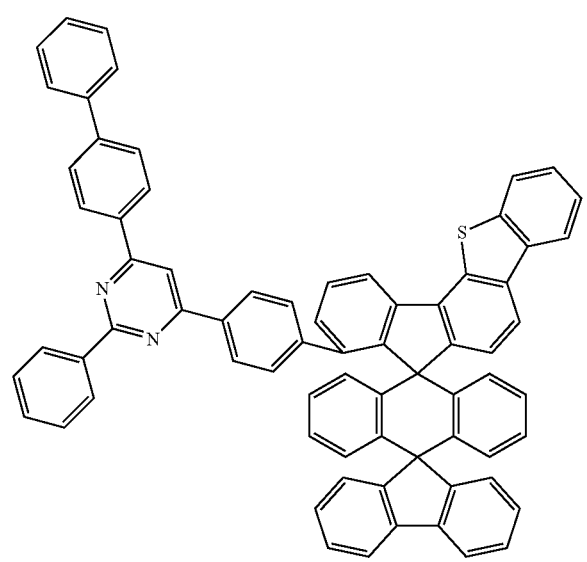
115
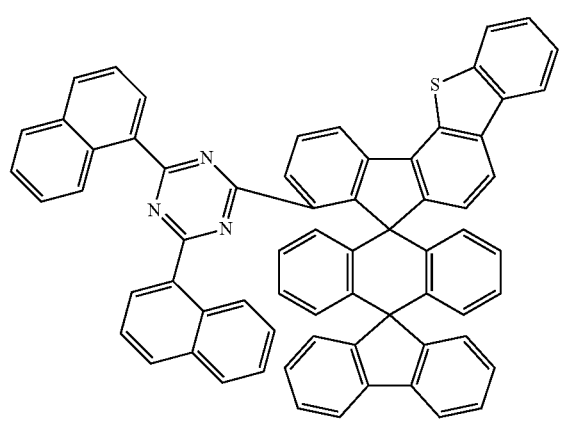
-continued
116
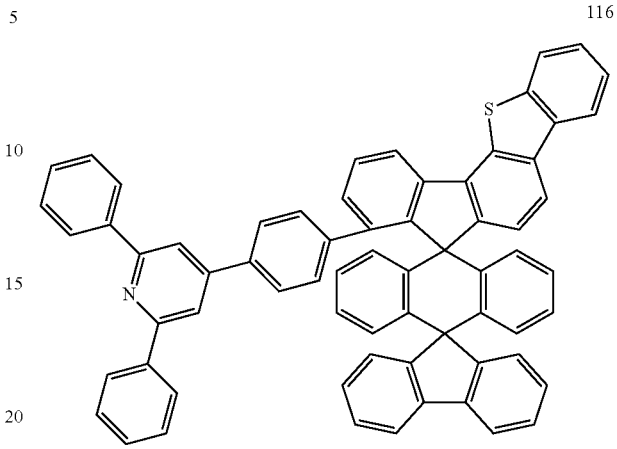
117
118
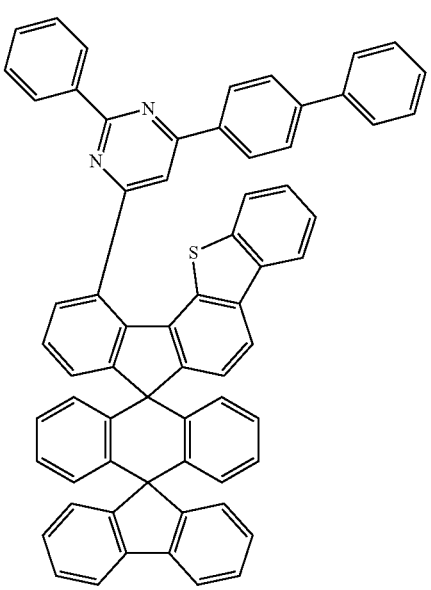

347
-continued
119
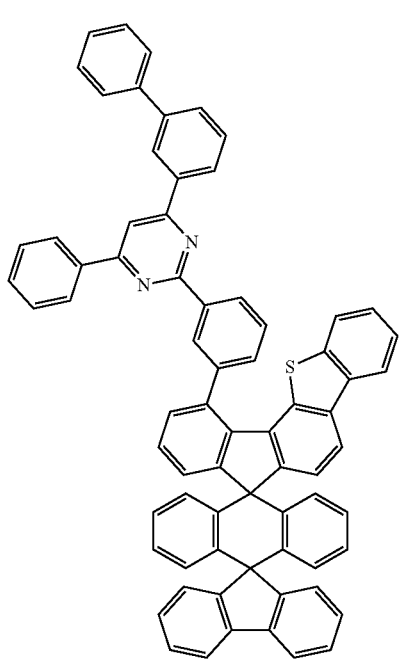
120
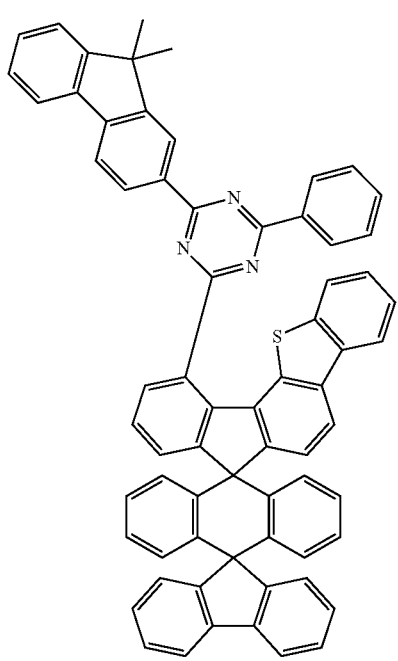
348
-continued
121
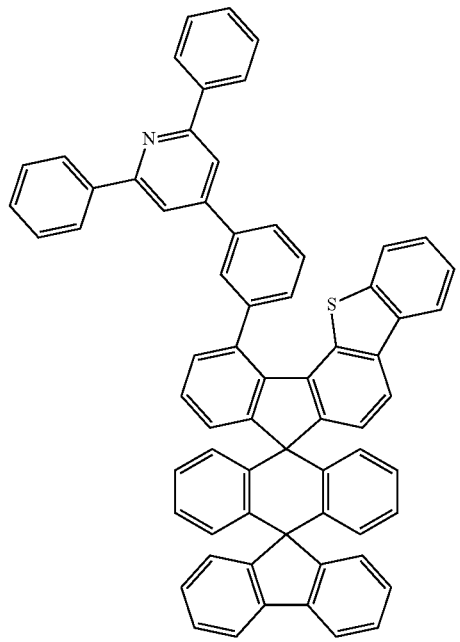
122
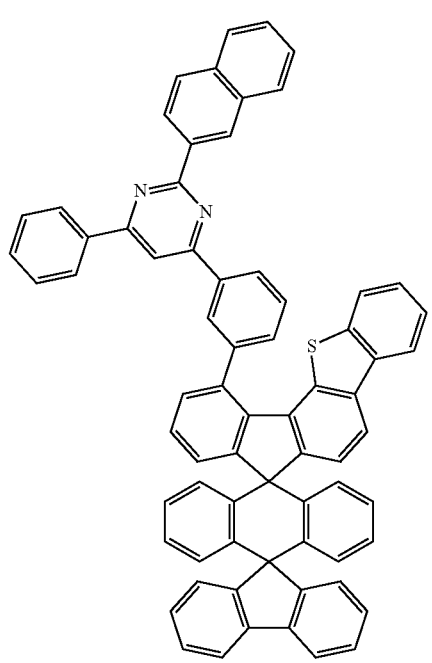

349
-continued
123
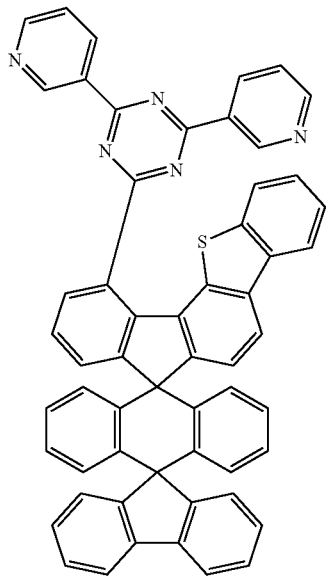
124
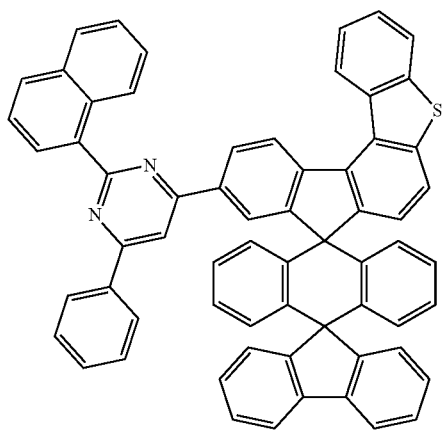
125
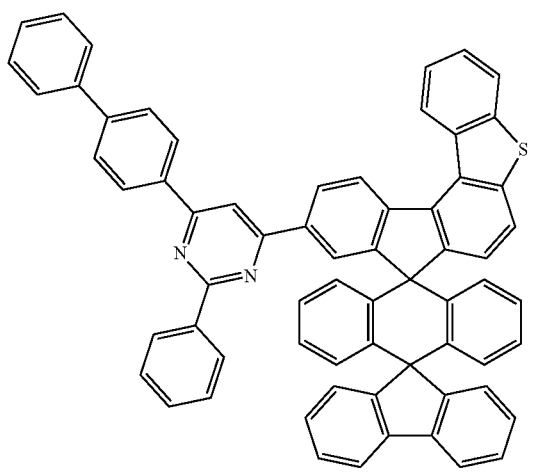
350
-continued
126
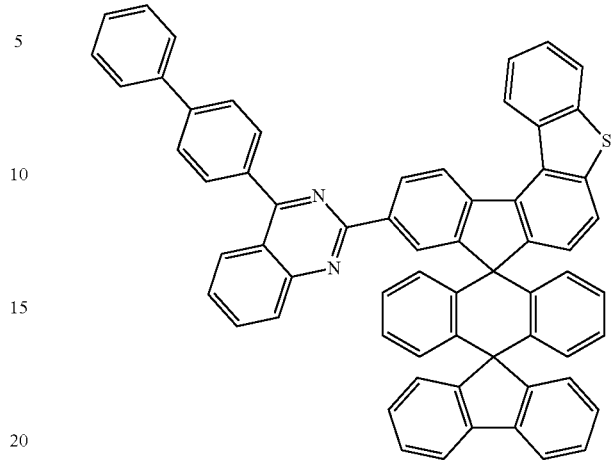
127
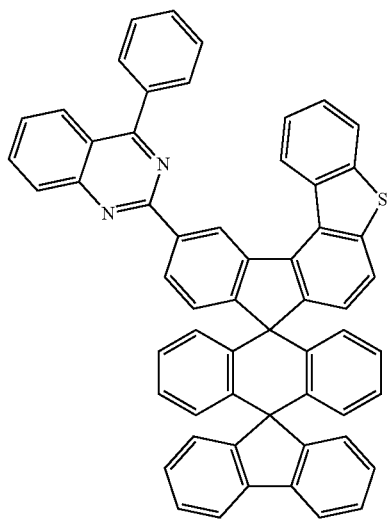
128
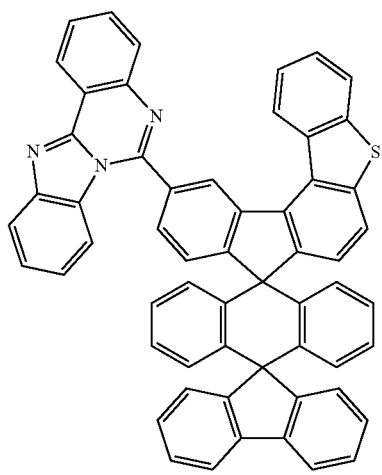

351
-continued
129
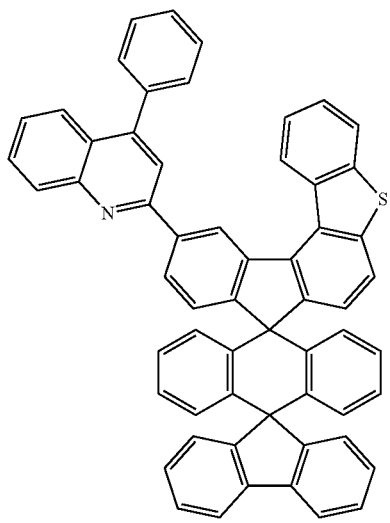
130
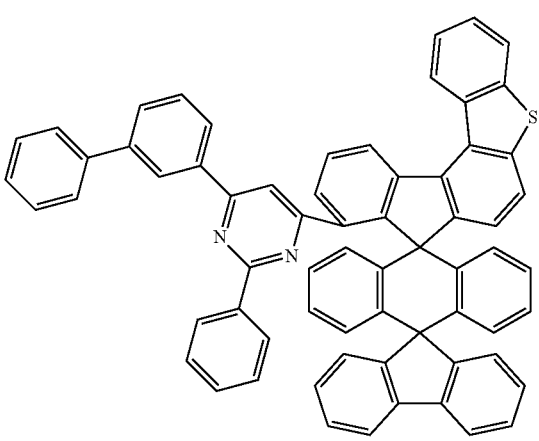
131
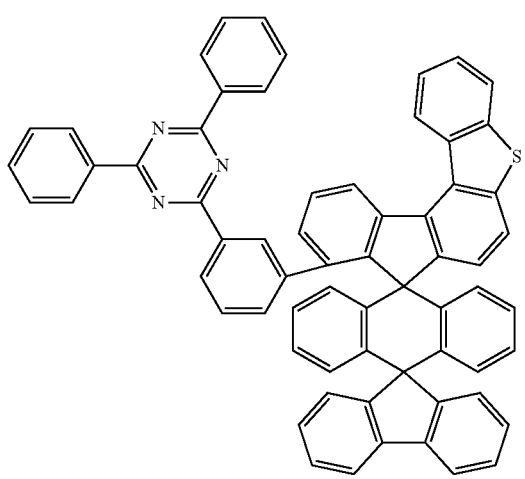
352
-continued
132
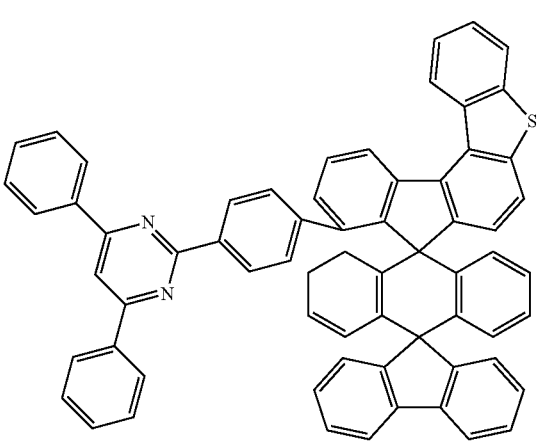
133
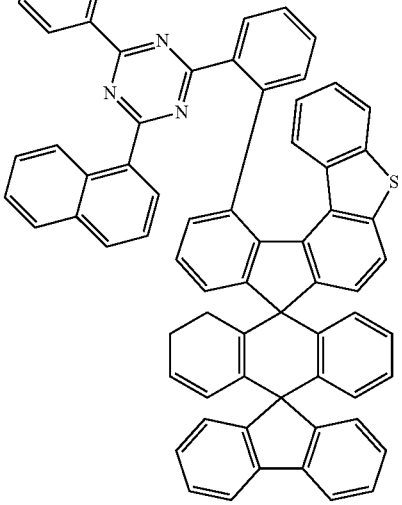
134
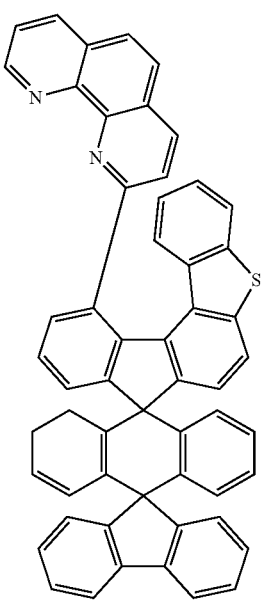

353
-continued
135
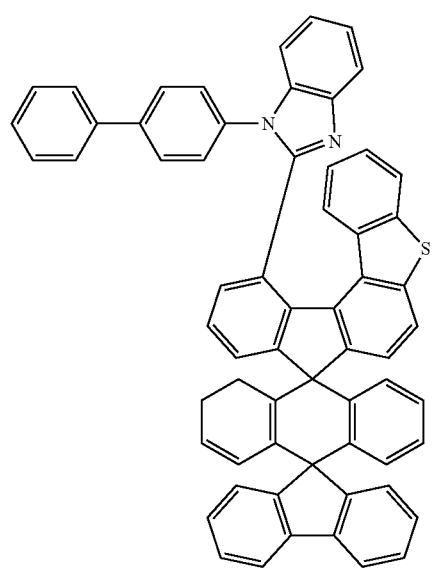
136
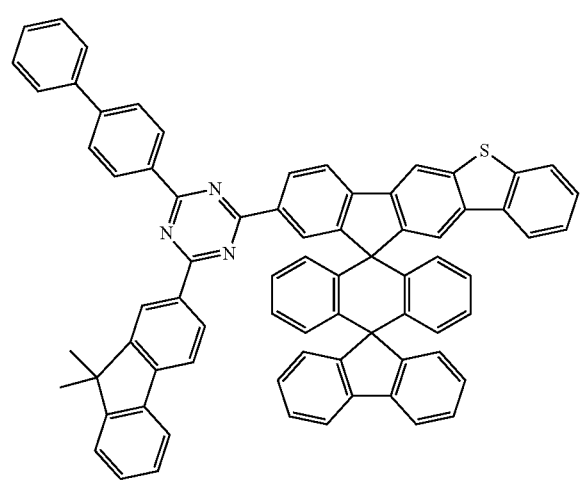
137
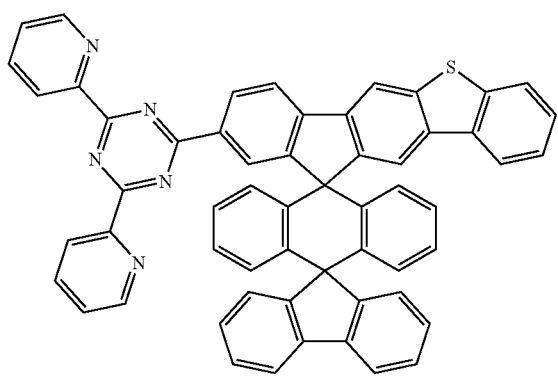
354
-continued
138
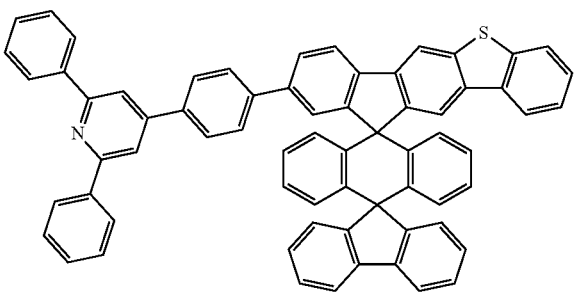
139
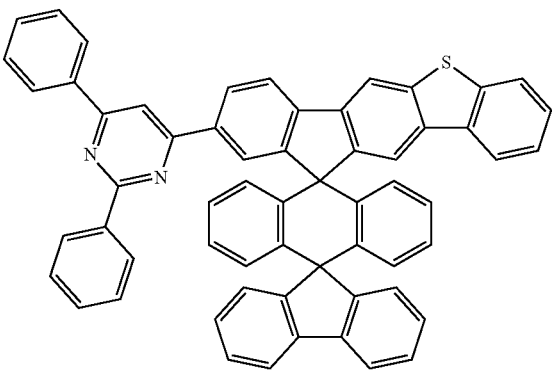
140

141 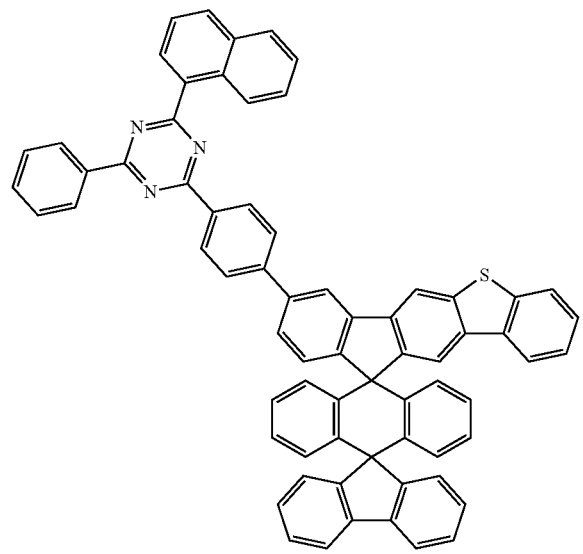
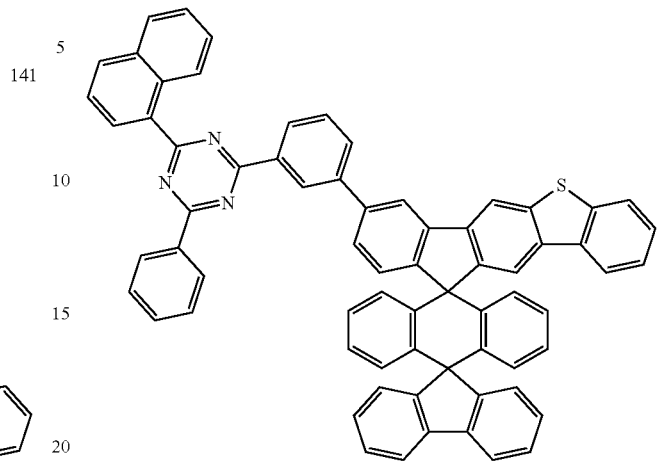
143
144 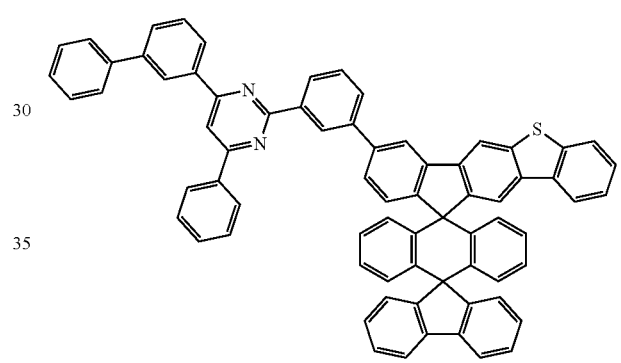
142 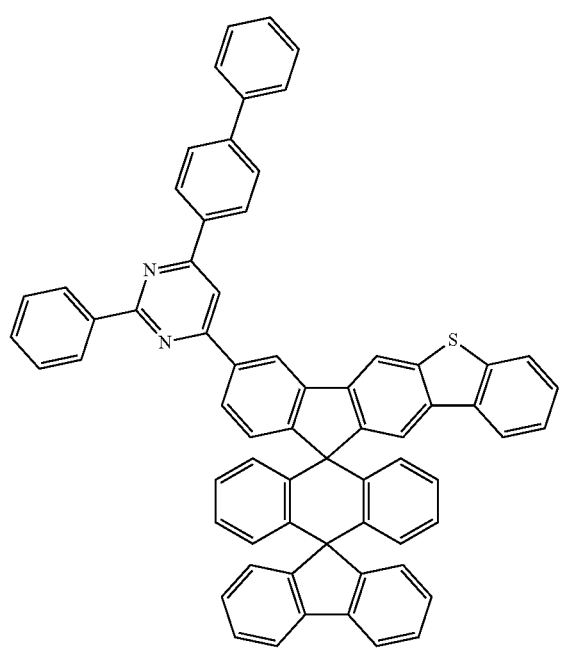
145 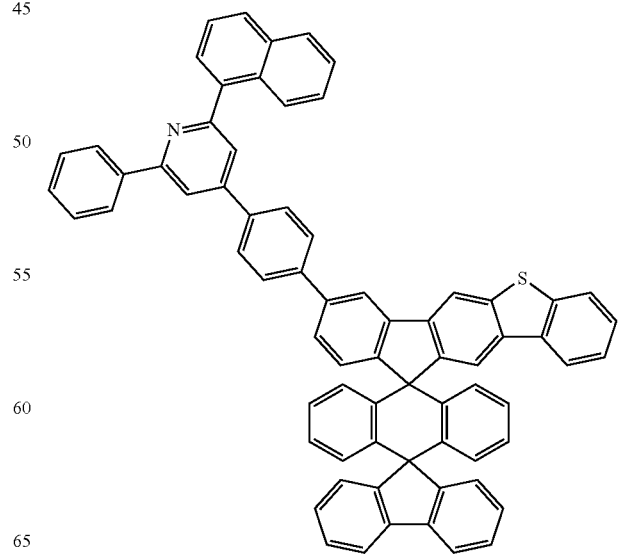

357
-continued
146
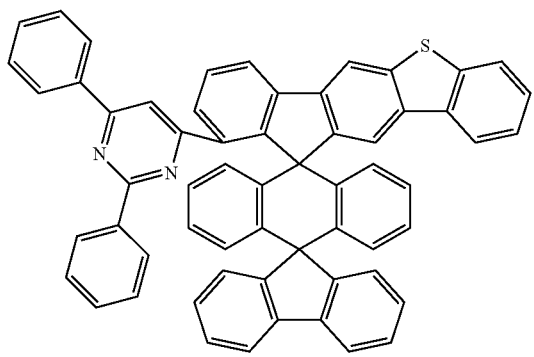
147
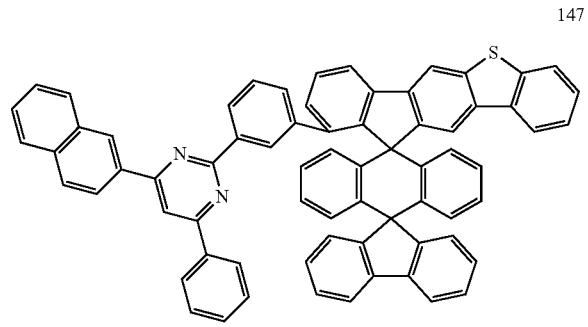
148
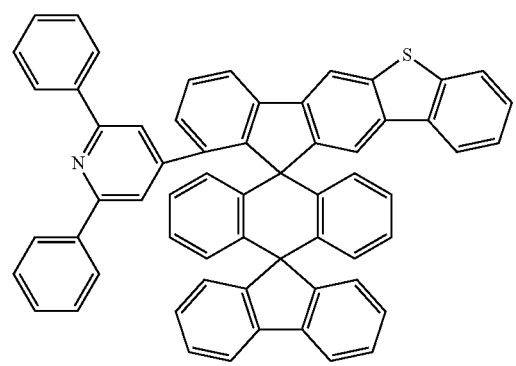
149
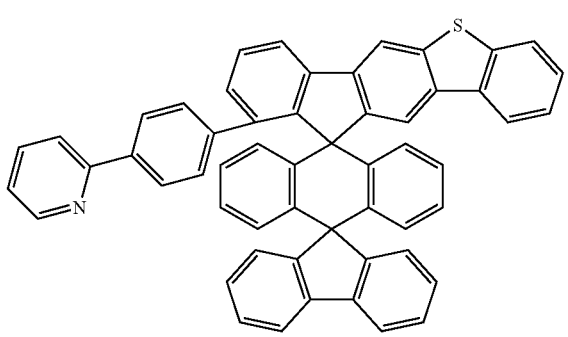
358
-continued
150
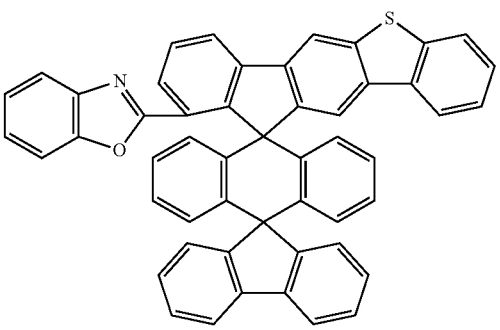
151
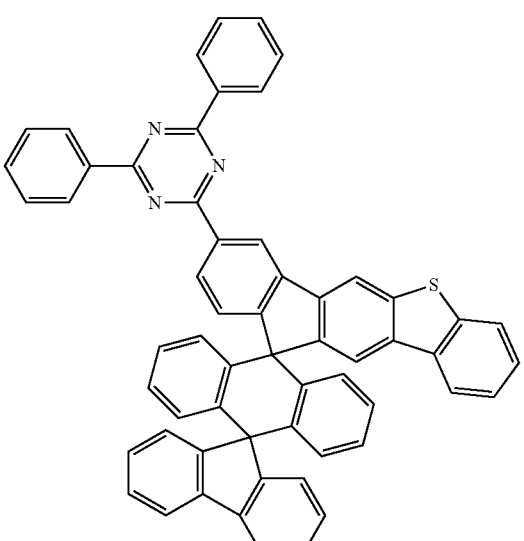
152

359
-continued
153
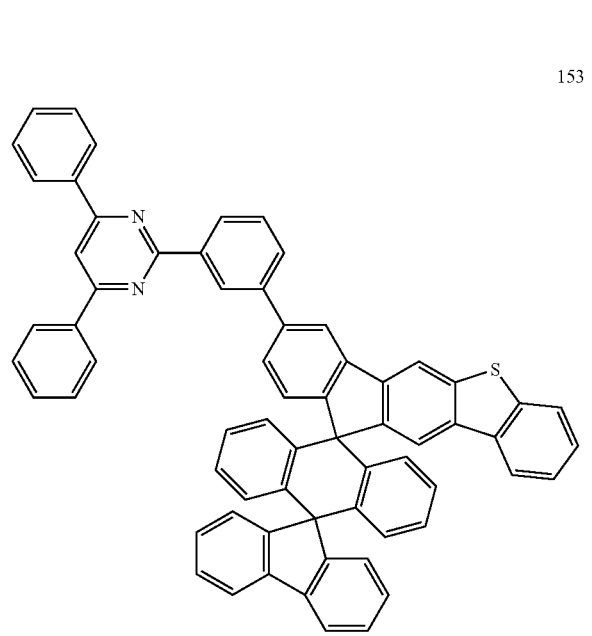
154
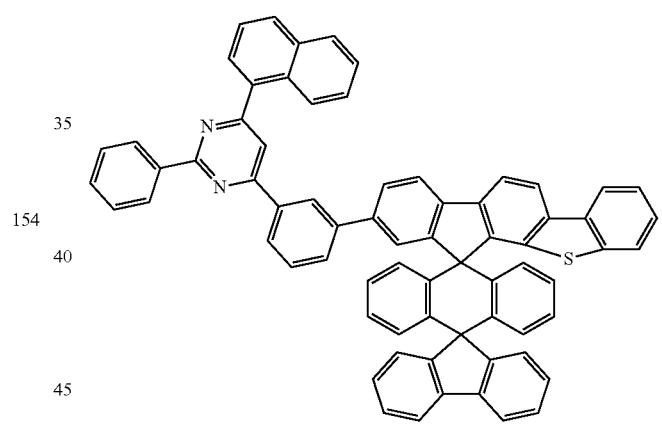
360
-continued
155
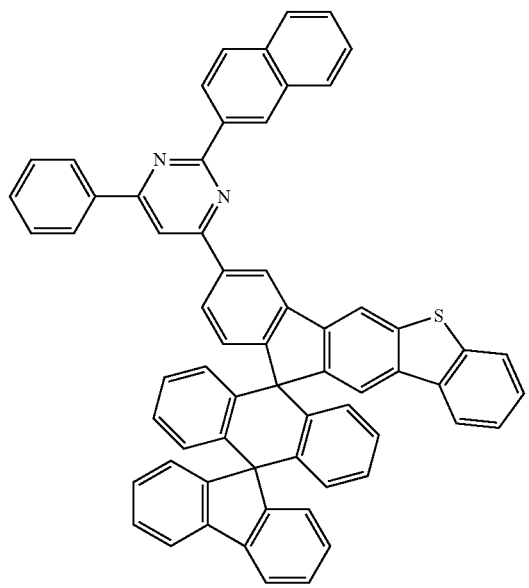
156
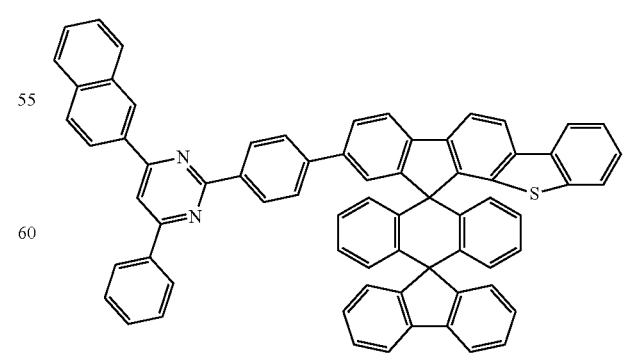
157

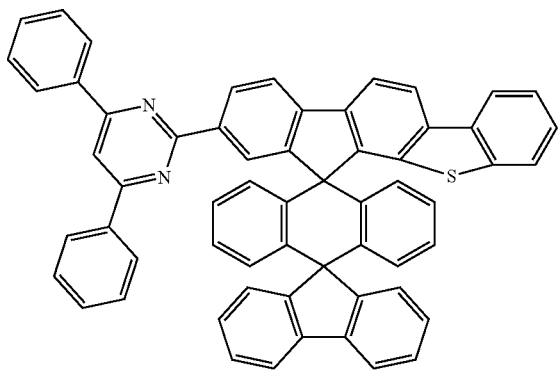
158
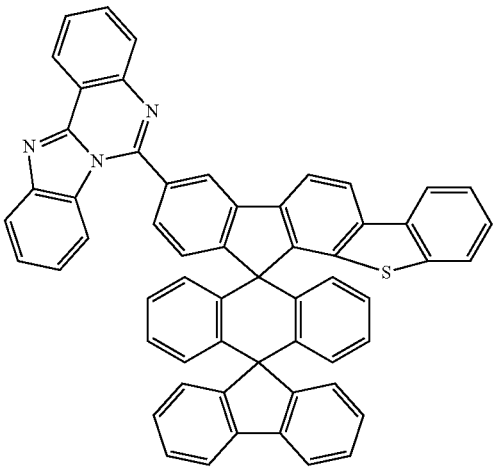
162
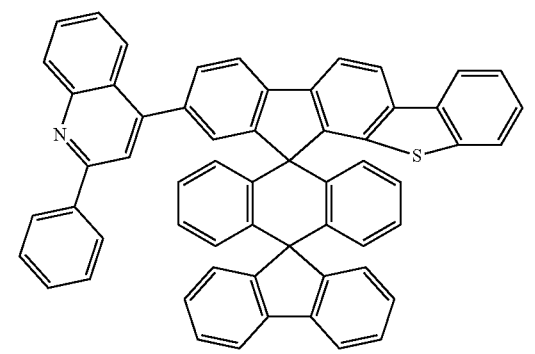
159
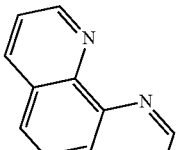
160
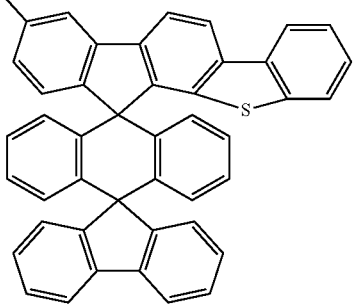
163
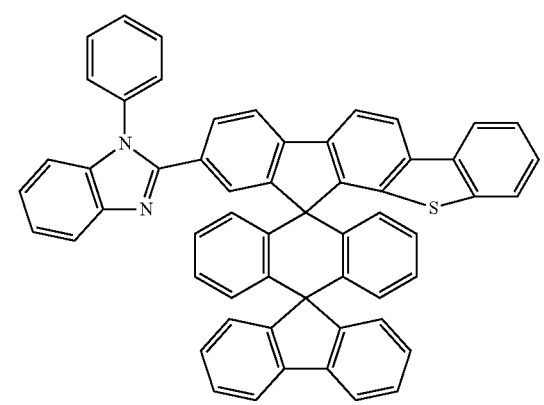
161
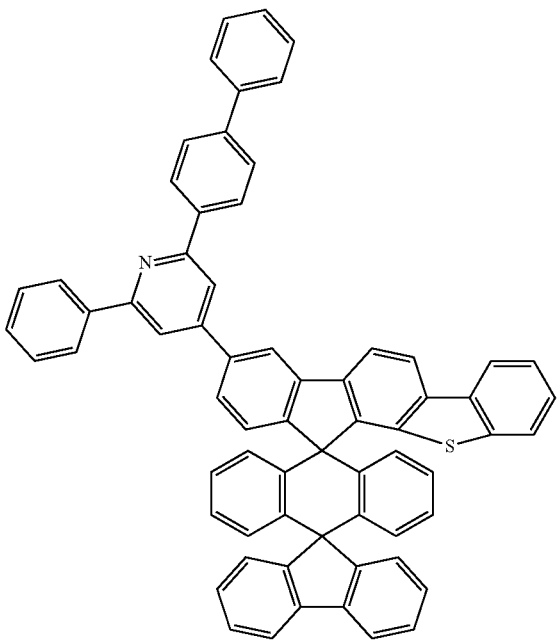
164

363
-continued
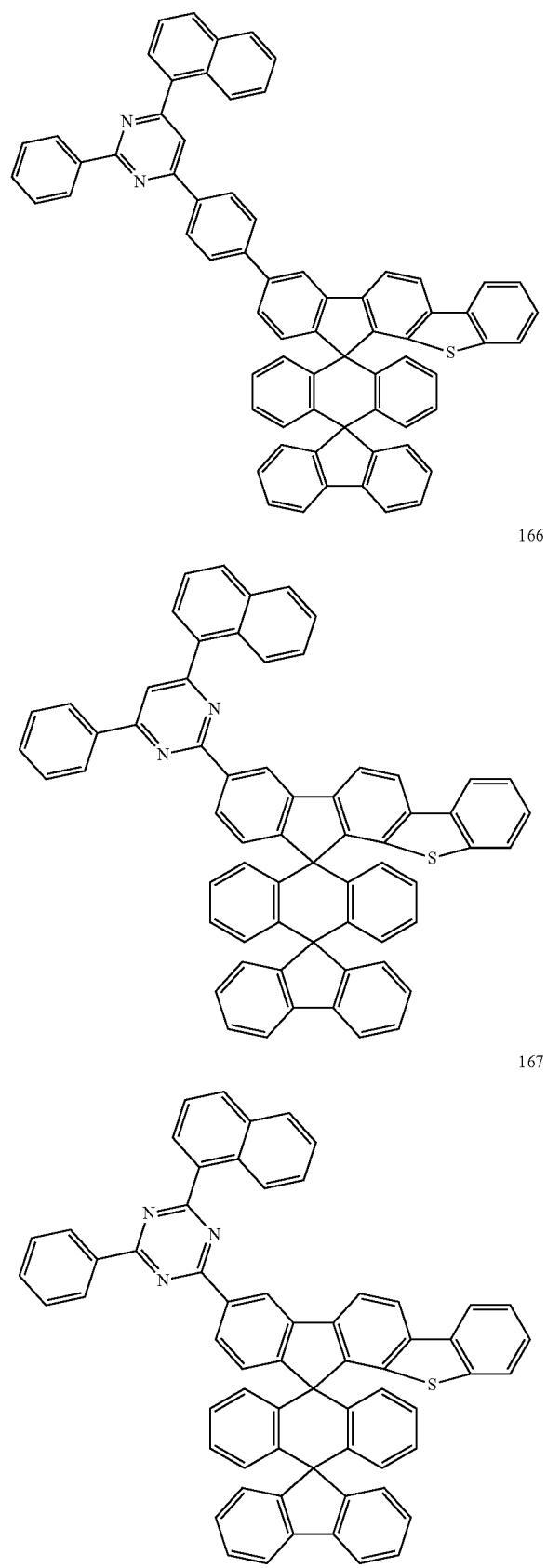
364
-continued
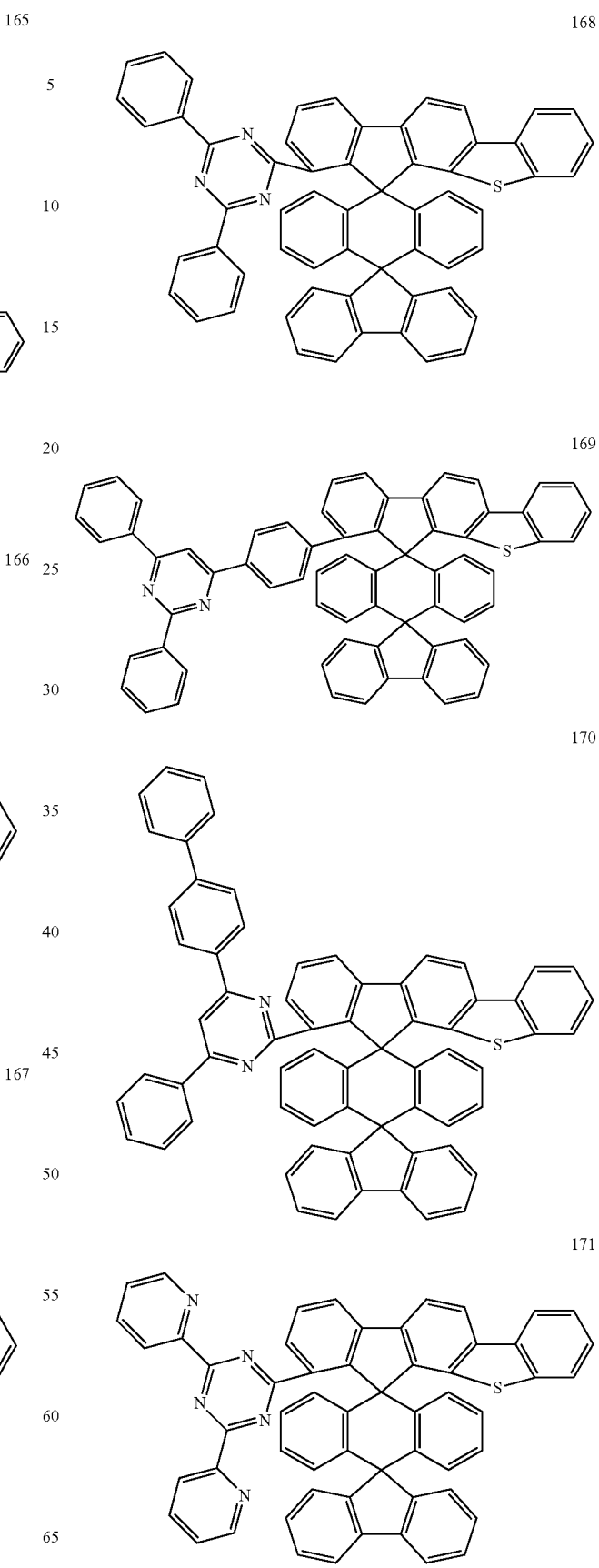

172
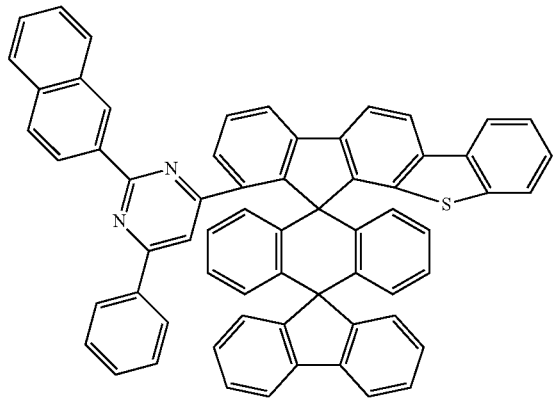
173
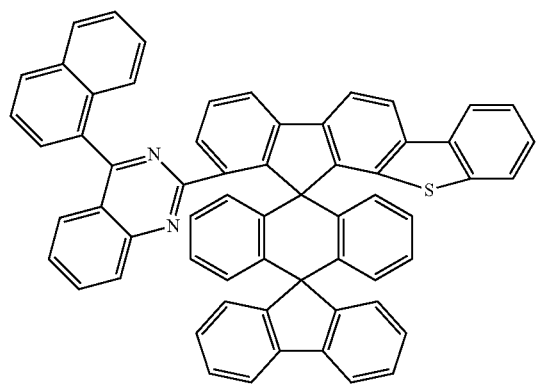
174
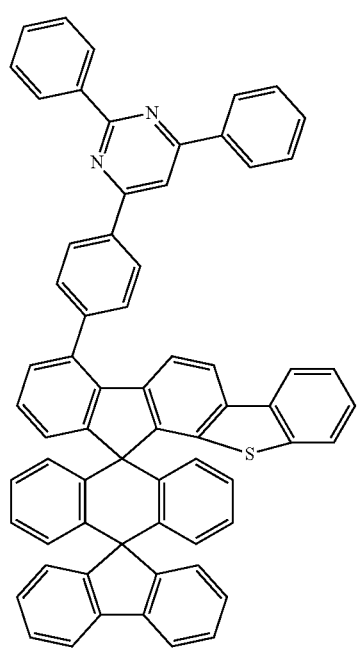
175
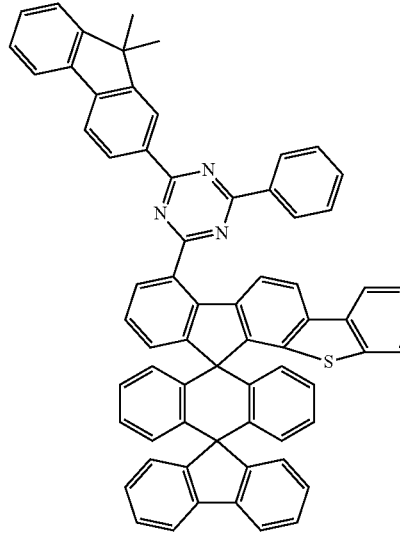
176
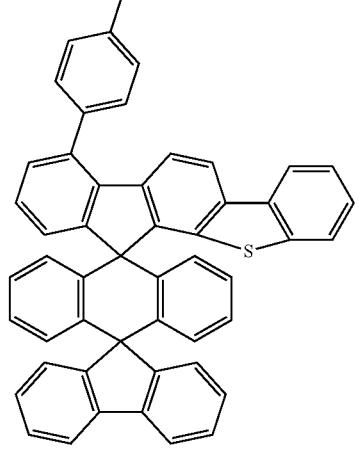
177
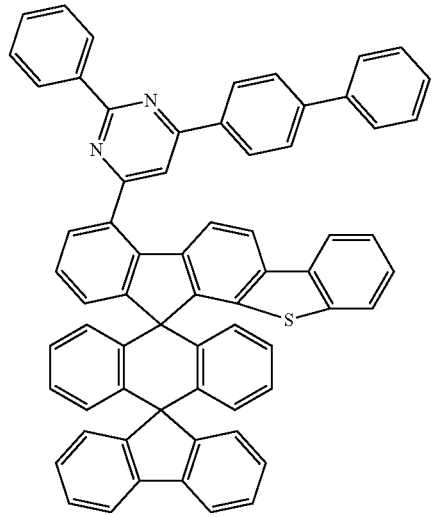

178
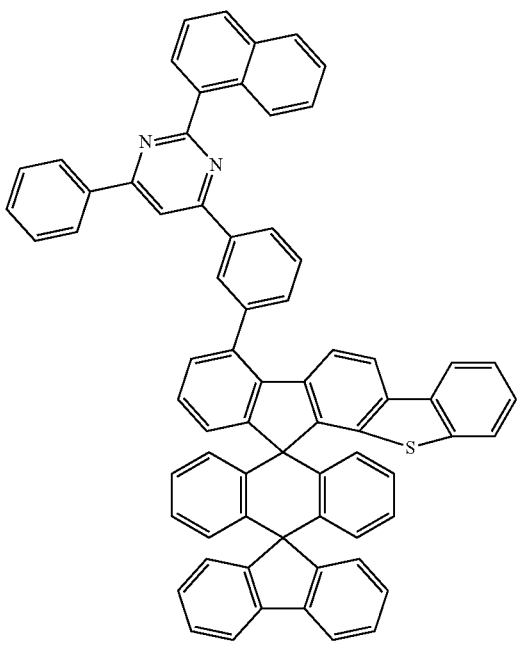
179
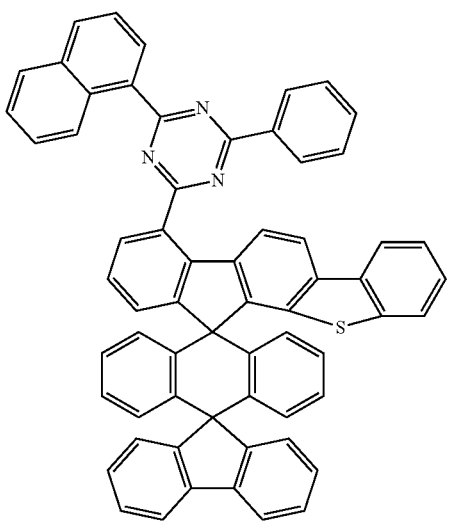
180
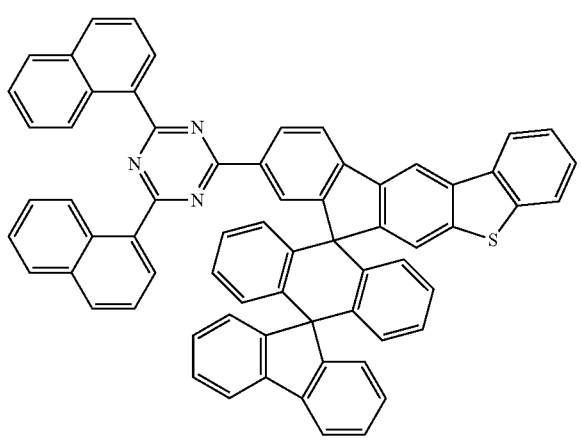
181
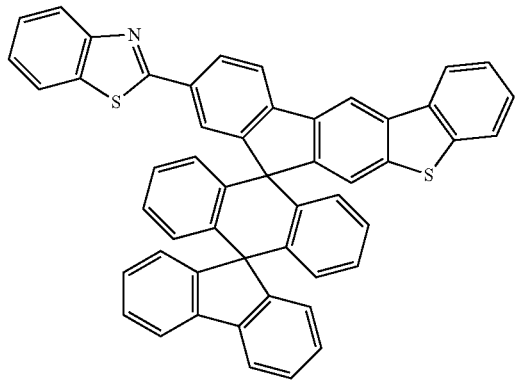
182
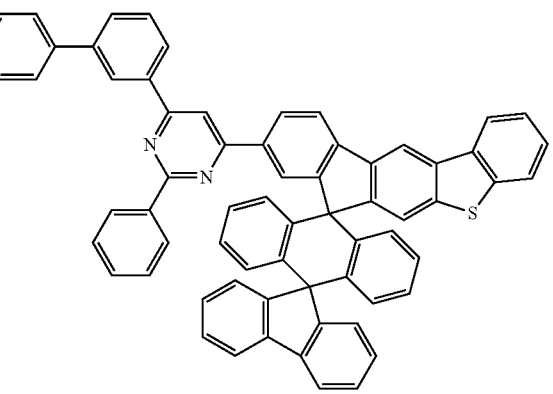
183
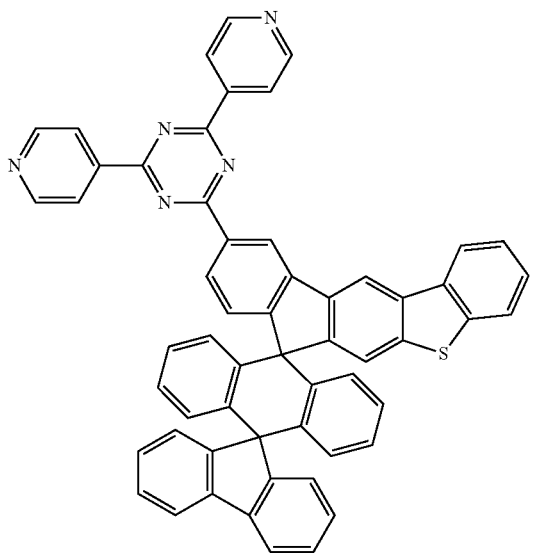

184
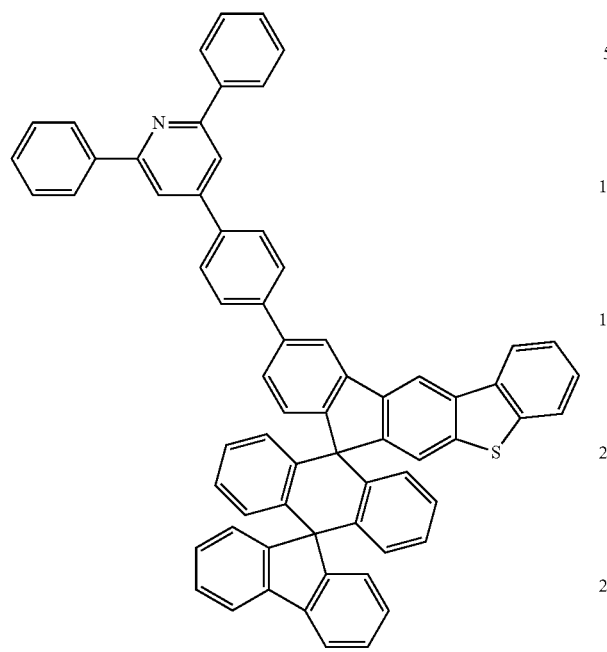
185
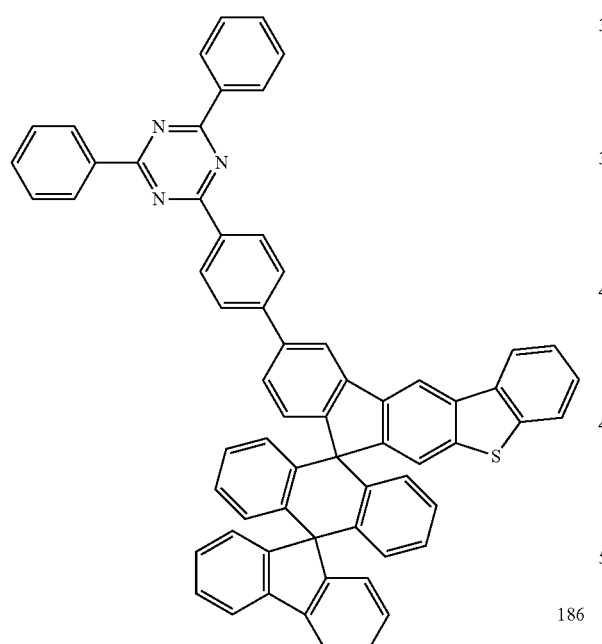
186
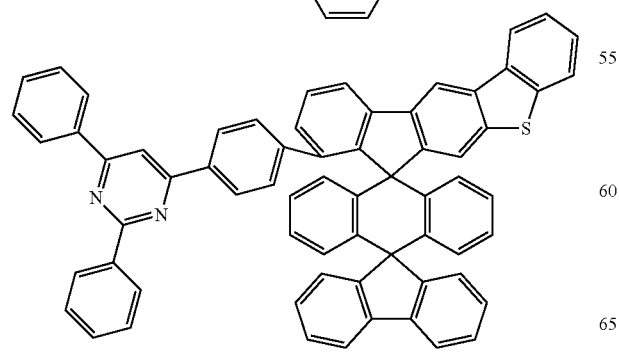
187
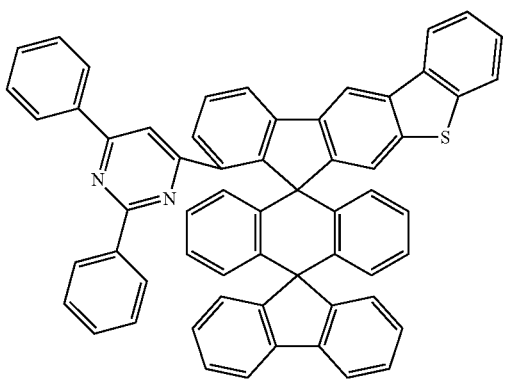
188
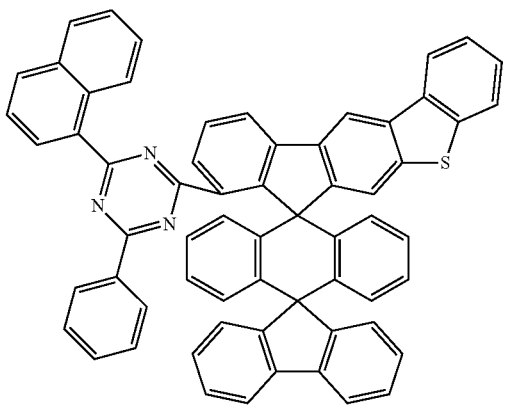
189
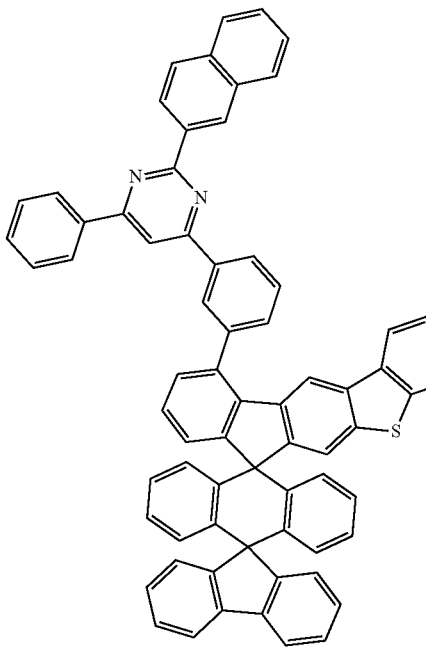

-continued
190
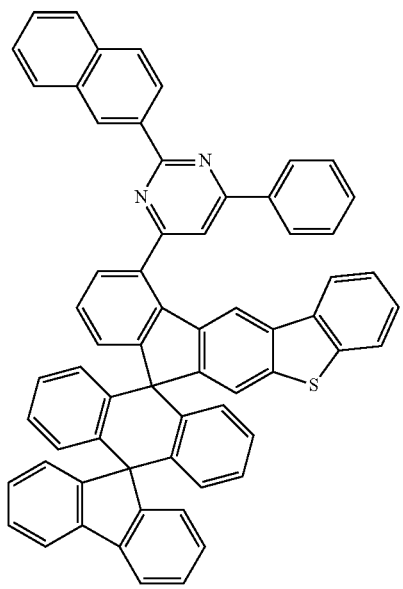
191
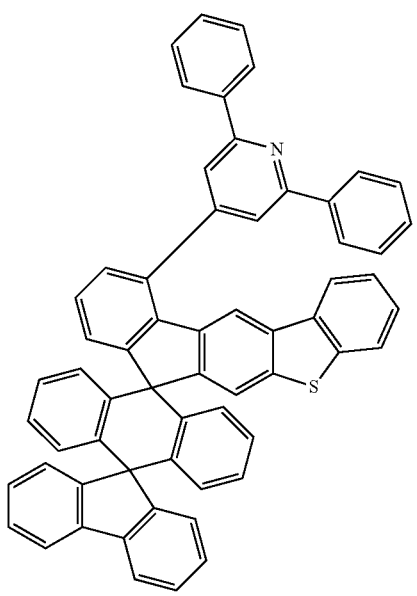
192
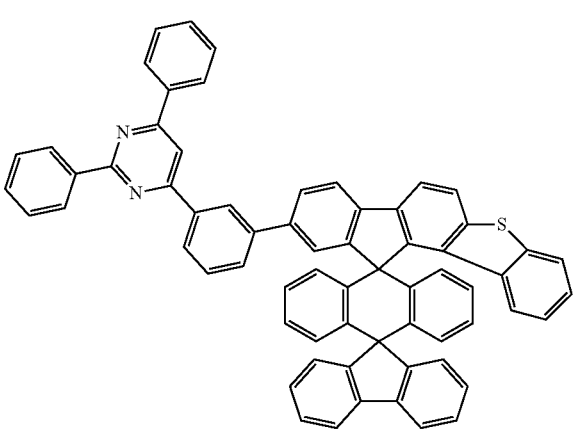
-continued
193
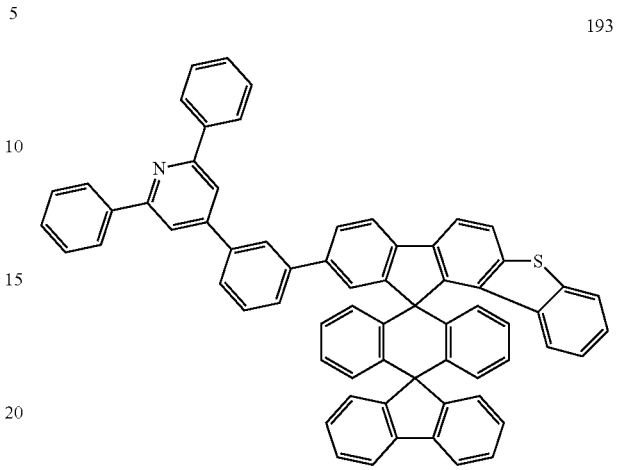
194
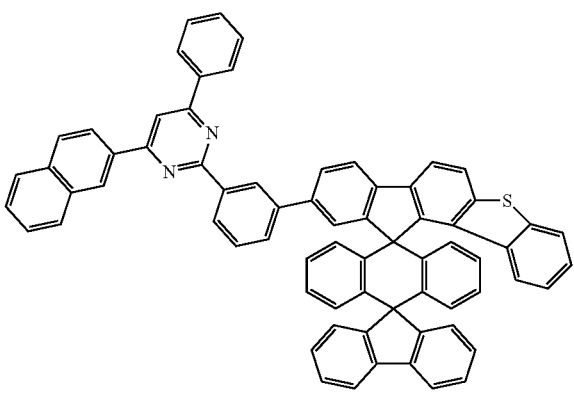
195
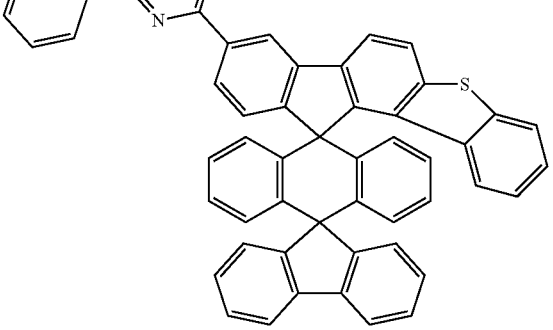

196
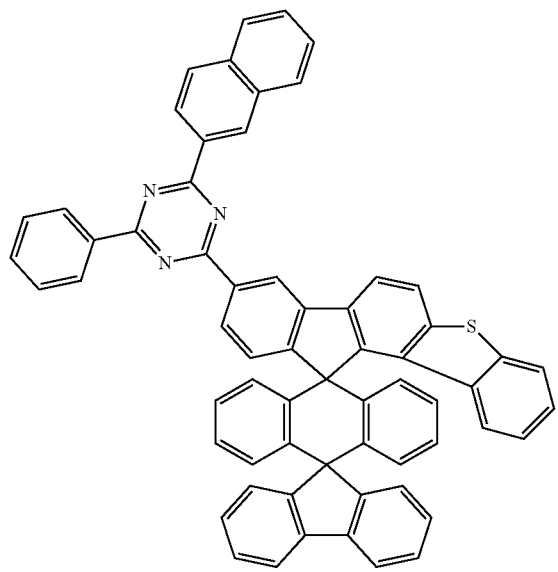
197
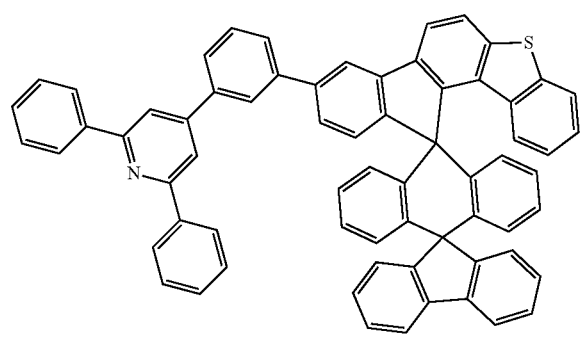
198
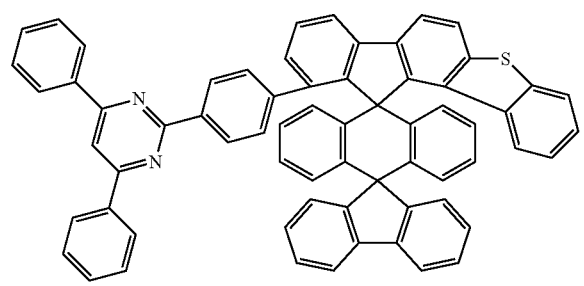
199
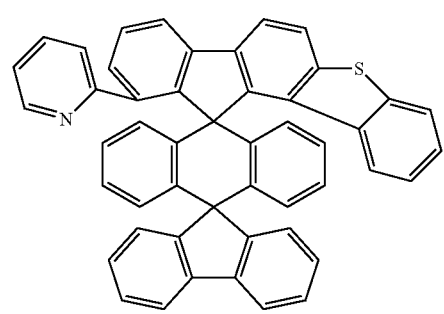
200
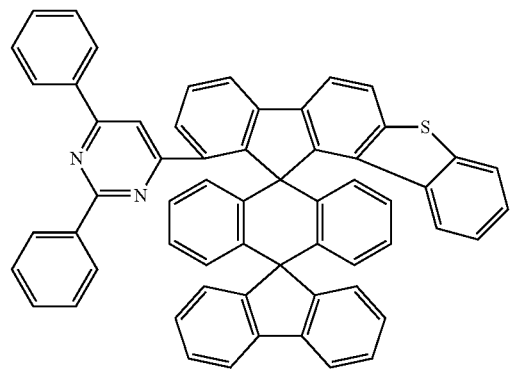
201
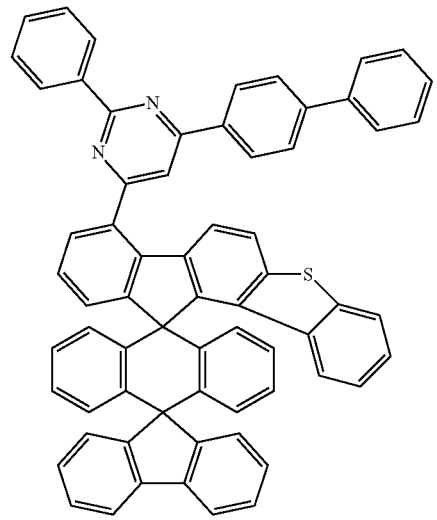
202
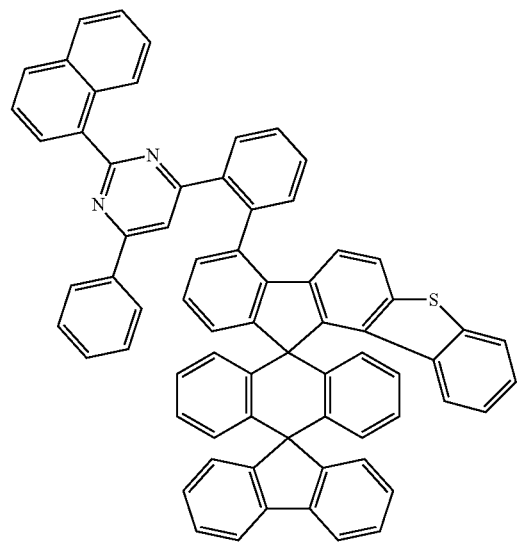

-continued

203

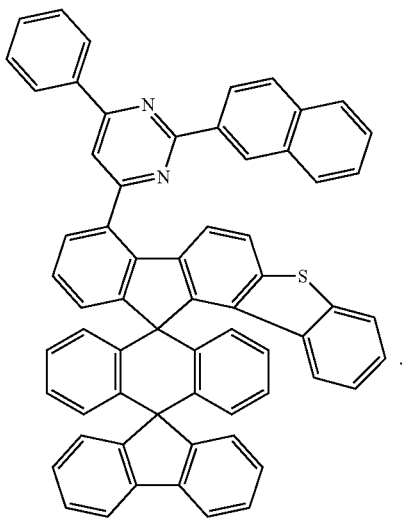

13. The organic light emitting device of claim 1, wherein the organic material layer comprising the compound of Chemical Formula 1 further comprises an n-type dopant.

14. The organic light emitting device of claim 13, wherein the n-type dopant is LiQ.

15. The organic light emitting device of claim 1, wherein the organic material layer comprising the compound of Chemical Formula 1 comprises at least one layer of an electron injection layer, an electron transport layer, or a layer which injects and transports electrons simultaneously, and the at least one layer comprises the compound.

16. The organic light emitting device of claim 15, wherein the light emitting layer comprises a compound represented by the following Chemical Formula 1-A:

[Chemical Formula 1-A]

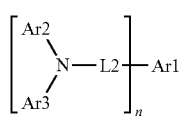

in Chemical Formula 1-A,
n is an integer of 1 or more,
Ar1 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L2 is a direct bond; a substituted or unsubstituted arylene group; or a substituted or unsubstituted heteroarylene group,
Ar2 and Ar3 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or optionally combine with each other to form a substituted or unsubstituted ring, and
when n is 2 or more, two or more structures in the parenthesis are the same as or different from each other.

17. The organic light emitting device of claim 16, wherein L2 is a direct bond, Ar1 is a divalent pyrene group, Ar2 and Ar3 are the same as or different from each other, and are each independently an aryl group which is unsubstituted or substituted with a germanium group substituted with an alkyl group, and n is 2.

18. The organic light emitting device of claim 16, wherein the light emitting layer comprises a compound represented by the following Chemical Formula 2-A:

[Chemical Formula 2-A]

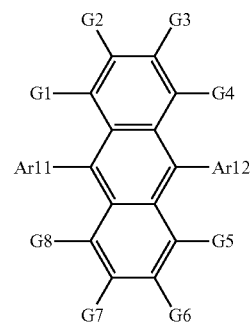

in Chemical Formula 2-A,
Ar11 and Ar12 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted monocyclic aryl group; or a substituted or unsubstituted polycyclic aryl group.

19. The organic light emitting device of claim 15, wherein the organic material layer comprises a light emitting layer, and the light emitting layer comprises a compound represented by the following Chemical Formula 2-A:

[Chemical Formula 2-A]

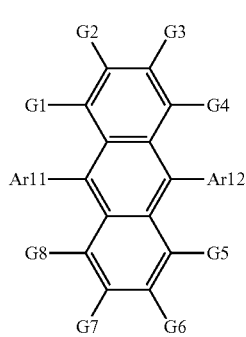

in Chemical Formula 2-A,
Ar11 and Ar12 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted monocyclic aryl group; or a substituted or unsubstituted polycyclic aryl group.

20. The organic light emitting device of claim 19, wherein Ar11 and Ar12 is a 2-naphthyl group, G6 is a 2-naphthyl group substituted with an anthracene group substituted with a phenyl group, and G1 to G5, G7, and G8 are hydrogen.

* * * * *